(12) United States Patent
Burns et al.

(10) Patent No.: US 9,403,850 B2
(45) Date of Patent: *Aug. 2, 2016

(54) BETA-LACTAMASE INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Bin Liu, Dayton, NJ (US); Daniel McGarry, Malvern, PA (US); Daniel C. Pevear, Downingtown, PA (US); Robert E. Lee Trout, Collegeville, PA (US); Randy W. Jackson, Livingston, MT (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/759,853

(22) PCT Filed: Jan. 10, 2014

(86) PCT No.: PCT/US2014/011144
§ 371 (c)(1),
(2) Date: Jul. 8, 2015

(87) PCT Pub. No.: WO2014/110442
PCT Pub. Date: Jul. 17, 2014

(65) Prior Publication Data
US 2016/0016978 A1  Jan. 21, 2016

Related U.S. Application Data

(60) Provisional application No. 61/751,161, filed on Jan. 10, 2013, provisional application No. 61/783,861, filed on Mar. 14, 2013.

(51) Int. Cl.
| | | |
|---|---|---|
| *A61K 31/407* | (2006.01) | |
| *C07F 5/02* | (2006.01) | |
| *A61K 31/69* | (2006.01) | |
| *A61K 45/06* | (2006.01) | |
| *A61K 31/496* | (2006.01) | |
| *A61K 31/546* | (2006.01) | |

(52) U.S. Cl.
CPC ............... *C07F 5/025* (2013.01); *A61K 31/407* (2013.01); *A61K 31/496* (2013.01); *A61K 31/546* (2013.01); *A61K 31/69* (2013.01); *A61K 45/06* (2013.01)

(58) Field of Classification Search
CPC .... C07F 5/025; A61K 31/407; A61K 31/496; A61K 31/546; A61K 45/06
See application file for complete search history.

(56) References Cited

U.S. PATENT DOCUMENTS

| 7,271,186 B1 | 9/2007 | Shoichet et al. | |
|---|---|---|---|
| 8,680,136 B2 | 3/2014 | Hirst et al. | |
| 8,912,169 B2* | 12/2014 | Burns | A61K 31/69 |
| | | | 514/64 |
| 9,040,504 B2* | 5/2015 | Burns | C07F 5/025 |
| | | | 514/64 |
| 9,101,638 B2* | 8/2015 | Reddy | C07F 5/025 |
| 2010/0056478 A1 | 3/2010 | Desarbre et al. | |
| 2010/0120715 A1* | 5/2010 | Burns | C07F 5/025 |
| | | | 514/64 |
| 2010/0286092 A1 | 11/2010 | Burns et al. | |
| 2010/0292185 A1 | 11/2010 | Burns et al. | |
| 2010/0317621 A1 | 12/2010 | Burns et al. | |
| 2011/0294777 A1 | 12/2011 | Blizzard et al. | |
| 2012/0040932 A1 | 2/2012 | Hirst et al. | |
| 2015/0224125 A1 | 8/2015 | Burns et al. | |

FOREIGN PATENT DOCUMENTS

| WO | WO-2005004799 A2 | 1/2005 |
|---|---|---|
| WO | WO-2009064413 A1 | 5/2009 |
| WO | WO-2009064414 A1 | 5/2009 |
| WO | WO-2010056827 A1 | 5/2010 |
| WO | WO-2010130708 A1 | 11/2010 |
| WO | WO-2013053372 A1 | 4/2013 |
| WO | WO-2013122888 A2 | 8/2013 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2014151959 A1 | 9/2014 |

OTHER PUBLICATIONS

U.S. Appl. No. 14/736,921, filed Jun. 2015, Trout.*
U.S. Appl. No. 14/737,156, filed Jun. 2015, Burns.*
U.S. Appl. No. 14/737,323, filed Jun. 2015, Burns.*
U.S. Appl. No. 14/693,318, filed Apr. 2015, Burns.*
U.S. Appl. No. 14/773,717, filed Sep. 2015, Burns.*
Bodner Research Web. The Chemistry of the Halogens. Available from <a href="http://web.archive.org/web/20090414155348/http://chemechem/topicreview/bp/ch10/group3.php">http://web.archive.org/web/20090414155348/http://chemechem/topicreview/bp/ch10/group3.php/</a>.
Burns et al. Caplus AN 2014-1130723 (2014).

(Continued)

*Primary Examiner* — D M Seaman

(74) *Attorney, Agent, or Firm* — Wilson Sonsini Goodrich & Rosati

(57) ABSTRACT

Described herein are compounds and compositions that modulate the activity of beta-lactamases. In some embodiments, the compounds described herein inhibit beta-lactamase. In certain embodiments, the compounds described herein are useful in the treatment of bacterial infections.

20 Claims, No Drawings

(56) References Cited

OTHER PUBLICATIONS

Co-pending U.S. Appl. No. 14/773,717, filed Sep. 8, 2015.
Isomer. https://en.wikipedia.org/wiki/Isomer (2015).
Lima et al. Bioisosterism: A Useful Strategy for Molecular Modification and Drug Design. Current Medicinal Chemistry 12:23-49 (2005).
PCT/US2015/035407 International Search Report and Written Opinion dated Oct. 20, 2015.
U.S. Appl. No. 14/649,527 Office Action dated Nov. 9, 2015.
U.S. Appl. No. 14/693,318 Office Action dated Sep. 1, 2015.
Co-pending U.S. Appl. No. 14/649,527, filed Jun. 3, 2015.
Co-pending U.S. Appl. No. 14/736,921, filed Jun. 11, 2015.
Co-pending U.S. Appl. No. 14/737,156, filed Jun. 11, 2015.
Co-pending U.S. Appl. No. 14/737,323, filed Jun. 11, 2015.
Eidam et al. Design, synthesis, crystal structures, and antimicrobial activity of sulfonamide boronic acids as β-lactamase inhibitors. J. Med. Chem. 53(21):7852-7863 (2010).
Ettmayer et al. Lessons Learned from Marketed and Investigational Prodrugs. J Medicinal Chem. 47(10):2393-2404. 2004.
Han. Targeted Prodrug Design to Optimize Drug Delivery. AAPS Pharmsci. 2(1)Article 6:1-11 (2000).
Morandi et al. Structure-based optimization of cephalothin-analogue boronic acids as β-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
PCT/US2013/073428 International Preliminary Report on Patentability dated Jun. 18, 2015.
PCT/US2013/073428 International Search Report dated Apr. 25, 2014.
PCT/US2014/011144 International Preliminary Report on Patentability dated Jul. 23, 2015.
PCT/US2014/011144 International Search Report dated May 12, 2014.
PCT/US2014/026727 International Search Report dated Jul. 25, 2014.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Testa. Prodrug research: futile or fertile? Biochem. Pharm. 68:2097-2106 (2004).
U.S. Appl. No. 14/152,916 Office Action dated Aug. 29, 2014.
Weston et al. Structure-based enhancement of boronic acid-based inhibitors of AmpC β-lactamase. J. Med. Chem. 41(23):4577-4586 (1998).
U.S. Appl. No. 14/737,323 Office Action dated Mar. 18, 2016.

* cited by examiner

BETA-LACTAMASE INHIBITORS

CROSS-REFERENCE TO RELATED APPLICATIONS

This application is a U.S. National Stage entry of International Application No. PCT/US14/11144, filed Jan. 10, 2014, which claims the benefit of prior from U.S. Provisional Application Ser. No. 61/751,161, filed Jan. 10, 2013, and U.S. Provisional Application Ser. No. 61/783,261 filed Mar. 14, 2013, each of which are hereby incorporated by reference in their entirety.

STATEMENT AS TO FEDERALLY SPONSORED RESEARCH

This invention was made with the support of the United States government under Contract number AI096679-01 by National Institutes of Health (NIH), AI096613-01 by National Institutes of Health (NIH), and AI089512-01 by National Institutes of Health (NIH). The government has certain rights in the invention.

FIELD OF INVENTION

The present invention relates to boron-containing compounds, compositions, preparations and their use as inhibitors of beta-lactamase enzymes and as antibacterial agents.

BACKGROUND OF THE INVENTION

Antibiotics are the most effective drugs for curing bacteria-infectious diseases clinically. They have a wide market due to their advantages of good antibacterial effect with limited side effects. Among them, the beta-lactam class of antibiotics (for example, penicillins, cephalosporins, and carbapenems) are widely used because they have a strong bactericidal effect and low toxicity.

To counter the efficacy of the various beta-lactams, bacteria have evolved to produce variants of beta-lactam deactivating enzymes called beta-lactamases, and in the ability to share this tool inter- and intra-species. These beta-lactamases are categorized as "serine" or "metallo" based, respectively, on presence of a key serine or zinc in the enzyme active site. The rapid spread of this mechanism of bacterial resistance can severely limit beta-lactam treatment options in the hospital and in the community.

SUMMARY OF THE INVENTION

Described herein are compounds that modulate the activity of beta-lactamases. In some embodiments, the compounds described herein inhibit beta-lactamases. In certain embodiments, the compounds described herein are useful in the treatment of bacterial infections.

In one aspect, provided herein are compounds of Formula I or Formula Ia, or pharmaceutically acceptable salts, polymorphs, solvates, tautomers, metabolites, or N-oxides thereof:

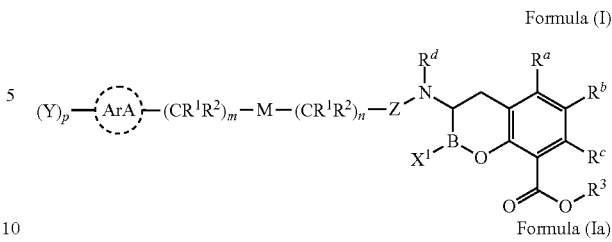

Formula (I)

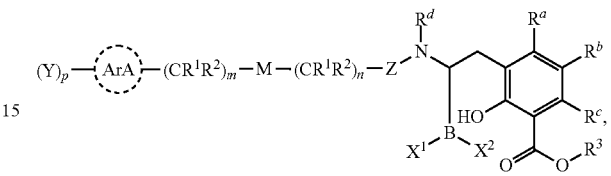

Formula (Ia)

wherein:
M is a bond, —O—, —S—, —S(O)—, $SO_2$—, or —N($R^4$)—;
m is 0, 1, or 2;
n is 0, 1, 2, or 3;
  provided that
    when n is 0, then M is a bond;
p is 2, 3, 4 or 5;
$X^1$ and $X^2$ are independently selected from —OH, —$OR^8$, or F;
Z is >C═O, >C═S, or >$SO_2$;
ArA is an aromatic or heteroaromatic ring system optionally substituted with one or more substituents from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, and —$SR^{10}$;
each Y is selected from the group consisting of
—$NR^4R^5$, —$(CR^6R^7)_vNR^4R^5$, —$NR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(═NR^7)NR^4(CR^6R^7)_vNR^4R^5$, —$N(R^4)C(═NR^5)R^6$, —$(CR^6R^7)_vN(R^4)C(═NR^5)R^6$, —$NR^4(CR^6R^7)_vN(R^4)C(═NR^5)R^6$, —$O(CR^6R^7)_vN(R^4)C(═NR^5)R^6$, —$S(O)_{0,1,2}(CR^6R^7)_vN(R^4)C(═NR^5)R^6$, —$(CR^6R^7)_vC(═NR^5)NR^4R^5$, —$NR^4(CR^6R^7)_vC(═NR^5)NR^4R^5$, —$O(CR^6R^7)_vC(═NR^5)NR^4R^5$, —$S(O)_{0,1,2}(CR^6R^7)_vC(═NR^5)NR^4R^5$, —$(CR^6R^7)_vN(R^4)C(═NR^5)NR^4R^5$, —$NR^4(CR^6R^7)_vN(R^4)C(═NR^5)NR^4R^5$, —$O(CR^6R^7)_vN(R^4)C(═NR^5)NR^4R^5$, —$S(O)_{0,1,2}(CR^6R^7)_vN(R^4)C(═NR^5)NR^4R^5$, —$NR^4C(═NR^5)NR^4C(═NR^5)NR^4R^5$, —$(CR^6R^7)_vC(═NR^4)NR^5C(═NR^4)NR^4R^5$, —$NR^4(CR^6R^7)_vC(═NR^4)NR^5C(═NR^4)NR^4R^5$, —$O(CR^6R^7)_vC(═NR^4)NR^5C(═NR^4)NR^4R^5$, —$S(O)_{0,1,2}$—$(CR^6R^7)_vC(═NR^4)NR^5C(═NR^4)NR^4R^5$, —$NR^4C(═NR^5)NR^4R^5$, —C(═$NR^4$)$NR^4R^5$, —C(═$NR^4$)$NR^4C(O)R^6$, —$NR^4SO_2R^6$, —$NR^4C(O)R^6$, —$NR^4C(═O)OR^6$, —C(O)$NR^4R^5$, —$(CR^6R^7)_vC(O)NR^4R^5$, —$SO_2NR^4R^5$, -Heteroaryl-$NR^4R^5$, -Heterocyclyl-$NR^4R^5$, -Heteroaryl-N($R^4$)C(═$NR^5$)$NR^4R^5$, -Heterocyclyl-N($R^4$)C(═$NR^5$)

NR$^4$R$^5$, —N(R$^4$)-Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$$_2$, —(CR$^6$R$^7$)$_v$(T)$^+$Q$^-$, and —O(CR$^6$R$^7$)$_v$NR$^4$R$^5$R$^{9+}$Q$^-$;

wherein:
T is pyridine-1-yl, pyrimidin-1-yl, or thiazol-3-yl;
Q is a pharmaceutically acceptable counterion; and
v is 1-4;
or two Ys taken together with the carbon atoms to which they are attached to ArA form an optionally substituted carbocycle or an optionally substituted heterocycle;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{10}$, —NR$^4$R$^5$, and —SR$^{10}$;

R$^1$ and R$^2$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$, or R$^1$ and R$^2$ taken together form an oxo, oxime, or an optionally substituted carbocycle or optionally substituted heterocycle with the carbon to which they are attached;

R$^3$ is hydrogen, optionally substituted C$_1$-C$_6$ alkyl, or a pharmaceutically acceptable prodrug;

R$^d$, R$^4$ and R$^5$ are independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^4$ and R$^5$ taken together form an optionally substituted heterocycle with the nitrogen to which they are attached;

R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;

or R$^6$ and R$^7$ taken together form an oxo, oxime, or an optionally substituted carbocycle or an optionally substituted heterocycle with the carbon to which they are attached;

R$^8$ is optionally substituted C$_1$-C$_6$ alkyl, optionally substituted C$_3$-C$_6$ cycloalkyl, or a pharmaceutically acceptable boronate ester group;

R$^9$ is optionally substituted C$_1$-C$_6$ alkyl;

R$^{10}$ is optionally substituted C$_1$-C$_6$ alkyl or optionally substituted C$_3$-C$_6$ cycloalkyl.

In some embodiments of a compound of Formula I or Formula Ia, R$^a$, R$^b$, and R$^c$ are independently selected from the group consisting of hydrogen, fluoro, chloro, optionally substituted C$_1$-C$_6$ alkyl, optionally substituted C$_3$-C$_6$ cycloalkyl, —OH, —OR$^{10}$, —NR$^4$R$^5$, and —SR$^{10}$. In certain embodiments, R$^a$, R$^b$, and R$^c$ are independently hydrogen, fluoro, or chloro. In preferred embodiments, R$^a$, R$^b$, and R$^c$ are hydrogen.

In some embodiments of a compound of Formula I or Formula Ia, R$^3$ is hydrogen, methyl, ethyl, propyl, butyl, or isopropyl. In preferred embodiments, R$^3$ is hydrogen.

In some embodiments of a compound of Formula I or Formula Ia, X$^1$ and X$^2$ are —OH.

In some embodiments of a compound of Formula I or Formula Ia, R$^d$ is hydrogen or C$_1$-C$_4$-alkyl. In preferred embodiments, R$^d$ is hydrogen.

In some embodiments of a compound of Formula I or Formula Ia, Z is >C=O or >SO$_2$. In preferred embodiments, Z is >C=O.

In some embodiments of a compound of Formula I or Formula Ia, each R$^1$ and R$^2$ is independently selected from the group consisting of fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$, or R$^1$ and R$^2$ taken together form an oxo, oxime, or an optionally substituted carbocycle or optionally substituted heterocycle with the carbon to which they are attached.

In some embodiments of a compound of Formula I or Formula Ia, ArA is selected from the group consisting of benzene, naphthalene, pyridine, pyrimidine pyrazine, pyridazine, triazine, thiophene, furan, pyrrole, pyrazole, triazole, imidazole, thiazole, isothiazole, oxazole, isoxazole. indole, indazole, azaindole, azaindazole, isoindole, indolizine, imidazopyridine, pyrazolo-pyridine, thiazolo-pyridine pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyrido-pyrimidine, pyrido-pyrazine, pyridopyridazine, isoxazolo-pyridine, and oxazolo-pyridine. In certain embodiments ArA is selected from the group consisting of benzene, pyridine, pyrimidine, thiophene, thiazole, triazole, indole, benzimidazole, azaindole, thienopyrazole, quinoline, quinazoline, and quinoxaline. In preferred embodiments, ArA is benzene, thiophene, pyridine, aza-indole, or quinoxaline.

In some embodiments of a compound of Formula I or Formula Ia, at least one Y is selected from the group consisting of NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —NR$^4$C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$, —C(=NR$^4$)

NR⁴R⁵, —O(CR⁶R⁷)ᵥC(=NR⁴)NR⁵C(=NR⁴)NR⁴R⁵, —NR⁴C(=NR⁵)NR⁴R⁵, —C(=NR⁴)NR⁴R⁵, —C(=NR⁴) NR⁴C(O)R⁶, —NR⁴SO₂R⁶, —NR⁴C(O)R⁶, —NR⁴C(=O) OR⁶, —C(O)NR⁴R⁵, —(CR⁶R⁷)ᵥC(O)NR⁴R⁵, -Heteroaryl-NR⁴R⁵, -Heterocyclyl-NR⁴R⁵, -Heteroaryl-N(R⁴)C(=NR⁵) NR⁴R⁵, -Heterocyclyl-N(R⁴)C(=NR⁵)NR⁴R⁵, —N(R⁴)-Heteroaryl-NR⁴R⁵, —N(R⁴)—Heterocyclyl-NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, —(CR⁶R⁷)ᵥHeterocyclyl-N(R⁴)C(=NR⁵)NR⁴R⁵, —(CR⁶R⁷)ᵥHeteroaryl, —(CR⁶R⁷)ᵥHeterocyclyl, —O-Heteroaryl, —O-Heterocyclyl, —NR⁴(CR⁶R⁷)ᵥHeteroaryl, —NR⁴(CR⁶R⁷)ᵥHeterocyclyl, —O(CR⁶R⁷)ᵥHeteroaryl, —O(CR⁶R⁷)ᵥHeterocyclyl, and —O(CR⁶R⁷)ᵥO-Heterocyclyl. In certain embodiments, at least one Y is selected from the group consisting of —NR⁴R⁵, —(CR⁶R⁷)ᵥNR⁴R⁵, —NR⁴(CR⁶R⁷)ᵥNR⁴R⁵, —O(CR⁶R⁷)ᵥNR⁴R⁵, —C(O)NR⁴ (CR⁶R⁷)ᵥNR⁴R⁵, —NR⁵C(O)NR⁴(CR⁶R⁷)ᵥNR⁴R⁵, —NR⁵C(=NR⁷)NR⁴(CR⁶R⁷)ᵥNR⁴R⁵, —N(R⁴)C(=NR⁵) R⁶, —(CR⁶R⁷)ᵥN(R⁴)C(=NR⁵)R⁶, —NR⁴(CR⁶R⁷)ᵥN(R⁴)C (=NR⁵)R⁶, —(CR⁶R⁷)ᵥC(=NR⁵)NR⁴R⁵, —NR⁴(CR⁶ R⁷)ᵥC(=NR⁵)NR⁴R⁵, —(CR⁶R⁷)ᵥN(R⁴)C(=NR⁵)NR⁴R⁵, —NR⁴(CR⁶R⁷)ᵥN(R⁴)C(=NR⁵)NR⁴R⁵, —NR⁴C(=NR⁵) NR⁴C(=NR⁵)NR⁴R⁵, —(CR⁶R⁷)ᵥC(=NR⁴)NR⁵C(=NR⁴) NR⁴R⁵, —NR⁴(CR⁶R⁷)ᵥC(=NR⁴)NR⁵C(=NR⁴)NR⁴R⁵, —NR⁴C(=NR⁵)NR⁴R⁵, —C(=NR⁴)NR⁴R⁵, —C(=NR⁴) NR⁴C(O)R⁶, —NR⁴C(O)R⁶, —(CR⁶R⁷)ᵥC(O)NR⁴R⁵, -Heterocyclyl-NR⁴R⁵, -Heterocyclyl-N(R⁴)C(=NR⁵)NR⁴R⁵, —N(R⁴)—Heterocyclyl-NR⁴R⁵, —(CR⁶R⁷)ᵥHeterocyclyl-NR⁴R⁵, —(CR⁶R⁷)ᵥHeterocyclyl-N(R⁴)C(=NR⁵)NR⁴R⁵, —(CR⁶R⁷)ᵥHeterocyclyl, and —NR⁴(CR⁶R⁷)ᵥHeterocyclyl. In further embodiments, at least one Y is selected from the group consisting of -Heteroaryl-NR⁴R⁵, -Heterocyclyl-NR⁴R⁵, -Heteroaryl-N(R⁴)C(=NR⁵)NR⁴R⁵, -Heterocyclyl-N(R⁴)C(=NR⁵)NR⁴R⁵, —N(R⁴)-Heteroaryl-NR⁴R⁵, —N(R⁴)—Heterocyclyl-NR⁴R⁵, -Heteroaryl-C(=NR⁵) NR⁴R⁵, -Heterocyclyl-C(=NR⁵)NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl-N(R⁴)C(=NR⁵)NR⁴R⁵, and —(CR⁶R⁷)ᵥHeterocyclyl-N(R⁴)C(=NR⁵)NR)NR⁴R⁵. In preferred embodiments, at least one Y is selected from the group consisting of —NR⁴R⁵, —NR⁴C(=NR⁵)NR⁴R⁵, —C(=NR⁴)NR⁴R⁵, —N(R⁴)C(=NR⁵)R⁶, —(CR⁶ R⁷)ᵥNR⁴R⁵, —(CR⁶R⁷)ᵥN(R⁴)C(=NR⁵)NR⁴R⁵, —NR⁴ (CR⁶R⁷)ᵥNR⁴R⁵, —NR⁴(CR⁶R⁷)ᵥOR¹⁰, —(CR⁶R⁷)ᵥNR⁴ (CR⁶R⁷)ᵥNR⁴R⁵, NR⁵C(=NR⁵)NR⁴(CR⁶R⁷)ᵥNR⁴R⁵, —NR⁴(CR⁶R⁷)ᵥN(R⁴)C(=NR⁵)NR⁴R⁵, —NR⁵C(O)CR⁶ (NR⁴R⁵)(CR⁶R⁷)ᵥNR⁴R⁵, —(CR⁶R⁷)ᵥC(=NR⁵)NR⁴R⁵, —(CR⁶R⁷)ᵥN(R⁴)C(O)(CR⁶R⁷)ᵥNR⁴R⁵, —C(=NR⁴)NR⁴C (O)R⁶, —NR⁴(CR⁶R⁷)ᵥHeteroaryl, and —O(CR⁶ R⁷)ᵥNR⁴R⁵. In preferred embodiments, at least one Y is —(CR⁶R⁷)ᵥNR⁴R⁵.

In certain embodiments, two Y groups taken together with the carbon atoms to which they are attached form an optionally substituted carbocycle or an optionally substituted heterocycle. In some embodiments, the carbocycle or heterocycle is optionally substituted with one to three substituents selected from the group consisting of fluoro, chloro, bromo, —CN, optionally substituted C₁-C₆ alkyl, optionally substituted C₃-C₆ cycloalkyl, optionally substituted heterocycle, optionally substituted aryl, optionally substituted heteroaryl, —OH, —OR¹⁰, —SR¹⁰, —NR⁴R⁵, —(CR⁶R⁷)ᵥNR⁴R⁵, —NR⁴(CR⁶R⁷)ᵥNR⁴R⁵, —O(CR⁶R⁷)ᵥNR⁴R⁵, —NR⁴C (=NR⁵)NR⁴R⁵, —C(=NR⁴)NR⁴R⁵, -Heteroaryl-NR⁴R⁵, -Heterocyclyl-NR⁴R⁵, —(CR⁶R⁷)ᵥHeteroaryl-NR⁴R⁵, —(CR⁶R⁷)ᵥHeterocyclyl-NR⁴R⁵, —(CR⁶R⁷)ᵥHeteroaryl, and —(CR⁶R⁷)ᵥHeterocyclyl. In certain embodiments, the two Y groups, together with the atoms to which they are attached form a pyrroline or tetrahydropyridine ring. In certain embodiments, the two Y groups, together with the atoms to which they are attached form a pyrroline ring.

In some embodiments, p is 2, 3, or 4. In certain embodiments, p is 2 or 3.

In some embodiments of a compound of Formula I or Formula Ia, R⁴ and R⁵ are independently selected from the group consisting of hydrogen, —OH, optionally substituted C₁-C₆ alkyl, optionally substituted alkoxyalkyl, optionally substituted hydroxyalkyl, and optionally substituted heterocyclyl. In preferred embodiments, R⁴ and R⁵ are independently hydrogen or optionally substituted C₁-C₆ alkyl. In certain embodiments, R⁴ and R⁵ are hydrogen.

In some embodiments of a compound of Formula I or Formula Ia, each R⁶ and R⁷ is independently selected from the group consisting of hydrogen, optionally substituted C₁-C₆ alkyl, —OH, —NR⁴R⁵, and optionally substituted heterocyclyl, or R⁶ and R⁷ taken together form an optionally substituted heterocycle with the carbon to which they are attached. In preferred embodiments, each R⁶ and R⁷ is independently hydrogen, fluoro, or optionally substituted C₁-C₆ alkyl. In some embodiments, R⁶ and R⁷ are hydrogen. In some preferred embodiments, v is 1.

In some embodiments of a compound of Formula I or Formula Ia, the compound comprises at least one basic amine. In some embodiments, the compound comprises at least two basic amines.

In certain embodiments of a compound of Formula I or Formula Ia, the compound is selected from the group represented by the following structures:

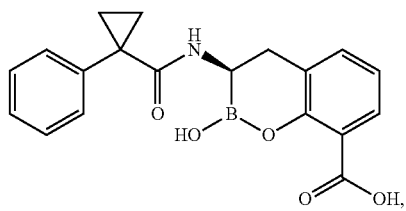

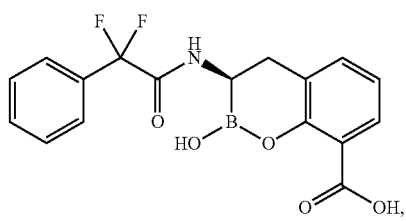

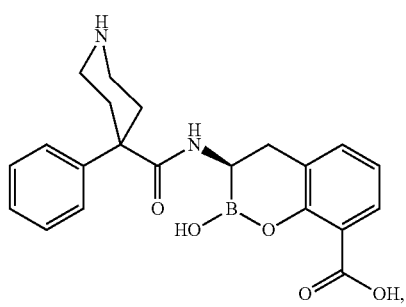

7
-continued
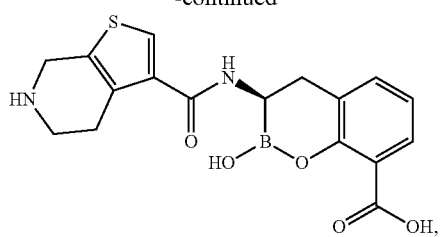
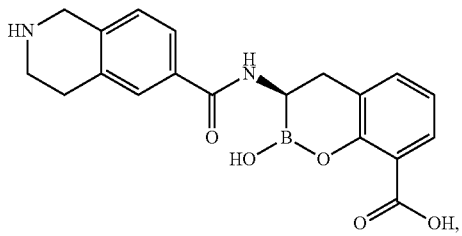
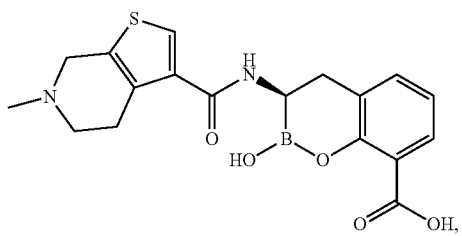
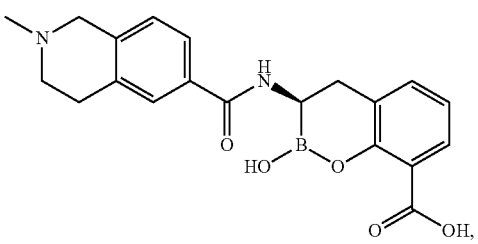
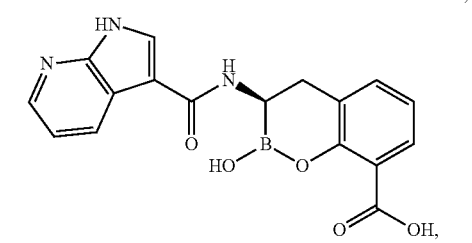
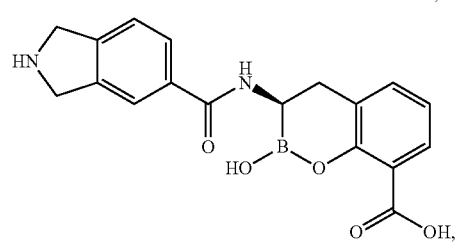
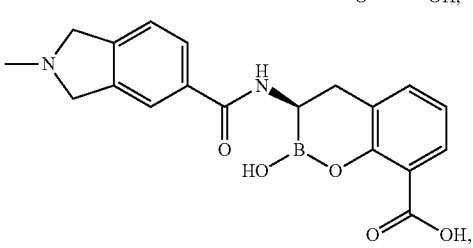
8
-continued
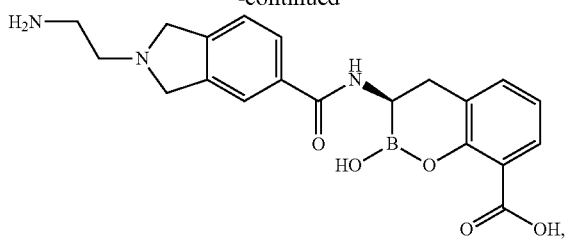
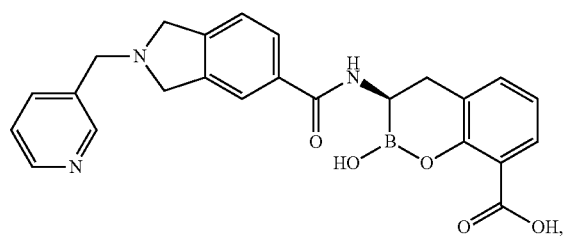
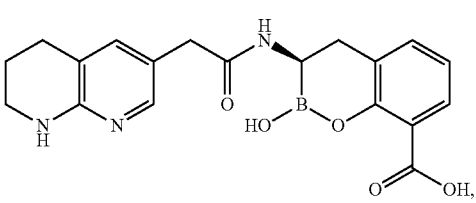
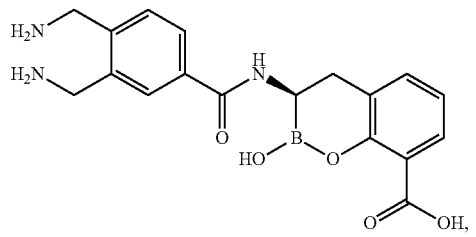
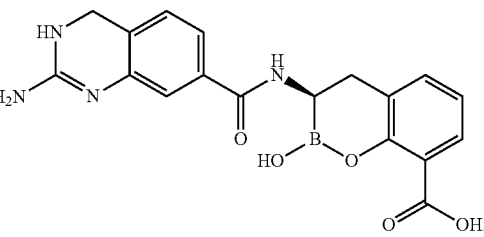
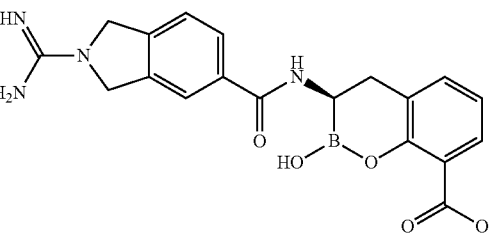
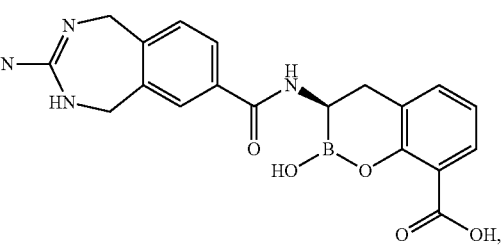

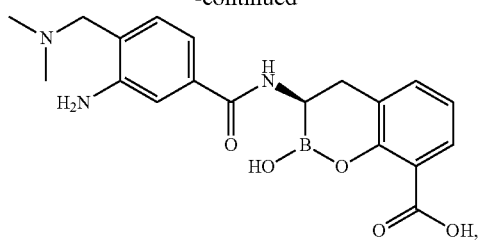
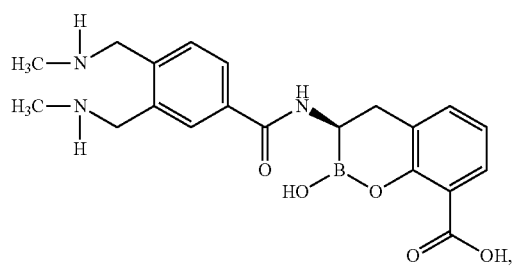
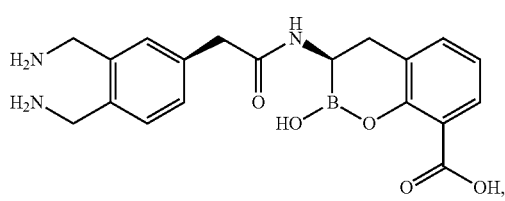
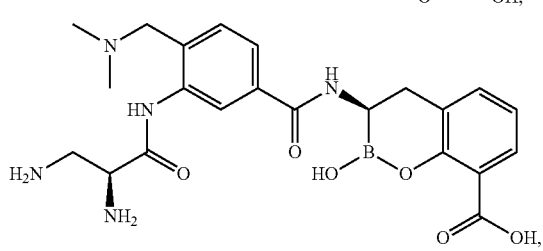
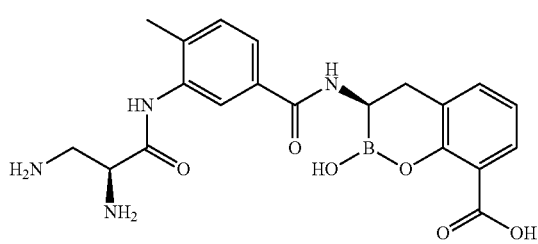
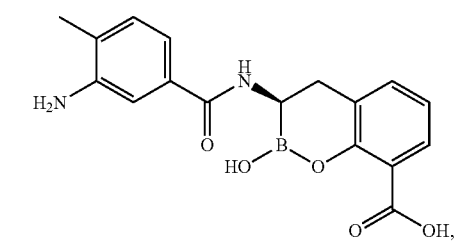
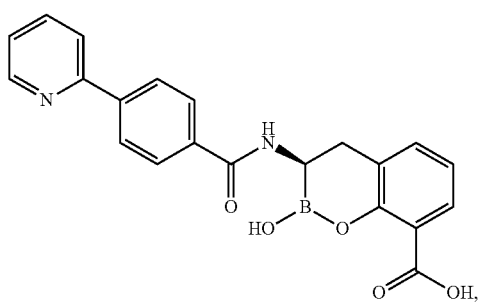
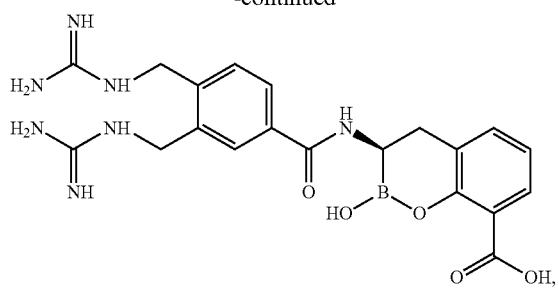
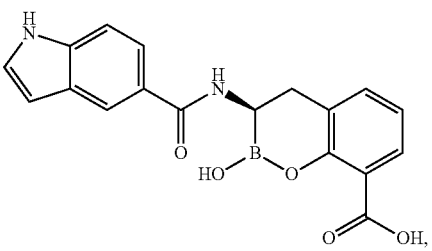
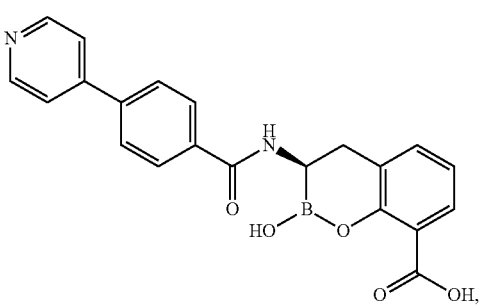
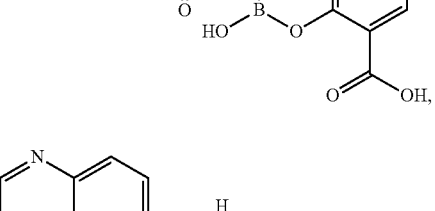
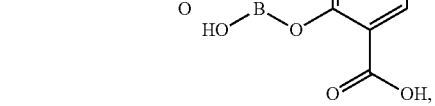
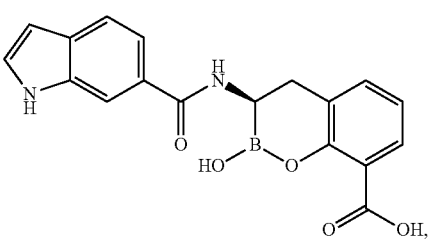

11
-continued
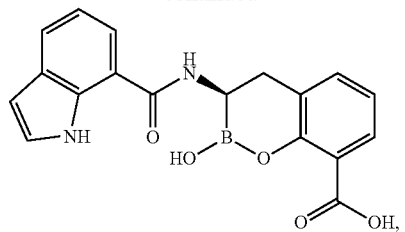
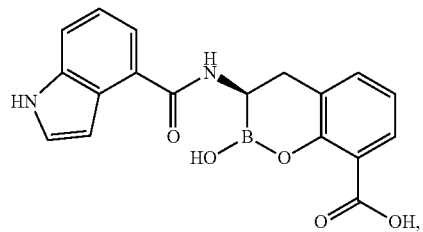
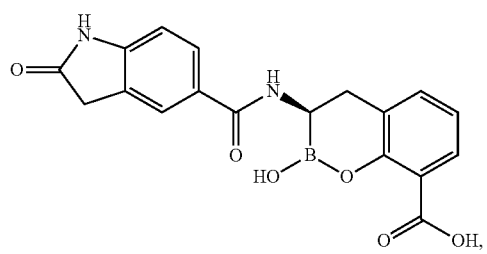
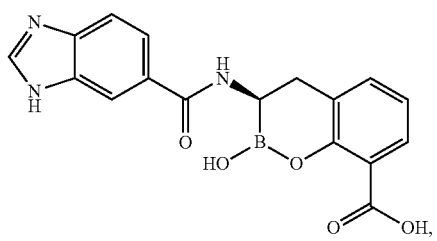
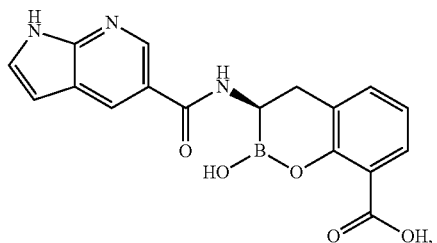
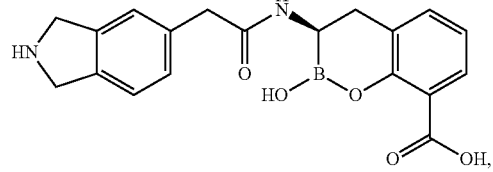
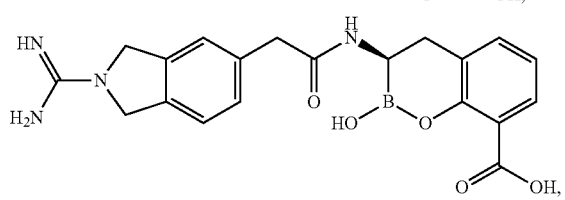
12
-continued
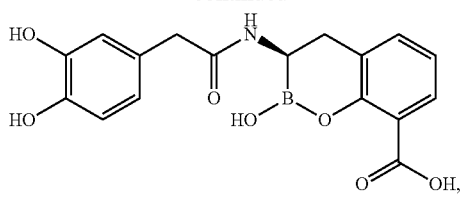
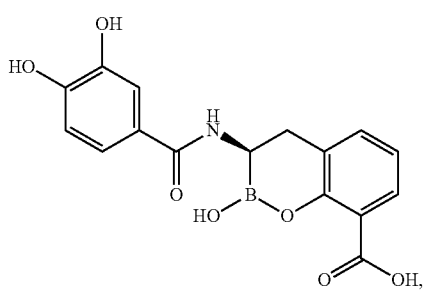
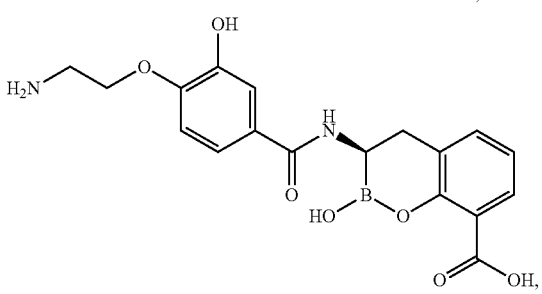
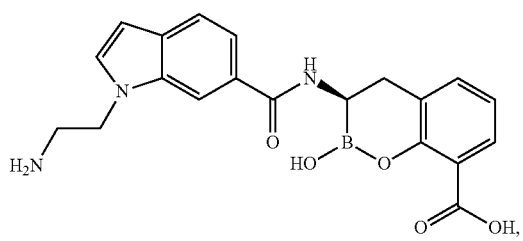
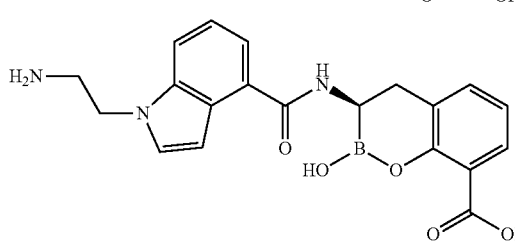
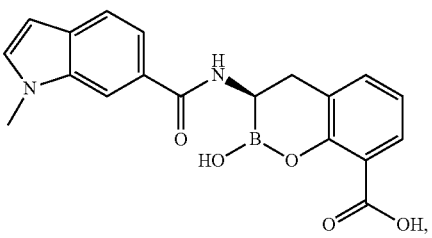
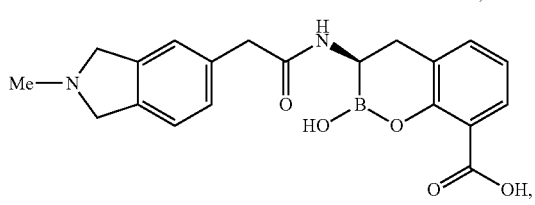

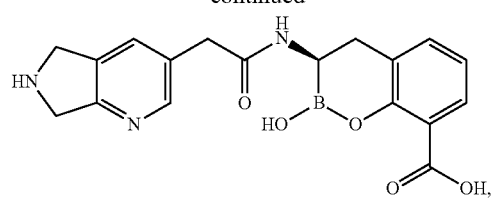
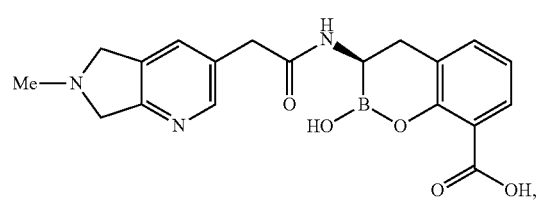
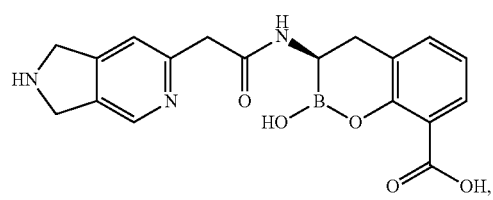
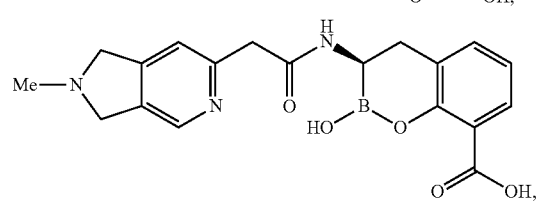
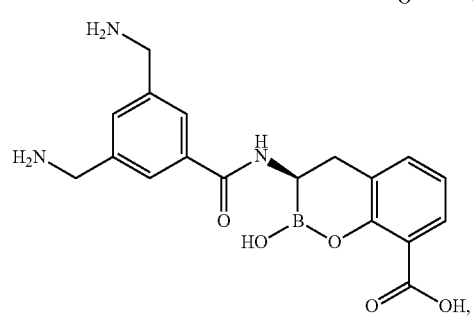
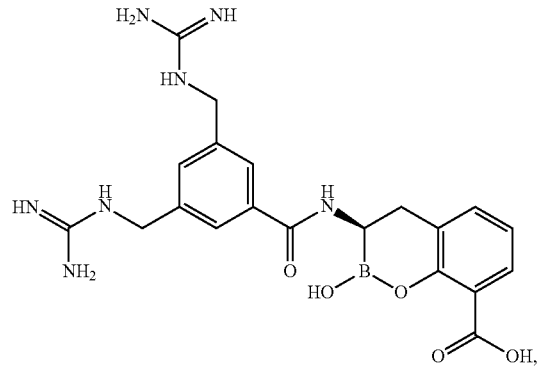
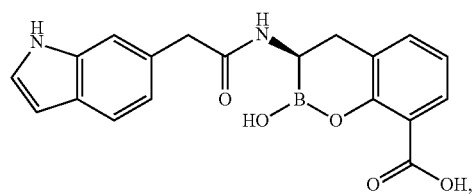
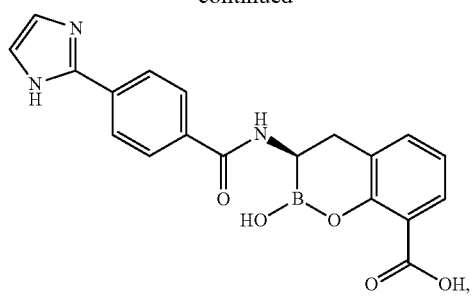
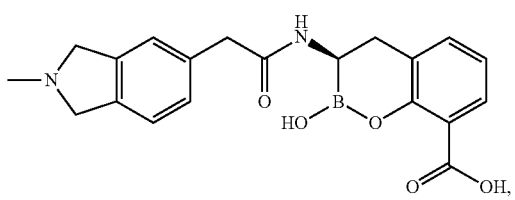
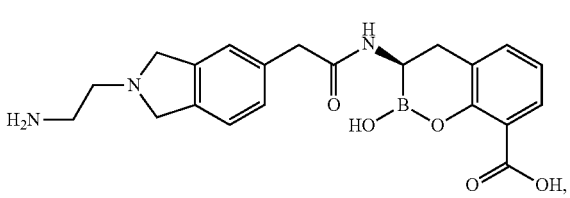
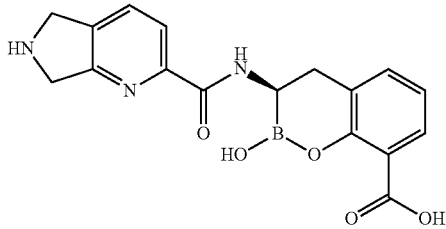
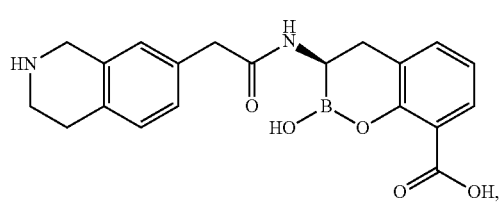
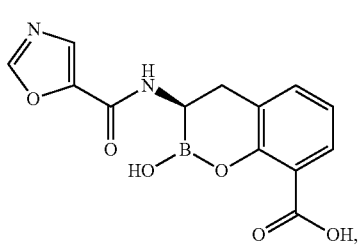
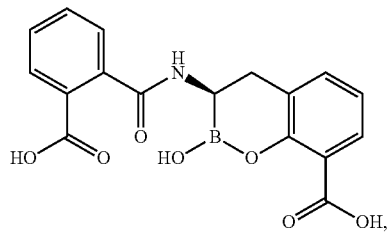

15
-continued
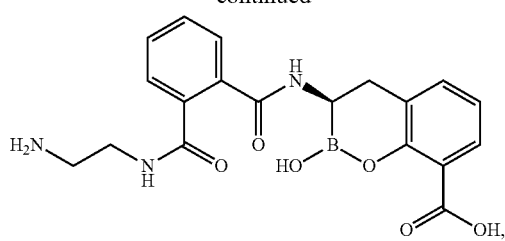
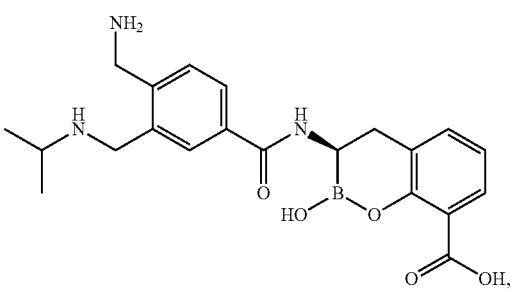
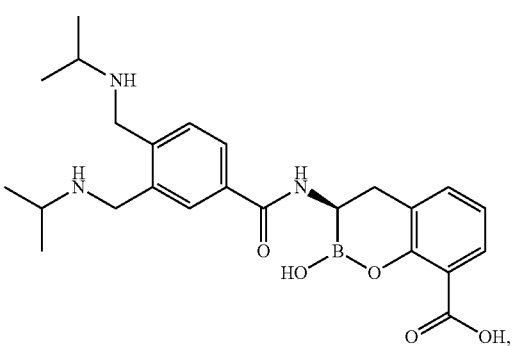
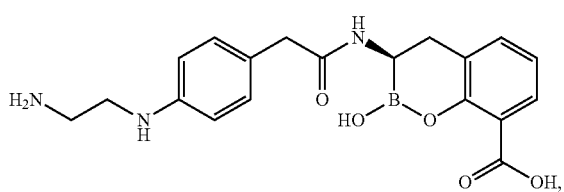
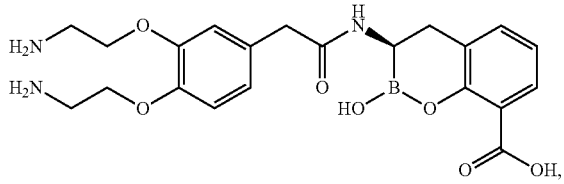
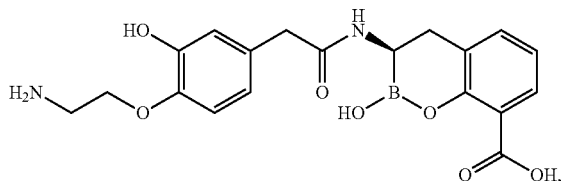
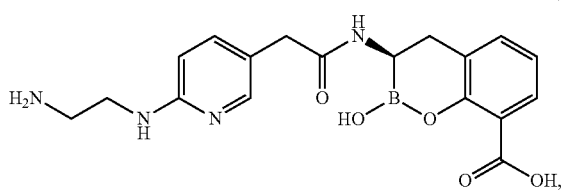
16
-continued
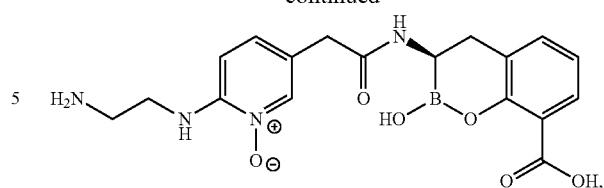
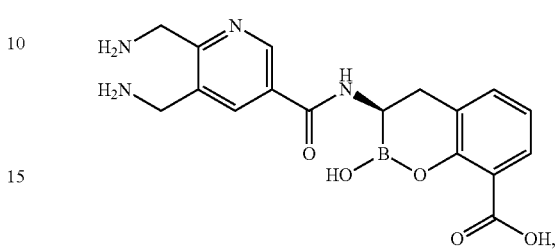
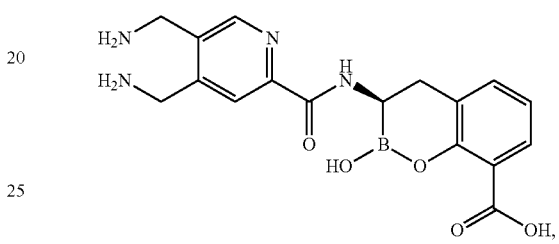
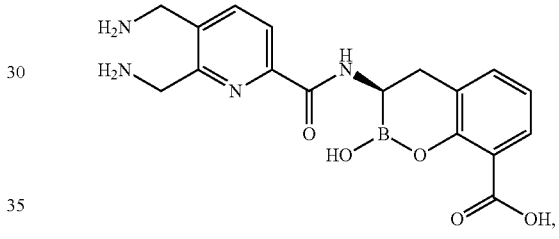
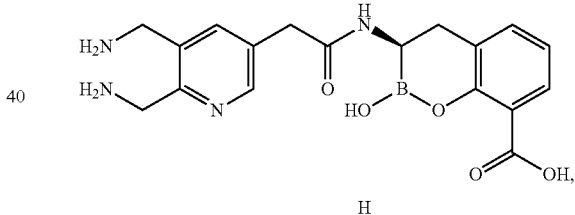
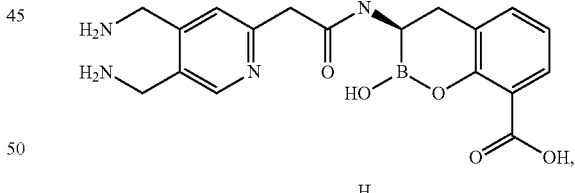
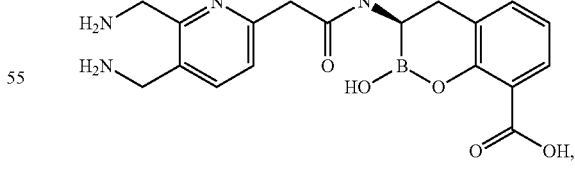
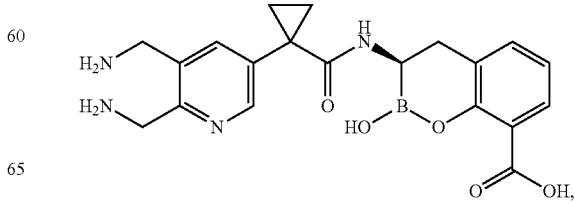

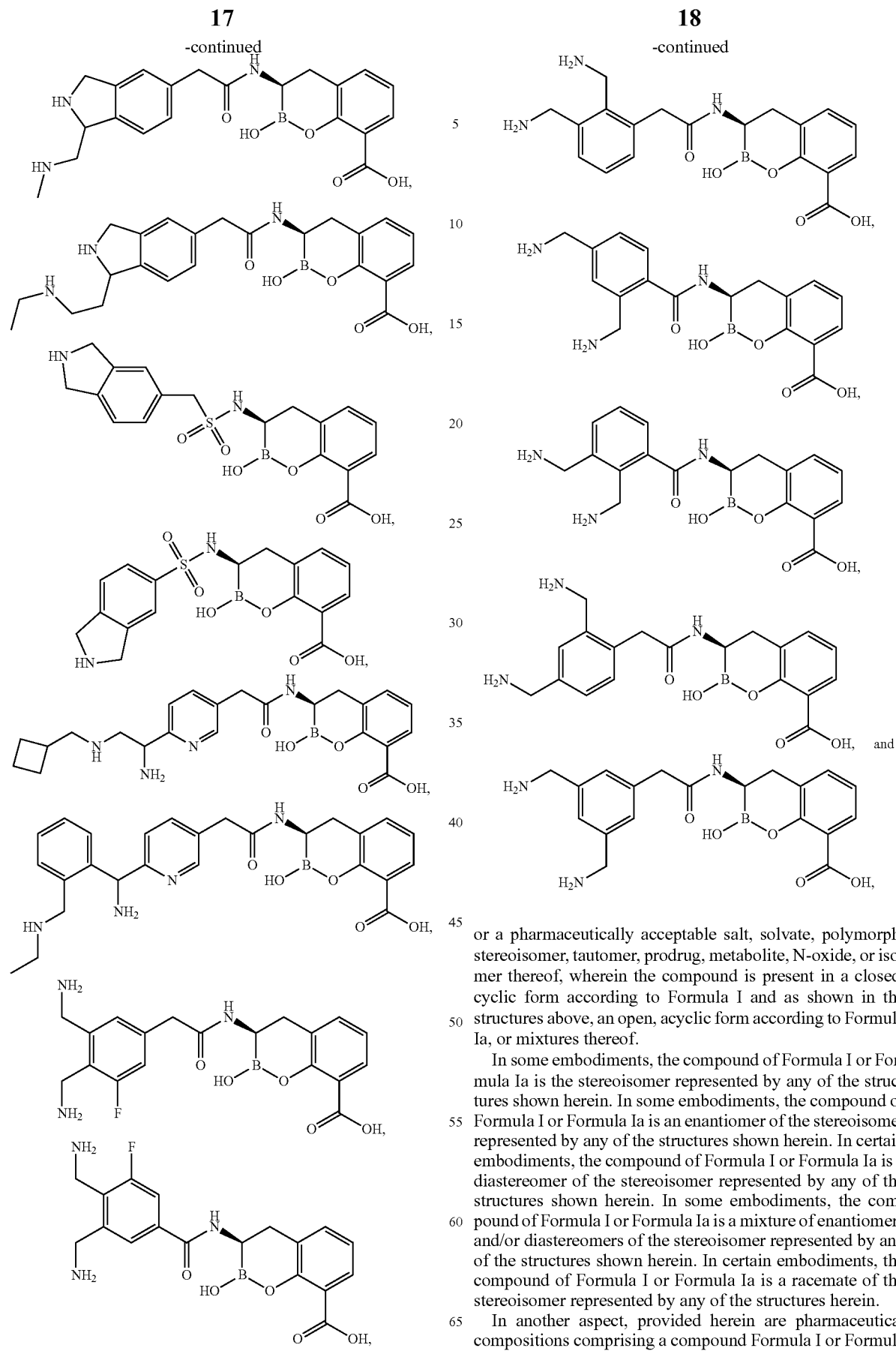

or a pharmaceutically acceptable salt, solvate, polymorph, stereoisomer, tautomer, prodrug, metabolite, N-oxide, or isomer thereof, wherein the compound is present in a closed, cyclic form according to Formula I and as shown in the structures above, an open, acyclic form according to Formula Ia, or mixtures thereof.

In some embodiments, the compound of Formula I or Formula Ia is the stereoisomer represented by any of the structures shown herein. In some embodiments, the compound of Formula I or Formula Ia is an enantiomer of the stereoisomer represented by any of the structures shown herein. In certain embodiments, the compound of Formula I or Formula Ia is a diastereomer of the stereoisomer represented by any of the structures shown herein. In some embodiments, the compound of Formula I or Formula Ia is a mixture of enantiomers and/or diastereomers of the stereoisomer represented by any of the structures shown herein. In certain embodiments, the compound of Formula I or Formula Ia is a racemate of the stereoisomer represented by any of the structures herein.

In another aspect, provided herein are pharmaceutical compositions comprising a compound Formula I or Formula Ia as described herein, or a pharmaceutically acceptable salt, polymorph, solvate, prodrug, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In an additional aspect, provided herein are methods of treating a bacterial infection in a subject, comprising administering to the subject a compound of Formula I or Formula Ia as described herein in combination with a therapeutically effective amount of beta-lactam antibiotic.

In a further aspect, provided herein are methods of treating a bacterial infection in a subject, comprising administering to the subject a pharmaceutical composition as described herein, optionally in combination with a beta-lactam antibiotic. In certain embodiments, the methods for treating a bacterial infection in a subject comprise administering to the subject a pharmaceutical composition as described herein in combination with a beta-lactam antibiotic.

Incorporation by Reference

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Beta-lactamases are typically grouped into 4 classes: Ambler classes A, B, C, and D, based on their amino acid sequences. Enzymes in classes A, C, and D are active-site serine beta-lactamases, while class B enzymes are Zn-dependent. Newer generation cephalosporins and carbapenems were developed partly based on their ability to evade the deactivating effect of the early serine-based beta-lactamase variants. However, a recent surge in new versions of serine-based beta-lactamases—for example Class A Extended-Spectrum Beta-Lactamase (ESBL) enzymes, Class A carbapenemases (e.g. KPC-2), chromosomal and plasmid mediated Class C cephalosporinases (AmpC, CMY, etc.), and Class D oxacillinases—as well as Class B metallo-beta-lactamases (e.g. VIM, NDM) has begun to diminish the utility of the beta-lactam antibiotic family, including the more recent generation beta-lactam drugs, leading to a serious medical problem. Indeed the number of catalogued serine-based beta-lactamases has exploded from less than ten in the 1970s to over 750 variants (see, e.g., Jacoby & Bush, "Amino Acid Sequences for TEM, SHV and OXA Extended-Spectrum and Inhibitor Resistant β-Lactamases", on the Lahey Clinic website).

The commercially available beta-lactamase inhibitors (clavulanic acid, sulbactam, tazobactam) were developed to address the beta-lactamases that were clinically relevant in the 1970s and 1980s (e.g. penicillinases). These beta-lactamase inhibitors are poorly active against the diversity of beta-lactamse enzymes (both serine- and metallo-based) now emergin clinically. In addition, these enzyme inhibitors are available only as fixed combinations with penicillin derivatives. No combinations with cephalosporins (or carbapenems) are clinically available. This fact, combined with the increased use of newer generation cephalosporins and carbapenems, is driving the selection and spread of the new beta-lactamase variants (ESBLs, carbapenemases, chromosomal and plasmid-mediated Class C, Class D oxacillinases, etc.). While maintaining good inhibitory activity against ESBLs, the legacy beta-lactamase inhibitors are largely ineffective against the new Class A and Class B carbapenemases, against the chromosomal and plasmid-mediated Class C cephalosporinases and against many of the Class D oxacillinases.

To address this growing therapeutic vulnerability, and because there are three major molecular classes of serine-based beta-lactamases, and one major class of metallo-beta-lactamases, and each of these classes contain significant numbers of beta-lactamase variants, we have identified an approach for developing novel beta-lactamase inhibitors with broad spectrum functionality. In particular, we have identified an approach for developing compounds that are active against both serine- and metallo-based beta-lactamase enzymes. Compounds of the current invention demonstrate potent activity across all four major classes of beta-lactamases.

The present invention is directed to certain boron-based compounds (boronic acids and cyclic boronic acid esters) which are beta-lactamase inhibitors and antibacterial compounds. The compounds and their pharmaceutically acceptable salts are useful alone and in combination with beta-lactam antibiotics for the treatment of bacterial infections, particularly antibiotic resistant bacterial infections. Some embodiments include compounds, compositions, pharmaceutical compositions, use and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent.

Examples of antibiotics suitable for use with respect to the present invention include penicillins, cephalosporins and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase. β-Lactamases of interest include those disclosed in an ongoing website that monitors beta-lactamase nomenclature (www.lahey.org) and in Bush, K. and G. A. Jacoby. 2010. An updated functional classification of β-lactamases. Antimicrob. Agents Chemother. 54:969-976. β-Lactamases of particular interest herein include β-lactamases found in bacteria such as class A β-lactamases including the SHV, CTX-M and KPC subclasses, class B β-lactamases such as VIM, class C (3-lactamases (both chromosomal and plasmid-mediated), and class D β-lactamases. The term "3-lactamase inhibitor" refers to a compound which is capable of inhibiting β-lactamase activity. Inhibiting β-lactamase activity means inhibiting the activity of a class A, B, C, or D β-lactamase. For antimicrobial applications inhibition at a 50% inhibitory concentration is preferably achieved at or below about 100 micrograms/mL, or at or below about 50 micrograms/mL, or at or below about 25 micrograms/mL. The terms "class A", "class B", "class C", and "class D" β-lactamases are understood by those skilled in the art and are described in Bush, K. and G. A. Jacoby. 2010. An updated functional classification of β-lactamases. Antimicrob. Agents Chemother. 54:969-976.

The terms below, as used herein, have the following meanings, unless indicated otherwise:

"Amino" refers to the —NH$_2$ radical.
"Cyano" or "nitrile" refers to the —CN radical.
"Hydroxy" or "hydroxyl" refers to the —OH radical.
"Nitro" refers to the —NO$_2$ radical.
"Oxo" refers to the =O substituent.
"Oxime" refers to the =N—OH substituent.
"Thioxo" refers to the =S substituent.
"Alkyl" refers to an optionally substituted straight-chain, or optionally substituted branched-chain saturated hydrocarbon monoradical having from one to about ten carbon atoms, more preferably one to six carbon atoms, wherein an sp3-hybridized carbon of the alkyl residue is attached to the rest of the molecule by a single bond. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. Unless stated otherwise specifically in the specification, an alkyl group may be optionally substituted as described below, for example, with oxo, amino, nitrile, nitro, hydroxyl, alkyl, alkylene, alkynyl, alkoxy, aryl, cycloalkyl, heterocyclyl, heteroaryl, and the like.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_2$-6 alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

"Alkylene" or "alkylene chain" refers to a straight or branched divalent hydrocarbon chain. Unless stated otherwise specifically in the specification, an alkylene group may be optionally substituted as described below.

"Alkoxy" refers to a radical of the formula —OR$_a$ where R$_a$ is an alkyl radical as defined. Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Unless otherwise stated specifically in the specification, a cycloalkyl or carbocycle group may be optionally substituted. Illustrative examples of cycloalkyl groups include, but are not limited to, the following moieties:

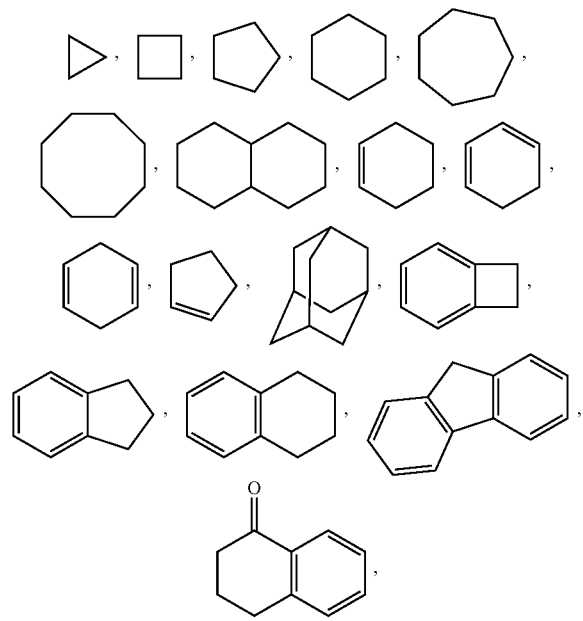

and the like.

"Aralkyl" means an -(alkylene)-R radical where R is aryl as defined above.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

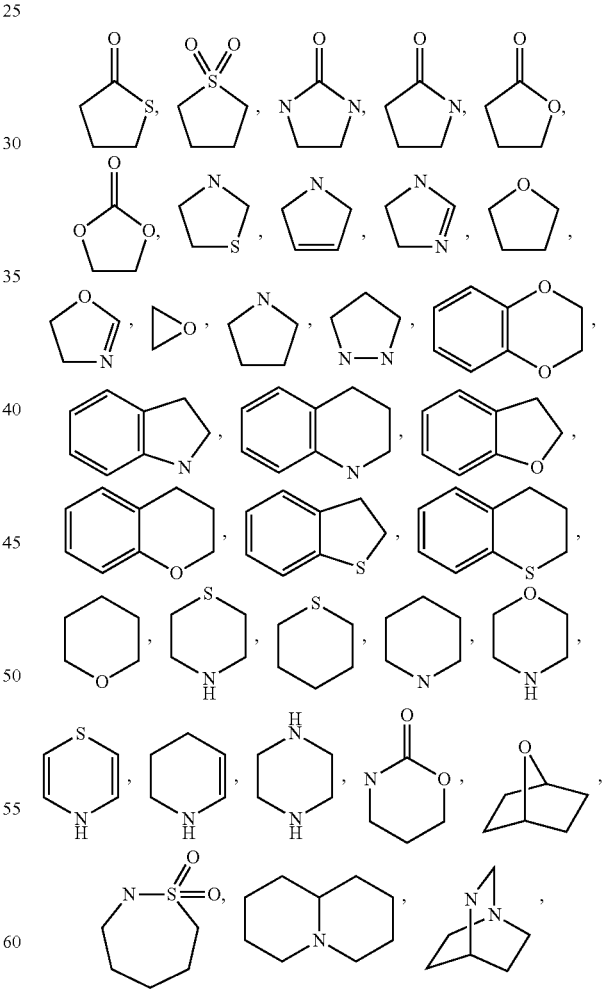

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —$CO_2H$, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—$N+R_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NH_2$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

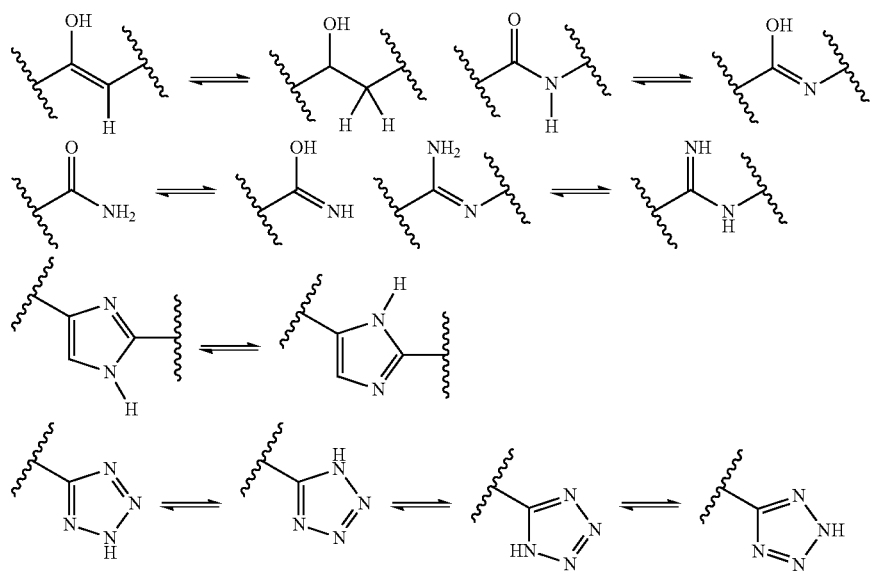

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Compounds

Described herein are compounds that modulate the activity of beta-lactamase. In some embodiments, the compounds described herein inhibit beta-lactamase. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula I or Formula Ia, or pharmaceutically acceptable salts, polymorphs, solvates, tautomers, metabolites, or N-oxides thereof:

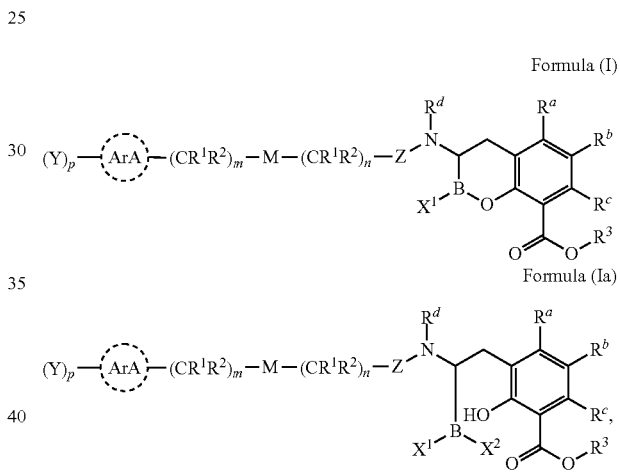

wherein:
M is a bond, —O—, —S—, —S(O)—, SO$_2$—, or —N(R$^4$)—;
m is 0, 1, or 2;
n is 0, 1, 2, or 3;
  provided that
    when n is 0, then M is a bond;
p is 0, 1, 2, or 3;
X$^1$ and X$^2$ are independently selected from —OH, —OR$^8$, or F;
Z is >C═O, >C═S, or >SO$_2$;
ArA is an optionally substituted aromatic or heteroaromatic ring system;
Each Y is selected from the group consisting of
  fluoro, chloro, bromo, —CN, optionally substituted C$_1$-C$_6$ alkyl, optionally substituted C$_3$-C$_6$ cycloalkyl, optionally substituted heterocycle, optionally substituted aryl, optionally substituted heteroaryl, ═O, —OH, —OR$^{10}$, —SR$^{10}$, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —S(O)$_{0,1,2}$(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —(CR$^6$R$^7$)$_v$NR$^4$(CR$^6$R$^7$)$_v$NR$^4$R$^5$, —NR$^4$(CR$^6$R$^7$)$_v$OR$^{10}$, —NR$^4$(CR$^6$R$^7$)$_v$S(O)$_{0,1,2}$R$^{10}$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —S(O)$_{0,1,2}$(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —S(O)$_{0,1,2}$(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —S(O)$_{0,1,2}$(CR$^6$R$^7$)$_v$N(R$^4$)C(=NR$^5$)NR$^4$R$^5$, —NR$^4$C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)$_v$C(=NR$^4$)NR$^5$C(=NR$^4$)NR$^4$R$^5$, —S(O)$_{0,1,2}$(CR$^6$R$^7$)$_v$C(=NR$^4$)NR$^5$C(=NR$^4$)NR$^4$R$^5$, —NR$^4$C(=NR$^5$)NR$^4$R$^5$, —C(=NR$^4$)NR$^4$R$^5$, —C(=NR$^4$)NR$^4$C(O)R$^6$, —NR$^4$SO$_2$R$^6$, —NR$^4$C(O)R$^6$, —NR$^4$C(=O)R$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)-Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-$$_2$, —(CR$^6$R$^7$)$_v$(T)$^+$Q$^-$, and —O(CR$^6$R$^7$)$_v$NR$^4$R$^5$R$^{9+}$Q$^-$;

wherein:
T is pyridine-1-yl, pyrimidin-1-yl, or thiazol-3-yl;
Q is a pharmaceutically acceptable counterion; and
v is 1-4;
or two Ys taken together with the carbon atoms to which they are attached form an optionally substituted carbocycle or an optionally substituted heterocycle;
R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{10}$, —NR$^4$R$^5$, and —SR$^{10}$;
R$^1$ and R$^2$ are independently selected from the group consisting of hydrogen, fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$,
or R$^1$ and R$^2$ taken together form an oxo, oxime, or an optionally substituted carbocycle or optionally substituted heterocycle with the carbon to which they are attached;
R$^3$ is hydrogen, optionally substituted C$_1$-C$_6$ alkyl, or a pharmaceutically acceptable prodrug;
R$^d$, R$^4$, and R$^5$ are independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;
or R$^4$ and R$^5$ taken together form an optionally substituted heterocycle with the nitrogen to which they are attached;
R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;
or R$^6$ and R$^7$ taken together form an oxo, oxime, or an optionally substituted carbocycle or an optionally substituted heterocycle with the carbon to which they are attached;
R$^8$ is optionally substituted C$_1$-C$_6$ alkyl, optionally substituted C$_3$-C$_6$ cycloalkyl, or a pharmaceutically acceptable boronate ester group;
R$^9$ is optionally substituted C$_1$-C$_6$ alkyl;
R$^{10}$ is optionally substituted C$_1$-C$_6$ alkyl or optionally substituted C$_3$-C$_6$ cycloalkyl.

In another aspect, provided herein are a compound of Formula (I) or Formula (Ia), a pharmaceutically acceptable salt, polymorph, solvate, prodrug, N-oxide, or isomer thereof:

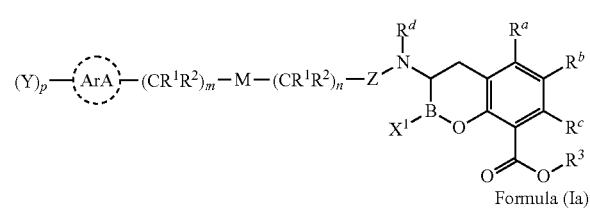

Formula (I)

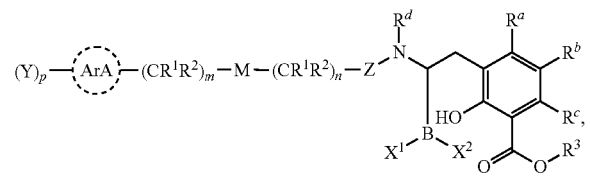

Formula (Ia)

wherein:
M is a bond, —O—, —S—, —S(O)—, SO$_2$—, or —N(R$^4$)—;
m is 0, 1, or 2;
n is 0, 1, 2, or 3;
provided that
when n is 0, then M is a bond;
p is 2, 3, 4, or 5;
X$^1$ and X$^2$ are independently selected from —OH, —OR$^8$, or F;
Z is >C=O, >C=S, or >SO$_2$;
ArA is an aromatic or heteroaromatic ring system optionally substituted with one or more substituents from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, and —$SR^{10}$;

each Y is selected from the group consisting of
—$NR^4R^5$, —$(CR^6R^7)_vNR^4R^5$, —$NR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$S(O)_{0,1,2}(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$S(O)_{0,1,2}(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$S(O)_{0,1,2}(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$S(O)_{0,1,2}(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, —$SO_2NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$—Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, —$NR^4(CR^6R^7)_vNR^5$-Heteroaryl, —$NR^4(CR^6R^7)_vNR^5$-Heterocyclyl, —$O(CR^6R^7)_vNR^5$-Heteroaryl, —$O(CR^6R^7)_vNR^5$-Heterocyclyl, —$O(CR^6R^7)_v$O-Heterocyclyl, —$NR^4R^5R^{9+}Q^-$, —$(CR^6R^7)_vNR^4R^5R^{9+}Q^-$; —$NR^4(CR^6R^7)_vNR^4R^5R^{9+}Q^-$, —$NR^{4+}(CR^6R^7)_vNR^4R^5R^{9+}Q^-_2$, —$(CR^6R^7)_v(T)^+Q^-$, and —$O(CR^6R^7)_vNR^4R^5R^{9+}Q^-$;

wherein:
T is pyridine-1-yl, pyrimidin-1-yl, or thiazol-3-yl;
Q is a pharmaceutically acceptable counterion; and
v is 1-4;
or two Ys taken together with the carbon atoms to which they are attached form an optionally substituted carbocycle or an optionally substituted heterocycle;

$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —$OR^{10}$, —$NR^4R^5$, and —$SR^{10}$;

$R^1$ and $R^2$ are independently selected from the group consisting of hydrogen, fluoro, chloro, bromo, optionally substituted $C_1$-$C_6$ alkyl, optionally substituted $C_3$-$C_6$ cycloalkyl, —OH, —$OR^{10}$, —$SR^{10}$, and —$NR^4R^5$, or $R^1$ and $R^2$ taken together form an oxo, oxime, or an optionally substituted carbocycle or optionally substituted heterocycle with the carbon to which they are attached;

$R^3$ is hydrogen, optionally substituted $C_1$-$C_6$ alkyl, or a pharmaceutically acceptable prodrug;

$R^d$, $R^4$ and $R^5$ are independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^4$ and $R^5$ taken together form an optionally substituted heterocycle with the nitrogen to which they are attached;

$R^6$ and $R^7$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{10}$, —$SR^{10}$, —$NR^4R^5$, —$NR^4C(O)R^5$, —$C(O)NR^4R^5$, —$NR^4SO_2R^5$, optionally substituted heterocyclyl, optionally substituted aryl, and optionally substituted heteroaryl;

or $R^6$ and $R^7$ taken together form an oxo, oxime, or an optionally substituted carbocycle or an optionally substituted heterocycle with the carbon to which they are attached;

$R^8$ is optionally substituted $C_1$-$C_6$ alkyl, optionally substituted $C_3$-$C_6$ cycloalkyl, or a pharmaceutically acceptable boronate ester group;

$R^9$ is optionally substituted $C_1$-$C_6$ alkyl;

$R^{10}$ is optionally substituted $C_1$-$C_6$ alkyl or optionally substituted $C_3$-$C_6$ cycloalkyl.

In some embodiments of a compound of Formula I or Formula Ia, $R^a$, $R^b$, and $R^c$ are independently selected from the group consisting of hydrogen, fluoro, chloro, optionally substituted $C_1$-$C_6$ alkyl, optionally substituted $C_3$-$C_6$ cycloalkyl, —OH, —$OR^{10}$, —$NR^4R^5$, and —$SR^{10}$. In certain embodiments, $R^a$, $R^b$, and $R^c$ are independently hydrogen, fluoro, or chloro. In preferred embodiments, $R^a$, $R^b$, and $R^c$ are hydrogen.

In some embodiments of a compound of Formula I or Formula Ia, $R^3$ is hydrogen, methyl, ethyl, propyl, butyl, or isopropyl. In preferred embodiments, $R^3$ is hydrogen.

In some embodiments of a compound of Formula I or Formula Ia, X and $X^2$ are —OH.

In some embodiments of a compound of Formula I or Formula Ia, $R^d$ is hydrogen or $C_1$-$C_4$-alkyl. In some embodiments, $R^d$ is methyl. In preferred embodiments, $R^d$ is hydrogen.

In some embodiments of a compound of Formula I or Formula Ia, Z is Z is >C=O or >$SO_2$. In preferred embodiments, Z is >C=O.

In some embodiments of a compound of Formula I or Formula Ia, ArA is selected from the group consisting of benzene, naphthalene, pyridine, pyrimidine pyrazine, pyridazine, triazine, thiophene, furan, pyrrole, pyrazole, triazole, imidazole, thiazole, isothiazole, oxazole, isoxazole. indole, indazole, azaindole, azaindazole, isoindole, indolizine, imidazopyridine, pyrazolo-pyridine, thiazolo-pyridine pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyridopyrimidine, pyrido-pyrazine, pyridopyridazine, isoxazolopyridine, and oxazolo-pyridine. In certain embodiments ArA is selected from the group consisting of benzene, pyridine, pyrimidine, thiophene, thiazole, triazole, indole, benzimidazole, azaindole, thienopyrazole, quinoline, quinazoline, and quinoxaline. In preferred embodiments, ArA is benzene, thiophene, pyridine, aza-indole, or quinoxaline.

In some embodiments of a compound of Formula I or Formula Ia, at least one Y is selected from the group consisting fluoro, chloro, —CN, optionally substituted $C_1$-$C_6$ alkyl, —OH, —$OR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$—Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, and —$O(CR^6R^7)_v$O-Heterocyclyl. In certain embodiments, at least one Y is selected from the group consisting fluoro, chloro, —CN, optionally substituted $C_1$-$C_6$ alkyl, —OH, —$NR^4R^5$, —$(CR^6R^7)_vNR^4R^5$, —$NR^4(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4C(O)R^6$, —$(CR^6R^7)_vC(O)NR^4R^5$, -Heterocyclyl-$NR^4R^5$, -Heterocyclyl-$N(R^4)C(=NR^5)NR^4R^5$, —$N(R^4)$—Heterocyclyl-$NR^4R^5$, —$(CR^6R^7)_v$Heterocyclyl-$NR^4R^5$, —$(CR^6R^7)_v$Heterocyclyl-$N(R^4)C(=NR^5)NR^4R^5$, —$(CR^6R^7)_v$Heterocyclyl, and —$NR^4(CR^6R^7)_v$Heterocyclyl. In further embodiments, at least one Y is selected from the group consisting of -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$—Heterocyclyl-$NR^4R^5$, -Heteroaryl-$C(=NR^5)NR^4R^5$, -Heterocyclyl-$C(=NR^5)NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, and —$(CR^6R^7)_v$Heterocyclyl-$N(R^4)C(=NR^5)NR^4R^5$. In specific embodiments, at least one Y is 2-($NR_4R_5$)-pyridyl, 2-($NR_4R_5$)-pyrimidinyl, 2-($NR_4R_5$)-thiazolyl, 2-($NR_4R_5$)-imidazolyl, 3-($NR_4R_5$)-pyrazolyl, 3-($R_4R_5N$)-isothiazolyl, 2-($R_4R_5N$)-oxazolyl, piperidine, pyrrolidine, 4-amino-piperidinyl, 3-amino-pyrrolidinyl, piperazine, or 4-carboximidoyl-piperazinyl. In preferred embodiments, at least one Y is selected from the group consisting of —$NR^4R^5$, —$NR^4C(=NR^5)NR^4R^5$, —$C(=NR^4)NR^4R^5$, —$N(R^4)C(=NR^5)R^6$, —$(CR^6R^7)_vNR^4R^5$, —$(CR^6R^7)_vN(R^4)C(=NR^5)NR^4R^5$, —$NR^4(CR^6R^7)_vNR^4R^5$, —$NR^4(CR^6R^7)_vOR^{10}$, —$(CR^6R^7)_vNR^4(CR^6R^7)_vNR^4R^5$, $NR^5C(=NR^5)NR^4(CR^6R^7)_vNR^4R^5$, —$NR^4(CR^6R^7)_vN(R^4)C(=NR^5)NR^4R^5$, —$NR^5C(O)CR^6(NR^4R^5)(CR^6R^7)_vNR^4R^5$, —$(CR^6R^7)_vC(=NR^5)NR^4R^5$, —$(CR^6R^7)_vN(R^4)C(O)(CR^6R^7)_vNR^4R^5$, —$C(=NR^4)NR^4C(O)R^6$, —$NR^4(CR^6R^7)_v$Heteroaryl, and —$O(CR^6R^7)_vNR^4R^5$.

In certain embodiments, two Y groups taken together with the carbon atoms to which they are attached form an optionally substituted carbocycle or an optionally substituted heterocycle. In some embodiments, the carbocycle or heterocycle is optionally substituted with one to three substituents selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, —$SR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$NR^4C(=NR^5)NR^4R^5$, —$C(=NR^4)NR^4R^5$, -Heteroaryl-$NR^4R^5$, -Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl, and —$(CR^6R^7)_v$Heterocyclyl. In certain embodiments, the two Y groups, together with the atoms to which they are attached form a pyrrolidine ring.

In some embodiments, p is 0, 1, 2, or 3. In certain embodiments, p is 1 or 2. In some embodiments, p is 2. In other embodiments, p is 1.

In some embodiments of a compound of Formula I or Formula Ia, $R^4$ and $R^5$ are independently selected from the group consisting of hydrogen, —OH, optionally substituted $C_1$-$C_6$ alkyl, optionally substituted alkoxyalkyl, optionally substituted hydroxyalkyl, and optionally substituted heterocyclyl. In preferred embodiments, $R^4$ and $R^5$ are independently hydrogen or optionally substituted $C_1$-$C_6$ alkyl.

In some embodiments of a compound of Formula I or Formula Ia, $R^6$ and $R^7$ are independently selected from the group consisting of hydrogen, optionally substituted $C_1$-$C_6$ alkyl, —OH, —$NR^4R^5$, and optionally substituted heterocyclyl, or $R^6$ and $R^7$ taken together form an optionally substituted heterocycle with the carbon to which they are attached. In preferred embodiments, $R^6$ and $R^7$ are independently hydrogen, fluoro, or optionally substituted $C_1$-$C_6$ alkyl.

In some embodiments of the compounds of Formula I or Formula Ia, $R^a$, $R^b$, $R^c$, $R^3$ are hydrogen; $X^1$ and $X^2$ are —OH; Z is >C=O; n is 0; m is 0 or 1; $R^1$ and $R^2$, when present are hydrogen; ArA is benzene or pyridine; p is 2; and at least one Y is —$(CH_2)_vNR^4R^5$; v is 1 or 2; and $R^4$ and $R^5$ are H or $C_1$-$C_6$ alkyl. In some embodiments of the compounds of Formula I or Formula Ia, $R^a$, $R^b$, $R^c$, $R^3$ are hydrogen; $X^1$ and $X^2$ are —OH; Z is >C=O; n is 0; m is 0 or 1; $R^1$ and $R^2$, when present are hydrogen; ArA is benzene or pyridine; p is 2; and at least two Y groups are —$(CH_2)_vNR^4R^5$; v is 1 or 2; and $R^4$ and $R^5$ are H or $C_1$-$C_6$ alkyl. In some embodiments of the compounds of Formula I or Formula Ia, $R^a$, $R^b$, $R^c$, $R^3$ are hydrogen; $X^1$ and $X^2$ are —OH; Z is >C=O; n is 0; m is 0; ArA is benzene or pyridine; p is 2; and two Y groups are —$(CH_2)_vNR^4R^5$; v is 1 or 2; and $R^4$ and $R^5$ are H or $C_1$-$C_6$ alkyl. In some embodiments of the compounds of Formula I or Formula Ia, $R^a$, $R^b$, $R^c$, $R^3$ are hydrogen; $X^1$ and $X^2$ are —OH; Z is >C═O; n is 0; m is 0; ArA is benzene or pyridine; p is 2; and two Y groups are —(CH$_2$)$_v$NR$^4$R$^5$; v is 1; and $R^4$ and $R^5$ are H or $C_1$-$C_6$ alkyl. In some embodiments of the compounds of Formula I or Formula Ia, $R^a$, $R^b$, $R^c$, $R^3$ are hydrogen; $X^1$ and $X^2$ are —OH; Z is >C═O; n is 0; m is 0; ArA is benzene or pyridine; p is 2; and two Y groups are —(CH$_2$)$_v$NR$^4$R$^5$; v is 1; and $R^4$ and $R^5$ are H. In some embodiments of the compounds of Formula I or Formula Ia, $R^a$, $R^b$, $R^c$, $R^3$ are hydrogen; $X^1$ and $X^2$ are —OH; Z is >C═O; n is 0; m is 0; ArA is benzene; p is 2; and two Y groups are —(CH$_2$)$_v$NR$^4$R$^5$; v is 1; and $R^4$ and $R^5$ are H.

In some embodiments of the compounds of Formula I or Formula Ia, $R^a$, $R^b$, $R^c$, $R^3$ are hydrogen; $X^1$ and $X^2$ are —OH; Z is >C═O; n is 0; m is 0 or 1; $R^1$ and $R^2$, when present are hydrogen; ArA is benzene or pyridine; p is 2; and two Y groups, together with the atoms to which they are attached form an optionally substituted carbocycle or an optionally substituted heterocycle. In some embodiments, two Y groups, together with the atoms to which they are attached form an optionally substituted pyrroline or tetrahydropyridine ring. In some embodiments, two Y groups together with the atoms to which they are attached form an optionally substituted pyrroline ring. In some embodiments, the carbocycle or heterocycle is substituted with one to three substituents selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —OR$^{10}$, —SR$^{10}$, —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —NR$^4$C(═NR$^5$)NR$^4$R$^5$, —C(═NR$^4$)NR$^4$R$^5$, -Heteroaryl-NR$^4$R$^5$, -Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl, and —(CR$^6$R$^7$)$_v$Heterocyclyl.

In some embodiments of the compounds of Formula I or Formula Ia, M is a bond; m and n are 0; p is 0, 1, 2, or 3; $X^1$ and $X^2$ are independently selected from —OH, —OR$^8$, or F; $R^a$, $R^b$, $R^c$, $R^3$ are hydrogen; ArA is an aromatic or heteroaromatic group optionally substituted with one or more substituents from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —OR$^{10}$, and —SR$^{10}$. In some embodiments, ArA is selected from the group consisting of pyrimidine, pyrazine, pyridazine, triazine, thiophene, furan, pyrrole, pyrazole, triazole, imidazole, isothiazole, oxazole, isoxazole, indole, indazole, azaindole, azaindazole, indolizine, imidazopyridine, pyrazolo-pyridine, thiazolo-pyridine pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyrido-pyrimidine, pyrido-pyrazine, pyridopyridazine, isoxazolo-pyridine, and oxazolo-pyridine. In some embodiments, ArA is a bicyclic aromatic group, for example, ArA is selected from the group consisting of indole, indazole, azaindole, azaindazole, indolizine, imidazopyridine, pyrazolo-pyridine, thiazolo-pyridine pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyrido-pyrimidine, pyrido-pyrazine, pyridopyridazine, isoxazolo-pyridine, and oxazolo-pyridine. In some embodiments, ArA is selected from the group consisting of pyrimidine, thiophene, oxazole, triazole, indole, benzimidazole, azaindole, thienopyrazole, quinoline, quinazoline, and quinoxaline.

In some embodiments of the compounds of Formula I or Formula Ia, M is a bond; m is 0; n is 1; p is 0, 1, 2, or 3; $X^1$ and $X^2$ are independently selected from —OH, —OR$^8$, or F; $R^a$, $R^b$, $R^c$, $R^3$ are hydrogen; ArA is an aromatic or heteroaromatic group optionally substituted with one or more substituents from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —OR$^{10}$, and —SR$^{10}$. In some embodiments, ArA is selected from the group consisting of pyrimidine, pyrazine, pyridazine, triazine, thiophene, furan, pyrrole, pyrazole, triazole, imidazole, isothiazole, oxazole, isoxazole, indole, indazole, azaindole, azaindazole, indolizine, imidazopyridine, pyrazolo-pyridine, thiazolo-pyridine pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyrido-pyrimidine, pyrido-pyrazine, pyridopyridazine, isoxazolo-pyridine, and oxazolo-pyridine. In preferred embodiments, ArA is a bicyclic aromatic group, for example, ArA is selected from the group consisting of indole, indazole, azaindole, azaindazole, indolizine, imidazopyridine, pyrazolo-pyridine, thiazolo-pyridine pyrrolo-pyrimidine, thieno-pyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyrido-pyrimidine, pyrido-pyrazine, pyridopyridazine, isoxazolo-pyridine, and oxazolo-pyridine. In some embodiments, ArA is indole, indazole, azaindole, azaindazole, indolizine or, benzimidazole. In certain embodiments, ArA is selected from the group consisting of pyrimidine, thiophene, oxazole, triazole, indole, benzimidazole, azaindole, thienopyrazole, quinoline, quinazoline, and quinoxaline.

In another aspect, provided herein are compounds of Formula I or Formula Ia, or pharmaceutically acceptable salts, polymorphs, solvates, tautomers, metabolites, or N-oxides thereof, wherein:

M is a bond;

m is 0;

n is 0, 1 or 2;
  provided that
    when n is 0, then M is a bond;

p is 0, 1, 2, or 3;

$X^1$ and $X^2$ are independently selected from —OH, —OR$^8$, or F;

Z is >C═O, >C═S, or >SO$_2$;

ArA is aromatic or heteroaromatic ring system optionally substituted with a substituent selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, ═O, —OH, —OR$^{10}$, and —SR$^{10}$;

Each Y is selected from the group consisting of
  —NR$^4$R$^5$, —(CR$^6$R$^7$)$_v$NR$^4$R$^5$, —NR$^4$(CR$^6$R$^7$)$_v$NR$^4$R$^5$, —O(CR$^6$R$^7$)$_v$NR$^4$R$^5$, —S(O)$_{0,1,2}$(CR$^6$R$^7$)$_v$NR$^4$R$^5$, —N(R$^4$)C(O)(CR$^6$R$^7$)$_v$NR$^4$R$^5$, —(CR$^6$R$^7$)$_v$N(R$^4$)C(O)(CR$^6$R$^7$)$_v$NR$^4$R$^5$, —(CR$^6$R$^7$)$_v$NR$^4$(CR$^6$R$^7$)$_v$NR$^4$R$^5$, —NR$^4$(CR$^6$R$^7$)$_v$OR$^{10}$, —NR$^4$(CR$^6$R$^7$)$_v$S(O)$_{0,1,2}$R$^{10}$, —C(O)NR$^4$(CR$^6$R$^7$)$_v$NR$^4$R$^5$, —S(O)$_{0,1,2}$NR$^4$(CR$^6$R$^7$)$_v$NR$^4$R$^5$, —NR$^5$C(O)NR$^4$(CR$^6$R$^7$)$_v$NR$^4$R$^5$, —OC(O)NR$^4$(CR$^6$R$^7$)$_v$NR$^4$R$^5$, —NR$^5$C(=NR$^7$)NR$^4$(CR$^6$R$^7$)$_v$NR$^4$R$^5$, —N(R$^4$)C(=NR$^5$)R$^6$, —(CR$^6$R$^7$)$_v$N(R$^4$)C(=NR$^5$)R$^6$, —NR$^4$(CR$^6$R$^7$)$_v$N(R$^4$)C(=NR$^5$)R$^6$, —O(CR$^6$R$^7$)$_v$N(R$^4$)C(=NR$^5$)R$^6$, —S(O)$_{0,1,2}$(CR$^6$R$^7$)$_v$N(R$^4$)C(=NR$^5$)R$^6$, —(CR$^6$R$^7$)$_v$C(=NR$^5$)NR$^4$R$^5$, —NR$^4$(CR$^6$R$^7$)$_v$C(=NR$^5$)NR$^4$R$^5$, —O(CR$^6$R$^7$)$_v$C(=NR$^5$)NR$^4$R$^5$, —S(O)$_{0,1,2}$(CR$^6$R$^7$)$_v$C(=NR$^5$)NR$^4$R$^5$, —(CR$^6$R$^7$)$_v$N(R$^4$)C(=NR$^5$)NR$^4$R$^5$, —NR$^4$(CR$^6$R$^7$)$_v$N(R$^4$)C(=NR$^5$)NR$^4$R$^5$, —O(CR$^6$R$^7$)$_v$N(R$^4$)C(=NR$^5$)NR$^4$R$^5$, —S(O)$_{0,1,2}$(CR$^6$R$^7$)$_v$N(R$^4$)C(=NR$^5$)NR$^4$R$^5$, —NR$^4$C(=NR$^5$)NR$^4$C(=NR$^5$)NR$^4$R$^5$, —(CR$^6$R$^7$)$_v$C(=NR$^4$)NR$^5$C(=NR$^4$)NR$^4$R$^5$, —NR$^4$(CR$^6$R$^7$)$_v$C(=NR$^4$)NR$^5$C(=NR$^4$)NR$^4$R$^5$, —O(CR$^6$R$^7$)$_v$C(=NR$^4$)NR$^5$C(=NR$^4$)NR$^4$R$^5$, —S(O)$_{0,1,2}$—(CR$^6$R$^7$)$_v$C(=NR$^4$)NR$^5$C(=NR$^4$)NR$^4$R$^5$, —NR$^4$C(=NR$^5$)NR$^4$R$^5$, —C(=NR$^4$)NR$^4$R$^5$, —C(=NR$^4$)NR$^4$C(O)R$^6$, —NR$^4$SO$_2$R$^6$, —NR$^4$C(O)R$^6$, —NR$^4$C(=O)OR$^6$, —C(O)NR$^4$R$^5$, —(CR$^6$R$^7$)$_v$C(O)NR$^4$R$^5$, —SO$_2$NR$^4$R$^5$, -Heteroaryl-NR$^4$R$^5$, -Heterocyclyl-NR$^4$R$^5$, -Heteroaryl-N(R$^4$)C(=NR$^5$)NR$^4$R$^5$, -Heterocyclyl-N(R$^4$)C(=NR$^5$)NR$^4$R$^5$, —N(R$^4$)-Heteroaryl-NR$^4$R$^5$, —N(R$^4$)—Heterocyclyl-NR$^4$R$^5$, —(CR$^6$R$^7$)$_v$Heteroaryl-NR$^4$R$^5$, —(CR$^6$R$^7$)$_v$Heterocyclyl-NR$^4$R$^5$, —(CR$^6$R$^7$)$_v$Heteroaryl-N(R$^4$)C(=NR$^5$)NR$^4$R$^5$, —(CR$^6$R$^7$)$_v$Heterocyclyl-N(R$^4$)C(=NR$^5$)NR$^4$R$^5$, —(CR$^6$R$^7$)$_v$Heteroaryl, —(CR$^6$R$^7$)$_v$Heterocyclyl, —O-Heteroaryl, —O-Heterocyclyl, —NR$^4$(CR$^6$R$^7$)$_v$Heteroaryl, —NR$^4$(CR$^6$R$^7$)$_v$Heterocyclyl, —O(CR$^6$R$^7$)$_v$Heteroaryl, —O(CR$^6$R$^7$)$_v$Heterocyclyl, —NR$^4$(CR$^6$R$^7$)$_v$NR$^5$-Heteroaryl, —NR$^4$(CR$^6$R$^7$)$_v$NR$^5$-Heterocyclyl, —O(CR$^6$R$^7$)$_v$NR$^5$-Heteroaryl, —O(CR$^6$R$^7$)$_v$NR$^5$-Heterocyclyl, —O(CR$^6$R$^7$)$_v$O-Heterocyclyl, —NR$^4$R$^5$R$^{9+}$Q$^-$, —(CR$^6$R$^7$)$_v$NR$^4$R$^5$R$^{9+}$Q$^-$, —NR$^4$(CR$^6$R$^7$)$_v$NR$^4$R$^5$R$^{9+}$Q$^-$, —NR$^4$R$^{9+}$(CR$^6$R$^7$)$_v$NR$^4$R$^5$R$^{9+}$Q$^-_2$, —(CR$^6$R$^7$)$_v$(T)$^+$Q$^-$, and —O(CR$^6$R$^7$)NR$^4$R$^5$R$^{9+}$Q$^-$;

wherein:
T is pyridine-1-yl, pyrimidin-1-yl, or thiazol-3-yl;
Q is a pharmaceutically acceptable counterion; and
v is 1-4;

or two Ys taken together with the carbon atoms to which they are attached form an optionally substituted carbocycle or an optionally substituted heterocycle;

R$^a$, R$^b$, and R$^c$ are independently selected from the group consisting of hydrogen, fluoro, chloro, bromo, optionally substituted C$_1$-C$_6$ alkyl, optionally substituted C$_3$-C$_6$ cycloalkyl, optionally substituted heterocyclyl, optionally substituted aryl, optionally substituted heteroaryl, —OH, —OR$^{10}$, —NR$^4$R$^5$, and —SR$^{10}$;

R$^1$ and R$^2$ are independently selected from the group consisting of fluoro, chloro, bromo, optionally substituted C$_1$-C$_6$ alkyl, optionally substituted C$_3$-C$_6$ cycloalkyl, —OH, —OR$^{10}$, —SR$^{10}$, and —NR$^4$R$^5$, or R$^1$ and R$^2$ taken together form an oxo, oxime, or an optionally substituted carbocycle or optionally substituted heterocycle with the carbon to which they are attached;

R$^3$ is hydrogen, optionally substituted C$_1$-C$_6$ alkyl, or a pharmaceutically acceptable prodrug;

R$^d$, R$^4$, and R$^5$ are independently selected from the group consisting of hydrogen, —OH, —CN, optionally substituted C$_1$-C$_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or R$^4$ and R$^5$ taken together form an optionally substituted heterocycle with the nitrogen to which they are attached;

R$^6$ and R$^7$ are independently selected from the group consisting of hydrogen, fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl;

or R$^6$ and R$^7$ taken together form an oxo, oxime, or an optionally substituted carbocycle or an optionally substituted heterocycle with the carbon to which they are attached;

R$^8$ is optionally substituted C$_1$-C$_6$ alkyl, optionally substituted C$_3$-C$_6$ cycloalkyl, or a pharmaceutically acceptable boronate ester group;

R$^9$ is optionally substituted C$_1$-C$_6$ alkyl;

R$^{10}$ is optionally substituted C$_1$-C$_6$ alkyl or optionally substituted C$_3$-C$_6$ cycloalkyl.

In some embodiments, R$^6$ and R$^7$ are independently selected from the group consisting of fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, —NR$^4$SO$_2$R$^5$, optionally substituted heterocyclyl, optionally substituted aryl, and optionally substituted heteroaryl; or R$^6$ and R$^7$ taken together form an optionally substituted carbocycle or an optionally substituted heterocycle with the carbon to which they are attached. In some embodiments, R$^6$ and R$^7$ are independently selected from the group consisting of fluoro, chloro, bromo, optionally substituted C$_1$-C$_6$ alkyl, optionally substituted alkoxyalkyl, optionally substituted hydroxyalkyl, optionally substituted C$_3$-C$_6$ cycloalkyl, —OH, —OR$^{10}$, —SR$^{10}$, —NR$^4$R$^5$, —NR$^4$C(O)R$^5$, —C(O)NR$^4$R$^5$, and —NR$^4$SO$_2$R$^5$. In some embodiments, v is 1; and R$^6$ and R$^7$ are fluoro. In some embodiments, v is 1; and R$^6$ and R$^7$ together with the carbon to which they are attached form a carbocycle such as cyclopropyl, cyclobutyl, cyclopentyl, cyclohexyl, cycloheptyl, or cyclooctyl group. In some embodiments, v is 1; and R$^6$ and R$^7$ together with the carbon to which they are attached form a heterocycle such as an aziridine, azetidine, pyrrolidine, or piperidine, for example. In some embodiments, ArA is phenyl or pyridine. In some embodiments, R$^1$ and R$^2$ are independently selected from the group consisting of fluoro, chloro, bromo. In certain embodiments, R$^1$ and R$^2$ taken together form an optionally substituted carbocycle or optionally substituted heterocycle with the carbon to which they are attached.

In some embodiments of the compound of Formula 1 or Formula 1a, p is 1, 2 or 3; and at least one Y is selected from the group consisting of —O(CR$^6$R$^7$)$_v$NR$^4$R$^5$, —(CR$^6$R$^7$)$_v$Heteroaryl-NR$^4$R$^5$, —NR$^4$(CR$^6$R$^7$)$_v$NR$^4$R$^5$, —C(O)NR$^4$(CR$^6$R$^7$)$_v$NR$^4$R$^5$, and —N(R$^4$)C(O)(CR$^6$R$^7$)$_v$NR$^4$R$^5$.

In some embodiments of the compound of Formula 1 or Formula 1a, p is 0; and ArA is aryl or heteroaryl substituted with a heteroaryl group. In some embodiments, p is 0; and ArA is selected from the group consisting of benzene, naphthalene, pyridine, pyrimidine pyrazine, pyridazine, triazine, thiophene, furan, pyrrole, pyrazole, triazole, imidazole, thiazole, isothiazole, oxazole, isoxazole, indole, indazole, azaindole, azaindazole, indolizine, imidazopyridine, pyrazolo-pyridine, thiazolo-pyridine pyrrolo-pyrimidine, thienopyrazole, benzimidazole, benzothiazole, benzoxazole, benzofuran, benzisoxazole, benzisothiazole, quinoline, isoquinoline, quinoxaline, quinazoline, cinnoline, benzotriazine napthyridine, pyrido-pyrimidine, pyrido-pyrazine, pyridopyridazine, isoxazolo-pyridine, and oxazolo-pyridine; wherein ArA is substituted with a heteroaryl group. In some embodiments, p is 0 and ArA is substituted with a heteroaryl group selected from azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). In some embodiments, p is 0 and ArA is benzene, pyridine, or pyrimidine substituted with a heteroaryl group selected from imidazolyl, pyridinyl, pyrimidinyl, pyridazinyl, and triazolyl.

Preparation of Compounds

Described herein are compounds of Formula I or Formula Ia that inhibit the activity of beta-lactamases, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds of Formula I or Formula Ia may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

In some embodiments, due to the oxophilic nature of the boron atom, the compounds described herein may convert to or exist in equilibrium with alternate forms, particularly in milieu that contain water (aqueous solution, plasma, etc.). Accordingly, the compounds described herein may exist in an equilibrium between the "closed" cyclic form shown in Formula I and the "open" acyclic form shown in FIG. I*a*. In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

In some embodiments, the compound of Formula I or Formula Ia is the stereoisomer represented by any of the structures shown herein. In some embodiments, the compound of Formula I or Formula Ia is an enantiomer of the stereoisomer represented by any of the structures shown herein. In certain embodiments, the compound of Formula I or Formula Ia is a diastereomer of the stereoisomer represented by any of the structures shown herein. In some embodiments, the compound of Formula I or Formula Ia is a mixture of enantiomers and/or diastereomers of the stereoisomer represented by any of the structures shown herein. In certain embodiments, the compound of Formula I or Formula Ia is a racemate of the stereoisomer represented by any of the structures herein.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\,alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quarternization of any basic nitrogen-containing groups they contain. It should be understood that the compounds described herein also include the quarternization of any boron-containing groups they contain. Such a quarternization could result from the treatment of the Lewis acidic bron with a Lewis base to form a complex or salt. In some embodiments, water or oil-soluble or dispersible products are obtained by such quarternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

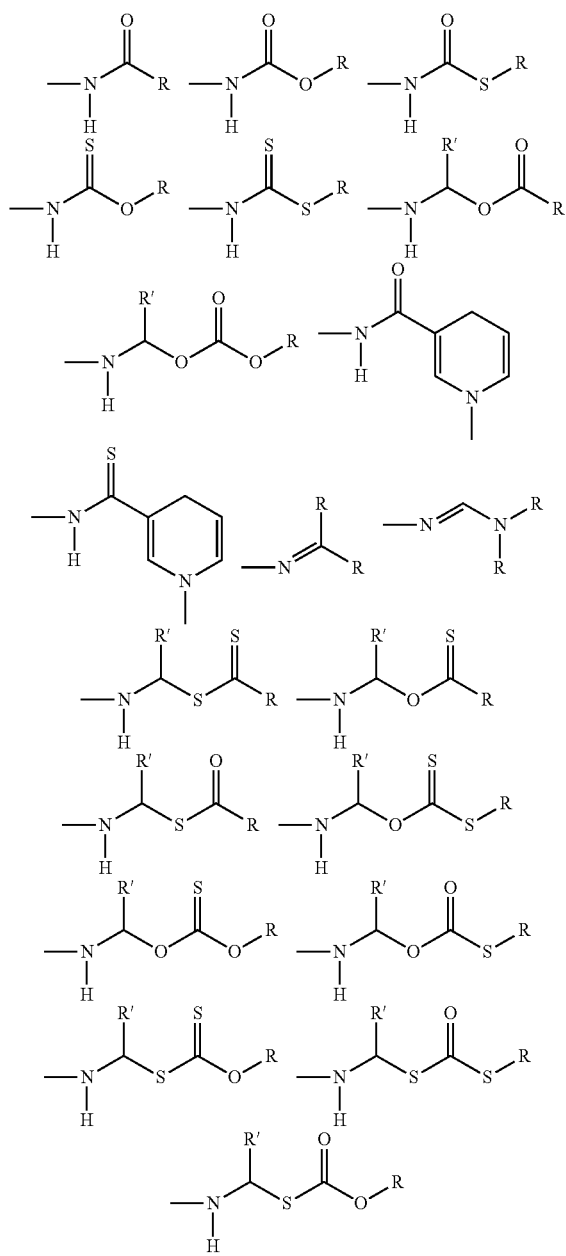

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds of Formula I or Formula Ia are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds of Formula I or Formula Ia described herein are metabolized upon administration to an organism in need to produce a metabolite that is then used to produce a desired effect, including a desired therapeutic effect.

Pharmaceutical Compositions/Formulations

In another aspect, provided herein are pharmaceutical composition comprising a compound of Formula I or Formula Ia as described herein, or a pharmaceutically acceptable salt, polymorph, solvate, prodrug, N-oxide, or isomer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula I or Formula Ia and at least one pharmaceutically acceptable inactive ingredient. In some embodiments, the compounds described herein are administered as pharmaceutical compositions in which a compound of Formula I or Formula Ia is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula I or Formula Ia with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound of Formula I or Formula Ia are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula I or Formula Ia as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

Combination Treatment

The compounds according to Formula I or Formula Ia may be used in combination with one or more antibiotics in the treatment of bacterial infections. Such antibiotics may be administered, by a route and in an amount commonly used therefore, contemporaneously or sequentially with a compound of Formula I or Ia. When a compound of Formula I or Ia is used contemporaneously with one or more antibiotic, a pharmaceutical composition in unit dosage form containing such other drugs and the compound of the present invention is preferred. However, the combination therapy may also include therapies in which the compound of Formula I or IA and one or more antibiotic are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound according to Formula I or Formula Ia. In some embodiments, a pharmaceutical composition comprising a compound of Formula I or Ia further comprises a beta-lactam antibiotic. In certain embodiments, the beta-lactam antibiotic is a penicillin, cephalosporin, carbapenem, monobactam, bridged monobactam, or a combination thereof.

The above combinations include combinations of a compound of Formula I or Ia not only with one antibiotic, but also with two or more antibiotics. Likewise, compounds of formula I or Ia, either in combination with an antibiotic or by themselves, may be used in combination with other drugs that are used in the prevention, treatment, control, amelioration, or reduction of risk of bacterial infections or conditions associated with bacterial infections. Such other drugs may be administered, by a route and in an amount commonly used therefore, contemporaneously or sequentially with a compound of Formula I or Ia. When a compound of Formula I or Ia is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of Formula I or Ia. The weight ratio of the compound of Formula I or Ia to the second active ingredient may be varied and will depend upon the effective dose of each ingredient. Generally, an effective dose of each will be used.

In some embodiments, the compounds according to Formula I or Formula Ia are used in combination with one or more antibiotics in the treatment of bacterial infections. In certain embodiments, the bacterial infection is a upper or lower respiratory tract infection, a urinary tract infection, a intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathine benzylpenicillin, benzathine phenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, ticarcillin. Penems include, but are not limited to, faropenem. Carbapenems include, but are not limited to, biapenem, ertapenem, doripenem, imipenem, meropenem, panipenem. Cephalosprins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftaroline fosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, loracarbef. Monobactams include, but are not limited to, aztreonam, carumonam, nocardicin A, tigemonam.

Administration of Pharmaceutical Composition

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, compounds of Formula I or Formula Ia and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

Assays for Antibacterial Activity

Assays for the inhibition of beta-lactamase activity are well known in the art. For instance, the ability of a compound to inhibit beta-lactamase activity in a standard enzyme inhibition assay may be used (see, e g, Page, *Biochem J,* 295:295-304 (1993)). Beta-lactamases for use in such assays may be purified from bacterial sources or preferably, are produced by recombinant DNA techniques, since genes and cDNA clones coding for many beta-lactamases are known (see, e g, Cartwright & Waley, *Biochem J* 221:505-12 (1984)).

Alternatively, the sensitivity of bacteria known, or engineered, to produce a beta-lactamase to an inhibitor may be determined. Other bacterial inhibition assays include agar disk diffusion and agar dilution (see, e.g, Traub & Leonhard, *Chemotherapy* 43 159-67 (1997)). Thus, a beta-lactamase may be inhibited by contacting the beta-lactamase enzyme with an effective amount of an inventive compound or by contacting bacteria that produce the beta-lactamase enzymes with an effective amount of such a compound so that the beta-lactamase in the bacteria is contacted with the inhibitor. The contacting may take place in vitro or in vivo. "Contacting" means that the beta-lactamase and the inhibitor are brought together so that the inhibitor can bind to the beta-lactamase. Amounts of a compound effective to inhibit a beta-lactamase may be determined empirically, and making such determinations is within the skill in the art. Inhibition includes both reduction and elimination of beta-lactamase activity.

Methods

The present disclosure also provides methods for inhibiting bacterial growth, by, e.g., reducing bacterial resistance to a β-lactam antibiotic, such methods comprising contacting a bacterial cell culture, or a bacterially infected cell culture, tissue, or organism, with a beta-lactamase inhibitor described herein. Preferably, the bacteria to be inhibited by administration of a beta-lactamase inhibitor of Formula I or Ia are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, a compound of Formula I or Ia is administered to an experimental cell culture in vitro to prevent the growth of beta-lactam resistant bacteria. In certain other embodiments, a compound of Formula I or Ia is administered to a mammal, including a human to prevent the growth of beta-lactam resistant bacteria in vivo. The method according to this embodiment comprises administering a therapeutically effective amount of a beta-lactamase inhibitor for a therapeutically effective period of time to a mammal, including a human. Preferably, the beta-lactamase inhibitor is administered in the form of a pharmaceutical composition as described above. In some embodiments, a beta-lactam antibiotic is co-administered with the beta-lactamase inhibitor as described above.

In another aspect provided herein are methods of treating a bacterial infection, which method comprises administering to a subject a pharmaceutical composition comprising a compound of Formula I or Formula Ia, or a pharmaceutically acceptable salt thereof, and a pharmaceutically acceptable excipient. In some embodiments, the methods of treating a bacterial infection in a subject comprises administering to the subject a pharmaceutical composition as described herein, optionally in combination with a beta-lactam antibiotic. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas aeruginosa, Pseudomonasfluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigellaflexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacterjejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroidesfragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcusfaecalis, Enterococcusfaecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus.*

In some embodiments, the infection that is treated or prevented comprises a bacteria that includes *Pseudomonas aeruginosa, Pseudomonasfluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus.*

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIEA diisopropylethylamine
DMAP 4-(N,N-dimethylamino)pyridine
DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
Me methyl
MeI methyliodide
MeOH methanol
MOMCl methoxymethylchloride
MOM methoxymethyl MS mass spectroscopy
NMP N-methyl-pyrrolidin-2-one
NMR nuclear magnetic resonance
PyBOP benzotriazole-1-yl-oxytris-pyrrolidino-phosphonium Hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl General Examples for the Preparation of Compounds of the Invention The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com). Certain compounds of the invention (I) (SCHEME 1) are prepared from the corresponding functional-group-protected boronic acid esters (II) by treatment with a Lewis acid such as $BCl_3$, in a solvent such as dichloromethane, at a temperature between −78° C. and 0° C. followed by an aqueous quench.

Alternatively, (I) is obtained from (II) by treatment of (II) with aqueous hydrochloric acid (around 3-5 Molar) in dioxane at a temperature between room temperature and 100° C.

The requisite boronic acid esters (II) are obtained (SCHEME 2) by coupling of amine (III) with (carboxylic or sulphonic) acid (IV). This transformation is effected by first activating the acid functionality as an acid chloride, anhydride or reactive ester (Va, Vb or Vc), followed by treatment of the activated substrate with (III) in a solvent such as DMF, DMA, NMP, THF or dichloromethane (or a mixture thereof) at about room temperature, usually in the presence of a non-nucleophilic base such as 4-methyl-morpholine, triethylamine or diisopropylethylamine.

Formation of the acid chloride (Va) involves treatment of (IV) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (Vb) (Z is C=O) involves treatment of (IV) with a sterically hindered acid chloride or chloroformate, such as trimethylacetyl chloride or isopropylchloroformate, in an inert solvent such as dichloromethane, in the presence of a non-nucleophilic base, such as triethyl amine or diisopropylamine at room temperature or below. Formation of the activated ester (Vc) involves treatment of (IV) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

The requisite acids (IV) are prepared by a number of different reaction sequences. While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

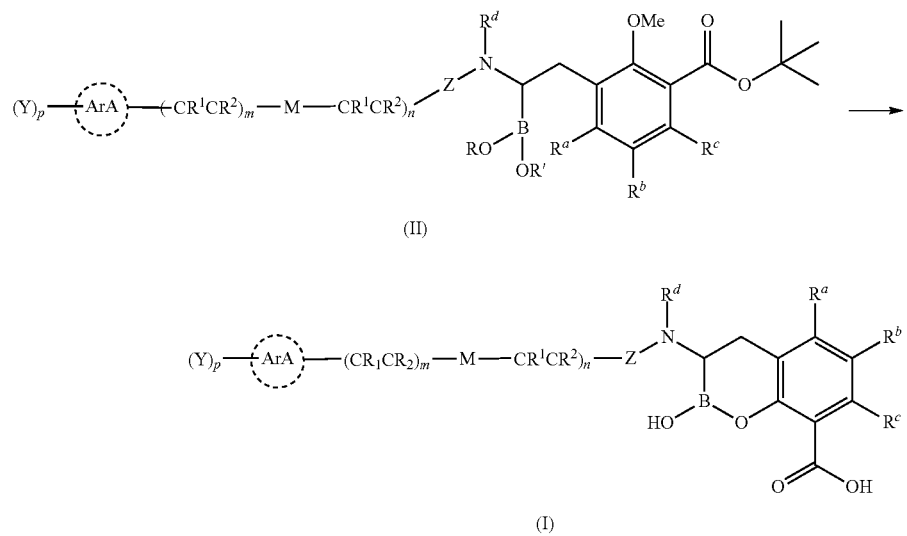

SCHEME 1

SCHEME 2

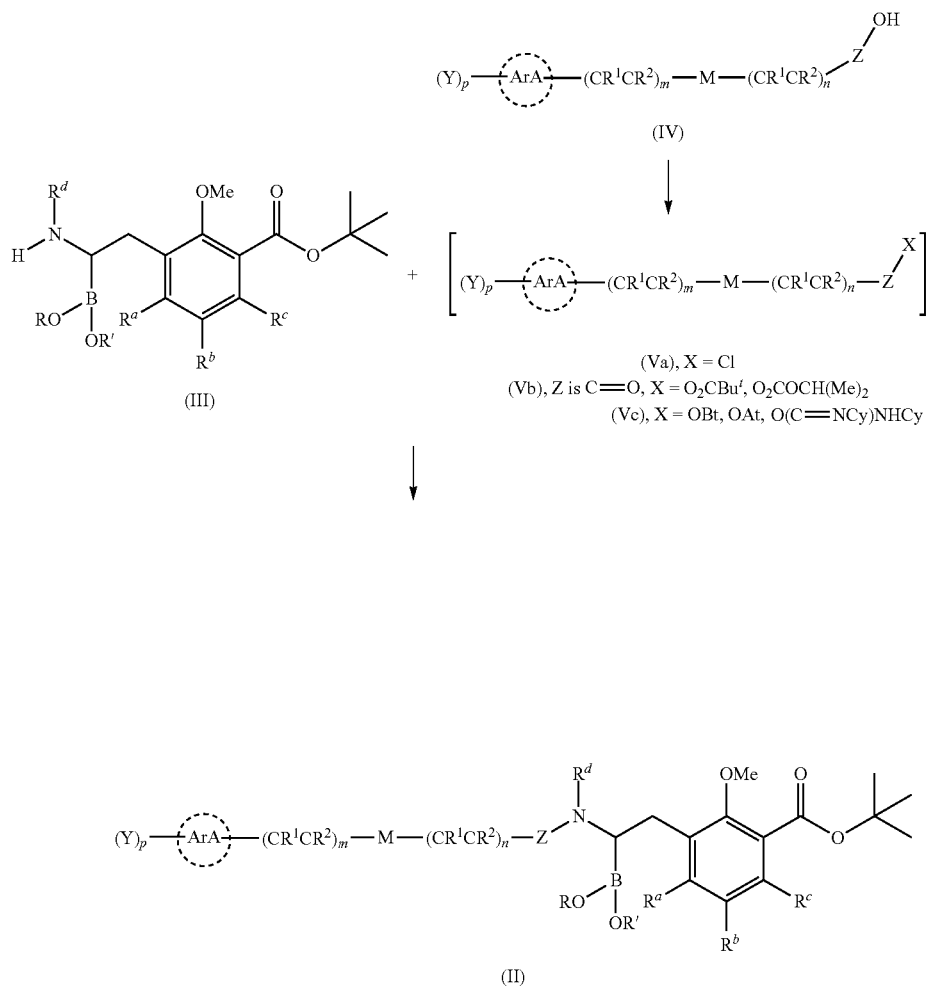

In the case where $Y_1$=an optionally substituted 1,3-diamino-propyl, or 1,4 diamino-butyl (SCHEME 3), the requisite acids (IV) are prepared by treatment of the appropriate benzyloxy-alkyl substituted benzaldehyde or phenyl-ketone (VIa VIb) with t-butylsulfinamine (*Chemical Reviews*, (2010), 110(6), 3600-3740), typically in a solvent such as dichloromethane, ether, benzene or toluene, in the presence of a Lewis acid or desiccant such as $MgSO_4$, $CuSO_4$, $Ti(OEt)_4$ or molecular sieves and, in some cases, in a Dean Stark type reactor system. The resulting t-butylsulphinimine (VII) is then condensed with an appropriate organometallic, such as an olefin substituted alkyl Grignard, in a solvent such as THF, ether, dichloromethane or toluene at a temperature between −60° and 0° C., to provide the sulfinamine substituted aromatic (VIII). Removal of the sulfinyl group is effected by treatment of (VIII) with an acid, such as trifluoroacetic acid, in a solvent such as dichloromethane or HCl in dioxane, at around room temperature, to yield the corresponding primary amine (IX).

SCHEME 3

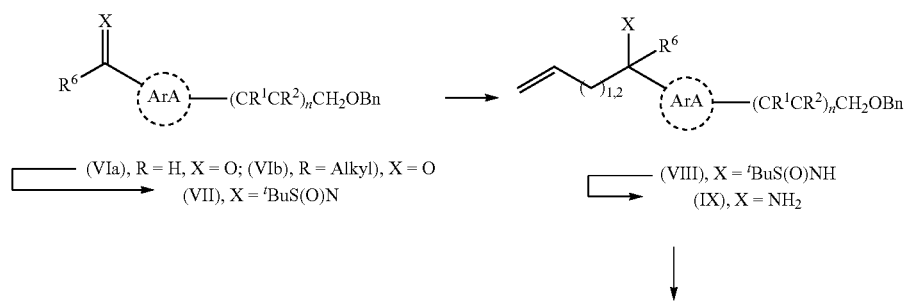

-continued

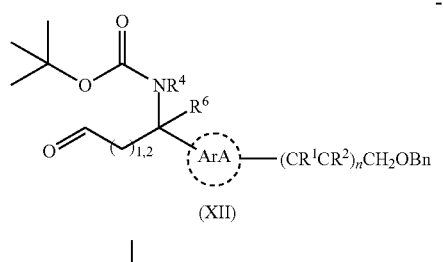

(XII)

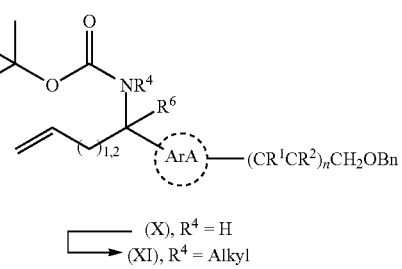

⎯⎯→ (X), R⁴ = H
⎯⎯→ (XI), R⁴ = Alkyl

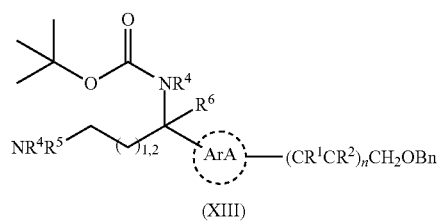

(XIII)

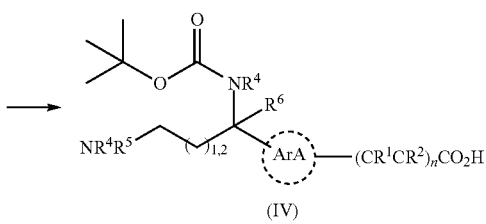

(IV)

The primary amine (IX) can be further functionalized using a variety of procedures. For example, protection of (IX) as a BOC or other appropriate derivative (Greene's Protective Groups in Organic Synthesis; 4th Edition: John Wiley & Sons, Inc., 2006) provides the carbamate (X). The carbamate is treated with an alkylating agent, such as an alkyl halide or alkyl-sulphonate, in the presence of a base, such as sodium hydride or potassium carbonate, in a solvent such as THF, DMF, DMA or acetonitrile, at a temperature between 0° C. and about 100° C. to give the N-alkylated derivative (XI). Oxidative cleavage of the olefin in (XI) is accomplished by treatment with catalytic amounts of osmium tetroxide (*Org. Synth. Oxid. Met. Compd.* (1986), 633-93. Plenum, N. Y.) in the presence of a co-oxidant such as N-methyl morpholine N-oxide, in a solvent system, such as tert-butanol/water or acetone/water, to give the corresponding vicinal di-hydroxy-derivative. This diol is then cleaved using sodium periodate, in a solvent such as THF/water, at around room temperature, to give (XII).

Installation of a second amino functionality is accomplished by treatment of (XII) with a secondary amine ($R^4R^5NH$), in the presence of a reducing agent (*Organic Reactions*, Vol. 59, E. W. Baxter & A. B. Reitz, Wiley 2002), such as $NaBH_4$, $NaCNBH_3$ or $Na(AcO)_3BH$, in a solvent such as dichloromethane, methanol, 1,4-dioxane, THF or acetic acid (or a combination thereof) at around room temperature or below, to give (XIII). (XIII) is converted to the requisite carboxylic acid by first, removal of the benzyl protecting group, typically by a hydrogenolysis reaction, using a heterogeneous catalyst, such as palladium on carbon, in a solvent such as ethyl acetate, THF methanol or acetic acid under a hydrogen atmosphere (1-5 bar) to yield the primary alcohol. This alcohol is oxidized to the corresponding acid using a two-step procedure; involving initial oxidation to the aldehyde, using a DMSO based oxidant system, such as Swem oxidation (*Organic Reactions.* (1990), 39, 297-572.) or by treatment with excess Dess-Martin periodinane (*Journal of Organic Chemistry*. (1983), 48, 4155) in a solvent such as dichloromethane at around room temperature. Subsequent oxidation of the intermediate aldehyde is accomplished by treatment with sodium chlorite/$NaH_2PO_4$ and 2,3-dimethyl-but-2-ene in a solvent such as t-butanol/water at around room temperature (*Journal of Organic Chemistry*, (1980), 45, 4825). In certain cases, the primary alcohol may also be oxidized to (IV) directly, using one of a number of oxidation protocols, such as with $NaIO_4$ and catalytic $RuCl_3$, in a solvent mixture of water/$CCl_4$/$CH_3CN$ in the ratio 3/2/2, at around room temperature (*Journal of Organic Chemistry*, (1981), 46(19), 3936-8) or with pyridinium dichromate in DMF (*Tetrahedron Letters*, (1979), 20 (52): 399) at around room temperature.

In the case where $Y_1$=an optionally substituted 1,2-di-amino-ethyl, the requisite acids (IV) are prepared (SCHEME 4) from a suitable aryl-halide (M=I, Br, Cl) or aryl-triflate (M=$O_3SCF_3$) (XIV) by treatment with an appropriate vinyl-boronic (XV) acid in the presence of a base such as $Na_2CO_3$, $Cs_2CO_3$, $Na_3PO_4$ and a palladium catalyst such as $(Ph_3P)_4Pd$, Dppf/$Pd(OAc)_2$ or the PEPPSI catalyst system, in a solvent such as aqueous 1,4-dioxane, DME, THF, at around room temperature to 100° C. to give the olefin derivative (XVI) (*Journal of Organometallic Chemistry*, (1999), 576, 147-168). Treatment of (XVI) with sodium azide, in the presence of a mild oxidant, such as $Mn(OAc)_3(H_2O)_2$ and an acid such as acetic acid or trifluoroacetic acid, in a solvent such as acetonitrile, at a temperature between −30° C. and 0° C. provides the diazide (XVII) (*Synthetic Communications*, 28(10), 1913-1922; 1998).

Subsequent reduction of the bis-azide by treatment with a reducing agent, such as triphenylphosphine, in a solvent such as THF, followed by in situ hydrolysis of the intermediate aza-phosphorane with excess water yields the bis-amine (XVIII). In certain instances, reduction of the bis-azide is achieved by treatment of (XVII) with hydrogen gas, in the presence of a catalyst, such as palladium on carbon, in a solvent such as THF or methanol. Subsequent functionalization of (XVIII) is accomplished as described above to yield (XIX). In particular, in the case where $R^4$ constitutes part of a piperazine ring structure, (XVIII) is treated with an alkyldihalide, such as 1,2-dibromoethane, in the presence of a base, such as triethylamine, in a solvent such as aqueous THF or dichloromethane, at around room temperature, to give (XIXa). The intermediate (XIXa) is converted to (XIXb) as described above. The requisite acids (IV) are obtained from the corresponding esters (XIX or XIXb) by formal hydrolysis of the ester functionality. The reaction conditions employed depends on the type of the ester used. In the case of a methyl, ethyl or other simple alkyl, hydrolysis is usually achieved by brief treatment with an aqueous base, such as sodium or lithium hydroxide in a solvent mixture of THF, water and methanol. However, other acid protecting groups can also be used, such as benzyl, 2-trimethylsilyl-ethyl or 2,2,2-trichloroethyl. In these cases, conversion of the ester to the corresponding acid is achieved using the standard deprotection procedures in the literature (*Greene's Protective Groups in Organic Synthesis*. Fourth Edition. John Wiley & Sons, Inc. 2006).

Alternatively, the 1,2 diamino-ethyl substructure can be prepared from a suitable aryl-alkyl ketone such as (XX) (SCHEME 5). For example, treatment of (XX) with trimethylsilyl-triflate, in ether, at about 0° C., in the presence of triethylamine provides silyl-enol ether (XXI). Treatment of (XXI) with a halogenating reagent, such as bromine, NCS, or pyridinium tribromide in an inert solvent such as dichloromethane or cyclohexane, at a temperature between −78° C. and room temperature furnishes the α-halo-ketone (XXII). (XXII) is condensed with an amine (NHR$^4$R$^5$) in an inert solvent such as toluene, THF, acetonitrile or DMA, at room temperature or above, to yield the α-amino-ketone (XXIII). Reductive amination of (XXIII) as described above, yields the diamino-ethyl derivative (XXIV) which is further processed (benzyl ether removal and oxidation) to provide the requisite acid (IV) as described above.

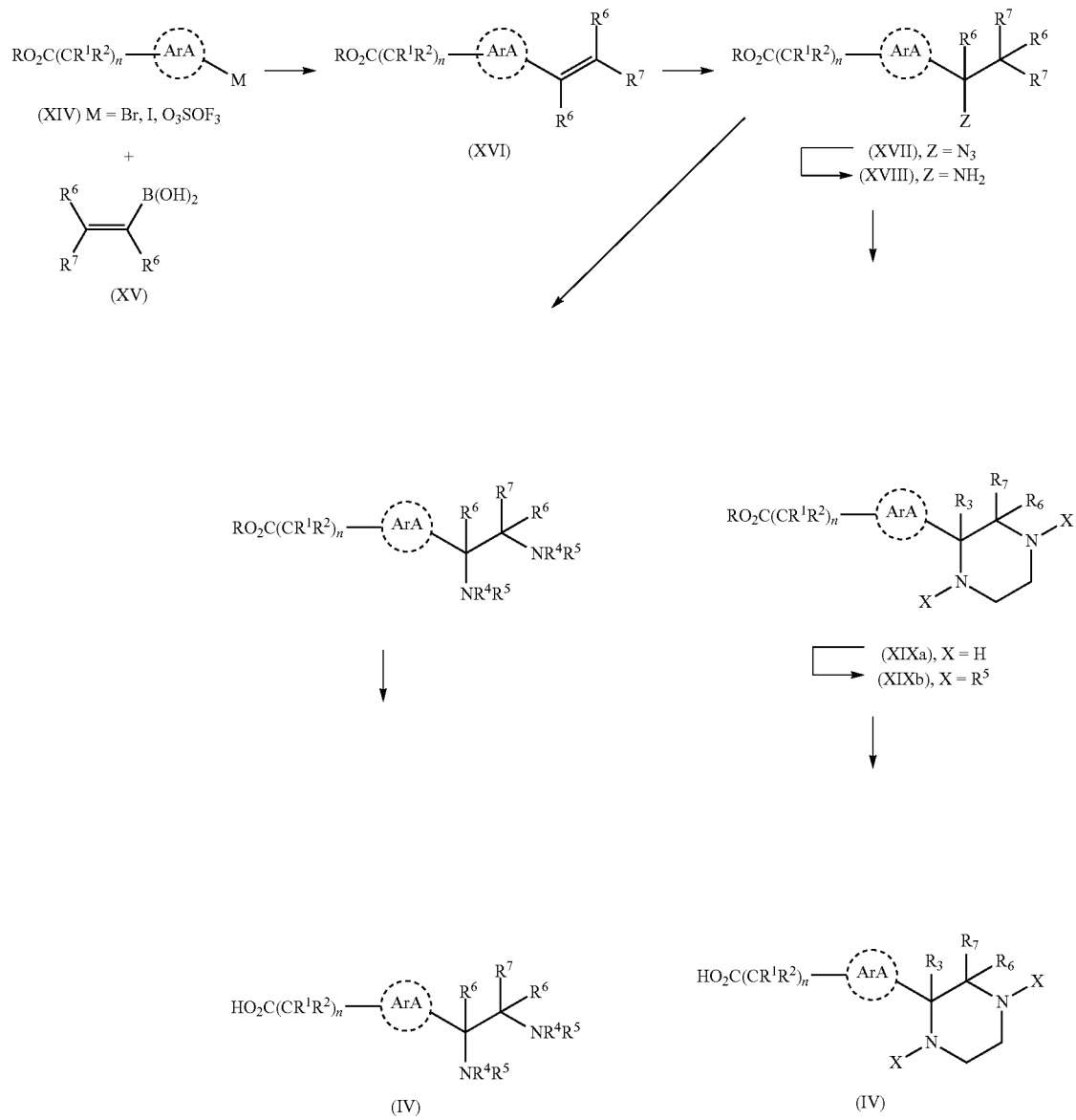

SCHEME 5

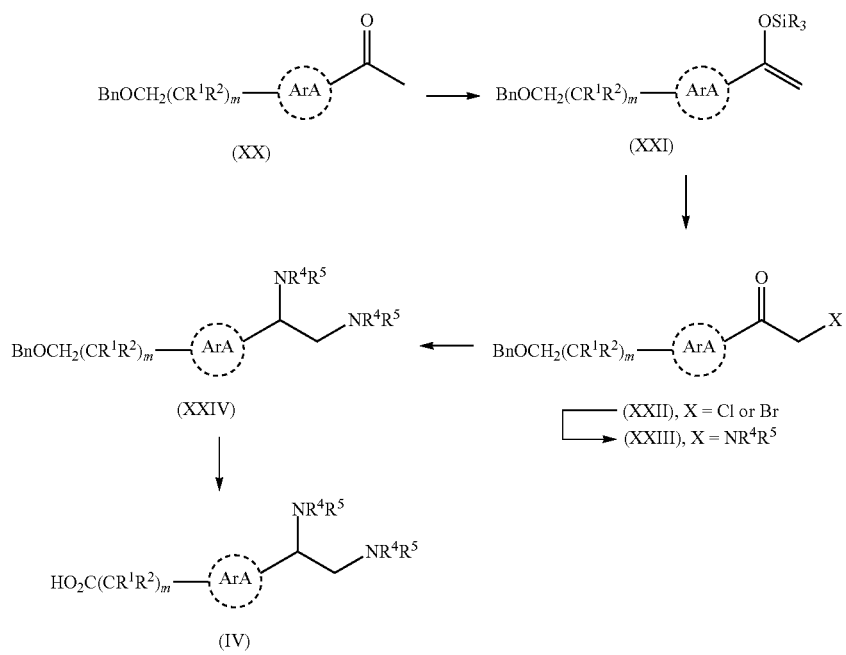

In the case where $Y_1$ is a 1,2-diamino-substituted-propyl or butyl group, the requisite alkene substrates for the aforementioned chemistry are prepared from the appropriate phenyl-halide (I, Br, Cl) or triflate and an allyl or buten-yl Grignard in the presence of a copper catalyst such as CuBr:DMS in a solvent such as THF at around room temperature.

In a variant of the 1,2-diamino system wherein, $Y_1$ is an amino-alkyl. $Y_2$ is an amino alkyl such that the substituent on the amine bearing carbon of $Y_1$ and the substituent on the amine bearing carbon of $Y_2$ together form a ring, the requisite acids (IV) are prepared from the appropriate benzo-fused cyclic alkene (XXV) (SCHEME 6). Bis azidination of (XXV) provides the cyclic bis azide (XXVI) which is processed as previously described to provide the requisite acid (IV).

SCHEME 6

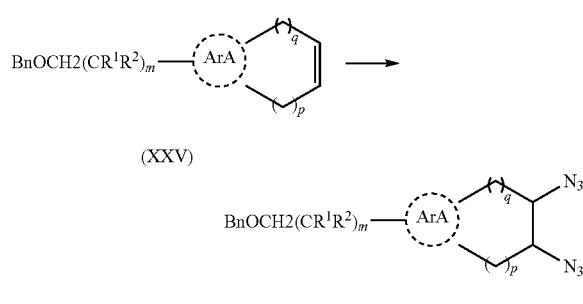

p = 0, 1, 2
q = 1, 2

In the case where $Y_1$=an optionally substituted amino-alkyl-amino, the requisite acids (IV) are prepared (SCHEME 7) by cross coupling of an appropriate aryl bromide (XXVII, M=Br), aryl iodides (XXVII; M=I), aryl chlorides (XXVII; M=Cl) or aryl-sulphonate ester (XXVII; M=$O_3$SR) with a diamine (or mono-N-protected-diamine) (XXVIII) (*Metal-Catalyzed Cross Coupling Reactions*, 2$^{nd}$ Ed., Wiley-VCH: 2004) to give intermediate (XXIX). This is followed by hydrolysis of the ester functionality to give (IV). The cross coupling of (XXVII) with amines is generally carried out under palladium catalysis, using a palladium source such as palladium bis(dibenzylidineacetone), Tris(dibenzylideneacetonyl)bis-palladium or palladium diacetate in a solvent such as toluene, THF, DMF or DMA at temperatures between 80 and 110° C. in the presence of a base such as sodium t-butoxide, potassium phosphate or lithium hexamethyldisilazide and a ligand such as 2-dicyclohexyl-phosphino-2'-dimethylamino-biphenyl, 2,2'-Bis(diphenyl-phosphino)-1,1'-binaphthylene, 9,9-Dimethyl-4,5-bis(diphenylphosphino)-xanthene, tri(tert-butyl)-phosphine, 2-(Di-tert-butylphosphino)-1,1'-biphenyl, 2,8,9-Triisobutyl-2,5,8,9-tetraaza-1-phosphabicyclo[3.3.3]undecane, 2-methyl-N,N'-bis(isobutyl)-2-[[(isobutyl)amino]-methyl]-1,3-propanediamine or the PEPPSI system (*Chemical Society Reviews*, (2011), 40, 5151-5169). In certain cases, cross coupling of (XXVII) and (XXVIII) employs a copper catalyst, such as Copper iodide and a 1,3 dicarbonyl ligand such as 2-isobutyryl-cyclohexanone in DMF in the presence of a base such as $Cs_2CO_3$ at a temperature between room temperature and 100° C. In the case where M is a nonaflate, the base is generally DBU or MTBD (7-methyl-1,5,7-triaza-bicyclo-[4.4.0]-dec-5-ene) and the ligands are 2,4,6,-triisopropyl-2'dicyclhexylphosphino-biphenyl or 9,9-Dimethyl-4,5-bis(diphenylphosphino)-xanthene in a solvent such as toluene, at a temperature of 100-150° C. (*Journal of Organic Chemistry* (2006), 71, 430.)

The N-protecting group employed in (XXVIII) is generally a carbamate, such as tert-butyl, benzyl or 2-trimethylsilyl-ethyl. Removal of such groups employs standard conditions described in the literature (*Greene's Protective Groups in Organic Synthesis*, Fourth Edition, John Wiley & Sons, Inc., 2006).

SCHEME 7

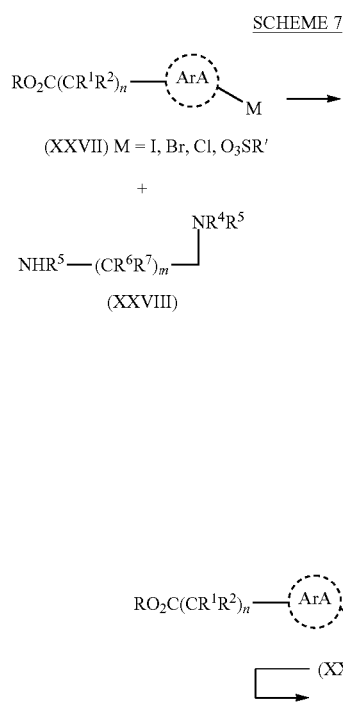

(XXVII) M = I, Br, Cl, O₃SR'

+

(XXVIII)

(XXIX), R = Alkyl
(IV), R = H

In the case where $Y_1$=an optionally substituted amino-alkyl and $Y_2$ is, independently, an optionally substituted amino alkyl, the requisite acids ((IV), FIG. 1) are usually prepared by sequential introduction of the amine functionality into the corresponding hydroxyl or oxo substituted carbon scaffold. The conversion of a hydroxyl functional group to an amine is accomplished by one of a number of reaction sequences known in the literature (*Comprehensive Organic Transformations*, VCH publishers. 1989). These generally involve conversion of the alcohol to a leaving group, such as an iodide, bromide, benzenesulphonate, mesylate or triflate, followed by displacement of the leaving group using an azide anion salt, such as sodium azide or tetrabutylammonium azide, in a solvent such as DMF, DMA DMSO or acetonitrile. The azide is then reduced to the corresponding primary amine by hydrogenation or Staudinger reaction, as described above. Alternatively, Introduction of the primary amino functionality is effected by conversion of the alcohol functionality to the corresponding pthalimide under Mitsunobu conditions (*Chemical Reviews*, (2009) 2551-2651), followed by deprotection of the pthalimide by treatment with excess hydrazine, in a solvent such as ethanol, at room temperature or above.

Conversion of an oxo functionality to the corresponding amine is achieved by reductive amination or t-butylsulphinimide formation and hydride addition/alkylation of the C=N functionality of the imine (*Chemical Reviews*, (2010), 110(6), 3600-3740). In a special case where the oxo is part of a carboxylic acid group, the amine functionality can be introduced by a Curtius rearrangement. (*Tetrahedron* (1974), 30 (14): 2151-2157).

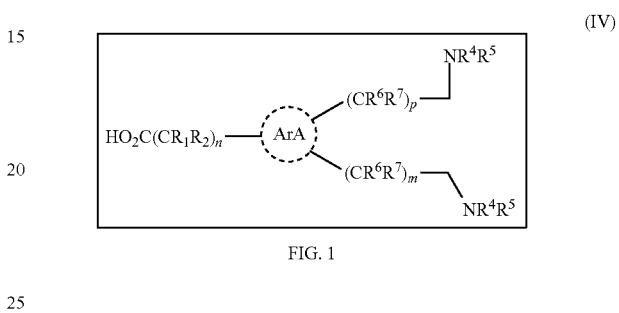

FIG. 1

The appropriate hydroxyl or oxo substituted carbon scaffold is prepared by one of a wide range of sequences known in the literature. The sequence employed in any given case depends on the specific arrangement of diamine functionality required. For example, in the case where p=0 and m=2 (IV), FIG. 1), the carbon scaffold is prepared as illustrated in SCHEME 8. Treatment of the 3-bromo-4-formyl-benzoate (XXX) with a secondary amine (R³R⁴NH) in the presence of a reducing agent such as sodium borohydride, as previously described, provides the benzylic amine (XXXI). Exposure of this intermediate to methyl-vinyl ketone under the conditions of the Heck reaction yields the α,β-unsaturated ketone (XXXII). Reduction of (XXXII) using a Pd, Rh or Pt catalyst, such as 10% Pd on carbon, or Wilkonson's catalyst under an atmosphere of hydrogen gas (1-4 atm), in a solvent such as toluene, ethyl acetate, methanol or THF (or a mixture thereof) at room temperature to 70° C. gives the saturated ketone (XXXIII). Alternatively, unsaturated-ketone (XXXII) is reduced by treatment with excess Magnesium, in a solvent such as methanol, at around room temperature (*Tetrahedron Letters*, (1986); 27(21), 2409-2410). Reductive amination of (XXXIII) with a secondary amine (R⁴'R⁵'NH), as described above provides (XXXIV). Finally, hydrolysis of the ester functionality in (XXXIV) yields the requisite acid (IV).

SCHEME 8

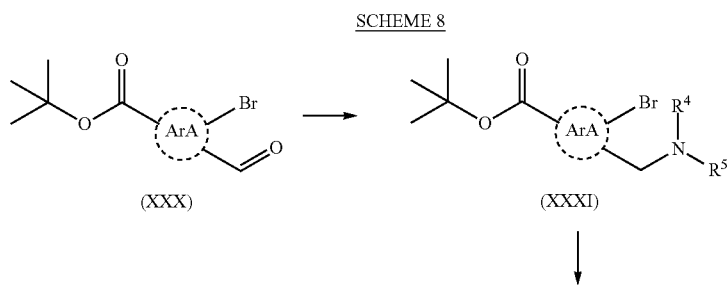

(XXX)   (XXXI)

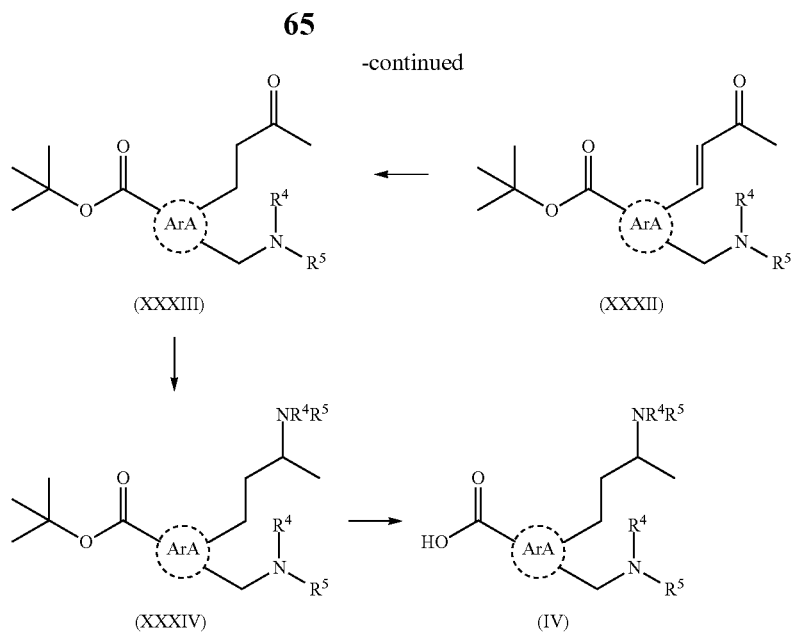

In addition to alcohol or carbonyl derivitization, the amino functionality may also be introduced, in latent form (such as a nitro, cyano, or amide) or directly during a C—C bond forming reaction employed in the construction of the carbon framework. For example (SCHEME 9), coupling of the aryl chloride (XXXV) with potassium (BOC-aminomethyl)-trifluoroborate in the presence of Pd(OAc)$_2$ and a phosphine ligand such as SPhos or XPhos and a base, such as potassium carbonate, in a solvent mixture of toluene and water, yields the benzyamine derivative (XXXVI) (*Organic Letters*, (2011), 13(15), 3956-3959). Functionalization of the BOC amine is achieved as described above to give (XXXVII). Coupling of this intermediate with a silyl-nitronate (XXXVIII) in the presence of a fluoride ion source provides the nitroaldol product (XXXIX) (*European Journal of Organic Chemistry*, (2007), 16, 2561-2574). Reduction of (XXXIX) with lithium aluminum hydride in THF yields the bis-amine (XL). This intermediate is again derivatized as described above to yield (XLI). (XLI) is then converted to the corresponding acid (IV) as described above.

SCHEME 9

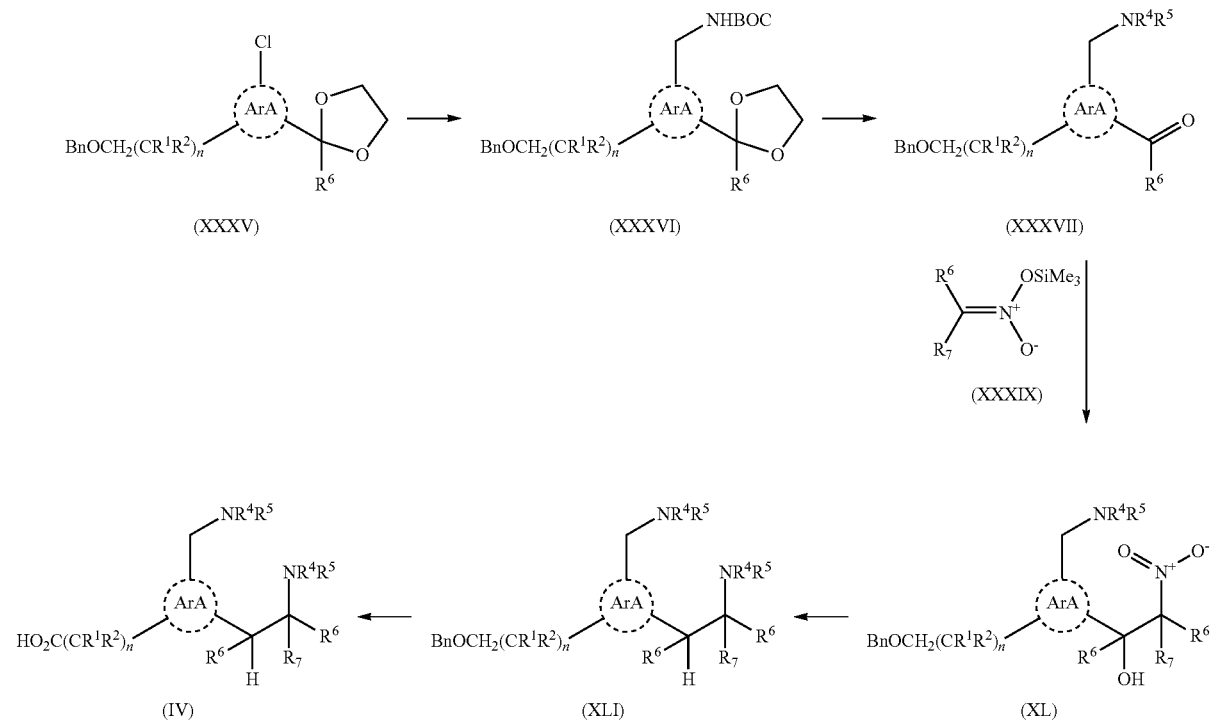

In the case where $Y_1$=an optionally substituted amino-alkyl and $Y_2$ is an optionally substituted amino group, the requisite acids (IV) are prepared from the corresponding bromide (XXVI) (SCHEME 10) by a palladium catalyzed amination as described above (*Metal-Catalyzed Cross Coupling Reactions*, 2nd Ed., Wiley-VCH: 2004) as illustrated in SCHEME 7.

In a variant of this system wherein, $Y_1$=a substituted amino-alkyl and $Y_2$ is a substituted amino group, such that the substituent on the amine-bearing carbon of $Y_1$ and N-substituent of $Y_2$ together form a ring, the requisite acids (IV) (SCHEME 11) are prepared, using a Povarov reaction, (*Name Reactions in Heterocyclic Chemistry II*, (2011), 385-399 Wiley) from the appropriately substituted aniline (XLIII), aldehyde or ketone (XLIV) and an N-vinyl carbamate (XLV) in the presence of an acid such as a diaryl phosphoric acid ester (for example, the phosphoric acid ester of BINOL (*Journal of the American Chemical Society*, (2011), 133(37), 14804-14813) in a solvent such as dichloromethane at around 0° C. to give (XLVI). Subsequent derivatization of the amine functionality in (XLVI), as previously described, followed by ester hydrolysis yields (IV).

SCHEME 10

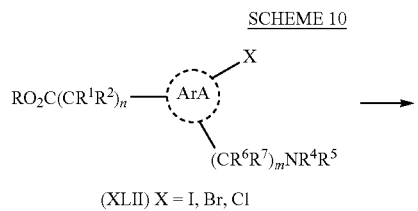

(XLII) X = I, Br, Cl

SCHEME 11

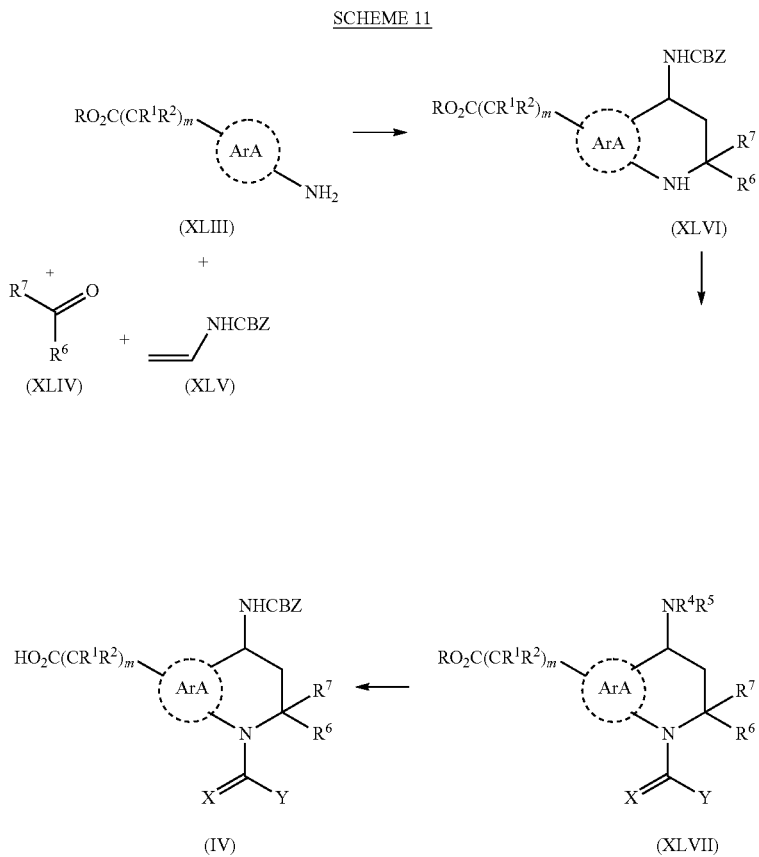

-continued

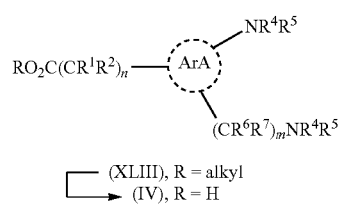

(XLIII), R = alkyl
(IV), R = H

In the case where $Y_1$=an optionally amino substituted piperidine and $Y_2$ is a H, the requisite acids (IV) (SCHEME 12) are prepared by reaction of an aryl Grignard reagent such as (XLIX) with an appropriately protected sulphinimide such as (XLVIII), as previously described, to provide intermediate (L). Treatment of (L) with an acid such as TFA in dichloromethane or HCl in dioxane yields the deprotected amino ester (LI). Boc protection of (LI), followed by conversion of the primary alcohol to the corresponding tosylate, using standard methods, yields (LII). Treatment of (LII) with a base such as $K_2CO_3$, NaH, DBU or TMG in a solvent such as DMA, NMP or DMF effects cyclization to give (LIII). (LIII) is de-protected and derivatized, as previously described, to yield the requisite acid (IV).

into the corresponding hydroxyl-substituted carbon scaffold (LVIII) as previously described (*Organic Letters*, (2207), 9(21), 4203-4206) or by reduction of the di-nitro derivative

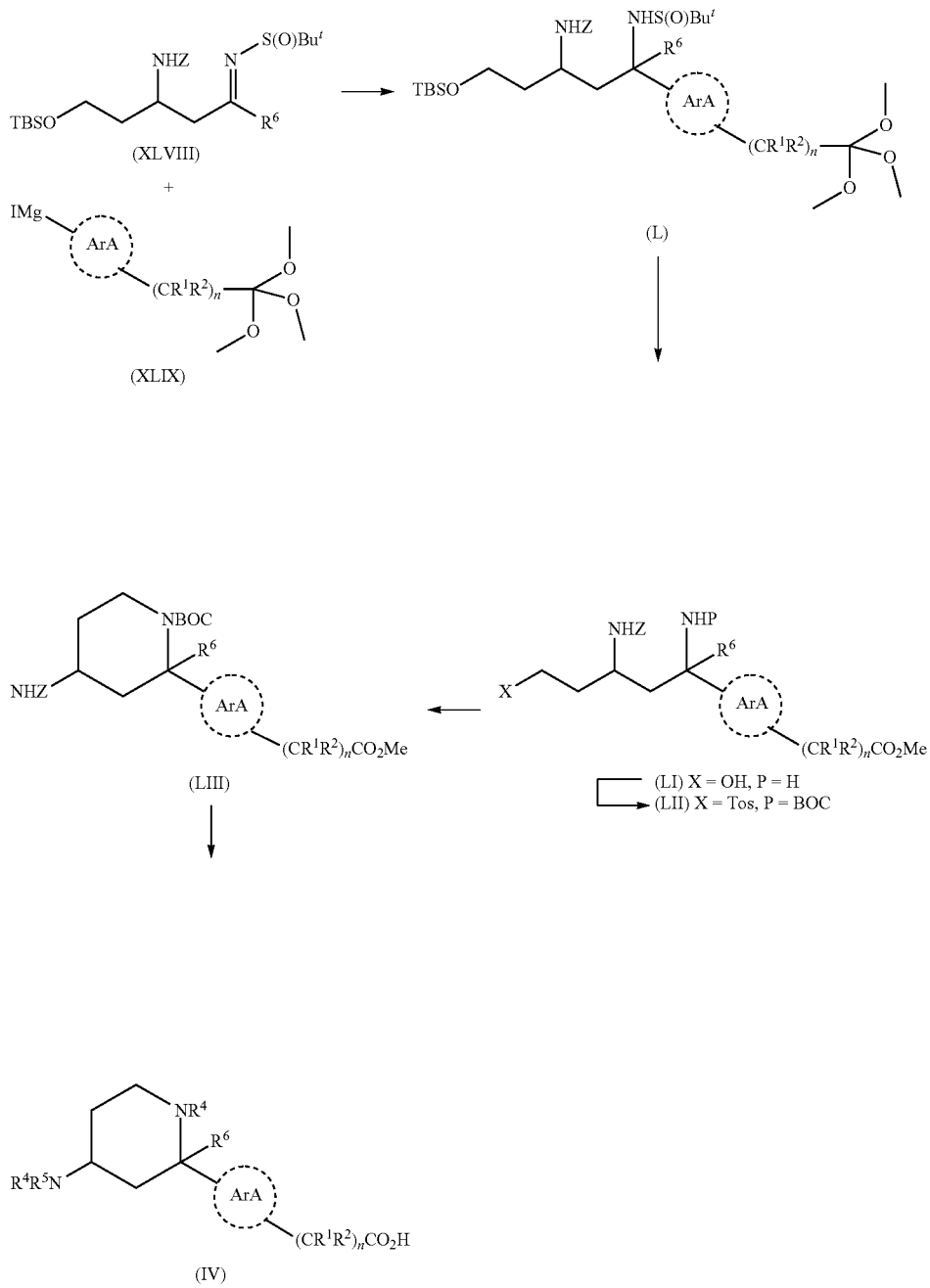

In a variant of this system, wherein $Y_1$=hexahydropyriminin-2-imine and $Y_2$ is a H, the requisite acids (IV) (SCHEME 13) are prepared by condensation of a 2-phenyl-1,3 diamino-propane (LIV) derivative with 2-Methyl-2-thiopseudourea sulfate (LV) (*Journal of Medicinal Chemistry*, (1985), 28(6), 694-8) to give (LVI) which is processed to give (IV) as previously described. The requisite 1,3 diamine (LIV) is obtained by Hofmann degradation of the bis amide (LVII); by introduction of the diamine functionality (LIX) with a hydride donor, such as lithium aluminum hydride, in a solvent such as THF. The di-nitro derivative is obtained from an appropriate aldehyde/ketone by condensation with nitromethane in the presence of alumina at room temperature (*European Journal of Organic Chemistry*, (2010), (3), 483-493) or by a nitro-alkene silyl-nitronate condensation in the presence of a quaternary ammonium fluoride ion source (*Angewandte Chemie International Edition*, (2006), 45, 7606-7608).

SCHEME 13

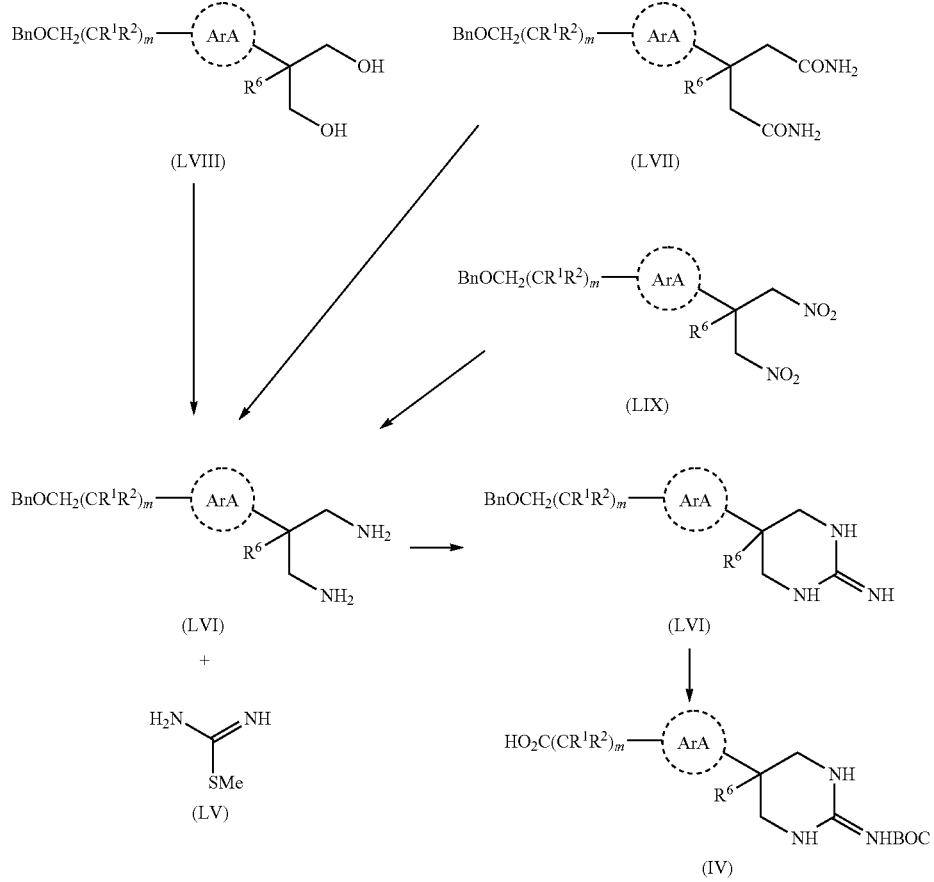

In the case where $Y_1$=an optionally amino-alkyl-substituted piperidine, the requisite acids (IV) (SCHEME 14) are prepared by alkylation of an appropriately substituted phenyl-acetonitrile, phenyl-acetone or phenyl acetic acid derivative such as (LX) with a bis-(chloroalkylamine), in the presence of a base such as, sodium hydride, potassium t-butoxide or sodium hydroxide, in a solvent such as THF, DMSO, toluene or DMF. In the case where aqueous NaOH is the base, a phase transfer catalyst, such as methyl-trioctanylammonium chloride can also be used (*Journal of Heterocyclic Chemistry*, (1986), 23(1), 73-5) to provide (LXI).

Functionalization of the iodide/bromide in (LXI) with a vinyl or allyl stannane, in a solvent such as DMF, in the presence of a palladium catalyst, such as $(Ph_3P)_4Pd$, yields the olefin functionalized piperidine (LXII). Treatment of (LXII) with a strong reducing agent such as lithium aluminum hydride, in a solvent such as THF or glyme, provides 4,4-disubstituted piperidine (LXIII). Derivitization of the amine functionality to give (LXIV) is achieved as already described. Installation of the carboxyl functionality to give (IV) is accomplished by hydroboration/oxidation to give the corresponding primary alcohol; or oxidative cleavage of the olefin functionality to give the one carbon truncated aldehyde, followed by further oxidation to the acid as previously described.

SCHEME 14

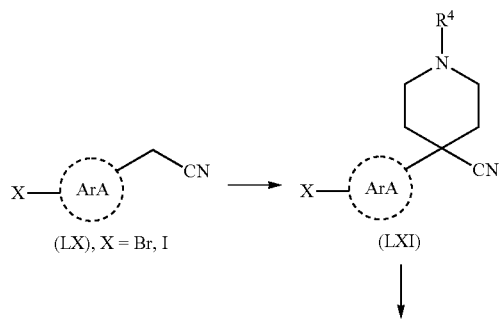

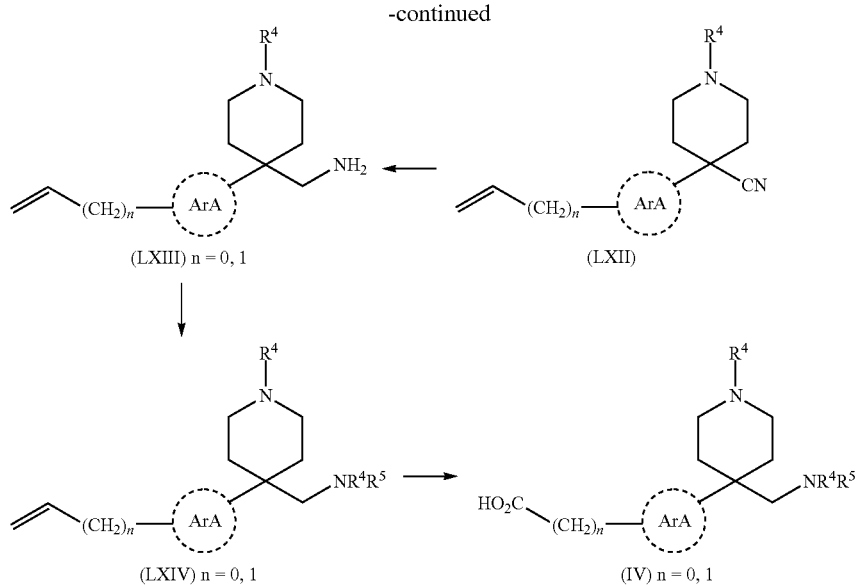

In a particular variant of this system, $Y_1$=a 4-substituted piperidine and $Y_2$ is a substituted amine such that the substituent on the 4 position of the piperidine and the substituent on the ($Y_2$) amine together form a ring, the requisite acids (IV) (SCHEME 15) are prepared from an appropriately substituted 2-fluoro-aryl/heteroarylacetonitrile (*Tetrahedron*, (2004), 60(22), 4874-4878). For example, treatment of a bromo or iodo substituted 2-fluoro-acetonitrile (LXV) with a bis-(2-chloroethyl)-amine derivative, as described above, provides the piperidine (LXVI). Functionalization of the iodide/bromide with a vinyl or allyl stannane, in a solvent such as DMF, in the presence of a palladium catalyst, such as $(Ph_3P)_4Pd$, yields the olefin functionalized piperidine (LXVII). Treatment of (LXVII) with a strong reducing agent such as lithium aluminum hydride/ethanol in a solvent such as glyme, provides the spiro-indole (LXVIII).

Scheme 15

Derivitization of the amine functionality to give (LXIX) is achieved as already described. Installation of the carboxyl functionality to give (IV) is accomplished by oxidation of the olefin functionality as previously described.

In another variant of this system, $Y_1$=a 4-substituted piperidine such that the substituent on the 4 position of the piperidine and the ortho substituent on A, taken together, form a carbocyclic ring. In this instance, the requisite acids (IV) (SCHEME 16) are prepared from an appropriate aryl fused cyclopentadiene. For example, Treatment of (LXX) with a bis-(2-chloroethyl)-amine derivative in the presence of a strong base, such as LHMDS, in a solvent such as THF, at around 0° C., yields the spiro-cyclopentadiene (LXXI)) (*Bioorganic and Medicinal Chemistry Letters*, (2012), 22(1), 363-366). Hydroboration of the olefin with 9-BBN in THF at around 0° C. followed by oxidative work up ($NaOH/H_2O_2$) provides the

SCHEME 16

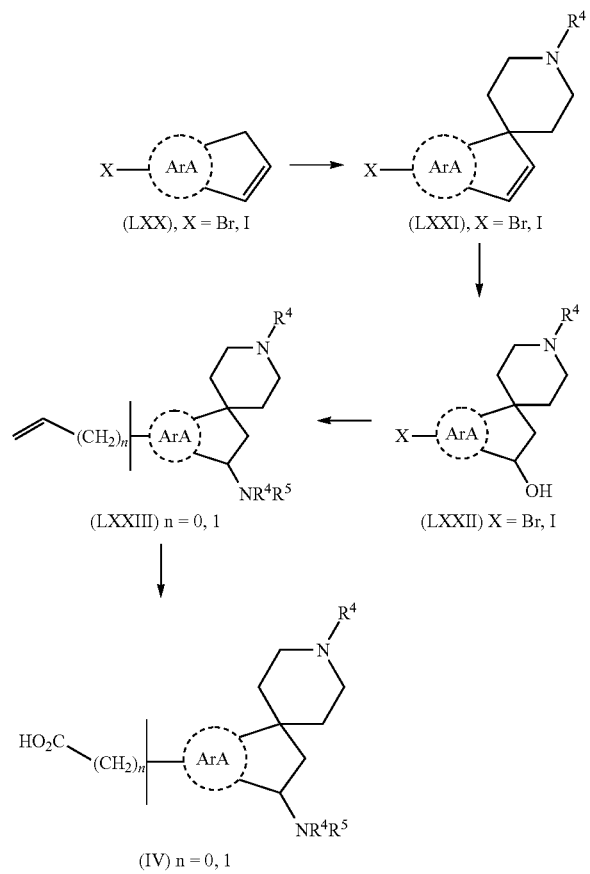

hydroxyl derivative (LXXII). Derivitization of the alcohol functionality, as described above, yields the diamine derivative (LXXIII). Installation of the acid functionality is accomplished, as described above, via Stille coupling of the bromide with an allyl or vinyl stannane followed by oxidation the olefin group and further oxidation of the resulting alcohol/aldehyde to the corresponding acid.

In the case where $Y_1$ is a piperidin-4-yl-substituted C1-C3 alkyl, $Y_2$ is a C1-amino-alkyl group such that the C4 of the piperidine of $Y_1$ and the C1-alkyl group of $Y_2$ are connected through a bond to form a 5, 6 or 7 membered ring, the requisite acids (IV) (SCHEME 17) are prepared from the appropriately substituted aryl/heteroaryl fused-carbocyclic ketone. For example, treatment of ketone (LXXIV) with a substituted bis-(bromoethyl)-amine in the presence of a base such as NaH, in a solvent such as DMF, DMA or NMP at around 50° C. (*Bioorganic & Medicinal Chemistry Letters*, (2010) 20(2), 746-754) yields the spiro-piperidine-ketone (LXXV). Installation of a second amino functionality is achieved by treatment of (LXXV) with an amine (NHR4'R5') in the presence of a Lewis acid such as TiCl$_n$(OiPr)$_{4-n}$ (n=0-4) in a solvent, such as benzene, at a temperature between room temperature and reflux to give imine (LXXVI) (*European Journal of Organic Chemistry*, (2007), 18, 2945-2957. *Journal of the Chemical Society, Perkin Transactions 1: Organic and Bio-Organic Chemistry* (1988), 12, 3399-406). The imine (LXXVI) is reduced with a hydride reducing agent such as NaBH$_4$ or LiBH$_4$ in a solvent such as THF, glyme or methanol to give (LXXVIII). Alternatively, treatment of (LXXV) with LHMDS to form the N-trimethylsilylimine (LXXVII) in situ, followed by reduction with NaBH$_4$ or LiBH$_4$ in a solvent such as THF provides the primary amine (LXXIX) which is then derivatized as already described. A third approach involves treatment of (LXXV) with NaBH$_4$ or LiBH$_4$ followed by reaction of the resulting alcohol (LXXX) with diphenylphosphoryl azide, in the presence of DBU, in a solvent such as benzene or toluene at around 0° C. followed by a period of heating at a temperature between 50 and 100° C. to give azide (LXXXI). The azide is reduced and the resulting primary amine (LXXIX) and derivatized as previously described. Processing of the benzyloxyalkyl side chain in (LXXXII) to provide (IV) is accomplished as described previously.

SCHEME 17

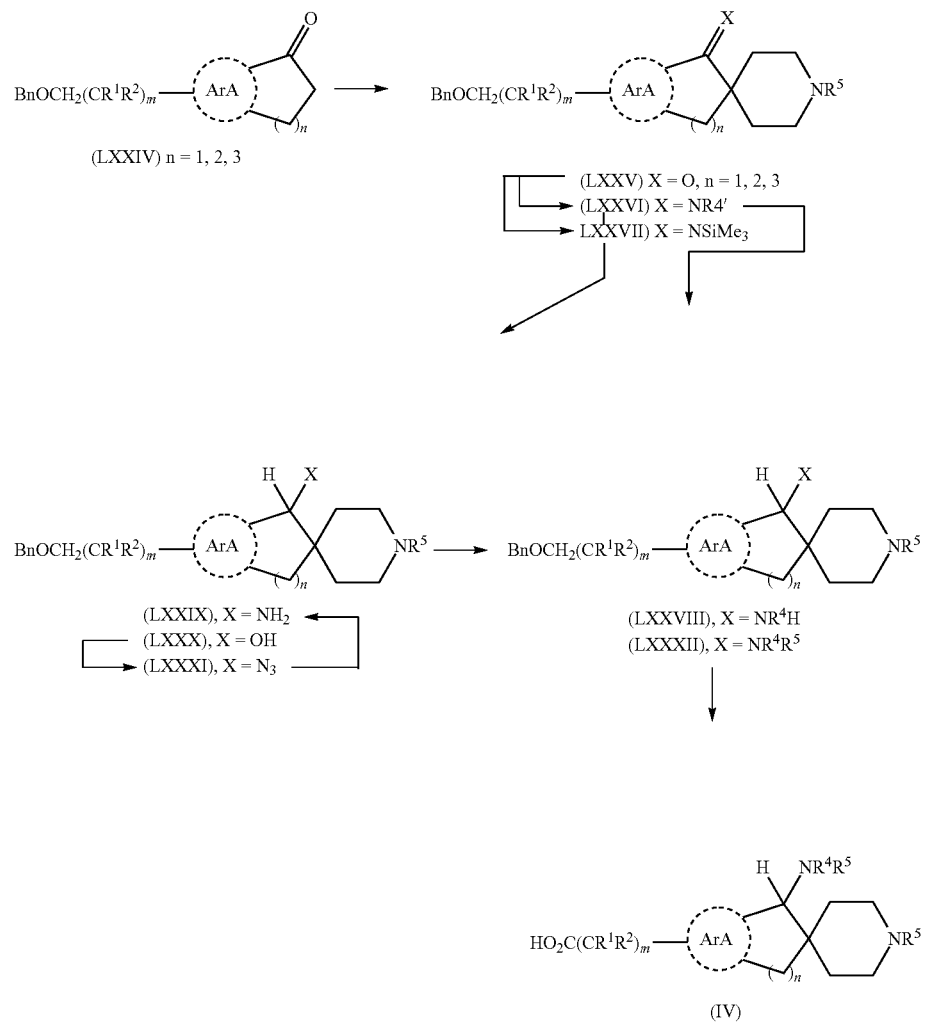

In a variant of this system, where $Y_1$ is an amino substituted C2-C4 alkyl, $Y_2$ is a piperidin-4yl group such that the C-4 substituent on the piperidine of $Y_2$ and the amino substituted carbon of $Y_1$ together form a 5, 6 or 7 membered ring, the requisite carboxylic acids (IV) (SCHEME 18) are prepared from the appropriate cyclic ketone (LXXXIII) using essentially the same methods for piperidine ring formation and amine installation as described above

SCHEME 18

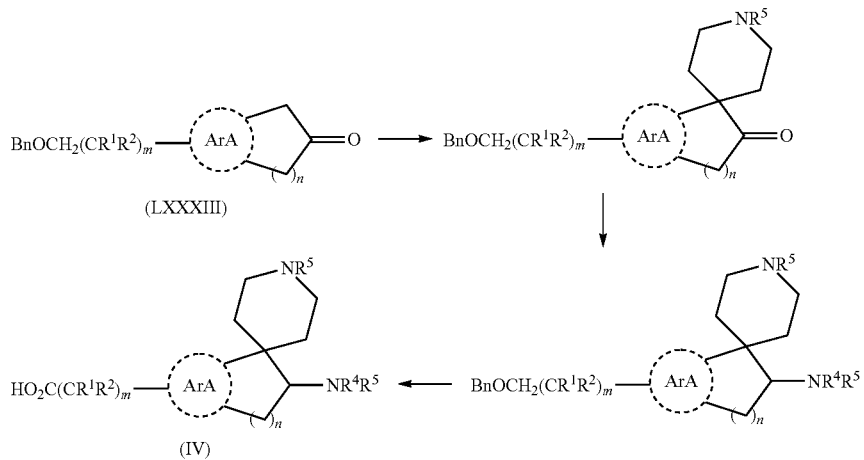

In a particular variant of this system, where $Y_1$ is a di-basic or cationic substituted C3-C4 alkyl, such that the C2 substituent on $Y_1$ and the substituent on ArA, positioned ortho- to $Y_1$, together form a ring, the requisite carboxylic acids (IV) (SCHEME 19) are prepared from the appropriate ary/heteroaryl-fused carbocyclic ketone (LXXXIV). For example, formation of the silyl-enol ether of (LXXXIV), under standard conditions, followed by condensation of the silyl enol ether with an appropriate nitro-alkene in the presence of a Lewis acid, such as TiClnOiPr4-n (n=0-4), in a solvent such as dichloromethane, provides the nitro-ethyl-substituted ketone (LXXXV) (*Journal of the American Chemical Society*, (1984) 106(7), 2149-56). Reduction of (LXXXV) with a hydride donor such as lithium aluminum hydride in THF yields the amino alcohol (LXXXVI). Derivatization of the primary amino group of (LXXXVI), as previously described, yields the alcohol (LXXXVII). Conversion of the alcohol to the azide and then the derivatized amine as previously described provides the diamine (LXXXVIII). This intermediate is processed to yield (IV) as described above. Similarly, reaction of the silyl-enol ether derived from (LXXXIV) with an amine acetal (*Tetrahedron*, (1988), 44(13), 4157-4172) in the presence of TMSOTf provides (LXXXIX) which is processed, via (XC) to provide (IV) as described above.

SCHEME 19

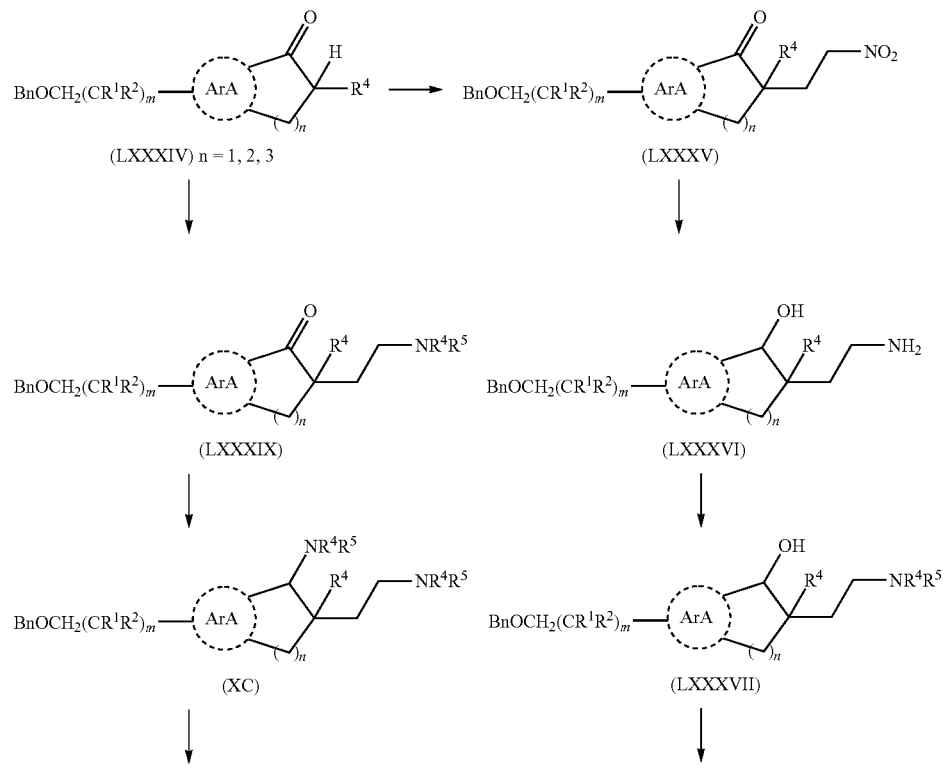

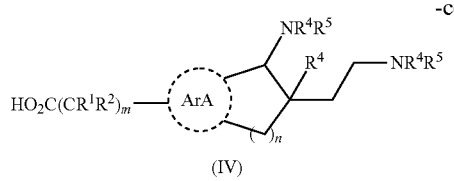
(IV)

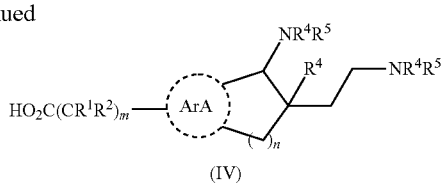
(IV)

In the case where $Y_1$ is an amino or aminomethyl-substituted pyrrolidine, the requisite carboxylic acids (IV) (SCHEME 20) are prepared from the appropriate cinnamate (XCI) and an N-(methoxymethyl)-N-(trimethylsilylmethyl)-amine derivative (XCII) in the presence of an acid, such as TFA, in a solvent such as toluene or dichloromethane, at 0° C. or above to give (XCIII). Ester (XCIII) is processed, via ester hydrolysis and a Curtius rearrangement, to provide (XCIV) or by amide formation to give (XCV) and reduction of the amide carbonyl to yield (XCVI) as previously described. The intermediate (XCIV) is derivitized to give (XCVII). Intermediates (XCV) and (XCVII) are converted to the corresponding acids (IV) by benzyl ether removal and oxidation of the resulting primary alcohol as previously described.

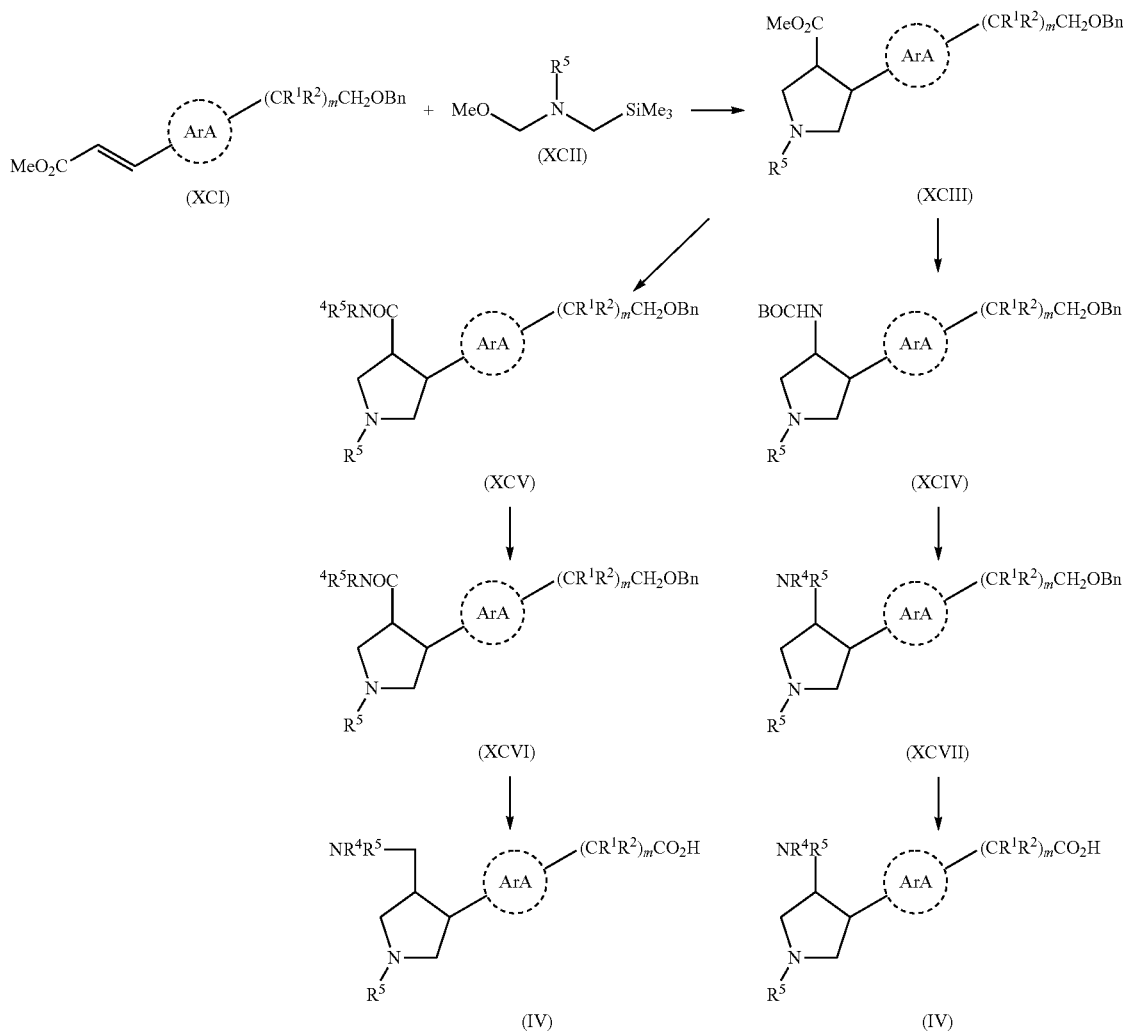

SCHEME 20

In a variant of this system, wherein $Y_1$ is a 3-amino or 3-aminomethyl-substituted piperidin-5-yl group, the requisite carboxylic acids (IV) (SCHEME 21) are prepared by treatment of an appropriate phenyl acetic acid ester (XCVIII) with a strong base, such as LDA or LHMDS, in a solvent such as THF, at a temperature between −78° C. and 0° C. to form the enolate, then reaction of this intermediate with a suitable 2-(N,N-dibenzylamino)-methacrylate (XCIX) ester to give (C). debenzylation of (C) by hydrogenolysis, as described above followed by cyclization of the resulting primary amino ester in the presence of a base such as DBU or TMG in a solvent such as toluene at a temperature between room temperature and 100° C. provides the lactam (CI).

Mitsunobu reaction conditions to give (CVII). De-protection of the latent carbonyl functionality in (CVII) under standard conditions provides (CVIII). Subsequent processing of (CVIII) yields the corresponding amine (CIX). Conversion of (CIX) to the amidine (CX) is accomplished by treatment with HCl in methanol to form the corresponding imidate ester followed by reaction of this intermediate with an appropriate amine ($R^4R^5NH$), in a solvent such as methanol or THF at around room temperature. Furthermore, in the case where $R^4R^5NH$ above is ammonia, the amidine functionality can also be introduced by treatment of the nitrile (CIX) with hydroxylamine to give the corresponding N-hydroxyl-amidine. This is followed by catalytic hydrogenolysis (Pd on carbon in acetic acid/acetic anhydride) to provide the amidine (CX). Acylation of the amidine functionality in (CX) and selective hydrolysis of the ester functionality yields (IV).

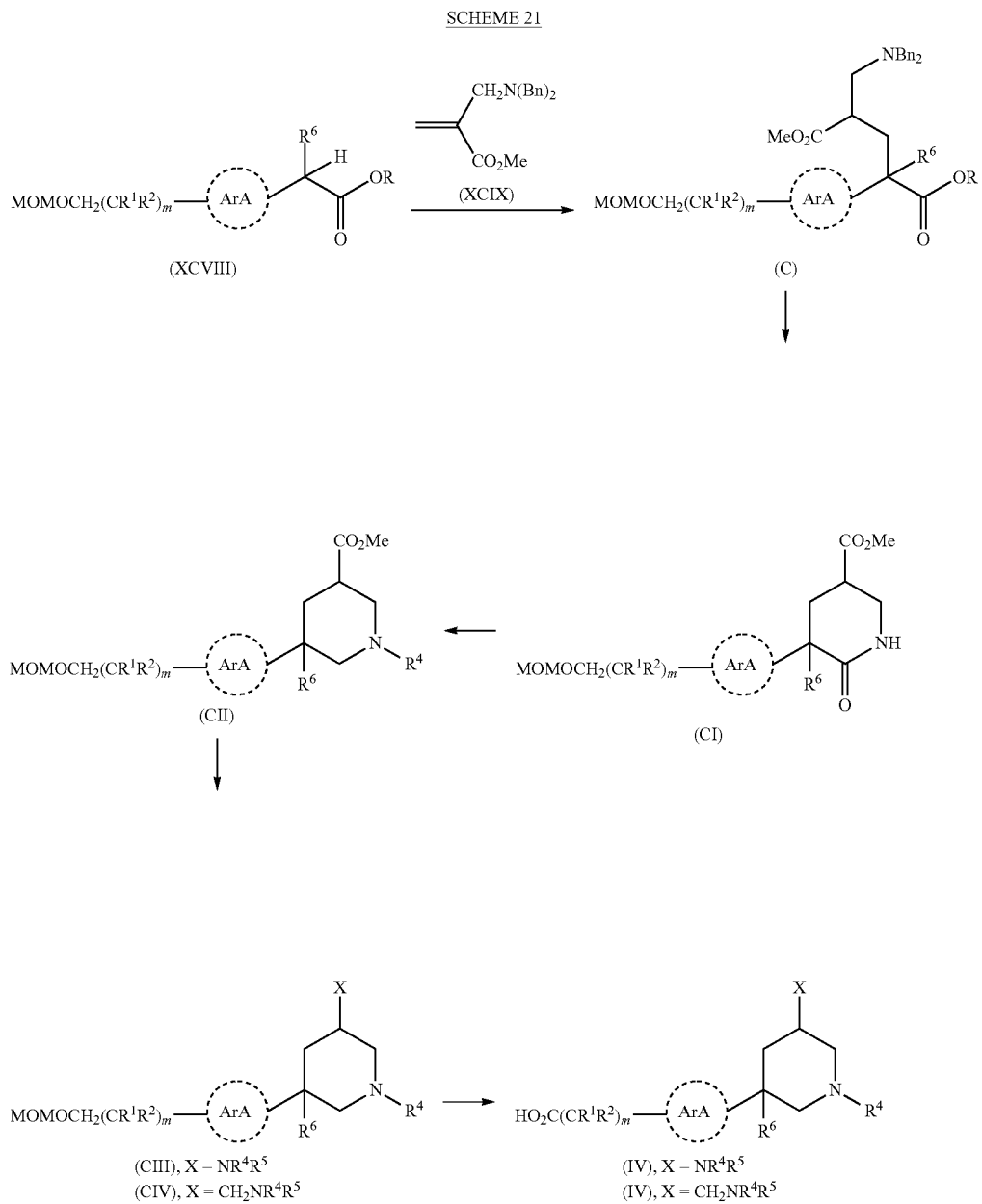

SCHEME 21

Derivitization of the amide nitrogen in (CI) and reduction of the amide carbonyl, as already described, provides piperidine (CII). Processing of the ester functionality in (CII) to yield (CIII) or (CIV) is carried out as previously described. Removal of the MOM protecting group, under standard conditions, followed by oxidation of the resulting primary alcohol provides the requisite acids (IV).

In the case where, $Y_1$ is an amino substituted alkoxy, and $Y_2$ is an amidine linked to the aryl ring through carbon, the requisite acids (IV) (SCHEME 22) are prepared from the appropriate cyano-substituted-phenol (CV) by treatment with a suitably functionalized alcohol (CVI) in the presence of an azodicarboxylate ester such as DEAD or DIAD and a phosphine such as $Ph_3P$, in a solvent such as THF under the

SCHEME 22

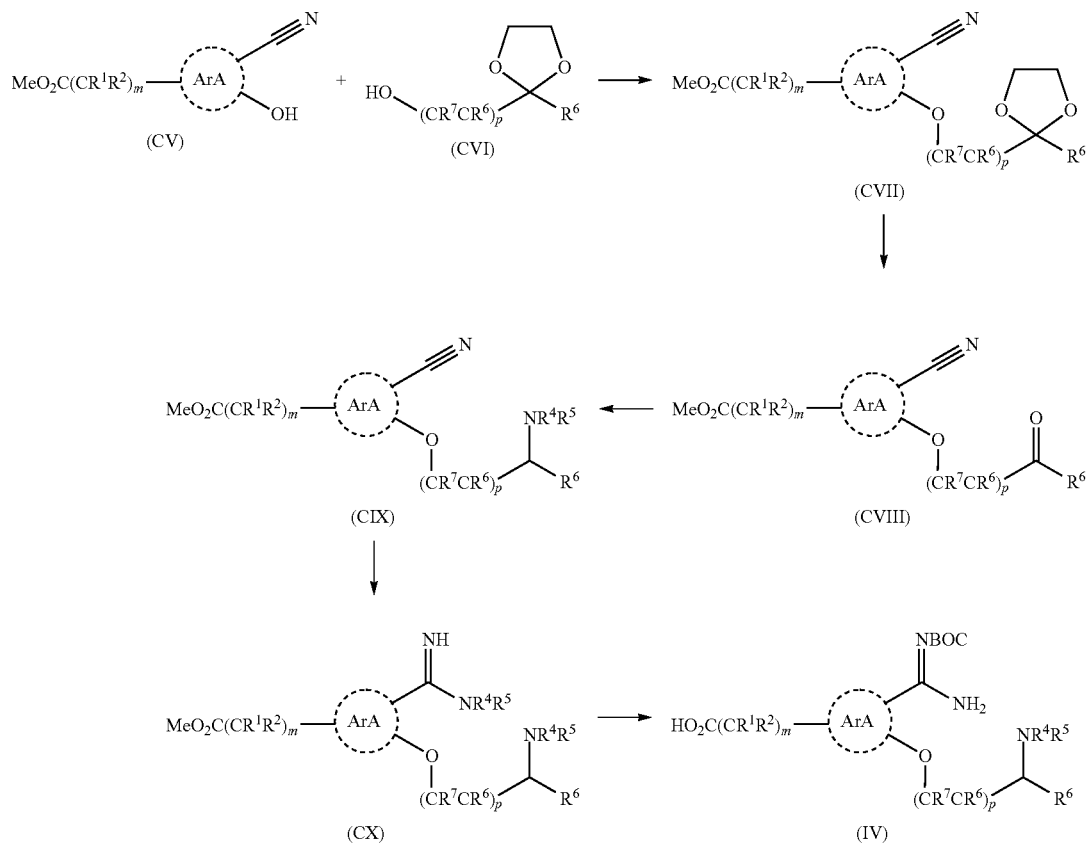

In the case where In the case where $Y_1$ is (or contains) a guanidine, the guanidino group is derived from the appropriate primary or secondary amine (CXI) (SCHEME 23) by treatment with a reagent such as 1,3-Di-tert-butyloxycarbonyl-S-methylisothiourea, in a solvent such as DMF, (*Synthesis*, (2004), 37-42) or pyridine at room temperature or above, or by treatment with N,N'Bis-(BOC)-1H-pyrazole-1-carboxamidine in the presence of a base such as diisopropylethylamine, in a solvent such as DMF or DMA at around room temperature to give (CXII). Selective cleavage of the ester functionality in (CXII), as already described, provides the corresponding acid (IV). Similarly, primary or secondary amine (CXI) is converted to the amidine functionality by treatment with a suitable alkyl thioimidate, such as the 2-napthylmethylthioimidate derivative (XVI), in a solvent such as ethanol at a temperature between 0° C. and room temperature (*Tetrahedron Letters*, (1997), 38(2), 179-182) to give (CXIII). Protection of the amidine (CXIII) as a carbamate derivative, such as BOC or Cbz (CXIV) under standard conditions, followed by selective ester hydrolysis provides acid (IV).

In certain instances, it is convenient to assemble $Y_1$ and or $Y_2$ prior to formation of the heteroaromatic ring. For example, in the case where ArA is a 1,2,3-triazole, the requisite carboxylic acids (IV) (SCHEME 24) are prepared by condensation of an appropriately substituted alkyne (CXV) with an appropriately substituted azide (CXVI) in the presence of a copper catalyst (*Chemical Society Reviews* (2010), 39(4), 1302-1315) such as copper sulphate/sodium ascorbate, in a solvent such as DMF/water to give (CXVII). Cleavage of the ester functionality in (CXVII) as previously described, provides (IV).

SCHEME 23

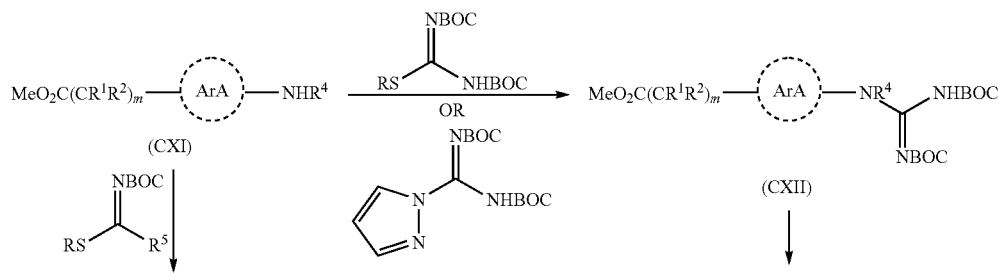

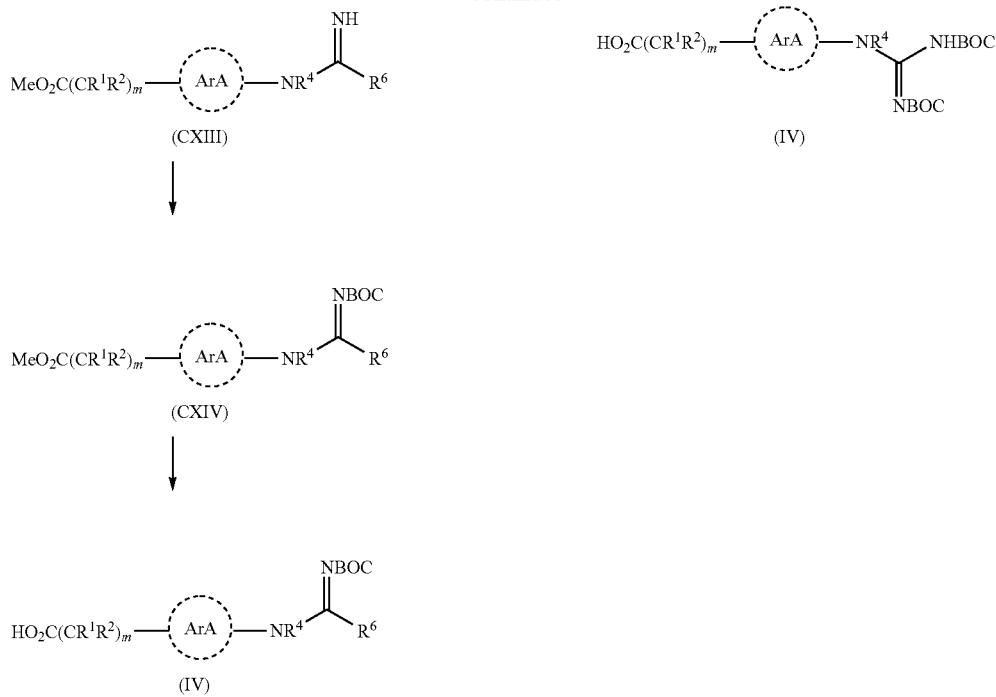

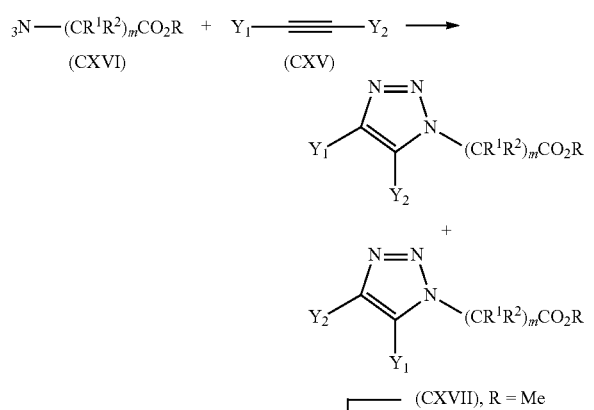

appropriately substituted α-halo-ketone (CXIX) in a solvent such as toluene, at a temperature between room temperature and 120° C. to give (CXX). Cleavage of the ester functionality in (CXX) as previously described provides (IV).

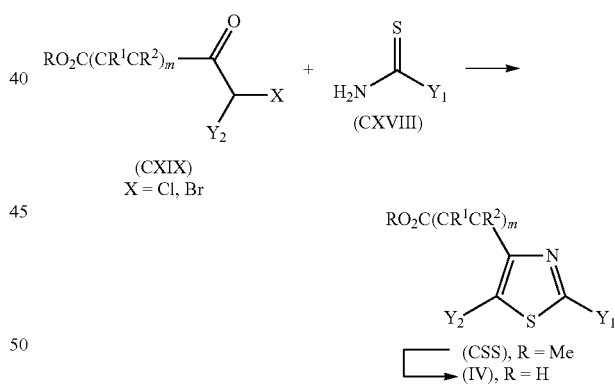

In the case where ArA is a thiazole, the requisite carboxylic acids (IV) (SCHEME 25) are prepared from an appropriately substituted primary-thioamide/thiourea (CXVIII) and an

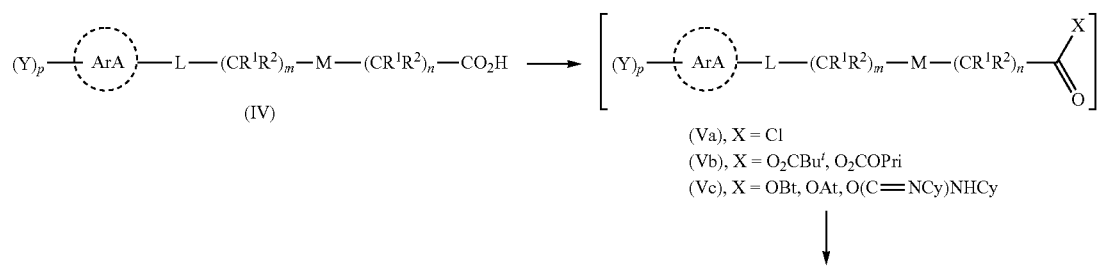

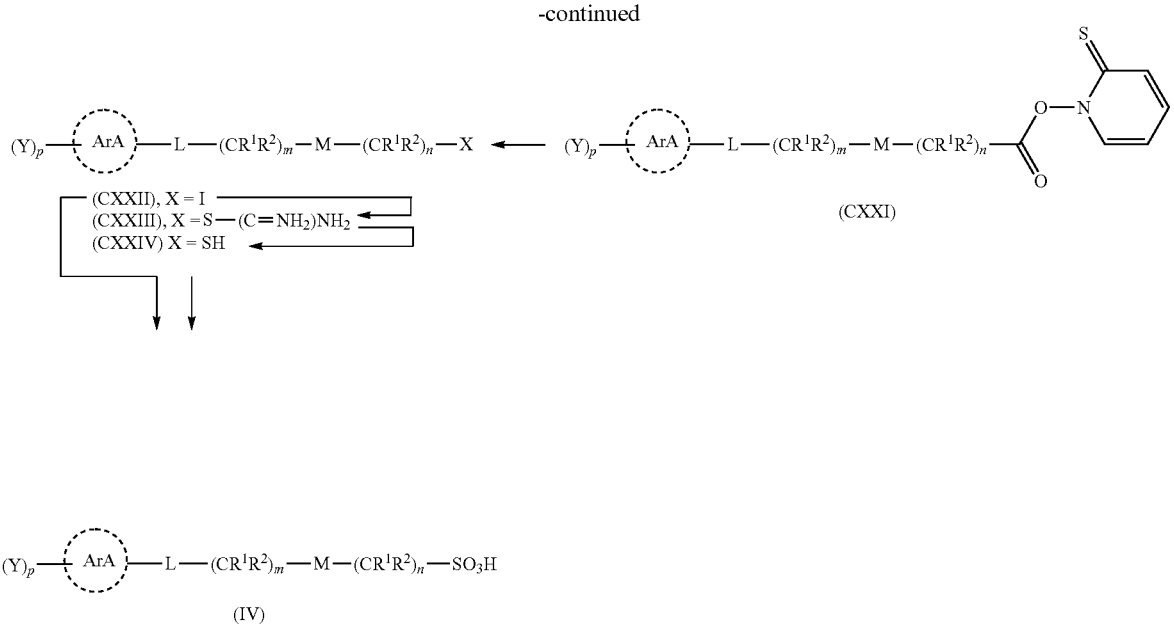

(IV)

In the case where Z is a sulphonyl group (SCHEME 26), the requisite sulphonic acid is prepared from the corresponding activated carboxylic acid (V) by treatment with sodium hydroxythiopyridone in a solvent such as dichloromethane, at around room temperature to yield the Barton ester intermediate (CXXI). (CXXI) is treated with iodoform in $CCl_4$ under a tungsten UV lamp at around reflux temperature to provide the de-carboxylative-iodination product (CXXII) (*Journal of Organic Chemistry*, 75(19), 6489-6501; 2010). Alternatively, treatment of acid (IV) with iodoso-benzene-diacetate and iodine in $CCl_4$, under a tungsten UV lamp, at around reflux temperature (*Journal of Organic Chemistry*, (1986), 51, 402) provides (CXXII) directly. Treatment of (CXXII) with sodium sulphite in aqueous ethanol, isopropanol or acetone, at a temperature between 60 and 90° C., followed by acidification yields the sulphonic acid (IV). Alternatively, treatment of (CXXII) with thiourea in acetone, at around 60° C., provides the isothiouronium salt derivative (CXXIII) (*Synthetic Letters*, (2010), 7, 1037). Cleavage of (CXXIII) with aq. sodium thiosulphate gives thiol (CXXIV). Treatment of (CXXIV) with performic acid (formic acid and aqueous $H_2O_2$ at around 0° C. to room temperature) provides (IV).

The requisite amines (III) are prepared according to literature methods (WO2010/130708).

SYNTHETIC EXAMPLES

The following preparations of compounds of Formula I or Formula Ia and intermediates are given to enable those of skill in the art to more clearly understand and to practice the present invention. They should not be considered as limiting the scope of the invention, but merely as illustrative and representative thereof.

Example 1

(R)-2-hydroxy-3-(1-phenylcyclopropanecarboxamido)-3,4-dihydro-2H-benzo[e][1,2]oxaborinine-8-carboxylic acid

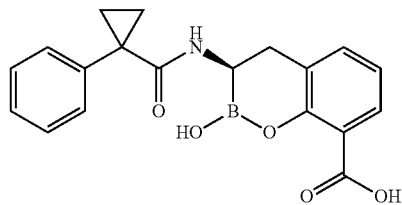 [SMILES: O=C(O)c1cccc2c1OB(O)[C@@H](NC(=O)C1(c3ccccc3)CC1)C2]

Step 1. Synthesis of tert-butyl 3-((2R)-2-(2,9,9-trimethyl-3,5-dioxa-4-bora-tricyclo[6.1.1.0$^{2,6}$]dec-4-yl)-2-(1-phenylcyclopropanecarboxamido)ethyl)-2-methoxybenzoate To anhydrous $CH_2Cl_2$ (0.61 mL, 9.4 mmol) in THF (20 mL) under Argon at −100° C. (MeOH/Liq. $N_2$) was added n-BuLi (2.7 mL, 2.5 M in hexane) dropwise and the reaction mixture was stirred at same temperature for 30 min. A THF (5 mL) solution of 2-methoxy-3-(2,9,9-trimethyl-3,5-dioxa-4-bora-tricyclo[6.1.1.0$^{2,6}$]dec-4-ylmethyl)-benzoic acid tert-butyl ester (2.37 g, 5.92 mmol) was added over a period of 10 min. After 20 min, the cooling bath was removed and the reaction mixture was slowly warmed up to 0° C. and stirred at same temperature for 1 hr. The reaction mixture was then cooled to −78° C., LHMDS (8.0 mL, 1M in THF) was added slowly and the resultant reaction mixture was stirred while warming up to room temperature gradually overnight. Anhydrous MeOH (0.29 mL, 7.1 mmol) was added at −10 OC, the reaction was stirred at same temperature for 1 hr and then at room temperature for 1 hr.

In a separated flask containing 1.1 g of 1-phenylcyclopropanecarboxylic acid (6.8 mmol), anhydrous $CH_2Cl_2$ (15 mL)

was added. To this reaction mixture was added NMM (0.92 mL, 8.4 mmol), followed by HATU (2.66 g, 7.0 mmol). DMF (1 mL) was added and the resultant solution was stirred at room temperature for 1 hr, at which time the solution from above reaction was added to the flask and the reaction was stirred for 2 hr. The reaction was quenched by addition of water (50 mL) and the aqueous phase extracted with EtOAc (3×50 mL). The organic phase was washed with brine, dried over $Na_2SO_4$, and concentrated in vacuo to afford the crude product, which was purified by flash chromatography on silica gel to afford the product (1.0 g, 29%)

Step 2. (R)-2-hydroxy-3-(1-phenylcyclopropanecarboxamido)-3,4-dihydro-2H-benzo[e][1,2]oxaborinine-8-carboxylic acid To a solution of tert-butyl 3-((2R)-2-(2,9,9-trimethyl-3,5-dioxa-4-bora-tricyclo[6.1.1.0$^{2,6}$]dec-4-yl)-2-(1-phenylcyclopropanecarboxamido)ethyl)-2-methoxybenzoate from step 1 (200 mg, 0.35 mmol) in anhydrous $CH_2Cl_2$ (5 mL) at −78° C. was added $BCl_3$ (2.5 mL, 1M in DCM, 2.5 mmol), and the reaction mixture was stirred at same temperature for 1 hr, at which time the reaction mixture was warmed up to 0° C. and stirred at same temperature for additional 1 hr. The reaction was quenched by addition of water (5 mL) at 0° C. The aqueous phase was extracted by EtOAc. The organic phase was washed with brine, dried over $Na_2SO_4$, and concentrated. The crude product was recrystallized in EtOAc/Hexane to afford the product (35 mg) as white solid. ESI-MS m/z 352 (MH)$^+$.

Example 2

(R)-3-(2,2-difluoro-2-phenylacetamido)-2-hydroxy-3,4-dihydro-2H-benzo[e][1,2]oxaborinine-8-carboxylic acid

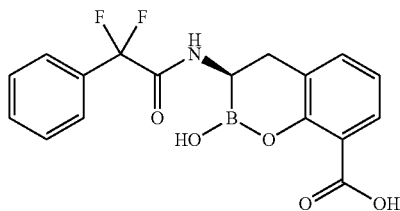 [SMILES: O=C(O)c1cccc2c1OB(O)[C@@H](NC(=O)C(F)(F)c1ccccc1)C2]

Synthesis of (R)-3-(2,2-difluoro-2-phenylacetamido)-2-hydroxy-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2,2-difluoro-2-phenylacetic acid following the procedure described in step 1 and step 2 of Example 1 to afford the product (5.5 mg) as white solid. ESI-MS m/z 362 (MH)$^+$.

Example 3

(R)-2-hydroxy-3-(4-phenylpiperidine-4-carboxamido)-3,4-dihydro-2H-benzo[e][1,2]oxaborinine-8-carboxylic acid

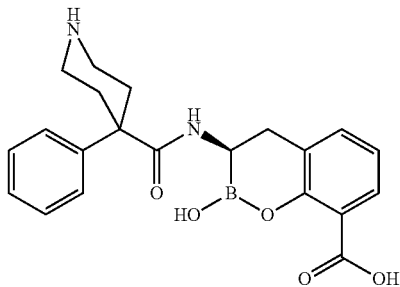 [SMILES: O=C(O)c1cccc2c1OB(O)[C@@H](NC(=O)C1(c3ccccc3)CCNCC1)C2]

Step 1. Synthesis of tert-butyl 4-((1R)-2-(3-(tert-butoxycarbonyl)-2-methoxyphenyl)-1-(2,9,9-trimethyl-3,5-dioxa-4-bora-tricyclo[6.1.1.0$^{2,6}$]dec-4-yl)ethylcarbamoyl)-4-phenylpiperidine-1-carboxylate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 1-(tert-butoxycarbonyl)-4-phenylpiperidine-4-carboxylic acid following the procedure described in step 1 of Example 1. The crude product was purified by flash chromatography on silica gel (Hexane/EtOAc, 2:1 to 1:2). ESI-MS m/z 717.1 (MH)$^+$.

Step 2. Synthesis of (R)-2-hydroxy-3-(4-phenylpiperidine-4-carboxamido)-3,4-dihydro-2H-benzo[e][1,2]oxaborinine-8-carboxylic acid To a solution of the product from step 1 (460 mg, 0.64 mmol) in anhydrous $CH_2Cl_2$ (15 mL) at −78° C. was added $BCl_3$ (5.0 mL, 1M in DCM, 5.0 mmol), and the reaction mixture was stirred at same temperature for 1 hr, at which time the reaction mixture was warmed up to 0° C. and stirred at same temperature for additional 1 hr. The reaction was quenched by addition of water (5 mL) at 0° C. After the phase separation, the product in aqueous phase was purified by reverse phase preparative HPLC [Phenomenex Luna, 5 μm, 30×75 mm, 5-100% AcCN:$H_2O$ (with 0.1% TFA)] and dried using lyophilization to afford the product (10 mg) as while solid. ESI-MS m/z 395 (MH)$^+$.

Example 4

(R)-2-hydroxy-3-(4,5,6,7-tetrahydrothieno[2,3-c]pyridine-3-carboxamido)-3,4-dihydro-2H-benzo[e][1,2]oxaborinine-8-carboxylic acid

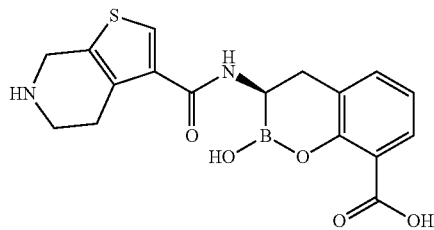 [SMILES: O=C(N[C@H]1Cc2cccc(C(=O)O)c2OB1O)c1csc2c1CCNC2]

Synthesis of (R)-2-hydroxy-3-(4,5,6,7-tetrahydrothieno[2,3-c]pyridine-3-carboxamido)-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 6-(tert-butoxycarbonyl)-4,5,6,7-tetrahydrothieno[2,3-c]pyridine-3-carboxylic acid following the procedure described in step 1 and step 2 of Example 3. The final product was purified by reverse phase preparative HPLC and dried using lyophilization. ESI-MS m/z 373 (MH)$^+$.

Example 5

(R)-3-(2-borono-2-(1,2,3,4-tetrahydroisoquinoline-6-carboxamido)ethyl)-2-hydroxybenzoic acid

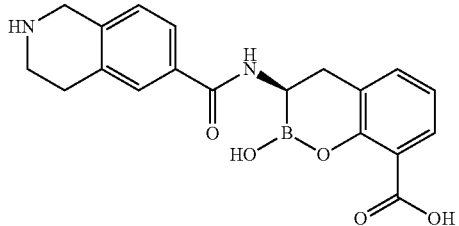 [SMILES: O=C(N[C@H]1Cc2cccc(C(=O)O)c2OB1O)c1ccc2c(c1)CCNC2]

Synthesis of (R)-3-(2-borono-2-(1,2,3,4-tetrahydroisoquinoline-6-carboxamido)ethyl)-2-hydroxybenzoic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(tert-butoxycarbonyl)-1,2,3,4-tetrahydroisoquinoline-6-carboxylic acid following the procedure described in step 1 and step 2 of Example 3. The final product was purified by reverse phase preparative HPLC and dried using lyophilization. ESI-MS m/z 367 (MH)$^+$.

Example 6

(R)-2-hydroxy-3-(6-methyl-4,5,6,7-tetrahydrothieno[2,3-c]pyridine-3-carboxamido)-3,4-dihydro-2H-benzo[e][1,2]oxaborinine-8-carboxylic acid

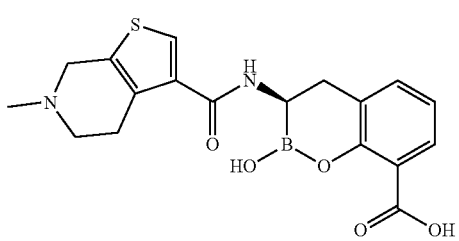 [SMILES: CN1CCc2c(C(=O)N[C@H]3Cc4cccc(C(=O)O)c4OB3O)csc2C1]

Synthesis of (R)-2-hydroxy-3-(6-methyl-4,5,6,7-tetrahydrothieno[2,3-c]pyridine-3-carboxamido)-3,4-dihydro-2H-benzo[e][1,2]oxaborinine-8-carboxylic acid To (R)-3-(2-borono-2-(4,5,6,7-tetrahydrothieno[2,3-c]pyridine-3-carboxamido)ethyl)-2-hydroxybenzoic acid (10.0 mg from Example 4) in MeOH (5 mL) was added formaldehyde (1.0 mL, 37% solution), followed by 10% Pd/C (20 mg). The reaction mixture was hydrogenated under H$_2$ balloon for 3 hr. The reaction mixture was filtrated and the solvent was removed under vacuum. The final product was purified by reverse phase preparative HPLC and dried using lyophilization. ESI-MS m/z 387 (MH)$^+$.

Example 7

(R)-2-hydroxy-3-(2-methyl-1,2,3,4-tetrahydroisoquinoline-6-carboxamido)-3,4-dihydro-2H-benzo[e][1,2]oxaborinine-8-carboxylic acid

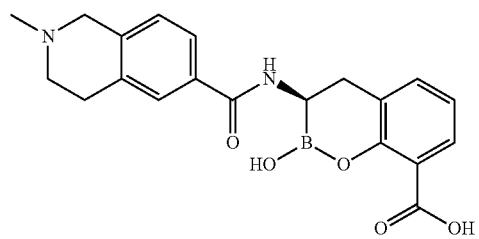 [SMILES: CN1CCc2cc(C(=O)N[C@H]3Cc4cccc(C(=O)O)c4OB3O)ccc2C1]

Synthesis of (R)-2-hydroxy-3-(2-methyl-1,2,3,4-tetrahydroisoquinoline-6-carboxamido)-3,4-dihydro-2H-benzo[e][1,2]oxaborinine-8-carboxylic acid Prepared from (R)-3-(2-borono-2-(1,2,3,4-tetrahydroisoquinoline-6-carboxamido)ethyl)-2-hydroxybenzoic acid (from Example 5) using the procedure described in Example 6. The final product was purified by reverse phase preparative HPLC and dried using lyophilization. ESI-MS m/z 381 (MH)$^+$.

Example 8

(R)-2-hydroxy-3-(1H-pyrrolo[2,3-b]pyridine-3-carboxamido)-3,4-dihydro-2H-benzo[e][1,2]oxaborinine-8-carboxylic acid

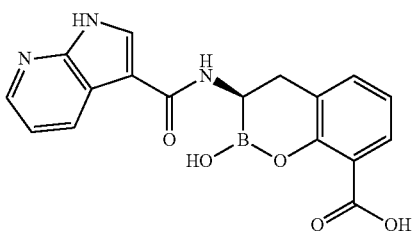 [SMILES: O=C(O)c1cccc2c1OB(O)[C@@H](NC(=O)c1c[nH]c3ncccc13)C2]

Synthesis of (R)-2-hydroxy-3-(1H-pyrrolo[2,3-b]pyridine-3-carboxamido)-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(tert-butoxycarbonyl)-1,2,3,4-tetrahydroisoquinoline-6-carboxylic acid following the procedure described in step 1 and step 2 of Example 3. The final product was purified by reverse phase preparative HPLC and dried using lyophilization. ESI-MS m/z 352 (MH)+.

Example 9

(R)-2-hydroxy-3-(isoindoline-5-carboxamido)-3,4-dihydro-2H-benzo[e][1,2]oxaborinine-8-carboxylic acid

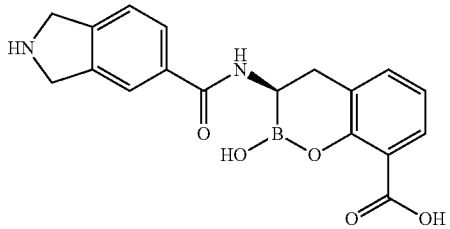 [SMILES: O=C(N[C@H]1Cc2cccc(C(=O)O)c2OB1O)c1ccc2c(c1)CNC2]

Step 1. Synthesis of benzyl 5-((1R)-2-(3-(tert-butoxycarbonyl)-2-methoxyphenyl)-1-(2,9,9-trimethyl-3,5-dioxa-4-bora-tricyclo[6.1.1.0$^{2,6}$]dec-4-yl)ethylcarbamoyl)isoindoline-2-carboxylate Prepared from 2-(benzyloxycarbonyl) isoindoline-5-carboxylic acid following the procedure described in step 1 Example 3. The crude product was purified by flash chromatography on silica gel (Hexane/EtOAc, 2:1 to 1:2). ESI-MS m/z 709.1 (MH)+.

Step 2. Synthesis of tert-butyl 3-((2R)-2-(2,9,9-trimethyl-3,5-dioxa-4-bora-tricyclo[6.1.1.0$^{2,6}$]dec-4-yl)-2-(isoindoline-5-carboxamido)ethyl)-2-methoxybenzoate To benzyl 5-((1R)-2-(3-(tert-butoxycarbonyl)-2-methoxyphenyl)-1-(2,9,9-trimethyl-3,5-dioxa-4-bora-tricyclo[6.1.1.0$^{2,6}$]dec-4-yl)ethylcarbamoyl)isoindoline-2-carboxylate (250 mg) in MeOH (10 mL) was added Pd on C (25 mg, 10%) and the reaction mixture was stirred under a hydrogen balloon for 4 hr. The catalyst was filtered and the solvent removed in vacuo to afford free amine (180 mg, 89%). ESI-MS m/z 575.1 (MH)+.

Step 3. Synthesis of (R)-2-hydroxy-3-(isoindoline-5-carboxamido)-3,4-dihydro-2H-benzo[e][1,2]oxaborinine-8-carboxylic acid Prepared from tert-butyl 3-((2R)-2-(2,9,9-trimethyl-3,5-dioxa-4-bora-tricyclo[6.1.1.0$^{2,6}$]dec-4-yl)-2-(isoindoline-5-carboxamido)ethyl)-2-methoxybenzoate and BCl$_3$ following the procedure described in Step 2 of Example 3. The crude product was purified by reverse phase preparative HPLC and dried using lyophilization. ESI-MS m/z 353 (MH)+.

Example 10

(R)-2-hydroxy-3-(2-methylisoindoline-5-carboxamido)-3,4-dihydro-2H-benzo[e][1,2]oxaborinine-8-carboxylic acid

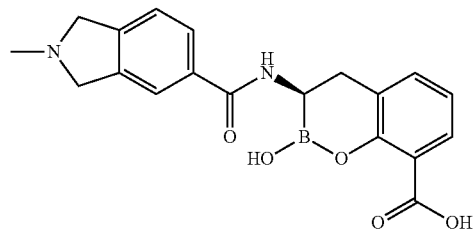 [SMILES: CN1Cc2ccc(C(=O)N[C@H]3Cc4cccc(C(=O)O)c4OB3O)cc2C1]

Synthesis of (R)-2-hydroxy-3-(2-methylisoindoline-5-carboxamido)-3,4-dihydro-2H-benzo[e][1,2]oxaborinine-8-carboxylic acid Prepared from (R)-3-(2-borono-2-(isoindoline-5-carboxamido)ethyl)-2-hydroxybenzoic acid following the procedure described in Example 6. The crude product was purified by reverse phase preparative HPLC and dried using lyophilization. ESI-MS m/z 367 (MH)+.

Example 11

(R)-3-(2-(2-aminoethyl)isoindoline-5-carboxamido)-2-hydroxy-3,4-dihydro-2H-benzo[e][1,2]oxaborinine-8-carboxylic acid

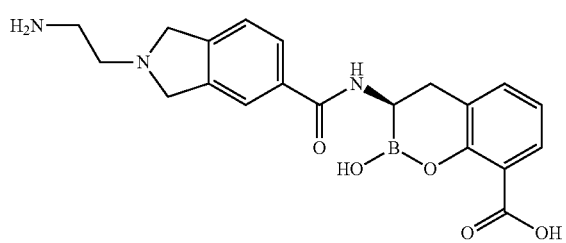 [SMILES: NCCN1Cc2ccc(C(=O)N[C@H]3Cc4cccc(C(=O)O)c4OB3O)cc2C1]

Step 1. Synthesis of tert-butyl 3-((2R)-2-(2-(2-(tert-butoxycarbonylamino)ethyl)isoindoline-5-carboxamido)-2-(2,9,9-trimethyl-3,5-dioxa-4-bora-tricyclo[6.1.1.0$^{2,6}$]dec-4-yl)ethyl)-2-methoxybenzoate To tert-butyl 3-((2R)-2-(2,9,9-trimethyl-3,5-dioxa-4-bora-tricyclo[6.1.1.0$^{2,6}$]dec-4-yl)-2-(isoindoline-5-carboxamido)ethyl)-2-methoxybenzoate from Example 9 step 2 (263 mg, 0.46 mmol) in DMF (5 mL) was added K$_2$CO$_3$ (252 mg, 1.84 mmol) and tert-butyl 2-bromoethylcarbamate (122 mg, 0.54 mmol). The resulting reaction was stirred at room temperature overnight. Water (15 mL) was added and the aqueous phase was extracted with EtOAc. The organic phase was washed with 1N HCl, brine, dried over Na$_2$SO$_4$ and concentrated in vacuo. The crude product was purified by flash chromatography on silica gel (Hexane/EtOAc, 2:1 to 1:2). ESI-MS m/z 718.1 (MH)⁺.

Step 2. Synthesis of (R)-3-(2-(2-aminoethyl)isoindoline-5-carboxamido)-2-hydroxy-3,4-dihydro-2H-benzo[e][1,2]oxaborinine-8-carboxylic acid Prepared from tert-butyl 3-((2R)-2-(2-(2-(tert-butoxycarbonylamino)ethyl)isoindoline-5-carboxamido)-2-(2,9,9-trimethyl-3,5-dioxa-4-bora-tricyclo[6.1.1.0²,⁶]dec-4-yl)ethyl)-2-methoxybenzoate and BCl₃ following the procedure described in Step 2 of Example 3. The crude product was purified by reverse phase preparative HPLC and dried using lyophilization. ESI-MS m/z 396 (MH)⁺.

Example 12

(R)-2-hydroxy-3-(2-(pyridin-3-ylmethyl)isoindoline-5-carboxamido)-3,4-dihydro-2H-benzo[e][1,2]oxaborinine-8-carboxylic acid

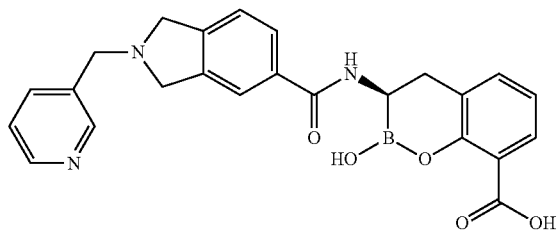 [SMILES: O=C(N[C@H]1Cc2cccc(C(=O)O)c2OB1O)c1ccc2c(c1)CN(Cc1cccnc1)C2]

Step 1. Synthesis of tert-butyl 2-methoxy-3-((2R)-2-(2-(pyridin-3-ylmethyl)isoindoline-5-carboxamido)-2-(2,9,9-trimethyl-3,5-dioxa-4-bora-tricyclo[6.1.1.0²,⁶]dec-4-yl)ethyl)benzoate To tert-butyl 3-((2R)-2-(2,9,9-trimethyl-3,5-dioxa-4-bora-tricyclo[6.1.1.0²,⁶]dec-4-yl)-2-(isoindoline-5-carboxamido) ethyl)-2-methoxybenzoate from Example 9 step 2 (240 mg, 0.42 mmol) in 1,2-dichloroethane (5 mL) was added nicotinaldehyde (90 mg, 0.84 mmol) and Na(OAc)₃BH₄ (211 mg, 1 mmol). The reaction mixture was stirred at room temperature for 6 hr. Water (10 mL) was added at 0° C. and the aqueous phase was extracted with EtOAc. The organic phase was washed brine, dried over Na₂SO₄ and concentrated in vacuo. The crude product was carried to the next step without further purification. ESI-MS m/z 666.1 (MH)⁺.

Step 2. Synthesis of (R)-2-hydroxy-3-(2-(pyridin-3-ylmethyl)isoindoline-5-carboxamido)-3,4-dihydro-2H-benzo[e][1,2]oxaborinine-8-carboxylic acid Prepared from tert-butyl 2-methoxy-3-((2R)-2-(2-(pyridin-3-ylmethyl)isoindoline-5-carboxamido)-2-(2,9,9-trimethyl-3,5-dioxa-4-bora-tricyclo[6.1.1.0²,⁶]dec-4-yl)ethyl) benzoate and BCl₃ following the procedure described in Step 2 of Example 3. The crude product was purified by reverse phase preparative HPLC and dried using lyophilization. ESI-MS m/z 344 (MH)⁺.

Example 13

(R)-2-hydroxy-3-(2-(5,6,7,8-tetrahydro-1,8-naphthyridin-3-yl)acetamido)-3,4-dihydro-2H-benzo[e][1,2]oxaborinine-8-carboxylic acid

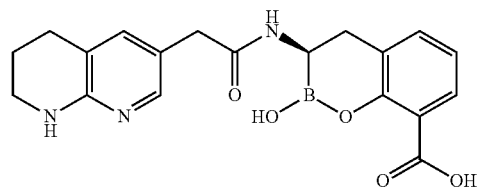 [SMILES: O=C(Cc1cnc2c(c1)CCCN2)N[C@H]1Cc2cccc(C(=O)O)c2OB1O]

Synthesis of (R)-2-hydroxy-3-(2-(5,6,7,8-tetrahydro-1,8-naphthyridin-3-yl)acetamido)-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0²,⁶]dec-4-ylmethyl)-benzoic acid tert-butyl ester and 2-(5,6,7,8-tetrahydro-1,8-naphthyridin-3-yl) acetic acid following the procedure described in step 1 and step 2 of Example 3. The final product was purified by reverse phase preparative HPLC and dried using lyophilization. ESI-MS m/z 382 (MH)⁺.

Example 14

(R)-3-(3,4-bis(aminomethyl)benzamido)-2-hydroxy-3,4-dihydro-2H-benzo[e][1,2]oxaborinine-8-carboxylic acid

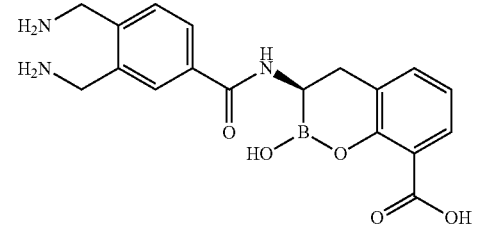 [SMILES: NCc1ccc(C(=O)N[C@H]2Cc3cccc(C(=O)O)c3OB2O)cc1CN]

Step 1. Synthesis of 3,4-bis((tert-butoxycarbonylamino)methyl)benzoic acid

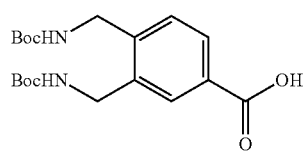 [SMILES: CC(C)(C)OC(=O)NCc1ccc(C(=O)O)cc1CNC(=O)OC(C)(C)C]

Step 1a. Synthesis of methyl 3,4-bis(bromomethyl)benzoate

A solution of 3,4-dimethyl benzoic acid (10 g), NBS (23.6 g) and AIBN (1.0 g) in CCl$_4$ (110 mL) were heated at reflux for 10 hr. After cooling and filtration, the solvent was removed and the residue was dissolved in DCM (200 mL) and the organic phase washed with water and aqueous saturated NaHCO$_3$ solution. The organic phase was dried over Na$_2$SO$_4$ and concentrated in vacuo. The product (20 g) was used directly to the next step without further purification.

Step 1b. Synthesis of methyl 3,4-bis(azidomethyl)benzoate

To methyl 3,4-bis(bromomethyl)benzoate (3.24 g, 10 mmol) in EtOH/THF/H$_2$O (100 mL, 4:2:1) was added NaN$_3$ (2.00 g, 30 mmol) and the resultant reaction mixture stirred at room temperature overnight. The aqueous was extracted with EtOAc (100 mL×3). The organic phase was combined, washed with brine, dried and concentrated. The residue (2.2 g) was used directly to the next step without further purification.

Step 1c. Synthesis of methyl 3,4-bis(aminomethyl)benzoate

The crude material from the above step (2.2 g, 20 mmol) was dissolved in MeOH (200 mL) and hydrogenated using Parr at 60 psi for 4 hr. The reaction mixture was filtrated over Celite and concentrated in vacuo to afford the product (1.5 g) which was used directly in the next step without further purification.

Step 1d. Synthesis of methyl 3,4-bis((tert-butoxycarbonylamino)methyl)benzoate To methyl 3,4-bis(aminomethyl)benzoate (1.0 g, 5.2 mmol) in DCM (10 mL) was added TEA (2.9 mL, 20 mmol) and di-tert-butyl dicarbonate (3.4 g, 15.5 mmol). The resultant reaction mixture was stirred at room temperature overnight. The organic phase was washed with 1N HCl, brine, dried and concentrated in vacuo. The residue was purified over silica gel to afford the product (1.0 g)

Step 1e. Synthesis of 3,4-bis((tert-butoxycarbonylamino)methyl)benzoic acid

The ester from the above step (1.0 g, 2.5 mmol) was dissolved in a mixture of MeOH/THF (50 mL, 2:1). 1N NaOH (10 mmol, 10 mL) was added and the reaction mixture was stirred at room temperature overnight. 1N HCl was added to adjust the pH of reaction to ~3. The aqueous layer was extracted with EtOAc. The organic phase was washed with 1N HCl, brine, dried and concentrated in vacuo to afford the product (0.55 g) as pale yellow solid.

Step 2. Synthesis of tert-butyl 3-((2R)-2-(3,4-bis((tert-butoxycarbonylamino)methyl)benzamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 3,4-bis((tert-butoxycarbonylamino)methyl) benzoic acid following the procedure described in step 1 of Example 3. The crude product was purified by flash chromatography on silica gel (Hexane/EtOAc, 2:1 to 1:2). ESI-MS m/z 792.1 (MH)$^+$.

Step 3. Synthesis of (R)-3-(3,4-bis(aminomethyl) benzamido)-2-hydroxy-3,4-dihydro-2H-benzo[e][1,2]oxaborinine-8-carboxylic acid Prepared from tert-butyl 3-((2R)-2-(3,4-bis((tert-butoxycarbonylamino)methyl)benzamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The crude product was purified by reverse phase preparative HPLC and dried using lyophilization. ESI-MS m/z 370 (MH)$^+$.

Example 15

(R)-3-(2-amino-3,4-dihydroquinazoline-7-carboxamido)-2-hydroxy-3,4-dihydro-2H-benzo[e][1,2]oxaborinine-8-carboxylic acid

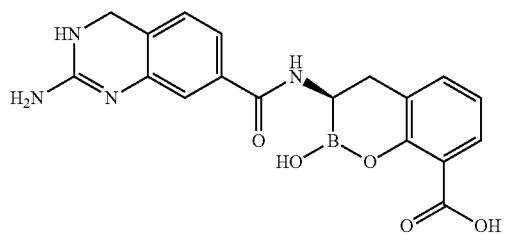

Step 1. Synthesis of 2-(2,4-dimethoxybenzylamino)-3,4-dihydroquinazoline-7-carboxylic acid

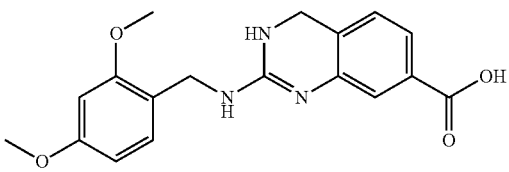 [SMILES: COc1ccc(CNC2=Nc3cc(C(=O)O)ccc3CN2)c(OC)c1]

Step 1a. Synthesis of Methyl 4-(bromomethyl)-3-nitrobenzoate

Methyl 4-(bromomethyl)-3-nitrobenzoate was prepared following the procedure described in step 1a in Example 14.

Step 1b. Synthesis of Methyl 4-(azidomethyl)-3-nitrobenzoate nitrobenzoate

Methyl 4-(azidomethyl)-3-nitrobenzoate nitrobenzoate was prepared following the procedure described in step 2 in Example 14.

Step 1c. Synthesis of Methyl 3-amino-4-(aminomethyl)benzoate

Methyl 3-amino-4-(aminomethyl)benzoate was prepared following the procedure describe in step 3 in Example 14.

Step 1d. Synthesis of methyl 2-thioxo-1,2,3,4-tetrahydroquinazoline-7-carboxylate Carbon disulfide (1.36 mL, 22.6 mmol) was added to a solution of methyl 3-amino-4-(aminomethyl)benzoate (2.0 g, 11.3 mmol) in pyridine (10 mL) and the resultant reaction mixture was stirred at 60° C. overnight. After cooling, water was added to the reaction mixture. The solid formed was filtrated to afford methyl 2-thioxo-1,2,3,4-tetrahydroquinazoline-7-carboxylate (2.2 g) which was carried to the next step without further purification.

Step 1e. Synthesis of methyl 2-(methylthio)-3,4-dihydroquinazoline-7-carboxylate To a suspension of methyl 2-thioxo-1,2,3,4-tetrahydroquinazoline-7-carboxylate (110 mg, 0.5 mmol) in anhydrous EtOH (5 mL) was added MeI (0.125 mL, 2 mmol). The reaction mixture was stirred at reflux for 1 hr. After cooling, the solid was isolated by filtration to afford methyl 2-(methylthio)-3,4-dihydroquinazoline-7-carboxylate (100 mg).

Step 1f. Synthesis of methyl 2-(2,4-dimethoxybenzylamino)-3,4-dihydroquinazoline-7-carboxylate Methyl 2-(methylthio)-3,4-dihydroquinazoline-7-carboxylate (1.30 g, 4.2 mmol) was dissolved in tBuOH (10 mL) and (2,4-dimethoxyphenyl)methanamine (2.8 g, 16.8 mmol) was added. The reaction mixture was heated at reflux overnight. After cooling, the solid was filtrated to afford methyl 2-(2,4-dimethoxybenzylamino)-3,4-dihydroquinazoline-7-carboxylate (1.0 g) as brown solid.

Step 1g. Synthesis of 2-(2,4-dimethoxybenzylamino)-3,4-dihydroquinazoline-7-carboxylic acid Hydrolysis of the ester to acid was prepared following the procedure described in step 1e of Example 14.

Step 2. Synthesis of tert-butyl 3-((2R)-2-(2-(2,4-dimethoxybenzylamino)-3,4-dihydroquinazoline-7-carboxamido)-2-(2,9,9-trimethyl-3,5-dioxa-4-bora-tricyclo[6.1.1.0²,⁶]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(2,4-dimethoxybenzylamino)-3,4-dihydroquinazoline-7-carboxylic acid following the procedure described in step 1 of Example 3. The crude product was purified by flash chromatography on silica gel (Hexane/EtOAc, 2:1 to 1:4). ESI-MS m/z 753.1 (MH)$^+$.

Step 3. Synthesis of (R)-3-(2-amino-3,4-dihydroquinazoline-7-carboxamido)-2-hydroxy-3,4-dihydro-2H-benzo[e][1,2]oxaborinine-8-carboxylic acid Prepared from tert-butyl 3-((2R)-2-(3,4-bis((tert-butoxycarbonylamino)methyl)benzamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The crude product was purified by reverse phase preparative HPLC and dried using lyophilization. ESI-MS m/z 381 (MH)$^+$.

Example 16

(R)-3-(2-carbamimidoylisoindoline-5-carboxamido)-2-hydroxy-3,4-dihydro-2H-benzo[e][1,2]oxaborinine-8-carboxylic acid

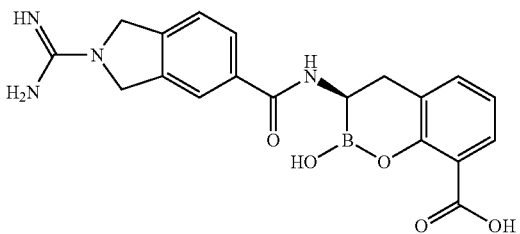 [SMILES: N=C(N)N1Cc2ccc(C(=O)N[C@H]3Cc4cccc(C(=O)O)c4OB3O)cc2C1]

Synthesis of (R)-3-(2-carbamimidoylisoindoline-5-carboxamido)-2-hydroxy-3,4-dihydro-2H-benzo[e][1,2]oxaborinine-8-carboxylic acid To (R)-3-(2-borono-2-(isoindoline-5-carboxamido)ethyl)-2-hydroxybenzoic acid from Example 9 (15 mg) in MeOH (2 mL) was added tert-butyl (1H-pyrazol-1-yl)methanediylidenedicarbamate (15 mg) and stirred for 4 hr. The solvent was removed in vacuo. The residue was dissolved in 4N HCl in dioxane (2 mL) and stirred for 2 hr. The solvent was removed in vacuo and the crude product was purified by reverse phase preparative HPLC and dried using lyophilization. ESI-MS m/z 395 (MH)$^+$.

Example 17

(R)-3-(3-amino-4,5-dihydro-1H-benzo[e][1,3]diazepine-7-carboxamido)-2-hydroxy-3,4-dihydro-2H-benzo[e][1,2]oxaborinine-8-carboxylic acid

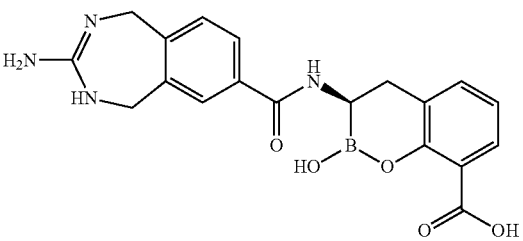 [SMILES: NC1=NCc2ccc(C(=O)N[C@H]3Cc4cccc(C(=O)O)c4OB3O)cc2CN1]

Synthesis of (R)-3-(3-amino-4,5-dihydro-1H-benzo[e][1,3]diazepine-7-carboxamido)-2-hydroxy-3,4-dihydro-2H-benzo[e][1,2]oxaborinine-8-carboxylic acid To (R)-3-(2-(3,4-bis(aminomethyl)benzamido)-2-boronoethyl)-2-hydroxybenzoic acid (10 mg) in DMF (1 mL) was added BrCN (10 mg) and the reaction was stirred for 5 hr. The crude product was purified by reverse phase preparative HPLC and dried using lyophilization. ESI-MS m/z 395 (MH)+.

Example 18

(R)-3-(3-amino-4-((dimethylamino)methyl)benzamido)-2-hydroxy-3,4-dihydro-2H-benzo[e][1,2]oxaborinine-8-carboxylic acid

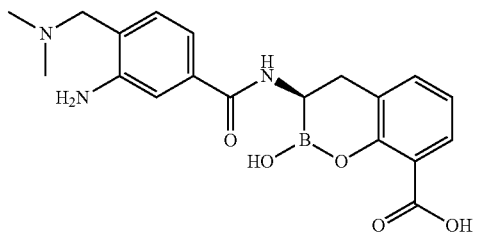 [SMILES: CN(C)Cc1ccc(C(=O)N[C@H]2Cc3cccc(C(=O)O)c3OB2O)cc1N]

Step 1 Synthesis of 4-((dimethylamino)methyl)-3-nitrobenzoic acid

Step 1a. Synthesis of methyl 4-(bromomethyl)-3-nitrobenzoate

Prepared from methyl 4-methyl-3-nitrobenzoate following the procedure described in step 1 in Example 14.

Step 1b. Synthesis methyl 4-((dimethylamino)methyl)-3-nitrobenzoate

To methyl 4-(bromomethyl)-3-nitrobenzoate (100 mg) in THF (5 mL) was added dimethyl amine (2 mL, 2 M in THF) and the resulting reaction mixture was stirred at room temperature overnight. The solvent was then removed to afford methyl 4-((dimethylamino)methyl)-3-nitrobenzoate which was carried on to the next step without further purification.

Step 1s. Synthesis of 4-((dimethylamino)methyl)-3-nitrobenzoic acid

Prepared from methyl 4-((dimethylamino)methyl)-3-nitrobenzoate using the procedure described in step 1e. of Example 14.

Step 2. Synthesis of tert-butyl 3-((2R)-2-(4-((dimethylamino)methyl)-3-nitrobenzamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 4-((dimethylamino)methyl)-3-nitrobenzoic acid following the procedure described in step 1 of Example 3. The crude product was purified by flash chromatography on silica gel (Hexane/EtOAc, 2:1 to 1:2).

Step 3. Synthesis of tert-butyl 3-((2R)-2-(3-amino-4-((dimethylamino)methyl)benzamido)-2-(3a,6,6-trimethylhexahydrobenzo[d][1,3,2]dioxaborol-2-yl)ethyl)-2-methoxybenzoate Prepared following the procedure described in step 2 in Example 9. ESI-MS m/z 606.1 (MH)+.

Step 4. Synthesis of (R)-3-(3-amino-4-((dimethylamino)methyl)benzamido)-2-hydroxy-3,4-dihydro-2H-benzo[e][1,2]oxaborinine-8-carboxylic acid Prepared from tert-butyl 3-((2R)-2-(3-amino-4-((dimethylamino)methyl)benzamido)-2-(3a,6,6-trimethylhexahydrobenzo[d][1,3,2]dioxaborol-2-yl)ethyl)-2-methoxybenzoate and BCl$_3$ following the procedure described in Step 2 of Example 3. The crude product was purified by reverse phase preparative HPLC and dried using lyophilization. ESI-MS m/z 384 (MH)+.

Example 19

(R)-3-(3,4-bis((methylamino)methyl)benzamido)-2-hydroxy-3,4-dihydro-2H-benzo[e][1,2]oxaborinine-8-carboxylic acid

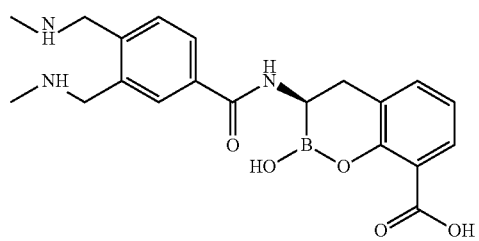 [SMILES: CNCc1ccc(C(=O)N[C@H]2Cc3cccc(C(=O)O)c3OB2O)cc1CNC]

Step 1. Synthesis of 3,4-bis((tert-butoxycarbonyl(methyl)amino)methyl)benzoic acid To 3,4-bis((tert-butoxycarbonylamino)methyl)benzoic acid (380 mg, 1 mmol) in THF (5 mL) was added NaH (200 mg, 60%). After stirring at room temperature for 20 min, MeI (4 eq) was added and the resultant solution stirred at room temperature overnight. Water was added and the aqueous phase extracted with EtOAc. The organic phase was washed with brine, dried and concentrated in vacuo to afford methyl 3,4-bis((tert-butoxycarbonylamino)methyl)benzoate (368 mg). The ester was hydrolyzed following the procedure described in step 1e of Example 14 to afford 3,4-bis((tert-butoxycarbonyl(methyl)amino)methyl)benzoic acid (300 mg).

Step 2. Synthesis of tert-butyl 3-((2R)-2-(3,4-bis((tert-butoxycarbonyl(methyl)amino)methyl)benzamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 3,4-bis((tert-butoxycarbonyl(methyl)amino)methyl)benzoic acid following the procedure described in step 1 of Example 3. The crude product was purified by flash chromatography on silica gel (Hexane/EtOAc, 2:1 to 1:2). ESI-MS m/z 820.1 (MH)+.

Step 3. Synthesis of (R)-3-(3,4-bis((methylamino)methyl)benzamido)-2-hydroxy-3,4-dihydro-2H-benzo[e][1,2]oxaborinine-8-carboxylic acid Prepared from tert-butyl 3-((2R)-2-(3,4-bis((tert-butoxycarbonyl(methyl)amino)methyl)benzamido)-2-(2,9,9-trimethyl-3,5-dioxa-4-bora-tricyclo[6.1.1.0$^{2,6}$]dec-4-yl)ethyl)-2-

Example 20

(R)-3-(2-(3,4-bis(aminomethyl)phenyl)acetamido)-2-hydroxy-3,4-dihydro-2H-benzo[e][1,2]oxaborinine-8-carboxylic acid

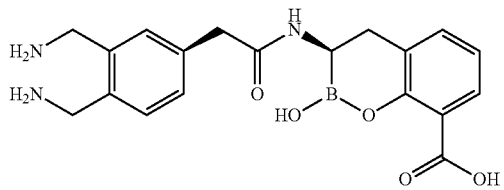

Step 1. Synthesis of 2-(3,4-bis(aminomethyl)phenyl)acetic acid 2-(3,4-dimethylphenyl)acetic acid methyl ester (1 g), NBS (2.2 g) and AIBN (0.1 g) in CCl$_4$ (10 mL) were heated at reflux for 10 hr. After cooling and filtration, the solvent was removed and the residue was dissolved in DCM and the organic phase washed with water and aqueous saturated NaHCO$_3$ solution. The organic phase was dried over Na$_2$SO$_4$ and concentrated in vacuo. The product (1.90 g) was used directly to the next step without further purification.

To methyl 2-(3,4-bis(bromomethyl)phenyl)acetate (1.9 g) in EtOH/THF/H$_2$O (70 mL, 4:2:1) was added NaN$_3$ (1.09 g, 17 mmol) and the resultant reaction mixture stirred at room temperature overnight. The aqueous layer was extracted with EtOAc (100 mL×3). The organic phases were combined, washed with brine, dried and concentrated. The residue was used directly to the next step without further purification.

The crude material from the above step was dissolved in MeOH (150 mL) and Pd on C (10%, 100 mg) was added. The reaction mixture was hydrogenated using Parr at 60 psi for 4 hr. The reaction mixture was filtrated over Celite and concentrated in vacuo to afford the product which was used directly in the next step without further purification.

To methyl 3,4-bis(aminomethyl)benzoate from the above step (2.6 g) in DCM (100 mL) was added TEA (5 mL) and di-tert-butyl dicarbonate (4.5 g). The resultant reaction mixture was stirred at room temperature overnight. The organic phase was washed with 1N HCl, brine, dried and concentrated in vacuo. The residue was purified over silica gel to afford the product (1.1 g)

The methyl 2-(3,4-bis((tert-butoxycarbonylamino)methyl)phenyl)acetate (1.1 g,) was dissolved in a mixture of MeOH/THF (50 mL, 2:1). 1N NaOH (10 mmol, 10 mL) was added and the reaction mixture was stirred at room temperature overnight. 1N HCl was added to adjust the pH of the reaction to ~3. The aqueous was extracted with EtOAc. The organic phase was washed with 1N HCl, brine, dried and concentrated in vacuo to afford the product (0.38 g) as yellow solid.

Step 2. Synthesis of tert-butyl 3-((2R)-2-(2-(3,4-bis((tert-butoxycarbonylamino)methyl)phenyl)acetamido)-2-(2,9,9-trimethyl-3,5-dioxa-4-bora-tricyclo[6.1.1.0$^{2,6}$]dec-4-yl)ethyl)-2-methoxybenzoate Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(3,4-bis(aminomethyl)phenyl)acetic acid following the procedure described in step 1 of Example 3. The crude product was purified by flash chromatography on silica gel (Hexane/EtOAc, 2:1 to 1:2). ESI-MS m/z 806.1 (MH)$^+$.

Step 3. Synthesis of (R)-3-(2-(3,4-bis(aminomethyl)phenyl)acetamido)-2-hydroxy-3,4-dihydro-2H-benzo[e][1,2]oxaborinine-8-carboxylic acid Prepared from tert-butyl 3-((2R)-2-(2-(3,4-bis((tert-butoxycarbonylamino)methyl)phenyl)acetamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The crude product was purified by reverse phase preparative HPLC and dried using lyophilization.

ESI-MS m/z 384 (MH)$^+$.

Example 21

(R)-3-(3-((S)-2,3-diaminopropanamido)-4-((dimethylamino)methyl)benzamido)-2-hydroxy-3,4-dihydro-2H-benzo[e][1,2]oxaborinine-8-carboxylic acid

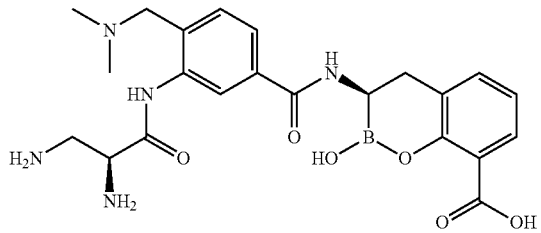 [SMILES: CN(C)Cc1ccc(C(=O)N[C@H]2Cc3cccc(C(=O)O)c3OB2O)cc1NC(=O)[C@@H](N)CN]

Step 1. Synthesis of tert-butyl 3-((2R)-2-(3-((S)-2-(benzyloxycarbonylamino)-3-(tert-butoxycarbonylamino)propanamido)-4-((dimethylamino)methyl)benzamido)-2-(2,9,9-trimethyl-3,5-dioxa-4-bora-tricyclo[6.1.1.0$^{2,6}$]dec-4-yl)ethyl)-2-methoxybenzoate To tert-butyl 3-((2R)-2-(3-amino-4-((dimethylamino)methyl)benzamido)-2-(2,9,9-trimethyl-3,5-dioxa-4-bora-tricyclo[6.1.1.0$^{2,6}$]dec-4-yl)ethyl)-2-methoxybenzoate from step 3 in Example 18 (130 mg, 0.22 mol) and (S)-2-(benzyloxycarbonylamino)-3-(tert-butoxycarbonylamino)propanoic acid (85 mg, 0.25 mol) in DCM/DMF (4 mL, 1/1) was added NMM (1.2 eq) followed by HATU (114 mg, 0.3 mol). The reaction mixture was stirred overnight at rt. Water was added and the aqueous phase extracted with EtOAc. The organic phase was washed with 1N HCl, sat. NaHCO$_3$, brine, dried and concentrated in vacuo to afford the product (0.130 g) as a brown oil. ESI-MS m/z 926.1 (MH)$^+$.

Step 2. Synthesis of tert-butyl 3-((2R)-2-(3-((S)-2-amino-3-(tert-butoxycarbonylamino)propanamido)-4-((dimethylamino)methyl)benzamido)-2-(2,9,9-trimethyl-3,5-dioxa-4-bora-tricyclo[6.1.1.0$^{2,6}$]dec-4-yl)ethyl)-2-methoxybenzoate To tert-butyl 3-((2R)-2-(3-((S)-2-(benzyloxycarbonylamino)-3-(tert-butoxycarbonylamino)propanamido)-4-((dimethylamino)methyl)benzamido)-2-(2,9,9-trimethyl-3,5-dioxa-4-bora-tricyclo[6.1.1.0$^{2,6}$]dec-4-yl)ethyl)-2- methoxybenzoate (130 mg) in MeOH (20 mL was added 10% Pd/C (20 mg). The reaction mixture was stirred under H2 balloon for 6 hr. The catalyst was removed by filtration and MeOH removed under reduced pressure to afford the product (90 mg) which was carried on to the next step.

Step 3. Synthesis of (R)-3-(3-((S)-2,3-diaminopropanamido)-4-((dimethylamino)methyl)benzamido)-2-hydroxy-3,4-dihydro-2H-benzo[e][1,2]oxaborinine-8-carboxylic acid Prepared from tert-butyl 3-((2R)-2-(3-((S)-2-amino-3-(tert-butoxycarbonylamino)propanamido)-4-((dimethylamino)methyl)benzamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The crude product was purified by reverse phase preparative HPLC and dried using lyophilization. ESI-MS m/z 470 (MH)$^+$.

Example 22

(R)-3-(3-((S)-2,3-diaminopropanamido)-4-methylbenzamido)-2-hydroxy-3,4-dihydro-2H-benzo[e][1,2]oxaborinine-8-carboxylic acid

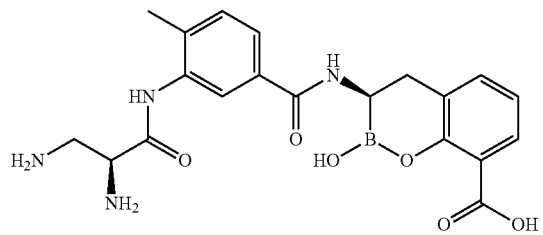 [SMILES: Cc1ccc(C(=O)N[C@H]2Cc3cccc(C(=O)O)c3OB2O)cc1NC(=O)[C@@H](N)CN]

Synthesis of (R)-3-(3-((S)-2,3-diaminopropanamido)-4-methylbenzamido)-2-hydroxy-3,4-dihydro-2H-benzo[e][1,2]oxaborinine-8-carboxylic acid 3-((R)-2-borono-2-(3-((S)-2,3-diaminopropanamido)-4-methylbenzamido)ethyl)-2-hydroxybenzoic acid was obtained as a byproduct from Example 21. ESI-MS m/z 427 (MH)$^+$.

Example 23

(R)-3-(3-amino-4-methylbenzamido)-2-hydroxy-3,4-dihydro-2H-benzo[e][1,2]oxaborinine-8-carboxylic acid

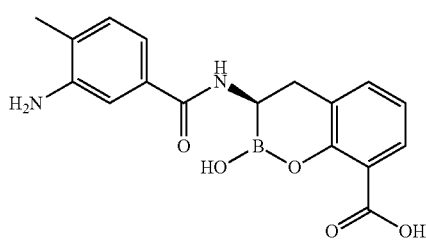 [SMILES: Cc1ccc(C(=O)N[C@H]2Cc3cccc(C(=O)O)c3OB2O)cc1N]

Synthesis of (R)-3-(3-amino-4-methylbenzamido)-2-hydroxy-3,4-dihydro-2H-benzo[e][1,2]oxaborinine-8-carboxylic acid (R)-3-(2-(3-amino-4-methylbenzamido)-2-boronoethyl)-2-hydroxybenzoic acid was obtained as a byproduct from Example 18. ESI-MS m/z 341 (MH)$^+$.

Example 24

(R)-2-hydroxy-3-(4-(pyridin-2-yl)benzamido)-3,4-dihydro-2H-benzo[e][1,2]oxaborinine-8-carboxylic acid

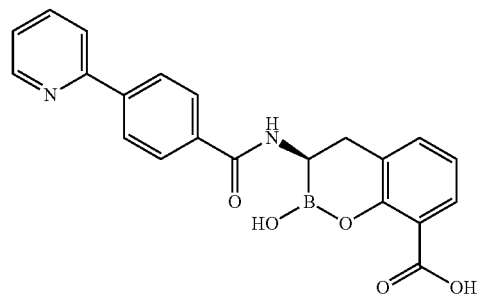 [SMILES: O=C(N[C@H]1Cc2cccc(C(=O)O)c2OB1O)c1ccc(-c2ccccn2)cc1]

(R)-2-hydroxy-3-(4-(pyridin-2-yl)benzamido)-3,4-dihydro-2H-benzo[e][1,2]oxaborinine-8-carboxylic acid was prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 4-(pyridin-2-yl)benzoic acid following the procedure described in step 1 and step 2 of Example 3. The final product was purified by reverse phase preparative HPLC and dried using lyophilization. ESI-MS m/z 389 (MH)$^+$.

Example 25

(R)-3-(3,4-bis(guanidinomethyl)benzamido)-2-hydroxy-3,4-dihydro-2H-benzo[e][1,2]oxaborinine-8-carboxylic acid

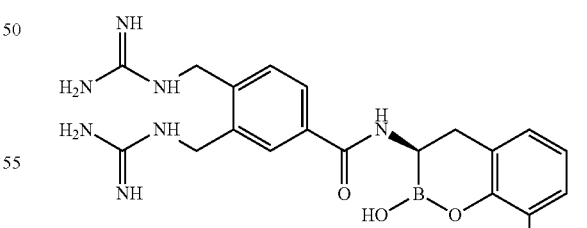

(R)-3-(3,4-bis(guanidinomethyl)benzamido)-2-hydroxy-3,4-dihydro-2H-benzo[e][1,2]oxaborinine-8-carboxylic acid was prepared from (R)-3-(2-(3,4-bis(aminomethyl)benzamido)-2-boronoethyl)-2-hydroxybenzoic acid (Example 14) using the procedure described in Example 16. ESI-MS m/z 454 (MH)$^+$.

Example 26

(R)-2-hydroxy-3-(1H-indole-5-carboxamido)-3,4-dihydro-2H-benzo[e][1,2]oxaborinine-8-carboxylic acid

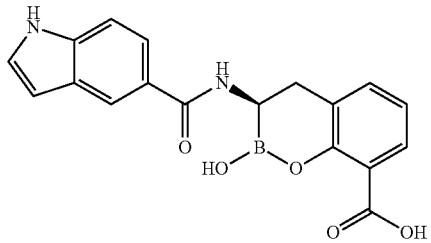 [SMILES: O=C(N[C@H]1Cc2cccc(C(=O)O)c2OB1O)c1ccc2[nH]ccc2c1]

Step 1. Synthesis of 3-[2-[(1H-Indole-5-carbonyl)-amino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.0$^{26}$]dec-4-ylmethyl)-benzoic acid tert-butyl ester and indole-5-carboxylic acid following the procedure described in step 1 of Example 3. The crude product was purified by flash chromatography on silica gel (EtOAc:Hexane, 0-100%). ESI-MS m/z 573.5 (MH)$^+$.

Step 2. Synthesis of 2-Hydroxy-3-[(1H-indole-5-carbonyl)-amino]-3,4-dihydro-2H-1-oxa-2-bora-naphthalene-8-carboxylic acid Prepared from 3-[2-[(1H-Indole-5-carbonyl)-amino]-2-(2,9,9-trimethyl-3,5-dioxa-4-bora-tricyclo[6.1.1.02,6]dec-4-yl)-ethyl]-2-methoxy-benzoic acid tert-butyl ester and BCl$_3$ following the procedure described in Step 2 of Example 3. The crude product was purified by reverse phase preparative HPLC and dried using lyophilization. ESI-MS m/z 351.0 (MH)$^+$.

Example 27

(R)-2-hydroxy-3-(4-(pyridin-4-yl)benzamido)-3,4-dihydro-2H-benzo[e][1,2]oxaborinine-8-carboxylic acid

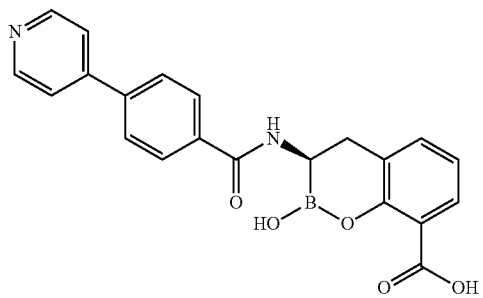 [SMILES: O=C(N[C@H]1Cc2cccc(C(=O)O)c2OB1O)c1ccc(-c2ccncc2)cc1]

Step 1. Synthesis of 2-Methoxy-3-[2-(4-pyridin-4-yl-benzoylamino)-2-(2,9,9-trimethyl-3,5-dioxa-4-bora-tricyclo[6.1.1.02,6]dec-4-yl)-ethyl]-benzoic acid tert-butyl ester Prepared from 2-methoxy-3-(2,9,9-trimethyl-3,5-dioxa-4-bora-tricyclo[6.1.1.0$^{26}$]dec-4-ylmethyl)-benzoic acid tert-butyl ester and 4-(4-pyridyl)benzoic acid following the procedure described in step 1 of Example 3. The crude product was purified by flash chromatography on silica gel (EtOAc:Hexane, 0-100%). ESI-MS m/z 611.5 (MH)$^+$.

Step 2. Synthesis of 2-Hydroxy-3-(4-pyridin-4-yl-benzoylamino)-3,4-dihydro-2H-1-oxa-2-bora-naphthalene-8-carboxylic acid Prepared from 2-Methoxy-3-[2-(4-pyridin-4-yl-benzoylamino)-2-(2,9,9-trimethyl-3,5-dioxa-4-bora-tricyclo[6.1.1.02,6]dec-4-yl)-ethyl]-benzoic acid tert-butyl ester and BCl$_3$ following the procedure described in Step 2 of Example 3. The crude product was purified by reverse phase preparative HPLC and dried using lyophilization. ESI-MS m/z 389.0 (MH)$^+$.

Example 28

(R)-2-hydroxy-3-(quinoline-6-carboxamido)-3,4-dihydro-2H-benzo[e][1,2]oxaborinine-8-carboxylic acid

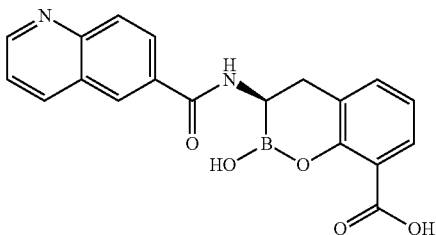 [SMILES: O=C(N[C@H]1Cc2cccc(C(=O)O)c2OB1O)c1ccc2ncccc2c1]

Step 1. Synthesis of 2-Methoxy-3-[2-[(quinoline-6-carbonyl)-amino]-2-(2,9,9-trimethyl-3,5-dioxa-4-bora-tricyclo[6.1.1.02,6]dec-4-yl)-ethyl]-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 6-quinolinecarboxylic acid following the procedure described in step 1 of Example 3. The crude product was purified by flash chromatography on silica gel (EtOAc:Hexane, 0-100%). ESI-MS m/z 585.5 (MH)$^+$.

Step 2. Synthesis of 2-Hydroxy-3-[(quinoline-6-carbonyl)-amino]-3,4-dihydro-2H-1-oxa-2-bora-naphthalene-8-carboxylic acid Prepared from 2-Methoxy-3-[2-[(quinoline-6-carbonyl)-amino]-2-(2,9,9-trimethyl-3,5-dioxa-4-bora-tricyclo[6.1.1.02,6]dec-4-yl)-ethyl]-benzoic acid tert-butyl ester and BCl$_3$ following the procedure described in Step 2 of Example 3. The crude product was purified by reverse phase preparative HPLC and dried using lyophilization. ESI-MS m/z 363.0 (MH)⁺.

Example 29

(R)-2-hydroxy-3-(quinoxaline-6-carboxamido)-3,4-dihydro-2H-benzo[e][1,2]oxaborinine-8-carboxylic acid

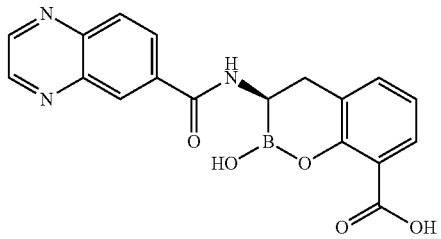 [SMILES: O=C(N[C@H]1Cc2cccc(C(=O)O)c2OB1O)c1ccc2nccnc2c1]

Step 1. Synthesis of 2-Methoxy-3-[2-[(quinoxaline-6-carbonyl)-amino]-2-(2,9,9-trimethyl-3,5-dioxa-4-bora-tricyclo[6.1.1.0²,⁶]dec-4-yl)-ethyl]-benzoic acid tert-butyl ester Prepared from 2-methoxy-3-(2,9,9-trimethyl-3,5-dioxa-4-bora-tricyclo[6.1.1.0²,⁶]dec-4-ylmethyl)-benzoic acid tert-butyl ester and quinoxaline-6-carboxylic acid following the procedure described in step 1 of Example 3. The crude product was purified by flash chromatography on silica gel (EtOAc:Hexane, 0-100%). ESI-MS m/z 586.5 (MH)⁺.

Step 2. Synthesis of 2-Hydroxy-3-[(quinoxaline-6-carbonyl)-amino]-3,4-dihydro-2H-1-oxa-2-bora-naphthalene-8-carboxylic acid Prepared from 2-Methoxy-3-[2-[(quinoxaline-6-carbonyl)-amino]-2-(2,9,9-trimethyl-3,5-dioxa-4-bora-tricyclo[6.1.1.02,6]dec-4-yl)-ethyl]-benzoic acid tert-butyl ester and BCl₃ following the procedure described in Step 2 of Example 3. The crude product was purified by reverse phase preparative HPLC and dried using lyophilization. ESI-MS m/z 364.0 (MH)⁺.

Example 30

(R)-2-hydroxy-3-(1H-indole-6-carboxamido)-3,4-dihydro-2H-benzo[e][1,2]oxaborinine-8-carboxylic acid

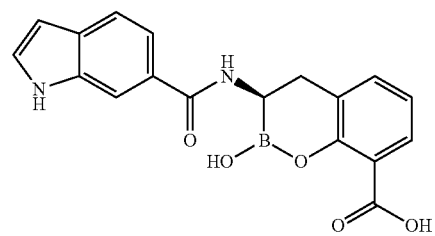 [SMILES: O=C(N[C@H]1Cc2cccc(C(=O)O)c2OB1O)c1ccc2cc[nH]c2c1]

Synthesis of (R)-2-Hydroxy-3-[(1H-indole-6-carbonyl)-amino]-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0²,⁶]dec-4-ylmethyl)-benzoic acid tert-butyl ester and indole-6-carboxylic acid following the procedure described in step 1 and step 2 of Example 3. The final product was purified by reverse phase preparative HPLC and dried using lyophilization. ESI-MS m/z 351 (MH)⁺.

Example 31

(R)-2-hydroxy-3-(1H-indole-7-carboxamido)-3,4-dihydro-2H-benzo[e][1,2]oxaborinine-8-carboxylic acid

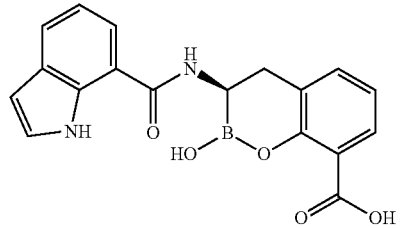 [SMILES: O=C(O)c1cccc2c1OB(O)[C@@H](NC(=O)c1cccc3cc[nH]c13)C2]

Synthesis of (R)-2-hydroxy-3-(1H-indole-7-carboxamido)-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0²,⁶]dec-4-ylmethyl)-benzoic acid tert-butyl ester and indole-7-carboxylic acid following the procedure described in step 1 and step 2 of Example 3. The final product was purified by reverse phase preparative HPLC and dried using lyophilization. ESI-MS m/z 351 (MH)⁺.

Example 32

(R)-2-Hydroxy-3-[(1H-indole-4-carbonyl)-amino]-3,4-dihydro-2H-benzo[e][1,2]oxaborinine-8-carboxylic acid

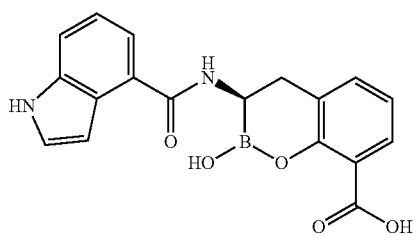 [SMILES: O=C(O)c1cccc2c1OB(O)[C@@H](NC(=O)c1cccc3[nH]ccc13)C2]

Synthesis of (R)-2-Hydroxy-3-[(1H-indole-4-carbonyl)-amino]-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0²,⁶]dec-4-ylmethyl)-benzoic acid tert-butyl ester and indole-4-carboxylic acid following the procedure described in step 1 and step 2 of Example 3. The final product was purified by reverse phase preparative HPLC and dried using lyophilization. ESI-MS m/z 351 (MH)+.

Example 33

(R)-2-Hydroxy-3-[(2-oxo-2,3-dihydro-1H-indole-5-carbonyl)-amino]-3,4-dihydro-2H-benzo[e][1,2]oxaborinine-8-carboxylic acid

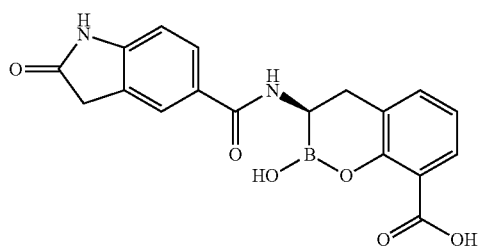 [SMILES: O=C1Cc2cc(C(=O)N[C@H]3Cc4cccc(C(=O)O)c4OB3O)ccc2N1]

Synthesis of (R)-2-Hydroxy-3-[(2-oxo-2,3-dihydro-1H-indole-5-carbonyl)-amino]-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 5-carboxyoxindole following the procedure described in step 1 and step 2 of Example 3. The final product was purified by reverse phase preparative HPLC and dried using lyophilization. ESI-MS m/z 367 (MH)+.

Example 34

(R)-3-[(3H-Benzoimidazole-5-carbonyl)-amino]-2-hydroxy-3,4-dihydro-2H-benzo[e][1,2]oxaborinine-8-carboxylic acid

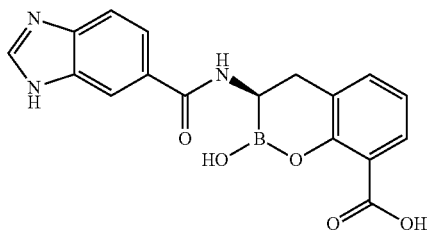

Synthesis of (R)-3-[(3H-Benzoimidazole-5-carbonyl)-amino]-2-hydroxy-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 1H-benzimidazole-6-carboxylic acid following the procedure described in step 1 and step 2 of Example 3. The final product was purified by reverse phase preparative HPLC and dried using lyophilization. ESI-MS m/z 352 (MH)+.

Example 35

(R)-2-Hydroxy-3-[(1H-pyrrolo[2,3-b]pyridine-5-carbonyl)-amino]-3,4-dihydro-2H-benzo[e][1,2]oxaborinine-8-carboxylic acid

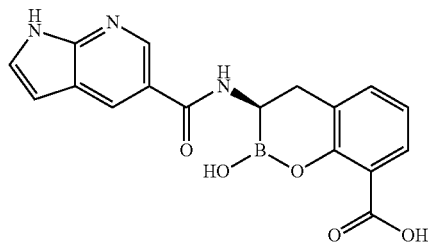

Synthesis of (R)-2-Hydroxy-3-[(1H-pyrrolo[2,3-b]pyridine-5-carbonyl)-amino]-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 1H-pyrrolo[2,3-b]pyridine-5-carboxylic acid following the procedure described in step 1 and step 2 of Example 3. The final product was purified by reverse phase preparative HPLC and dried using lyophilization. ESI-MS m/z 352 (MH)+.

Example 36

(3R)-2-hydroxy-3-[(2-isoindolin-5-ylacetyl)amino]-3,4-dihydro-1,2-benzoxaborinine-8-carboxylic acid

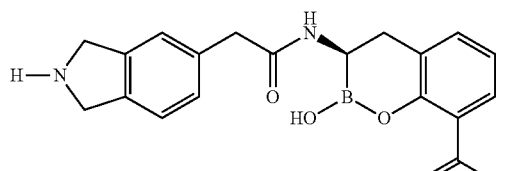

Step 1. Synthesis of 4-bromo-1,2-bis(bromomethyl)benzene

To a solution of 4-bromo-1,2-dimethyl-benzene (3.7 g, 20 mmol) in carbon tetrachloride (40 mL) was added N-bromosuccinamide (7.83 g, 44 mmol). To this mixture was added azo-bis-isobutyronitrile (AIBN, 150 mg). The resulting suspension was warmed to reflux and stirred at this temperature for 3 hr. A further portion of AIBN was added (75 mg) and stirring continued for 15 hr. The reaction mixture was cooled to room temperature, filtered and the filtrate concentrated under vacuum. The residue was purified by silica chromatography (50 g silica eluted with hexane) to give a semi solid product. This material is triturated with hexane and filtered to give the title compound as a white solid.

Step 2. Synthesis of 5-bromo-2-(p-tolylsulfonyl)isoindoline

To a suspension of sodium hydride (440 mg, 60% dispersion in mineral oil, 11 mmol) in N,N-dimethylacetamide (24 mL) was added, dropwise, a solution of p-toluenesulfonamide (1.45 g, 8.5 mmol) in N,N-dimethylacetamide (8 mL) over about 5 min. The frothy solution was stirred for 1 hr at room temperature then heated to 60° C. and stirred at this temperature for 0.5 hr. To this mixture was added, dropwise a solution of 4-bromo-1,2-bis(bromomethyl)benzene (2.9 g 8.4 mmol) in N,N-dimethylacetamide (6 mL). The resulting mixture was stirred for 1 hr then cooled to room temperature and stirred for 17 hr. The mixture was then diluted with ether, washed with water (2×) then brine, dried over sodium sulfate and concentrated. The residue was triturated with ethyl acetate and filtered to give the title compound as a white solid.

Step 3. Synthesis of 5-bromoisoindoline

To a solution of aqueous hydrobromic acid (16 mL, 48% solution in water), propionic acid (2.8 mL) and phenol (2 g) was added 5-bromo-2-(p-tolylsulfonyl)isoindoline (2.4 g, 6.8 mmol). The resulting mixture was heated to reflux and stirred at this temperature for 10 hr then cooled to room temperature. This mixture was diluted with water (20 mL) and extracted with ether (2×50 mL). The aqueous extract was brought to pH 14 with 5M sodium hydroxide solution. This solution was extracted with ether (3×). The ether extract is washed with brine, dried over magnesium sulfate, and concentrated to give the title compound as an oil.

Step 4. Synthesis of benzyl 5-bromoisoindoline-2-carboxylate

To a cooled solution of 5-bromoisoindoline (1.1 g, 5.5 mmol) in dichloromethane (15 mL) was added N,N-diisopropylethylamine (1.16 mL, 6.6 mmol) followed by benzyl chloroformate (942 µL, 6.6 mmol). The cold bath was removed and stirring continued for 2 hr. The reaction mixture was then diluted with dichloromethane, washed with water, dried over magnesium sulfate and concentrated under vacuum. The residue was purified by silica chromatography (25 g silica eluted with 0-50% ethyl acetate in hexane) to give the title compound as a white solid.

Step 5. Synthesis of benzyl 5-allylisoindoline-2-carboxylate

To a mixture of benzyl 5-bromoisoindoline-2-carboxylate (332 mg, 1 mmol), tetrakistriphenylphosphine palladium (0) (80 mg, 0.07 mmol), and cesium fluoride (604 mg, 4 mmol) was added THF (7 mL). The system was degassed and flushed with argon. To this mixture was added allyl boronic acid pinacol ester (285 µL, 1.5 mmol). The resulting mixture was heated to 72° C. and stirred at this temperature for 4 hr then cooled to room temperature. The mixture was diluted with ethyl acetate, washed with brine, dried over magnesium sulfate and concentrated under vacuum. The residue was purified by silica chromatography (25 g silica eluted with 3-40% ethyl acetate in hexane) to give the title compound as a white solid.

Step 6. Synthesis of benzyl 5-(2,3-dihydroxypropyl)isoindoline-2-carboxylate To a suspension of benzyl 5-allylisoindoline-2-carboxylate (294 mg, 1 mmol) in tert-butanol (2.5 mL) and water (2.5 mL) was added N-methylmorpholine-N-oxide (257 mg, 2.2 mmol) followed by osmium tetroxide solution (0.1 mL of 4% wt in water). The resulting mixture was stirred for 3 hr (during which time the mixture becomes homogeneous). This solution was diluted with ethyl acetate, washed with saturated sodium thiosulfate solution then brine, dried over magnesium sulfate and concentrated under vacuum. The residue was purified by silica chromatography (25 g silica eluted with 3-40% ethyl acetate in hexane) to give the title compound as a white solid.

Step 7. Synthesis of benzyl 5-(2-oxoethyl)isoindoline-2-carboxylate

To a solution of benzyl 5-(2,3-dihydroxypropyl)isoindoline-2-carboxylate (327 mg, 1 mmol) in THF (7 mL) and water (7 mL) was added sodium periodate (426 mg, 2 mmol). The resulting mixture was stirred for 20 min diluted with ethyl acetate, washed with water and brine, dried over magnesium sulfate and concentrated to give the title compound a white solid. This material is used without further purification.

Step 8. Synthesis of 2-(2-benzyloxycarbonylisoindolin-5-yl)acetic acid

To a solution of benzyl 5-(2-oxoethyl)isoindoline-2-carboxylate (290 mg, 1 mmol) in tert-butanol (10 mL) was added 2,3-dimethyl-but-2-ene (1.1 mL). To this mixture was added a solution comprising sodium dihydrogenphosphate hydrate (1.08 g, 8 mmol) and sodium chlorite (1.08 g, 9.5 mmol tech grade). This mixture was stirred for 20 min diluted with ethyl acetate, washed with brine, dried over magnesium sulfate and concentrated under vacuum. The residue was purified by silica chromatography (25 g silica eluted with 3-20% methanol in dichloromethane) to give the title compound as a white solid.

Step 9. Synthesis of [(1S)-2-(3-tert-butoxycarbonyl-2-methoxy-phenyl)-1-chloro-ethyl]boronic acid (+) pinanediol ester Method 1: To a cooled (−100° C. external temperature) solution of dichloromethane (2.27 mL, 35 mmol) in THF (44 mL) was added, dropwise down the side of the flask, BuLi (8.88 mL, 2.5 M in hexanes, 22 mmol) over 45 min. After approx. 80% of the BuLi is added, a white precipitate forms. On complete addition, the reaction mixture was stirred 30 min. To this mixture was added, dropwise down the side of the flask, 2-methoxy-3-(2,9,9-trimethyl-3,5-dioxa-4-bora-tricyclo[6.1.1.0$^{2,6}$]dec-4-ylmethyl)-benzoic acid tert-butyl ester (8.0 g, 20 mmol) in THF (20 mL) over approximately 30 min. On complete addition, the resulting solution was stirred for 5 min. To this solution was added $ZnCl_2$ (22 mL, 1M in ether) dropwise down the side of the flask, over approximately 12 min. On complete addition, the cold bath was removed and replaced with a −10° C. bath. The reaction mixture was stirred for 1.25 hr. To this solution is added ice cold ether (300 mL) and ice cold saturated aqueous $NH_4Cl$ (125 mL). The organic phase was washed with brine, dried over magnesium sulfate and concentrated under reduced pressure. The residue was purified by silica chromatography (120 g silica eluted with 2-20% ethyl acetate in hexane) to give the title compound as a colorless oil. This material slowly crystallizes at −10° C.

Method 2: 2-methoxy-3-(2,9,9-trimethyl-3,5-dioxa-4-bora-tricyclo[6.1.1.0$^{2,6}$]dec-4-ylmethyl)-benzoic acid tert-butyl ester (2.0 g, 5 mmol) and dichloromethane (1.6 mL, 25 mmol) in THF (20 mL) was stirred at −60° C. for 30 min. To this solution was added LDA (6.5 mmol, 2 M solution from Aldrich) over a period of 10 min. The resulting reaction mixture is stirred at −60° C. for 20 min. ZnCl$_2$ (8.75 mmol, 1M solution in ether) was added at −60° C. slowly. The reaction mixture was stirred at −50 to −60° C. for 30 min. This resulting mixture was warmed up to 0° C. over a period of 1 h, at which time, 10% H$_2$SO$_4$ solution (10 mL) was added and the reaction mixture stirred for 10 min. After phase separation, the organic phase was washed with water and brine. The organic phase was then dried and concentrated in vacuo. The residue was then purified by flash silica chromatography (EtOAc/Hexane:4/1) to give the title compound.

Step 10. Synthesis of tert-butyl 3-((2R)-2-(2-benzyloxycarbonylisoindolin-5-yl)acetamido)-2-(2,9,9-trimethyl-3,5-dioxa-4-bora-tricyclo[6.1.1.0$^{2,6}$]dec-4-yl)ethyl)-2-methoxybenzoate To a cooled (−78° C.) solution of [(1S)-2-(3-tert-butoxycarbonyl-2-methoxy-phenyl)-1-chloro-ethyl]boronic acid (+) pinanediol ester (450 mg, 1 mmol) in THF (3 mL) was added lithium bis-trimethylsilylamide (1.0 mL, 1M in THF) dropwise. On complete addition, the cold bath was removed and stirring continued for 19 hr to give a solution of [(1R)-1-[bis(trimethylsilyl)amino]-2-(3-tert-butoxycarbonyl-2-methoxy-phenyl)ethyl]boronic acid (+) pinanediol ester, approximately 0.25M in THF. This solution was used directly in the next operation.

In a separate flask: To a mixture of 2-(2-benzyloxycarbonylisoindolin-5-yl)-acetic acid (311 mg, 1 mmol) and HATU (418 mg, 1.1 mmol) was added DMA (3 mL) followed by N-methylmorpholine (122 μL, 1.1 mmol). The resulting solution was stirred for 1.5 hr then the solution of [(1R)-1-[bis(trimethylsilyl)amino]-2-(3-tert-butoxycarbonyl-2-methoxy-phenyl)ethyl]boronic acid (+) pinanediol in THF (prepared above) was added. This mixture was stirred for 4 h, diluted with ethyl acetate, washed with water and brine, dried over magnesium sulfate and concentrated. The residue was purified by silica chromatography (10 g silica, eluted with 40-100% ethyl acetate in hexanes) to give the title compound as a foam. ESI-MS m/z 745 (M+Na)$^+$.

Step 11. Synthesis of tert-butyl 3-((2R)-2-(isoindolin-5-yl)acetamido)-2-(2,9,9-trimethyl-3,5-dioxa-4-bora-tricyclo[6.1.1.0$^{2,6}$]dec-4-yl)ethyl)-2-methoxybenzoate To a solution of tert-butyl 3-((2R)-2-(2-benzyloxycarbonylisoindolin-5-yl)acetamido)-2-(2,9,9-trimethyl-3,5-dioxa-4-bora-tricyclo[6.1.1.0$^{2,6}$]dec-4-yl)ethyl)-2-methoxybenzoate (460 mg, 0.63 mmol) in methanol (4 mL) was added palladium on carbon (46 mg, 10% palladium by weight). This mixture was flushed with hydrogen gas and stirred under this atmosphere for 2.5 hr. The mixture was flushed with nitrogen, diluted with dichloromethane and filtered. The filtrate was concentrated to give the title compound as a tan oil that is used without further purification.

Step 12. Synthesis of (3R)-2-hydroxy-3-[(2-isoindolin-5-ylacetyl)amino]-3,4-dihydro-1,2-benzoxaborinine-8-carboxylic acid To a solution of tert-butyl 3-((2R)-2-(isoindolin-5-yl)acetamido)-2-(2,9,9-trimethyl-3,5-dioxa-4-bora-tricyclo[6.1.1.0$^{2,6}$]dec-4-yl)ethyl)-2-methoxybenzoate (150 mg, 0.25 mmol) in dioxane (2 mL) was added HCl (2 mL, 3M aqueous). The resulting solution was heated to reflux and stirred at this temperature for 2.5 hr. The resulting mixture was cooled to room temperature and extracted with ether (2×). The aqueous extract concentrated to about ½ volume and the residue was purified by reverse phase HPLC. Pure fractions are concentrated by lyophilization to give the title compound as a white solid. ESI-MS m/z 367 (MH)$^+$.

Example 37

(3R)-3-[[2-(2-carbamimidoylisoindolin-5-yl)acetyl]amino]-2-hydroxy-3,4-dihydro-1,2-benzoxaborinine-8-carboxylic acid

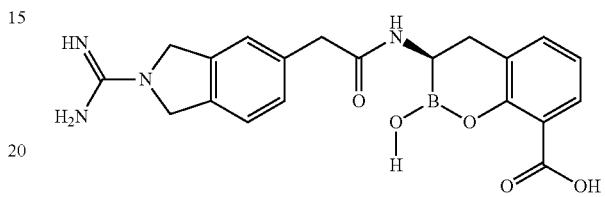

Step 1. Synthesis of tert-butyl (3R)-3-[[2-[2-[(Z)—N,N'-bis(tert-butoxycarbonyl)carbamimidoyl]isoindolin-5-yl]acetyl]amino]-2-(2,9,9-trimethyl-3,5-dioxa-4-bora-tricyclo[6.1.1.0$^{2,6}$]dec-4-yl)ethyl)-2-methoxybenzoate To a solution of tert-butyl 3-((2R)-2-(isoindolin-5-yl)acetamido)-2-(2,9,9-trimethyl-3,5-dioxa-4-bora-tricyclo[6.1.1.0$^{2,6}$]dec-4-yl)ethyl)-2-methoxybenzoate (190 mg, 0.31 mmol) in methanol (3 mL) was added bis-BOC-(pyrazol-1-yl)-carboxamidine (124 mg, 0.4 mmol). The resulting solution was stirred for 3 hr then concentrated under reduced pressure. The residue was purified by silica chromatography (10 g silica eluted with 20-100% ethyl acetate in hexane) to give the title compound.

Step 2. Synthesis of (3R)-3-[[2-(2-carbamimidoylisoindolin-5-yl)acetyl]amino]-2-hydroxy-3,4-dihydro-1,2-benzoxaborinine-8-carboxylic acid Prepared from tert-butyl (3R)-3-[[2-[2-[(Z)—N,N'-bis(tert-butoxycarbonyl)carbamimidoyl]isoindolin-5-yl]acetyl]amino]-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 1. The crude product was purified by reverse phase HPLC. Pure fractions are concentrated by lyophilization to give the title compound as a white solid. ESI-MS m/z 409 (MH)$^+$.

Example 38

(R)-3-(2-(3,4-dihydroxyphenyl)acetamido)-2-hydroxy-3,4-dihydro-2H-benzo[e][1,2]oxaborinine-8-carboxylic acid

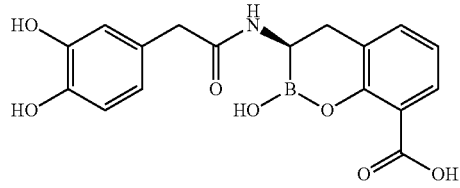 [SMILES: O=C(Cc1ccc(O)c(O)c1)N[C@H]1Cc2cccc(C(=O)O)c2OB1O]

Step 1. Synthesis of tert-butyl 3-((2R)-2-(2-(3,4-dihydroxyphenyl)acetamido)-2-(2,9,9-trimethyl-3,5-dioxa-4-bora-tricyclo[6.1.1.0²,⁶]dec-4-yl)ethyl)-2-methoxybenzoate Prepared from 2-methoxy-3-(2,9,9-trimethyl-3,5-dioxa-4-bora-tricyclo[6.1.1.0²,⁶]dec-4-ylmethyl)-benzoic acid tert-butyl ester and 2-(3,4-dihydroxyphenyl)acetic acid following the procedure described in step 1 of Example 1. The crude product was purified by flash chromatography on silica gel (Hexane/EtOAc 4:1 to 1:2). ESI-MS m/z 580.1 (MH)⁺.

Step 2. Synthesis of (R)-3-(2-(3,4-dihydroxyphenyl)acetamido)-2-hydroxy-3,4-dihydro-2H-benzo[e][1,2]oxaborinine-8-carboxylic acid tert-Butyl 3-((2R)-2-(2-(3,4-dihydroxyphenyl)acetamido)-2-(2,9,9-trimethyl-3,5-dioxa-4-bora-tricyclo[6.1.1.02,6]dec-4-yl)ethyl)-2-methoxybenzoate (200 mg) was mixed with 3 ml of 3N HCl and the reaction mixture was heated at reflux for 1 hr. The reaction solution was cooled and washed with dichloromethane three times. The crude product in the aqueous phase was purified by reverse phase preparative HPLC and dried using lyophilization. ESI-MS m/z 358 (MH)+.

Example 39

(R)-3-(3,4-dihydroxybenzamido)-2-hydroxy-3,4-dihydro-2H-benzo[e][1,2]oxaborinine-8-carboxylic acid

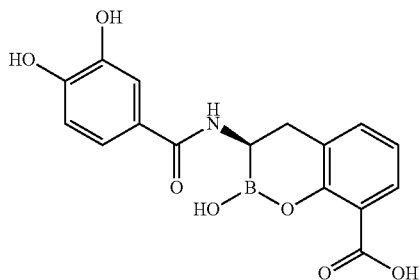 [SMILES: O=C(N[C@H]1Cc2cccc(C(=O)O)c2OB1O)c1ccc(O)c(O)c1]

Step 1. Synthesis of 3,4-diacetoxybenzoic acid

To a solution of 3,4-dihydroxybenzoic acid (0.84 g) and DMAP (80 mg) in pyridine (5 mL) at 0° C. was added acetic anhydride (1.2 mL). The reaction mixture was stirred overnight. The reaction mixture was then poured over crushed ice. The solution was acidified (pH<2) and extracted with EtOAc. The combined extracts were dried over Na₂SO₄ and concentrated in vacuo to afford the product (0.9 g).

Step 2. Synthesis of (R)-3-(3,4-dihydroxybenzamido)-2-hydroxy-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0²,⁶]dec-4-ylmethyl)-benzoic acid tert-butyl ester and 3,4-diacetoxybenzoic acid (step 1) following the procedure described in step 1 and step 2 of Example 39. The crude product was purified by reverse phase preparative HPLC and dried using lyophilization. ESI-MS m/z 344 (MH)+.

Example 40

(R)-3-(4-(2-aminoethoxy)-3-hydroxybenzamido)-2-hydroxy-3,4-dihydro-2H-benzo[e][1,2]oxaborinine-8-carboxylic acid

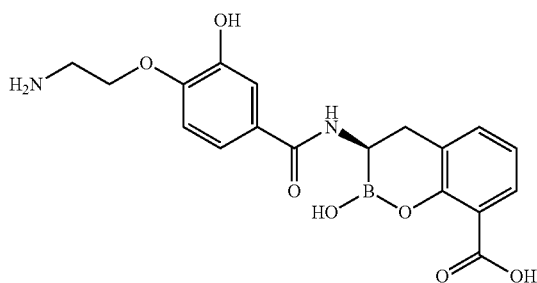 [SMILES: NCCOc1ccc(C(=O)N[C@H]2Cc3cccc(C(=O)O)c3OB2O)cc1O]

Step 1. Synthesis of tert-butyl 3-((2R)-2-(3-acetoxy-4-hydroxybenzamido)-2-(2,9,9-trimethyl-3,5-dioxa-4-bora-tricyclo[6.1.1.02,6]dec-4-yl)ethyl)-2-methoxybenzoate The titled product was obtained as a side product in step 2 of Example 39 during chromatography.

Step 2. Synthesis of tert-butyl 3-((2R)-2-(3-acetoxy-4-(2-aminoethoxy)benzamido)-2-(2,9,9-trimethyl-3,5-dioxa-4-bora-tricyclo[6.1.1.02,6]dec-4-yl)ethyl)-2-methoxybenzoate To tert-butyl 3-((2R)-2-(3-acetoxy-4-hydroxybenzamido)-2-(2,9,9-trimethyl-3,5-dioxa-4-bora-tricyclo[6.1.1.02,6]dec-4-yl)ethyl)-2-methoxybenzoate (100 mg from step 1) in DMF (3 mL) was added K₂CO₃ (100 mg) followed by tert-butyl 2-bromoethylcarbamate (100 mg). The resulting reaction mixture was stirred at room temperature overnight. Water was added to the reaction mixture and extracted with EtOAc three times. The combined organic phases were dried and concentrated to afford the product which was carried on to the next step without further purification.

Step 3. Synthesis of (R)-3-(4-(2-aminoethoxy)-3-hydroxybenzamido)-2-hydroxy-3,4-dihydro-2H-benzo[e][1,2]oxaborinine-8-carboxylic acid Prepared from tert-butyl 3-((2R)-2-(3-acetoxy-4-(2-aminoethoxy)benzamido)-2-(2,9,9-trimethyl-3,5-dioxa-4-bora-tricyclo[6.1.1.02,6]dec-4-yl)ethyl)-2-methoxybenzoate following the procedure described in step 2 of Example 38. The crude product was purified by reverse phase preparative HPLC and dried using lyophilization. ESI-MS m/z 387 (MH)⁺.

Example 41

(R)-3-{[1-(2-Amino-ethyl)-1H-indole-6-carbonyl]-amino}-2-hydroxy-3,4-dihydro-2H-benzo[e][1,2]oxaborinine-8-carboxylic acid

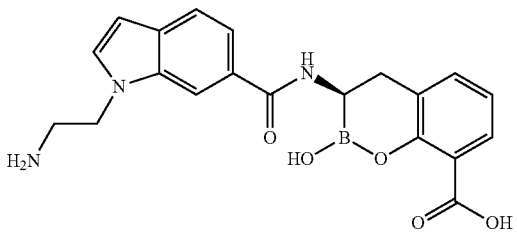 [SMILES: NCCn1ccc2ccc(C(=O)N[C@H]3Cc4cccc(C(=O)O)c4OB3O)cc21]

Step 1. Synthesis of 1H-Indole-6-carboxylic acid methyl ester

Iodomethane (0.75 mL, 12.0 mmol) was added to a suspension of indole-6-carboxylic acid (1.68 g, 10.5 mmol) and potassium carbonate (2.16 g, 15.7 mmol) in DMF (30 mL) under argon. The reaction was stirred at room temperature for 19 hr. The reaction was quenched with sat. $NH_4Cl$ and extracted with ethyl acetate (2×). The combined organic layers were washed with brine, dried over $Na_2SO_4$, filtered, and concentrated. The crude product was purified by flash chromatography on silica gel (0-60% EtOAc:Hexane). ESI-MS m/z 176 $(MH)^+$.

Step 2. Synthesis of 1-(2-tert-Butoxycarbonylamino-ethyl)-1H-indole-6-carboxylic acid methyl ester A solution of 1H-Indole-6-carboxylic acid methyl ester (0.503 g, 2.87 mmol) and DMF (9.0 mL) under argon was cooled to 0° C. for 10 min. Sodium hydride (~48%, 0.190 g, 3.80 mmol) was added and reaction warmed to room temperature for 30 min. 2-(Boc-amino)ethyl bromide (0.787 g, 3.52 mmol) was added and the reaction stirred for 17 hr. The reaction was quenched with $H_2O$ and extracted with ethyl acetate (3×). The combined organic layers were washed with $H_2O$ and brine, dried over $Na_2SO_4$, filtered, and concentrated. The crude product was purified by flash chromatography on silica gel (0-50% EtOAc:Hexane). ESI-MS m/z 319 $(MH)^+$.

Step 3. Synthesis of 1-(2-tert-Butoxycarbonylamino-ethyl)-1H-indole-6-carboxylic acid Sodium hydroxide (1N, 6.0 mL, 6.00 mmol) was added to a solution of 1-(2-tert-Butoxycarbonylamino-ethyl)-1H-indole-6-carboxylic acid methyl ester (0.501 g, 1.57 mmol) in methanol (12 mL) and THF (4.0 mL). The reaction was stirred at room temperature for 68 hr. The reaction was concentrated in vacuo. The aqueous residue was acidified to pH~1 with 1N HCl and extracted with ethyl acetate (3×). The combined organic layers were dried over $Na_2SO_4$, filtered, and concentrated. The crude product was carried forward without purification. ESI-MS m/z 327 (M+Na).

Step 4. Synthesis of (R)-3-{[1-(2-Amino-ethyl)-1H-indole-6-carbonyl]-amino}-2-hydroxy-3,4-dihydro-2H-benzo[e][1,2]oxaborinine-8-carboxylic acid Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 1-(2-tert-Butoxycarbonylamino-ethyl)-1H-indole-6-carboxylic acid following the procedure described in step 1 and step 2 of Example 3. The final product was purified by reverse phase preparative HPLC and dried using lyophilization.
ESI-MS m/z 394 $(MH)^+$.

Example 42

(R)-3-{[1-(2-Amino-ethyl)-1H-indole-4-carbonyl]-amino}-2-hydroxy-3,4-dihydro-2H-benzo[e][1,2]oxaborinine-8-carboxylic acid

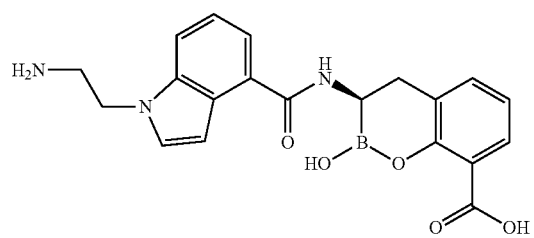 [SMILES: NCCn1ccc2c(C(=O)N[C@H]3Cc4cccc(C(=O)O)c4OB3O)cccc21]

Synthesis of (R)-3-{[1-(2-Amino-ethyl)-1H-indole-4-carbonyl]-amino}-2-hydroxy-3,4-dihydro-2H-benzo[e][1,2]oxaborinine-8-carboxylic acid Prepared from indole-4-carboxylic acid following the procedure described in steps 1 through 4 of Example 40. The final product was purified by reverse phase preparative HPLC and dried using lyophilization. ESI-MS m/z 394 $(MH)^+$.

Example 43

(R)-2-Hydroxy-3-[(1-methyl-1H-indole-6-carbonyl)-amino]-3,4-dihydro-2H-benzo[e][1,2]oxaborinine-8-carboxylic acid

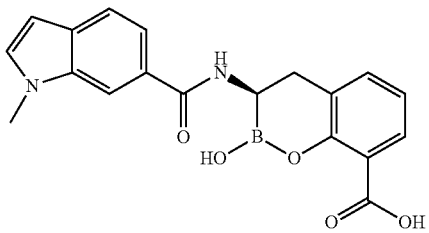 [SMILES: Cn1ccc2ccc(C(=O)N[C@H]3Cc4cccc(C(=O)O)c4OB3O)cc21]

Step 1. Synthesis of 1-Methyl-1H-indole-6-carboxylic acid methyl ester

Iodomethane (2.3 mL, 36.9 mmol) was added to a suspension of indole-6-carboxylic acid (1.55 g, 9.62 mmol) and potassium carbonate (1.98 g, 14.3 mmol) in DMF (32 mL) under argon. The reaction was stirred at room temperature for 24 hr. The reaction was quenched with sat. $NH_4Cl$ and extracted with ethyl acetate (2×). The combined organic layers were washed with brine, dried over $Na_2SO_4$, filtered, and concentrated. The crude product was purified by flash chromatography on silica gel (0-60% EtOAc:Hexane). ESI-MS m/z 190 $(MH)^+$.

Step 2. Synthesis of (R)-2-Hydroxy-3-[(1-methyl-1H-indole-6-carbonyl)-amino]-3,4-dihydro-2H-benzo[e][1,2]oxaborinine-8-carboxylic acid Prepared from 1-Methyl-1H-indole-6-carboxylic acid methyl ester following the procedure described in steps 3 and 4 of Example 40. The final product was purified by reverse phase preparative HPLC and dried using lyophilization. ESI-MS m/z 365 (MH)$^+$.

Example 44

(R)-3-(3,5-bis(aminomethyl)benzamido)-2-hydroxy-3,4-dihydro-2H-benzo[e][1,2]oxaborinine-8-carboxylic acid

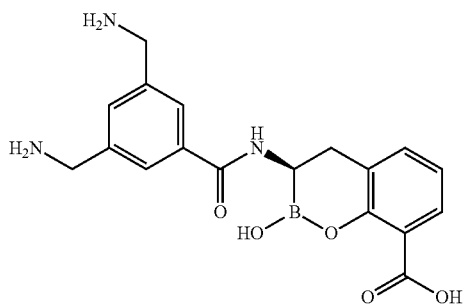 [SMILES: NCc1cc(CN)cc(C(=O)N[C@H]2Cc3cccc(C(=O)O)c3OB2O)c1]

Step 1. Synthesis of 3,5-bis((tert-butoxycarbonylamino)methyl)benzoic acid

Prepared from 3,5-dimethylbenzoic acid following the procedures described in step 1a-1e, Example 14.

Step 2. Synthesis of tert-butyl 3-((2R)-2-(3,4-bis((tert-butoxycarbonylamino)methyl)benzamido)-2-(2,9,9-trimethyl-3,5-dioxa-4-bora-tricyclo[6.1.1.0$^{2,6}$]dec-4-yl)ethyl)-2-methoxybenzoate Prepared from [(1S)-2-(3-tert-butoxycarbonyl-2-methoxy-phenyl)-1-chloro-ethyl]boronic acid (+) pinanediol ester and 3,5-bis((tert-butoxycarbonylamino)methyl)benzoic acid following the procedure described in step 10 of Example 36. The crude product was purified by flash chromatography on silica gel (Hexane/EtOAc, 2:1 to 1:2). ESI-MS m/z 792.1 (MH)$^+$.

Step 3. Synthesis of (R)-3-(3,5-bis(aminomethyl)benzamido)-2-hydroxy-3,4-dihydro-2H-benzo[e][1,2]oxaborinine-8-carboxylic acid Prepared from tert-butyl 3-((2R)-2-(3,5-bis((tert-butoxycarbonylamino)methyl)benzamido)-2-(2,9,9-trimethyl-3,5-dioxa-4-bora-tricyclo[6.1.1.0$^{2,6}$]dec-4-yl)ethyl)-2-methoxy-benzoate and BCl$_3$ following the procedure described in Step 2 of Example 3. The crude product was purified by reverse phase preparative HPLC and dried using lyophilization. ESI-MS m/z 370 (MH)$^+$.

Example 45

(R)-3-(3,5-bis(guanidinomethyl)benzamido)-2-hydroxy-3,4-dihydro-2H-benzo[e][1,2]oxaborinine-8-carboxylic acid

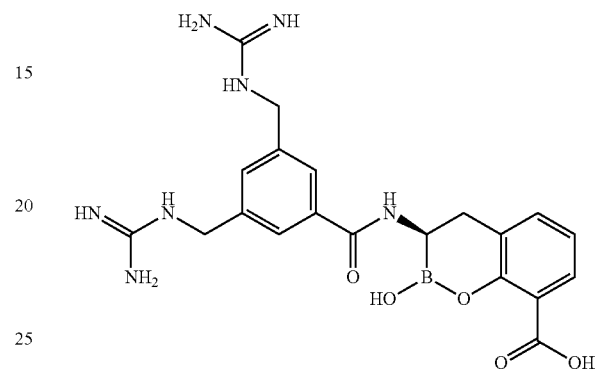

Synthesis of (R)-3-(3,5-bis(guanidinomethyl)benzamido)-2-hydroxy-3,4-dihydro-2H-benzo[e][1,2]oxaborinine-8-carboxylic acid (R)-3-(3,5-bis(guanidinomethyl)benzamido)-2-hydroxy-3,4-dihydro-2H-benzo[e][1,2]oxaborinine-8-carboxylic acid was prepared from (R)-3-(2-(3,5-bis(aminomethyl)benzamido)-2-boronoethyl)-2-hydroxybenzoic acid (Example 44) using the procedure described in Example 16. The product was purified by reverse phase HPLC and dried using lyophilization. ESI-MS m/z 454 (MH)$^+$.

Example 46

(R)-2-Hydroxy-3-(2-1H-indol-6-yl-acetylamino)-3,4-dihydro-2H-benzo[e][1,2]oxaborinine-8-carboxylic acid

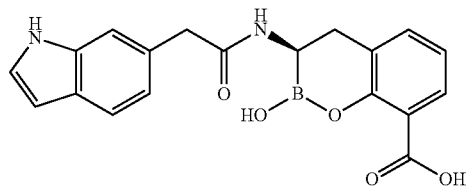 [SMILES: O=C(Cc1ccc2cc[nH]c2c1)N[C@H]1Cc2cccc(C(=O)O)c2OB1O]

Step 1. Synthesis of 3-[2-(2-1H-Indol-6-yl-acetylamino)-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-(1H-indol-6-yl)acetic acid following the procedure described in Step 1 of Example 1. The crude product was purified by flash chromatography on silica gel (EtOAc:Hexane, 25-100%). ESI-MS m/z 587 (MH)+.

Step 2. Synthesis of (R)-2-Hydroxy-3-(2-1H-indol-6-yl-acetylamino)-3,4-dihydro-2H-benzo[e][1,2]oxaborinine-8-carboxylic acid Prepared from 3-[2-(2-1H-Indol-6-yl-acetylamino)-2-(2,9,9-trimethyl-3,5-dioxa-4-bora-tricyclo[6.1.1.0 2,6]dec-4-yl)-ethyl]-2-methoxy-benzoic acid tert-butyl ester and BCl₃ following the procedure described in Step 2 of Example 1. The crude product was purified by reverse phase preparative HPLC and dried using lyophilization. ESI-MS m/z 365 (MH)+.

Example 47

(R)-2-Hydroxy-3-[4-(1H-imidazol-2-yl)-benzoylamino]-3,4-dihydro-2H-benzo[e][1,2]oxaborinine-8-carboxylic acid

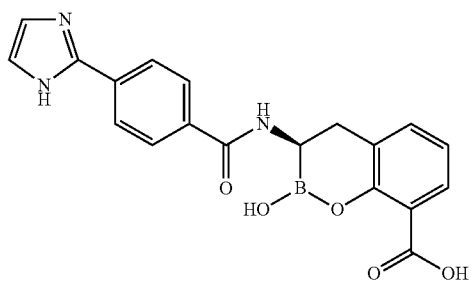 [SMILES: O=C(N[C@H]1Cc2cccc(C(=O)O)c2OB1O)c1ccc(-c2ncc[nH]2)cc1]

Step 1. Synthesis of 3-[2-[4-(1H-Imidazol-2-yl)-benzoylamino]-2-(2,9,9-trimethyl-3,5-dioxa-4-bora-tricyclo[6.1.1.02,6]dec-4-yl)-ethyl]-2-methoxy-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 4-(1H-imidazol-2-yl)benzoic acid following the procedure described in Step 1 of Example 1. The crude product was purified by flash chromatography on silica gel (CH₃OH:CH₂Cl₂, 0-15%). ESI-MS m/z 600 (MH)+.

Step 2. Synthesis of (R)-2-Hydroxy-3-[4-(1H-imidazol-2-yl)-benzoylamino]-3,4-dihydro-2H-benzo[e][1,2]oxaborinine-8-carboxylic acid Prepared from 3-[2-[4-(1H-Imidazol-2-yl)-benzoylamino]-2-(2,9,9-trimethyl-3,5-dioxa-4-bora-tricyclo[6.1.1.02,6]dec-4-yl)-ethyl]-2-methoxy-benzoic acid tert-butyl ester and BCl₃ following the procedure described in Step 2 of Example 1. The crude product was purified by reverse phase preparative HPLC and dried using lyophilization. ESI-MS m/z 378 (MH)+.

Example 48

(R)-2-Hydroxy-3-[2-(2-methyl-2,3-dihydro-1H-isoindol-5-yl)-acetylamino]-3,4-dihydro-2H-benzo[e][1,2]oxaborinine-8-carboxylic acid

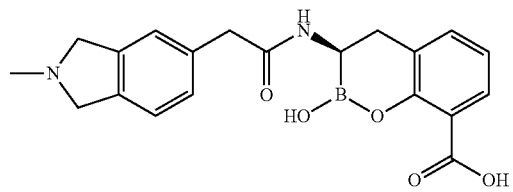 [SMILES: CN1Cc2ccc(CC(=O)N[C@H]3Cc4cccc(C(=O)O)c4OB3O)cc2C1]

Step 1. Synthesis of Di-prop-2-ynyl-carbamic acid tert-butyl ester

A mixture of N-Boc-propargylamine (2.63 g, 16.9 mmol) and DMF (35 mL) was prepared under argon and cooled to 0° C. for 20 min. Sodium hydride (60%, 0.714 g, 17.9 mmol) was added and the reaction stirred at 0° C. for 30 min. Propargyl bromide (80% in toluene, 2.7 mL, 24.2 mmol) in DMF (5 mL) was added slowly and the reaction stirred at 0° C. for 15 min then warmed to room temperature and stirred for additional 17 hr. The reaction mixture was quenched with water and extracted two times with EtOAc. The combined organic layers were washed with water (3×) and brine, dried over Na₂SO₄, filtered, and concentrated. The crude product was carried to the next reaction without purification. ESI-MS m/z 194 (MH)+.

Step 2. Synthesis of 5-Carboxymethyl-1,3-dihydro-isoindole-2-carboxylic acid tert-butyl ester A mixture of di-prop-2-ynyl-carbamic acid tert-butyl ester (4.78 g, 24.7 mmol) and ethanol (120 mL) was prepared under argon and cooled to 0° C. for 15 min. 3-Butynoic acid (3.64 g, 43.3 mmol) and tris(triphenylphosphine)rhodium (I) chloride (1.14 g, 1.23 mmol) were added and reaction was gradually warmed to room temperature over 1.3 hr. The reaction was then heated to 45° C. for 17 hr. The reaction was cooled to room temperature and concentrated in vacuo. The residue was diluted with IN NaOH and extracted with diethyl ether (3×). The aqueous layer was acidified to pH~1 with IN HCl and extracted with EtOAc (3×). The combined EtOAc layers were dried over Na₂SO₄, filtered, and concentrated. The crude product was purified by flash chromatography on silica gel (EtOAc:Hexane, 5-100%). ESI-MS m/z 278 (MH)+.

Step 3. Synthesis of 5-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-1,3-dihydro-isoindole-2-carboxylic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 5-carboxymethyl-1,3-dihydro-isoindole-2-carboxylic acid tert-butyl ester following the procedure described in Step 1 of Example 1. The crude product was purified by flash chromatography on silica gel (EtOAc:Hexane, 30-100%). ESI-MS m/z 689 (MH)+.

Step 4. Synthesis of 3-[2-(2-2,3-Dihydro-1H-isoindol-5-yl-acetylamino)-2-(2,9,9-trimethyl-3,5-dioxa-4-bora-tricyclo[6.1.1.02,6]dec-4-yl)-ethyl]-2-methoxy-benzoic acid Trifluoroacetic acid (0.60 mL, 8.08 mmol) was added to a solution of 5-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-1,3-dihydro-isoindole-2-carboxylic acid tert-butyl ester (0.285 g, 0.414 mmol) in CH$_2$Cl$_2$ (3.0 mL) under argon. The reaction was stirred at room temperature for 2 hr then concentrated in vacuo and carried to the next step without purification. ESI-MS m/z 533 (MH)+.

Step 5. Synthesis of 2-Methoxy-3-[2-[2-(2-methyl-2,3-dihydro-1H-isoindol-5-yl)-acetylamino]-2-(2,9,9-trimethyl-3,5-dioxa-4-bora-tricyclo[6.1.1.02,6]dec-4-yl)-ethyl]-benzoic acid A solution of 3-[2-(2-2,3-Dihydro-1H-isoindol-5-yl-acetylamino)-2-(2,9,9-trimethyl-3,5-dioxa-4-bora-tricyclo[6.1.1.02,6]dec-4-yl)-ethyl]-2-methoxy-benzoic acid (0.110 g, 0.207 mmol), formaldehyde (37% in H$_2$O, 0.06 mL, 0.740 mmol), and methanol (2.5 mL) was purged with argon. Palladium on carbon (10%, 0.049 g) was added, the flask evacuated, and the reaction placed under hydrogen for 18 hr. The reaction mixture was filtered through a Celite-plugged filter frit, washed with CH$_3$OH and CH$_2$Cl$_2$, and concentrated. The crude product was carried forward without purification. ESI-MS m/z 547 (MH)+.

Step 6. Synthesis of (R)-2-Hydroxy-3-[2-(2-methyl-2,3-dihydro-1H-isoindol-5-yl)-acetylamino]-3,4-dihydro-2H-benzo[e][1,2]oxaborinine-8-carboxylic acid To a mixture of 2-Methoxy-3-[2-[2-(2-methyl-2,3-dihydro-1H-isoindol-5-yl)-acetylamino]-2-(2,9,9-trimethyl-3,5-dioxa-4-bora-tricyclo[6.1.1.02,6]dec-4-yl)-ethyl]-benzoic acid (0.113 g, 0.207 mmol) and 1,4-dioxane (2.0 mL) was added 3N HCl (1.7 mL, 5.10 mmol) and the reaction was heated at 100° C. for 1 hr. The reaction was cooled to room temperature and extracted with diethyl ether (3×). The product remained in the aqueous layer and was purified by reverse phase preparative HPLC and dried using lyophilization. ESI-MS m/z 381 (MH)+.

Example 49

(R)-3-{2-[2-(2-Amino-ethyl)-2,3-dihydro-1H-isoindol-5-yl]-acetylamino}-2-hydroxy-3,4-dihydro-2H-benzo[e][1,2]oxaborinine-8-carboxylic acid

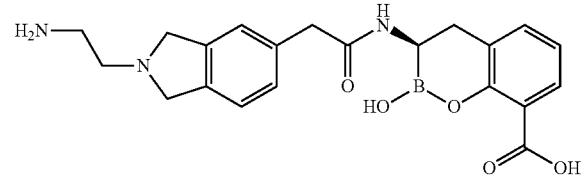 [SMILES: NCCN1Cc2ccc(CC(=O)N[C@H]3Cc4cccc(C(=O)O)c4OB3O)cc2C1]

Step 1. Synthesis of 3-[2-{2-[2-(2-tert-Butoxycarbonylamino-ethyl)-2,3-dihydro-1H-isoindol-5-yl]-acetylamino}-2-(2,9,9-trimethyl-3,5-dioxa-4-bora-tricyclo[6.1.1.02,6]dec-4-yl)-ethyl]-2-methoxy-benzoic acid A solution of 3-[2-(2-2,3-Dihydro-1H-isoindol-5-yl-acetylamino)-2-(2,9,9-trimethyl-3,5-dioxa-4-bora-tricyclo[6.1.1.02,6]dec-4-yl)-ethyl]-2-methoxy-benzoic acid (0.110 g, 0.207 mmol) (prepared following the procedures in Steps 1-4 in Example 48), N-Boc-2-aminoacetaldehyde (0.06 g, 0.427 mmol), and methanol (2.5 mL) was purged with argon. Palladium on carbon (10%, 0.051 g) was added, the flask evacuated, and the reaction placed under hydrogen for 91 hr. The reaction mixture was filtered through a Celite-plugged filter frit, washed with CH$_3$OH and CH$_2$Cl$_2$, and concentrated. The crude product was carried forward without purification. ESI-MS m/z 676 (MH)+.

Step 2. Synthesis of (R)-3-{2-[2-(2-Amino-ethyl)-2,3-dihydro-1H-isoindol-5-yl]-acetylamino}-2-hydroxy-3,4-dihydro-2H-benzo[e][1,2]oxaborinine-8-carboxylic acid Prepared from 3-[2-{2-[2-(2-tert-Butoxycarbonylamino-ethyl)-2,3-dihydro-1H-isoindol-5-yl]-acetylamino}-2-(2,9,9-trimethyl-3,5-dioxa-4-bora-tricyclo[6.1.1.02,6]dec-4-yl)-ethyl]-2-methoxy-benzoic acid and HCl following the procedure described in Step 6 of Example 48. The crude product was purified by reverse phase preparative HPLC and dried using lyophilization. ESI-MS m/z 410 (MH)+.

Example 50

(3R)-3-(6,7-dihydro-5H-pyrrolo[3,4-b]pyridine-3-carbonylamino)-2-hydroxy-3,4-dihydro-1,2-benzoxaborinine-8-carboxylic acid

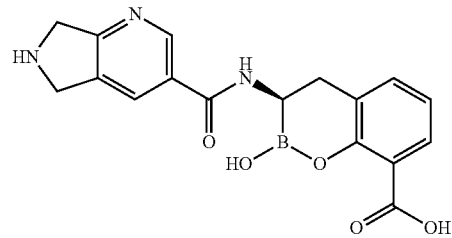 [SMILES: O=C(N[C@H]1Cc2cccc(C(=O)O)c2OB1O)c1cnc2c(c1)CNC2]

Step 1. Synthesis of 5-bromo-2,3-dimethyl-pyridine

To a stirred solution of 2,3-dimethyl-pyridine (6.79 mL, 60 mmol) in fuming sulfuric acid (80 mL) held at 150° C. in a round bottom flask fitted with a water cooled reflux condenser and a calcium chloride filled drying tube, was added, dropwise, bromine (3.1 mL, 60 mmol) over 2 hr. The resulting dark red solution was stirred for 16 hr then cooled to room temperature and allowed to stand overnight. This mixture was poured into approximately 400 g of ice. This mixture was brought to pH 12 with cooling in an ice bath. The resulting mixture was extracted with ether and the ether extract washed with brine, dried over magnesium sulfate and concentrated under reduced pressure. The residue was purified by silica chromatography (50 g silica, eluted with 2-20% ethyl acetate in hexanes) to give the title compound (8.3 g) as a colorless oil.

Step 2. Synthesis of 5-bromo-2,3-bis(bromomethyl)pyridine

To a solution of 5-bromo-2,3-dimethyl-pyridine (8.3 g, 44.6 mmol) in $CCl_4$ (120 mL) was added N-bromo-succinimide (16.77 g, 93.7 mmol) followed by AIBN (167 mg, 1 mmol). The resulting solution was heated to 82° C. and stirred at this temperature for 2 hr. To this mixture was added AIBN (167 mg, 1 mmol). This mixture was stirred for a further 2 hr at 82° C. then cooled to room temperature. The solid precipitate was removed by filtration and the filtrate concentrated under reduced pressure. The residue was purified by silica chromatography (50 g silica, eluted with 2-20% ethyl acetate in hexanes) to give the title compound as a mixture with starting material and tri-brominated derivative.

Step 3. Synthesis of 3-bromo-6-trityl-5,7-dihydropyrrolo[3,4-b]pyridine

To a solution of 5-bromo-2,3-bis(bromomethyl)pyridine (Step 2 above, 5.6 g, approximately 16.3 mmol) in DMF (40 mL) was added trityl amine (5.3 g, 20.6 mmol) followed by diisopropylethylamine (8.6 mL, 49 mmol). The resulting solution was warmed to 60° C. and stirred at this temperature for 2.5 hr. The mixture was then concentrated under reduced pressure and the residue was purified by silica chromatography (50 g silica, eluted with 10-100% dichloromethane in hexanes) to give the title compound as a foam.

Step 4. Synthesis of 3-bromo-6,7-dihydro-5H-pyrrolo[3,4-b]pyridine

To a cooled (0° C.) solution of 3-bromo-6-trityl-5,7-dihydropyrrolo[3,4-b]pyridine (1.57 g, 3.66 mmol) in chloroform (15 mL) and methanol (15 mL) was added trifluoroacetic acid (30 mL) over 1 min. On complete addition, the solution was stirred for 5 min then the cold bath removed and stirring continued for 30 min. This solution was concentrated under reduced pressure and the residue taken up in HCl (30 mL, 1M aq.). This mixture was extracted with ether (2×20 mL) then the aqueous phase basified with sodium hydroxide (5M aq.). This mixture was extracted with dichloromethane (3×20 mL). The combined dichloromethane extract was dried over magnesium sulfate and concentrated under reduced pressure to give the title compound as a solid.

Step 5. Synthesis of tert-butyl 3-bromo-5,7-dihydropyrrolo[3,4-b]pyridine-6-carboxylate To a solution of 3-bromo-6,7-dihydro-5H-pyrrolo[3,4-b]pyridine (755 mg, 3.79 mmol) in dichloromethane (15 mL) was added diisopropylethylamine (791 µL, 4.54 mmol) followed by di-tert-butyl dicarbonate (989 mg, 4.54 mmol). The resulting solution was stirred for 1 hr then diluted with ether, washed with brine, dried over magnesium sulfate and concentrated. The residue was purified by silica chromatography (25 g silica, eluted with 5-40% ethyl acetate in hexanes) to give the title compound as a solid.

Step 6. Synthesis of tert-butyl 3-allyl-5,7-dihydropyrrolo[3,4-b]pyridine-6-carboxylate A mixture of tert-butyl 3-bromo-5,7-dihydropyrrolo[3,4-b]pyridine-6-carboxylate (857 mg, 2.87 mmol), cesium fluoride (1.7 g, 11.5 mmol), and tetrakis-(triphenylphosphine) palladium (0) (229 mg, 0.2 mmol) in THF (15 mL) was degassed and flushed with nitrogen. To this mixture was added allyl-boronic acid pinacol ester (820 µL, 4.3 mmol). The resulting mixture was heated to reflux and stirred at this temperature for 2.5 hr then cooled to room temperature, diluted with ether, washed with water and brine, dried over magnesium sulfate and concentrated. The residue was purified by silica chromatography (25 g silica, eluted with 5-40% ethyl acetate in hexanes) to give the title compound as a solid.

Step 7. Synthesis of tert-butyl 3-(2,3-dihydroxypropyl)-5,7-dihydropyrrolo[3,4-b]pyridine-6-carboxylate To a solution of tert-butyl 3-allyl-5,7-dihydropyrrolo[3,4-b]pyridine-6-carboxylate (430 mg, 1.64 mmol) in tert-butanol (5 mL) and water (5 mL) was added N-methyl-morpholine N-oxide (422 mg, 3.6 mmol) followed by osmium tetroxide (20 µl, 4% aqueous solution). The resulting solution was stirred for 48 hr then diluted with ether, washed with 10% sodium thiosulphate solution and brine, dried over magnesium sulfate and concentrated to give the title compound as a solid.

Step 8. Synthesis of 6-tert-butoxycarbonyl-5,7-dihydropyrrolo[3,4-b]pyridine-3-carboxylic acid and 2-(6-tert-butoxycarbonyl-5,7-dihydropyrrolo[3,4-b]pyridin-3-yl)acetic acid To a solution of tert-butyl 3-(2,3-dihydroxypropyl)-5,7-dihydropyrrolo[3,4-b]pyridine-6-carboxylate (450 mg, 1.52 mmol) in THF (4.5 mL) and water (4.5 mL) was added sodium periodate (648 mg, 3 mmol). The resulting mixture was stirred for 20 min then diluted with ethyl acetate, washed with water and brine, dried over magnesium sulfate and concentrated. The residue was taken up in tert-butanol (15 mL). To this solution was added 2,3-dimethyl-but-2-ene (1.7 mL) followed by a solution comprising sodium chlorite (1.6 g, technical grade approximately 14 mmol) and disodium hydrogen phosphate hydrate (1.6 g, 12 mmol) in water (15 mL). The resulting mixture was stirred for 20 min then diluted with ethyl acetate, washed with water and brine, dried over magnesium sulfate, and concentrated to give the title compounds (approximately 1:9 ratio) as a solid. This product was used without further purification.

Step 9. Synthesis of [(1R)-2-(3-tert-butoxycarbonyl-2-methoxy-phenyl)-1-[(6-tert-butoxycarbonyloxycarbonyl-5,7-dihydropyrrolo[3,4-b]pyridine-3-carbonyl)amino]ethyl]boronic acid (+) pinanediol ester The title compound was prepared using essentially the same procedure described in Example 36 step 10 except using 6-tert-butoxycarbonyl-5,7-dihydropyrrolo[3,4-b]pyridine-3-carboxylic acid and 2-(6-tert-butoxycarbonyl-5,7-dihydropyrrolo[3,4-b]pyridin-3-yl)acetic acid in place of 2-(2-benzyloxycarbonylisoindolin-5-yl)-acetic acid.

Step 10. Synthesis of (3R)-3-(6,7-dihydro-5H-pyrrolo[3,4-b]pyridine-3-carbonylamino)-2-hydroxy-3,4-dihydro-1,2-benzoxaborinine-8-carboxylic acid The title compound was prepared using essentially the same procedure described in Example 36, step 12 except using [(1R)-2-(3-tert-butoxycarbonyl-2-methoxy-phenyl)-1-[(6-tert-butoxycarbonyloxycarbonyl-5,7-dihydropyrrolo[3, 4-b]pyridine-3-carbonyl)amino]ethyl]boronic acid (+) pinanediol ester in place of [(1R)-2-(3-tert-butoxycarbonyl-2-methoxy-phenyl)-1-[(2-isoindolin-5-ylacetyl)amino]ethyl]boronic acid (+) pinanediol ester. Purification was by reverse phase HPLC (Phenomenex Luna; 5 micron C18 column; 35×75 mm; flow rate 40 ml/min eluted with 5-40% CH$_3$CN/H$_2$O/0.1% TFA over 8 min). Purified fractions were isolated by lyophilization. ESI-MS m/z 354 (MH)$^+$.

Example 51

(R)-2-Hydroxy-3-(2-1,2,3,4-tetrahydro-isoquinolin-7-yl-acetylamino)-3,4-dihydro-2H-benzo[e][1,2]oxaborinine-8-carboxylic acid

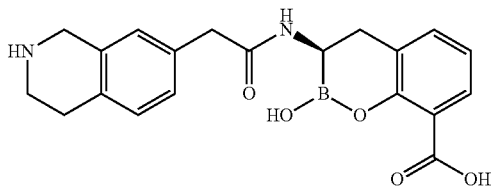 [SMILES: O=C(Cc1ccc2c(c1)CNCC2)N[C@H]1Cc2cccc(C(=O)O)c2OB1O]

Step 1. Synthesis of 7-{[2-(3-tert-Butoxycarbonyl-2-methoxy-phenyl)-1-(2,9,9-trimethyl-3,5-dioxa-4-bora-tricyclo[6.1.1.0²,⁶]dec-4-yl)-ethylcarbamoyl]-methyl}-3,4-dihydro-1H-isoquinoline-2-carboxylic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and 2-Boc-1,2,3,4-tetrahydro-7-isoquinolineacetic acid following the procedure described in Step 1 of Example 1. The crude product was purified by flash chromatography on silica gel (EtOAc:Hexane, 25-100%). ESI-MS m/z 703 (MH)$^+$.

Step 2. Synthesis of (R)-2-Hydroxy-3-(2-1,2,3,4-tetrahydro-isoquinolin-7-yl-acetylamino)-3,4-dihydro-2H-benzo[e][1,2]oxaborinine-8-carboxylic acid Prepared from 7-{[2-(3-tert-Butoxycarbonyl-2-methoxy-phenyl)-1-(2,9,9-trimethyl-3,5-dioxa-4-bora-tricyclo[6.1.1.02,6]dec-4-yl)-ethylcarbamoyl]-methyl}-3,4-dihydro-1H-isoquinoline-2-carboxylic acid tert-butyl ester and HCl following the procedure described in Step 6 of Example 48. The crude product was purified by reverse phase preparative HPLC and dried using lyophilization. ESI-MS m/z 381 (MH)$^+$.

Example 52

(R)-2-Hydroxy-3-[(oxazole-5-carbonyl)-amino]-3,4-dihydro-2H-benzo[e][1,2]oxaborinine-8-carboxylic acid

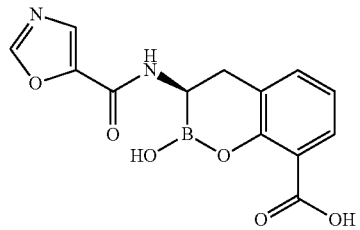 [SMILES: O=C(N[C@H]1Cc2cccc(C(=O)O)c2OB1O)c1cnco1]

Step 1. Synthesis of 2-Methoxy-3-[2-[(oxazole-5-carbonyl)-amino]-2-(2,9,9-trimethyl-3,5-dioxa-4-bora-tricyclo[6.1.1.02,6]dec-4-yl)-ethyl]-benzoic acid tert-butyl ester Prepared from 2-methoxy-3-(2,9,9-trimethyl-3,5-dioxa-4-bora-tricyclo[6.1.1.0$^{2,6}$]dec-4-ylmethyl)-benzoic acid tert-butyl ester and oxazole-5-carboxylic acid following the procedure described in Step 1 of Example 1. The crude product was purified by flash chromatography on silica gel (EtOAc:Hexane, 10-100%). ESI-MS m/z 525 (MH)$^+$.

Step 2. Synthesis of (R)-2-Hydroxy-3-[(oxazole-5-carbonyl)-amino]-3,4-dihydro-2H-benzo[e][1,2]oxaborinine-8-carboxylic acid Aluminum chloride (0.132 g, 0.990 mmol) was added to a solution of 2-Methoxy-3-[2-[(oxazole-5-carbonyl)-amino]-2-(2,9,9-trimethyl-3,5-dioxa-4-bora-tricyclo[6.1.1.02,6]dec-4-yl)-ethyl]-benzoic acid tert-butyl ester (0.064 g, 0.122 mmol) in CH$_2$Cl$_2$ (3.0 mL). The reaction was stirred at room temperature for 16 hr. The reaction was quenched with H$_2$O and CH$_3$OH and extracted with hexane (2×). The crude product remained in the aqueous layer and was purified by reverse phase preparative HPLC and dried using lyophilization. ESI-MS m/z 303 (MH)$^+$.

Example 53

(R)-3-(2-carboxybenzamido)-2-hydroxy-3,4-dihydro-2H-benzo[e][1,2]oxaborinine-8-carboxylic acid

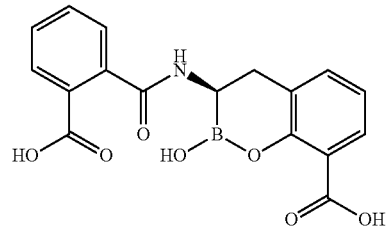 [SMILES: O=C(O)c1ccccc1C(=O)N[C@H]1Cc2cccc(C(=O)O)c2OB1O]

Step 1. Synthesis of tert-butyl 3-((2R)-2-(1,3-dioxoisoindolin-2-yl)-2-(2,9,9-trimethyl-3,5-dioxa-4-bora-tricyclo[6.1.1.0$^{2,6}$]dec-4-yl)ethyl)-2-methoxybenzoate To [(1S)-2-(3-tert-butoxycarbonyl-2-methoxy-phenyl)-1-chloro-ethyl]boronic acid (+) pinanediol ester (1.3 g from Step 9, Example 36) in 10 mL DMSO was added potassium phthalimide (1.2 g). The resulting reaction mixture was stirred at room temperature for 4 hr.

Water was added to the reaction solution and extracted with EtOAc. The organic phase was dried and concentrated to afford the title product (1.8 g).

Step 2. Synthesis of (R)-3-(1,3-dioxoisoindolin-2-yl)-2-hydroxy-3,4-dihydro-2H-benzo[e][1,2]oxaborinine-8-carboxylic acid Prepared from tert-butyl 3-((2R)-2-(1,3-dioxoisoindolin-2-yl)-2-(2,9,9-trimethyl-3,5-dioxa-4-bora-tricyclo-

[6.1.1.0$^{2,6}$]dec-4-yl)ethyl)-2-methoxybenzoate and BCl$_3$ following the procedure described in Step 2 of Example 3. ESI-MS m/z 338 (MH)$^+$.

Step 3. Synthesis of (R)-3-(2-carboxybenzamido)-2-hydroxy-3,4-dihydro-2H-benzo[e][1,2]oxaborinine-8-carboxylic acid To 20 mg of (R)-3-(1,3-dioxoisoindolin-2-yl)-2-hydroxy-3,4-dihydro-2H-benzo[e][1,2]oxaborinine-8-carboxylic acid in a mixture of methanol and H$_2$O (2 mL, 1:1) was added 1 N NaOH (0.5 mL) and the resulting reaction mixture was stirred at room temperature for 3 hr. 1N HCl was added to adjust the pH of the solution to 3. The product was then purified by reverse phase HPLC and dried using lyophilization. ESI-MS m/z 356 (MH)$^+$.

Example 54

(R)-3-(2-(2-aminoethylcarbamoyl)benzamido)-2-hydroxy-3,4-dihydro-2H-benzo[e][1,2]oxaborinine-8-carboxylic acid

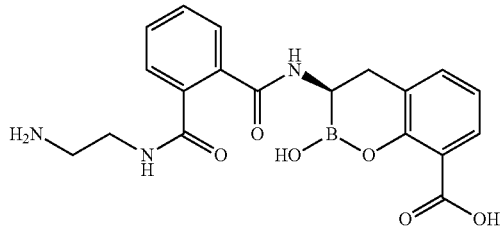 [SMILES: NCCNC(=O)c1ccccc1C(=O)N[C@H]1Cc2cccc(C(=O)O)c2OB1O]

Step 1. Synthesis of tert-butyl 3-((2R)-2-(2-(2-(tert-butoxycarbonylamino)ethylcarbamoyl)benzamido)-2-(2,9,9-trimethyl-3,5-dioxa-4-bora-tricyclo[6.1.1.0$^{2,6}$]dec-4-yl)ethyl)-2-methoxybenzoate To tert-butyl 3-((2R)-2-(1,3-dioxoisoindolin-2-yl)-2-(2,9,9-trimethyl-3,5-dioxa-4-bora-tricyclo[6.1.1.0$^{2,6}$]dec-4-yl)ethyl)-2-methoxybenzoate (100 mg from Step 1, Example 53) in 2 mL methanol was added tert-butyl 2-aminoethylcarbamate (1.1 eq). The resulting reaction mixture was stirred at reflux for 2 hr. Methanol was then removed under reduced pressure. The crude product was used in the next step without further purification.

Step 2. Synthesis of (R)-3-(2-(2-aminoethylcarbamoyl)benzamido)-2-hydroxy-3,4-dihydro-2H-benzo[e][1,2]oxaborinine-8-carboxylic acid Prepared from tert-butyl 3-((2R)-2-(2-(2-(tert-butoxycarbonylamino)ethylcarbamoyl)benzamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The product was then purified by reverse phase HPLC and dried using lyophilization. ESI-MS m/z 398 (MH)$^+$.

Example 55

(R)-3-(4-(aminomethyl)-3-((isopropylamino)methyl)benzamido)-2-hydroxy-3,4-dihydro-2H-benzo[e][1,2]oxaborinine-8-carboxylic acid

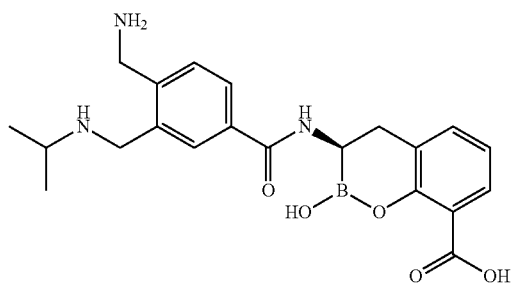 [SMILES: CC(C)NCc1cc(C(=O)N[C@H]2Cc3cccc(C(=O)O)c3OB2O)ccc1CN]

Synthesis of (R)-3-(4-(aminomethyl)-3-((isopropylamino)methyl)benzamido)-2-hydroxy-3,4-dihydro-2H-benzo[e][1,2]oxaborinine-8-carboxylic acid To (R)-3-(3,4-bis(aminomethyl)benzamido)-2-hydroxy-3,4-dihydro-2H-benzo[e][1,2]oxaborinine-8-carboxylic acid from Example 14 (44.1 mg) in methanol (2 mL) was added TEA (0.042 mL), AcOH (0.050 mL), acetone (0.030 mL), and sodium triacetoxyborohydride (70 mg). The resulting reaction mixture was stirred at room temperature for overnight. After removal of the solvents, the product was then purified by reverse phase HPLC and dried using lyophilization. ESI-MS m/z 412 (MH)$^+$.

Example 56

(R)-3-(3,4-bis((isopropylamino)methyl)benzamido)-2-hydroxy-3,4-dihydro-2H-benzo[e][1,2]oxaborinine-8-carboxylic acid

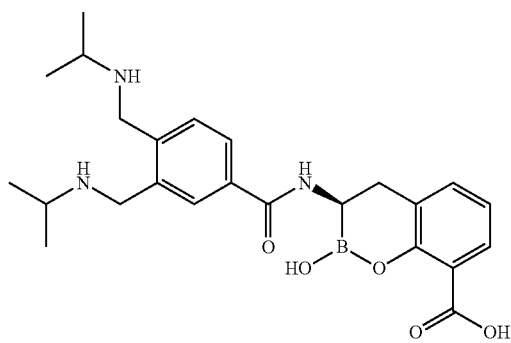 [SMILES: CC(C)NCc1ccc(C(=O)N[C@H]2Cc3cccc(C(=O)O)c3OB2O)cc1CNC(C)C]

The product was prepared in the same reaction described in Example 55. The product was purified by reverse phase HPLC and dried using lyophilization. ESI-MS m/z 454 (MH)+.

Example 57

(R)-3-(2-(4-(2-aminoethylamino)phenyl)acetamido)-2-hydroxy-3,4-dihydro-2H-benzo[e][1,2]oxaborinine-8-carboxylic acid

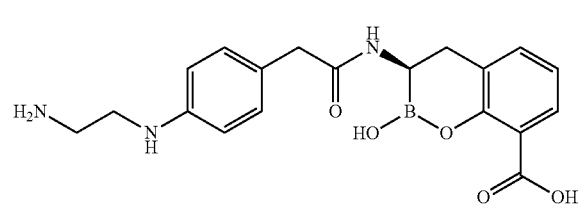 [SMILES: NCCNc1ccc(CC(=O)N[C@H]2Cc3cccc(C(=O)O)c3OB2O)cc1]

Step 1. Synthesis of 2-(4-(tert-butoxycarbonyl(2-(tert-butoxycarbonylamino)ethyl)amino)phenyl) acetic acid To 2-(4-aminophenyl)acetic acid (600 mg) in methanol (10 mL) was added tert-butyl 2-oxoethylcarbamate (800 mg) and sodium triacetoxyborohydride (1.3 g). The resulting reaction mixture was stirred at room temperature overnight. The solvent was them removed under reduced pressure. Water was then added and extracted with EtOAc. The organic phase was dried and concentrated. The residue was dissolved in 20 mL dioxane and 20 mL $H_2O$. To this solution was added di-tert-butyl dicarbonate (1.3 g) and $Na_2CO_3$ (936 mg). The resulting reaction mixture was stirred at room temperature for overnight. After removal of the solvent, the residue was purified by reverse phase chromatography to afford the acid (0.5 g).

Step 2. Synthesis of tert-butyl 3-((2R)-2-(2-(4-(tert-butoxycarbonyl(2-(tert-butoxycarbonylamino)ethyl) amino)phenyl)acetamido)-2-(2,9,9-trimethyl-3,5-dioxa-4-bora-tricyclo[6.1.1.0$^{2,6}$]dec-4-yl)ethyl)-2-methoxybenzoate Prepared from [(1S)-2-(3-tert-butoxycarbonyl-2-methoxy-phenyl)-1-chloro-ethyl]boronic acid (+) pinanediol ester and 2-(4-(tert-butoxycarbonyl(2-(tert-butoxycarbonylamino)ethyl)amino)phenyl)acetic acid following the procedure described in step 10 of Example 36. The crude product was purified by flash chromatography on silica gel (Hexane/EtOAc, 2:1 to 1:2). ESI-MS m/z 806.1 (MH)+.

Step 3. Synthesis of (R)-3-(2-(4-(2-aminoethylamino)phenyl)acetamido)-2-hydroxy-3,4-dihydro-2H-benzo[e][1,2]oxaborinine-8-carboxylic acid Prepared from tert-butyl 3-((2R)-2-(2-(4-(tert-butoxycarbonyl(2-(tert-butoxycarbonylamino)ethyl)amino)phenyl)acetamido)-2-(2,9,9-trimethyl-3,5-dioxa-4-bora-tricyclo[6.1.1.0$^{2,6}$]dec-4-yl)ethyl)-2-methoxybenzoate and $BCl_3$ following the procedure described in Step 2 of Example 3.

The crude product was purified by reverse phase preparative HPLC and dried using lyophilization. ESI-MS m/z 384 (MH)+.

Example 58

(R)-3-(2-(3,4-bis(2-aminoethoxy)phenyl)acetamido)-2-hydroxy-3,4-dihydro-2H-benzo[e][1,2]oxaborinine-8-carboxylic acid Step 1. Synthesis of 2-(3,4-bis(2-(tert-butoxycarbonylamino)ethoxy)phenyl)acetic acid To methyl 2-(3,4-dihydroxyphenyl)acetate (1.0 g) in DMF (10 mL) was added tert-butyl 2-bromoethylcarbamate (2.7 g) and $K_2CO_3$ (1.7 g). The resulting reaction mixture was stirred at 60° C. overnight. Water was added and the aqueous phase extracted with EtOAc. The organic phase was then dried and concentrated. The residue was purified by flash chromatography. The product was obtained as a mixture of mono- and bis-alkylation. The mixture was then dissolved in MeOH and THF (10 mL, 1:1) and IN NaOH was added. The resulting reaction mixture was stirred at room temperature overnight. IN HCl was added to acidify the solution. The aqueous phase was extracted with EtOAc (3×). The organic phases were combined, dried and concentrated. The title product was obtained by reverse phase chromatography purification (0.5 g).

Step 2. Synthesis of tert-butyl 3-((2R)-2-(2-(3,4-bis (2-(tert-butoxycarbonylamino)ethoxy)phenyl)acetamido)-2-(2,9,9-trimethyl-3,5-dioxa-4-bora-tricyclo [6.1.1.0$^{2,6}$]dec-4-yl)ethyl)-2-methoxybenzoate Prepared from [(1S)-2-(3-tert-butoxycarbonyl-2-methoxy-phenyl)-1-chloro-ethyl]boronic acid (+) pinanediol ester and 2-(3,4-bis(2-(tert-butoxycarbonylamino)ethoxy)phenyl) acetic acid following the procedure described in step 10 of Example 36. The product was purified by flash chromatography on silica gel (Hexane/EtOAc, 2:1 to 1:2).

Step 3. Synthesis of (R)-3-(2-(3,4-bis(2-aminoethoxy)phenyl)acetamido)-2-hydroxy-3,4-dihydro-2H-benzo[e][1,2]oxaborinine-8-carboxylic acid Prepared from tert-butyl 3-((2R)-2-(2-(3,4-bis(2-(tert-butoxycarbonylamino)ethoxy)phenyl)acetamido)-2-(2,9,9-trimethyl-3,5-dioxa-4-bora-tricyclo[6.1.1.0$^{2,6}$]dec-4-yl)ethyl)-2-methoxybenzoate and $BCl_3$ following the procedure described in Step 2 of Example 3. The crude product was purified by reverse phase preparative HPLC and dried using lyophilization. ESI-MS m/z 444 (MH)+.

Example 59

(R)-3-(2-(4-(2-aminoethoxy)-3-hydroxyphenyl)acetamido)-2-hydroxy-3,4-dihydro-2H-benzo[e][1,2]oxaborinine-8-carboxylic acid

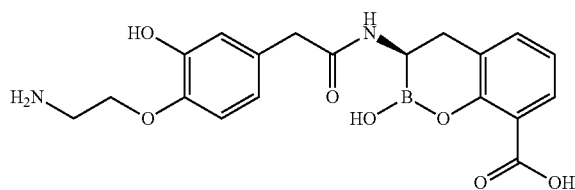 [SMILES: NCCOc1ccc(CC(=O)N[C@H]2Cc3cccc(C(=O)O)c3OB2O)cc1O]

Synthesis of (R)-3-(2-(4-(2-aminoethoxy)-3-hydroxyphenyl)acetamido)-2-hydroxy-3,4-dihydro-2H-benzo[e][1,2]oxaborinine-8-carboxylic acid 2-(4-(2-(tert-butoxycarbonylamino)ethoxy)-3-hydroxyphenyl)acetic acid was prepared from the reaction described in Step 1, Example 58. (R)-3-(2-(4-(2-aminoethoxy)-3-hydroxyphenyl)acetamido)-2-hydroxy-3,4-dihydro-2H-benzo[e][1,2]oxaborinine-8-carboxylic acid was obtained following the procedure described in Steps 2 and 3, Example 58. The product was purified by reverse phase preparative HPLC and dried using lyophilization. ESI-MS m/z 401 (MH)+.

Example 60

(R)-3-(2-(6-(2-aminoethylamino)pyridin-3-yl)acetamido)-2-hydroxy-3,4-dihydro-2H-benzo[e][1,2]oxaborinine-8-carboxylic acid

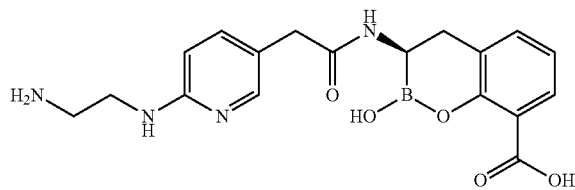

Step 1. Synthesis of methyl 2-(6-chloropyridin-3-yl)acetate

To a stirred solution of MeOH (25 mL) was added slowly acetyl chloride (3.5 mL).

After 30 min, 2-(6-chloropyridin-3-yl)acetic acid (2.5 g) was added and the resulting reaction mixture stirred at room temperature for 2 hr. Solvents were then removed. The residue was dissolved in EtOAc and washed with 10% NaHCO₃. The organic phase was dried and concentrated to afford the product (2.5 g).

Step 2. Synthesis of 2-chloro-5-(2-methoxy-2-oxoethyl)pyridine 1-oxide

To methyl 2-(6-chloropyridin-3-yl)acetate (2.5 g) in DCM (100 mL) was added mCPBA (4.6 g). The resulting reaction mixture was stirred at room temperature for 4 hr. The organic phase was washed with sat. NaHCO₃, dried over Na₂SO₄, and concentrated. The crude product was purified by flash chromatography to afford the title product (2.5 g).

Step 3. Synthesis 2-(2-(tert-butoxycarbonylamino)ethylamino)-5-(2-methoxy-2-oxoethyl)pyridine 1-oxide To 2-chloro-5-(2-methoxy-2-oxoethyl)pyridine 1-oxide (2.5 g) in t-BuOH (50 mL) was added DIEA (3.4 mL) and tert-butyl 2-aminoethylcarbamate (3.0 g). The resulting reaction mixture was stirred at 80° C. for 2 days. The solvent was then removed and the residue purified by reverse phase chromatography to afford the desired product (1.3 g).

Step 4. Synthesis of 2-(tert-butoxycarbonyl(2-(tert-butoxycarbonylamino)ethyl)amino)-5-(2-methoxy-2-oxoethyl)pyridine 1-oxide To 2-(2-(tert-butoxycarbonylamino)ethylamino)-5-(2-methoxy-2-oxoethyl)pyridine 1-oxide (1.3 g) in DCM (20 mL) was added di-tert-butyl dicarbonate (1.7 g), TEA (1.2 mL), and DMAP (0.1 mg). The resulting reaction mixture was stirred at room temperature for overnight. The solvent was removed and the residue was used in the next step without further purification.

Step 5. Synthesis of 2-(tert-butoxycarbonyl(2-(tert-butoxycarbonylamino)ethyl)amino)-5-(carboxymethyl)pyridine 1-oxide To 2-(tert-butoxycarbonyl(2-(tert-butoxycarbonylamino)ethyl)amino)-5-(2-methoxy-2-oxoethyl)pyridine 1-oxide from step 4 in a mixture of MeOH/THF (20 mL, 1:1) was added 1 N NaOH. The reaction mixture was stirred at room temperature overnight. IN HCl was added to acidify the solution to pH 4. The aqueous phase was extracted with EtOAc (3×). The combined organic phases were dried and concentrated. The residue was then purified by reverse phase chromatography to afford the product (1.4 g).

Step 6. Synthesis of 2-(6-(tert-butoxycarbonyl(2-(tert-butoxycarbonylamino)ethyl)amino)pyridin-3-yl)acetic acid To 2-(tert-butoxycarbonyl(2-(tert-butoxycarbonylamino)ethyl)amino)-5-(carboxymethyl)pyridine 1-oxide (0.78 g) in a mixture of THF (10 mL) and sat. NH₄Cl (10 mL) was added Zinc dust (0.65 g). The reaction mixture was stirred at room temperature for overnight. EtOAc was then added and washed with water. The organic phase was dried and concentrated to afford the desired product (0.5 g).

137

Step 7. Synthesis of tert-butyl 3-((2R)-2-(2-(6-(tert-butoxycarbonyl(2-(tert-butoxycarbonylamino)ethyl)amino)pyridin-3-yl)acetamido)-2-(2,9,9-trimethyl-3,5-dioxa-4-bora-tricyclo[6.1.1.0$^{2,6}$]dec-4-yl)ethyl)-2-methoxybenzoate Prepared from [(1S)-2-(3-tert-butoxycarbonyl-2-methoxy-phenyl)-1-chloro-ethyl]boronic acid (+) pinanediol ester and 2-(6-(tert-butoxycarbonyl(2-(tert-butoxycarbonylamino)ethyl)amino)pyridin-3-yl)acetic acid following the procedure described in Step 10 of Example 36. The crude product was purified by flash chromatography on silica gel. ESI-MS m/z 807.1 (MH)$^+$.

Step 8. Synthesis of (R)-3-(2-(6-(2-aminoethylamino)pyridin-3-yl)acetamido)-2-hydroxy-3,4-dihydro-2H-benzo[e][1,2]oxaborinine-8-carboxylic acid Prepared from tert-butyl 3-((2R)-2-(2-(6-(tert-butoxycarbonyl(2-(tert-butoxycarbonylamino)ethyl)amino)pyridin-3-yl)acetamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The crude product was purified by reverse phase preparative HPLC and dried using lyophilization. ESI-MS m/z 385 (MH)$^+$.

Example 61

(R)-2-(2-aminoethylamino)-5-(2-(8-carboxy-2-hydroxy-3,4-dihydro-2H-benzo[e][1,2]oxaborinin-3-ylamino)-2-oxoethyl)pyridine 1-oxide

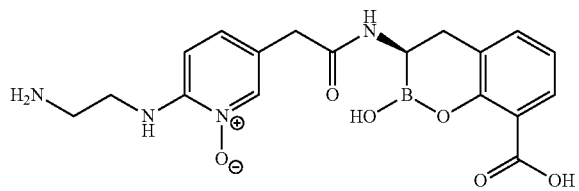 [SMILES: NCCNc1ccc(CC(=O)N[C@H]2Cc3cccc(C(=O)O)c3OB2O)c[n+]1[O-]]

Synthesis of (R)-2-(2-aminoethylamino)-5-(2-(8-carboxy-2-hydroxy-3,4-dihydro-2H-benzo[e][1,2]oxaborinin-3-ylamino)-2-oxoethyl)pyridine 1-oxide Prepared from 2-(tert-butoxycarbonyl(2-(tert-butoxycarbonylamino)ethyl)amino)-5-(carboxymethyl)pyridine 1-oxide (step 5, Example 60) following the same procedure described in Steps 7 and 8, Example 60. The product was purified by reverse phase preparative HPLC and dried using lyophilization. ESI-MS m/z 401 (MH)$^+$.

138

Example 62

(R)-3-(5,6-bis(aminomethyl)nicotinamido)-2-hydroxy-3,4-dihydro-2H-benzo[e][1,2]oxaborinine-8-carboxylic acid

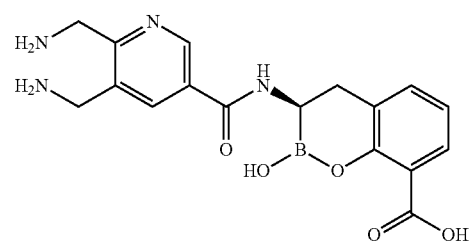 [SMILES: NCc1cc(C(=O)N[C@H]2Cc3cccc(C(=O)O)c3OB2O)cnc1CN]

Step 1. Synthesis of 5,6-bis((tert-butoxycarbonylamino)methyl)nicotinic acid

To methyl 5-bromo-6-chloronicotinate (1.1 g) in a flask was added potassium t-butoxycarbonyl amino methyl trifluoroborate (2.2 g), K$_2$CO$_3$ (3.62 g), and XPhos-Pd-G2 (500 mg). The mixture was flushed with argon three times. A mixture of t-BuOH and H$_2$O (18 mL, 1:1) was added. The reaction mixture was stirred at 80° C. for overnight. The reaction was diluted with EtOAc. The organic phase was washed with water and brine, dried, and concentrated. The product was obtained by flash chromatography on silica gel to afford methyl 5,6-bis((tert-butoxycarbonylamino)methyl)nicotinate (0.1 g). The ester was hydrolyzed to acid following the procedure described in Step 5, Example 60.

Step 2. Synthesis of tert-butyl 3-((2R)-2-(5,6-bis((tert-butoxycarbonylamino)methyl)nicotinamido)-2-(2,9,9-trimethyl-3,5-dioxa-4-bora-tricyclo[6.1.1.0$^{2,6}$]dec-4-yl)ethyl)-2-methoxybenzoate tert-butyl 3-((2R)-2-(2-(6-(tert-butoxycarbonyl(2-(tert-butoxycarbonylamino)ethyl)amino)pyridin-3-yl)acetamido)-2-(2,9,9-trimethyl-3,5-dioxa-4-bora-tricyclo[6.1.1.0$^{2,6}$]dec-4-yl)ethyl)-2-methoxybenzoate Prepared from [(1S)-2-(3-tert-butoxycarbonyl-2-methoxy-phenyl)-1-chloro-ethyl]boronic acid (+) pinanediol ester and 5,6-bis((tert-butoxycarbonylamino)methyl)nicotinic acid following the procedure described in Step 10 of Example 36. The crude product was purified by flash chromatography on silica gel. ESI-MS m/z 793.1 (MH)$^+$.

Step 3. Synthesis of (R)-3-(5,6-bis(aminomethyl)nicotinamido)-2-hydroxy-3,4-dihydro-2H-benzo[e][1,2]oxaborinine-8-carboxylic acid Prepared from tert-butyl 3-((2R)-2-(5,6-bis((tert-butoxycarbonylamino)methyl)nicotinamido)-2-(2,9,9-trimethyl-3,5-dioxa-4-bora-tricyclo[6.1.1.0$^{2,6}$]dec-4-yl)ethyl)-2-methoxybenzoate and BCl$_3$ following the procedure described in Step 2 of Example 3. The crude product was purified by reverse phase preparative HPLC and dried using lyophilization. ESI-MS m/z 371 (MH)$^+$.

TABLE 1

| | Examples of compounds | | |
|---|---|---|---|
| Example | Structure | MW | ESI-MS (m/z) for[MH]+ |
| 1 | | 351 | 352 |
| 2 | | 361 | 362 |
| 3 | | 394 | 395 |
| 4 | | 372 | 373 |
| 5 | | 366 | 367 |
| 6 | | 386 | 387 |

TABLE 1-continued

Examples of compounds

| Example | Structure | MW | ESI-MS (m/z) for [MH]+ |
|---|---|---|---|
| 7 | 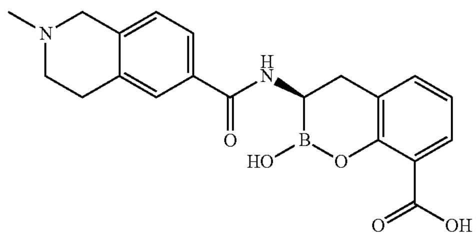 [SMILES: CN1CCc2cc(C(=O)N[C@H]3Cc4cccc(C(=O)O)c4OB3O)ccc2C1] | 380 | 381 |
| 8 | 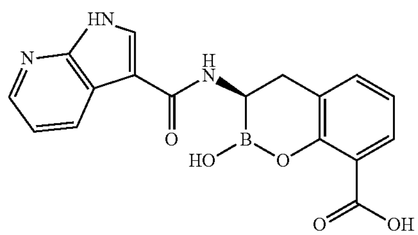 [SMILES: O=C(O)c1cccc2c1OB(O)[C@@H](NC(=O)c1c[nH]c3ncccc13)C2] | 351 | 352 |
| 9 | 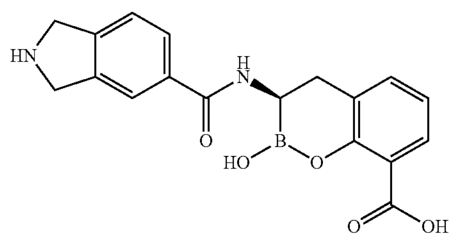 [SMILES: O=C(N[C@H]1Cc2cccc(C(=O)O)c2OB1O)c1ccc2c(c1)CNC2] | 352 | 353 |
| 10 | 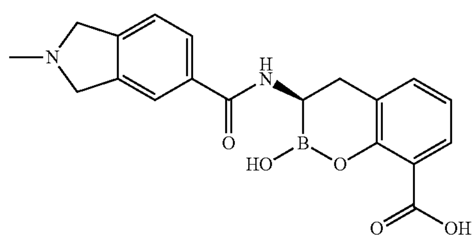 [SMILES: CN1Cc2ccc(C(=O)N[C@H]3Cc4cccc(C(=O)O)c4OB3O)cc2C1] | 366 | 367 |
| 11 | 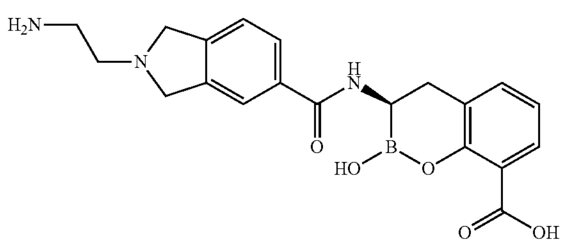 [SMILES: NCCN1Cc2ccc(C(=O)N[C@H]3Cc4cccc(C(=O)O)c4OB3O)cc2C1] | 395 | 396 |
| 12 | 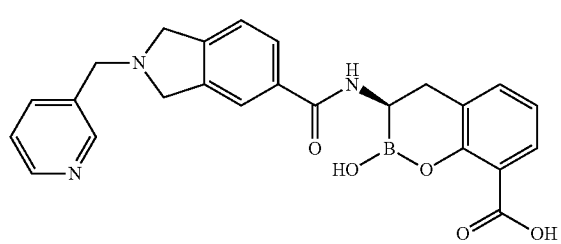 [SMILES: O=C(N[C@H]1Cc2cccc(C(=O)O)c2OB1O)c1ccc2c(c1)CN(Cc1cccnc1)C2] | 343 | 344 |

TABLE 1-continued

Examples of compounds

| Example | Structure | MW | ESI-MS (m/z) for[MH]+ |
|---------|-----------|-----|----------------------|
| 13 | 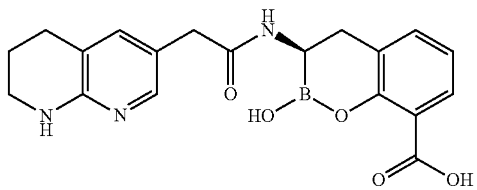 [SMILES: O=C(Cc1cnc2c(c1)CCCN2)N[C@H]1Cc2cccc(C(=O)O)c2OB1O] | 381 | 382 |
| 14 | 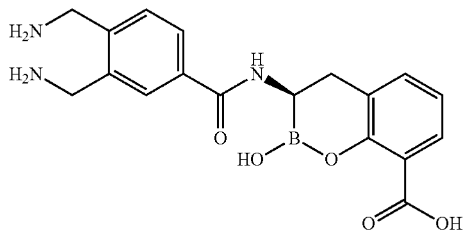 [SMILES: NCc1ccc(C(=O)N[C@H]2Cc3cccc(C(=O)O)c3OB2O)cc1CN] | 369 | 370 |
| 15 | 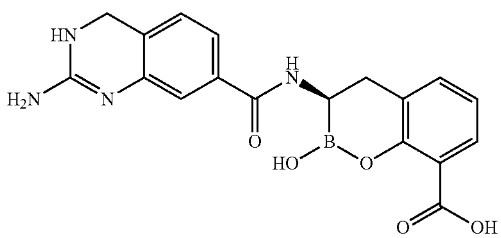 [SMILES: NC1=Nc2cc(C(=O)N[C@H]3Cc4cccc(C(=O)O)c4OB3O)ccc2CN1] | 380 | 381 |
| 16 | 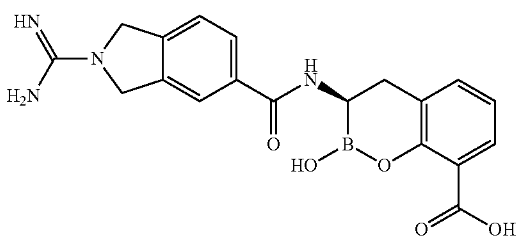 [SMILES: N=C(N)N1Cc2ccc(C(=O)N[C@H]3Cc4cccc(C(=O)O)c4OB3O)cc2C1] | 394 | 395 |
| 17 | 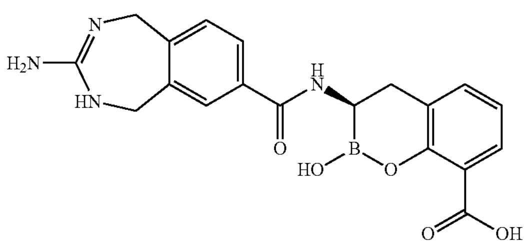 [SMILES: NC1=NCc2ccc(C(=O)N[C@H]3Cc4cccc(C(=O)O)c4OB3O)cc2CN1] | 394 | 395 |
| 18 | 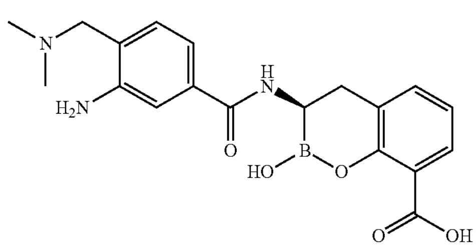 [SMILES: CN(C)Cc1ccc(C(=O)N[C@H]2Cc3cccc(C(=O)O)c3OB2O)cc1N] | 383 | 384 |

TABLE 1-continued

Examples of compounds

| Example | Structure | MW | ESI-MS (m/z) for[MH]+ |
|---|---|---|---|
| 19 | 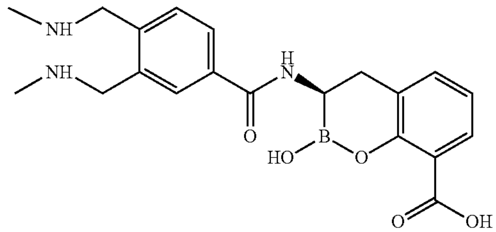 [SMILES: CNCc1ccc(C(=O)N[C@H]2Cc3cccc(C(=O)O)c3OB2O)cc1CNC] | 397 | 398 |
| 20 | 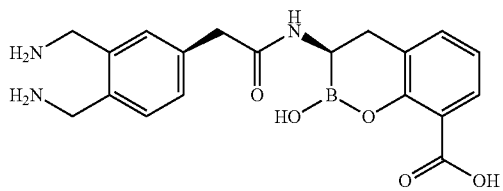 | 383 | 384 |
| 21 | 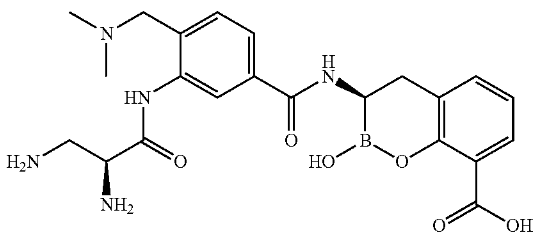 [SMILES: CN(C)Cc1ccc(C(=O)N[C@H]2Cc3cccc(C(=O)O)c3OB2O)cc1NC(=O)[C@@H](N)CN] | 469 | 470 |
| 22 | 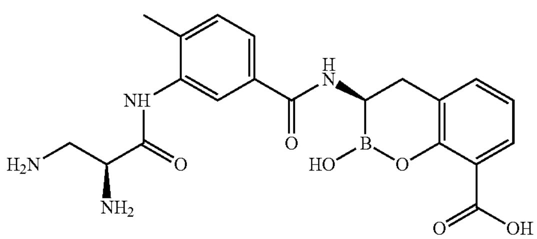 [SMILES: Cc1ccc(C(=O)N[C@H]2Cc3cccc(C(=O)O)c3OB2O)cc1NC(=O)[C@@H](N)CN] | 426 | 427 |
| 23 | 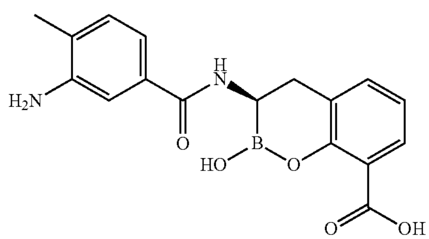 [SMILES: Cc1ccc(C(=O)N[C@H]2Cc3cccc(C(=O)O)c3OB2O)cc1N] | 340 | 341 |
| 24 | 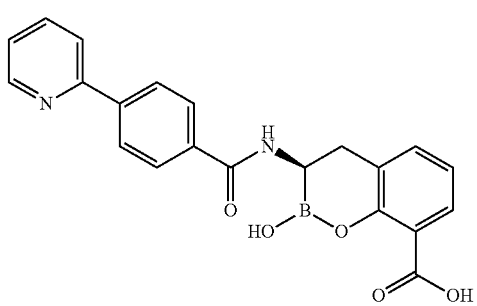 [SMILES: O=C(N[C@H]1Cc2cccc(C(=O)O)c2OB1O)c1ccc(-c2ccccn2)cc1] | 388 | 389 |

TABLE 1-continued

Examples of compounds

| Example | Structure | MW | ESI-MS (m/z) for[MH]+ |
|---|---|---|---|
| 25 | 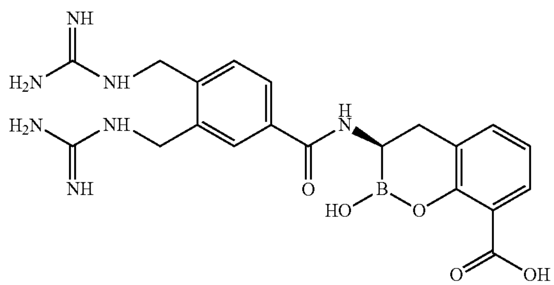 [SMILES: N=C(N)NCc1ccc(C(=O)N[C@H]2Cc3cccc(C(=O)O)c3OB2O)cc1CNC(=N)N] | 453 | 454 |
| 26 | 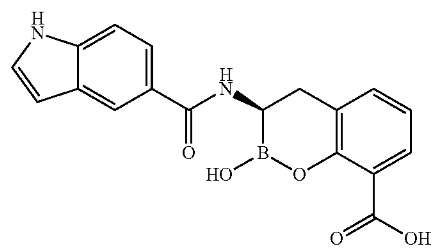 [SMILES: O=C(N[C@H]1Cc2cccc(C(=O)O)c2OB1O)c1ccc2[nH]ccc2c1] | 350 | 351 |
| 27 | 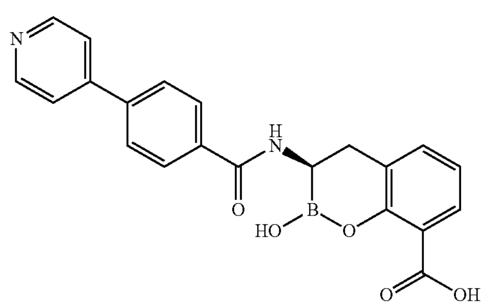 [SMILES: O=C(N[C@H]1Cc2cccc(C(=O)O)c2OB1O)c1ccc(-c2ccncc2)cc1] | 388 | 389 |
| 28 | 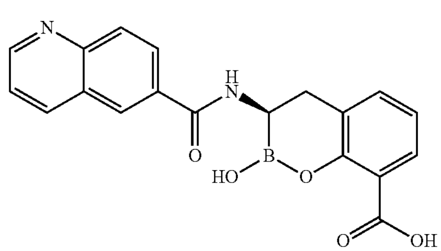 | 362 | 363 |
| 29 | 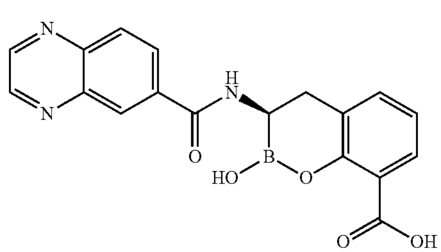 | 363 | 364 |

TABLE 1-continued

Examples of compounds

| Example | Structure | MW | ESI-MS (m/z) for [MH]+ |
|---|---|---|---|
| 30 | 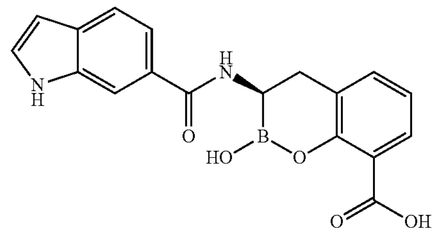 [SMILES: O=C(N[C@H]1Cc2cccc(C(=O)O)c2OB1O)c1ccc2cc[nH]c2c1] | 350.1 | 351 |
| 31 | 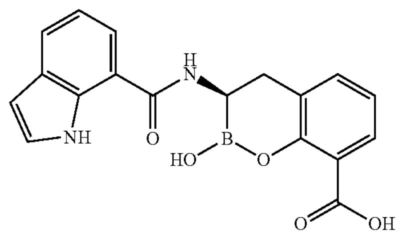 [SMILES: O=C(O)c1cccc2c1OB(O)[C@@H](NC(=O)c1cccc3cc[nH]c13)C2] | 350.1 | 351 |
| 32 | 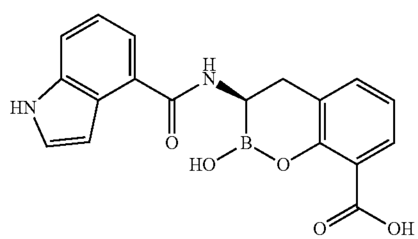 [SMILES: O=C(O)c1cccc2c1OB(O)[C@@H](NC(=O)c1cccc3[nH]ccc13)C2] | 350.1 | 351 |
| 33 | 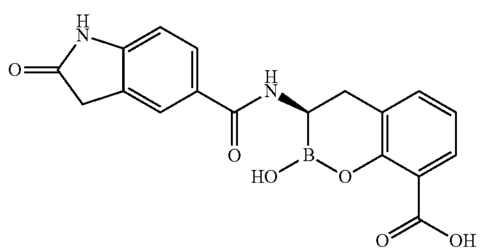 [SMILES: O=C1Cc2cc(C(=O)N[C@H]3Cc4cccc(C(=O)O)c4OB3O)ccc2N1] | 366.1 | 357 |
| 34 | 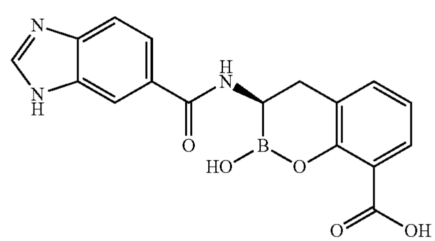 | 351.1 | 352 |
| 35 | 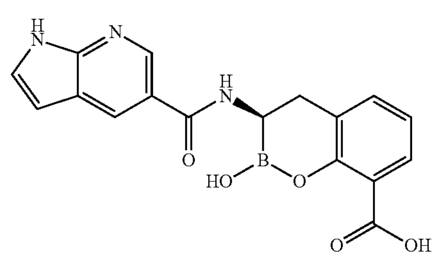 [SMILES: O=C(N[C@H]1Cc2cccc(C(=O)O)c2OB1O)c1cnc2[nH]ccc2c1] | 351.1 | 352 |

TABLE 1-continued

Examples of compounds

| Example | Structure | MW | ESI-MS (m/z) for[MH]+ |
|---------|-----------|------|------|
| 36 | 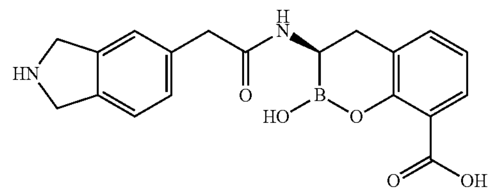 [SMILES: O=C(Cc1ccc2c(c1)CNC2)N[C@H]1Cc2cccc(C(=O)O)c2OB1O] | 366.1 | 367 |
| 37 | 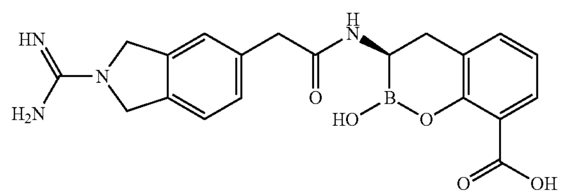 [SMILES: N=C(N)N1Cc2ccc(CC(=O)N[C@H]3Cc4cccc(C(=O)O)c4OB3O)cc2C1] | 408.2 | 409 |
| 38 | 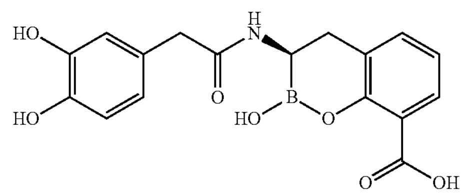 [SMILES: O=C(Cc1ccc(O)c(O)c1)N[C@H]1Cc2cccc(C(=O)O)c2OB1O] | 357.1 | 358 |
| 39 | 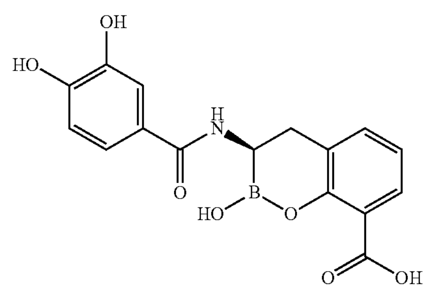 [SMILES: O=C(N[C@H]1Cc2cccc(C(=O)O)c2OB1O)c1ccc(O)c(O)c1] | 343.1 | 344 |
| 40 | 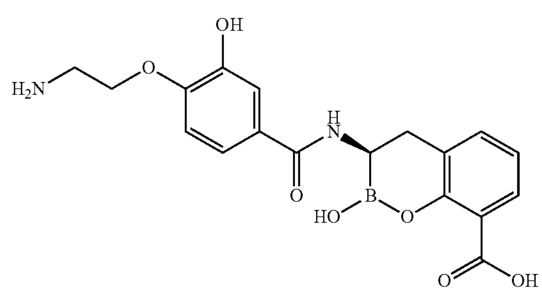 [SMILES: NCCOc1ccc(C(=O)N[C@H]2Cc3cccc(C(=O)O)c3OB2O)cc1O] | 386.1 | 387 |
| 41 | 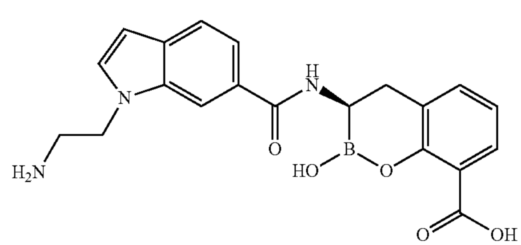 [SMILES: NCCn1ccc2ccc(C(=O)N[C@H]3Cc4cccc(C(=O)O)c4OB3O)cc21] | 393.2 | 394 |

TABLE 1-continued

Examples of compounds

| Example | Structure | MW | ESI-MS (m/z) for[MH]+ |
|---------|-----------|------|------------------------|
| 42 | 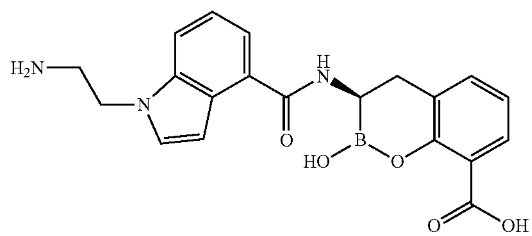 [SMILES: NCCn1ccc2c(C(=O)N[C@H]3Cc4cccc(C(=O)O)c4OB3O)cccc21] | 393.2 | 394 |
| 43 | 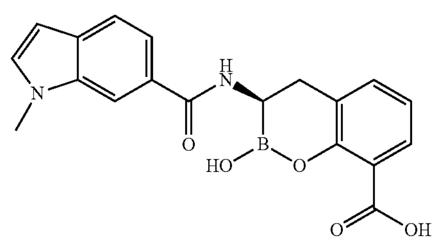 [SMILES: Cn1ccc2ccc(C(=O)N[C@H]3Cc4cccc(C(=O)O)c4OB3O)cc21] | 364.1 | 365 |
| 44 | 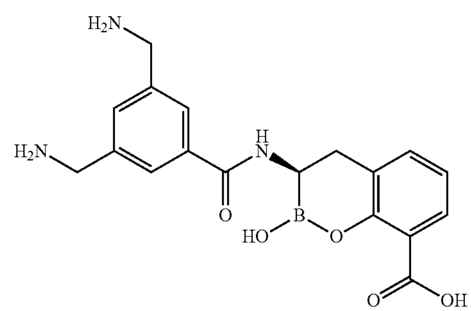 [SMILES: NCc1cc(CN)cc(C(=O)N[C@H]2Cc3cccc(C(=O)O)c3OB2O)c1] | 369.1 | 370 |
| 45 | 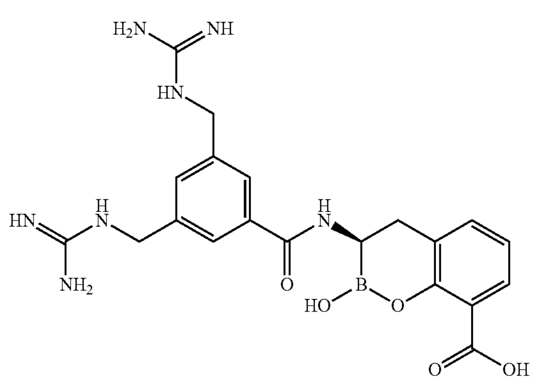 [SMILES: N=C(N)NCc1cc(CNC(=N)N)cc(C(=O)N[C@H]2Cc3cccc(C(=O)O)c3OB2O)c1] | 453.2 | 454 |
| 46 | 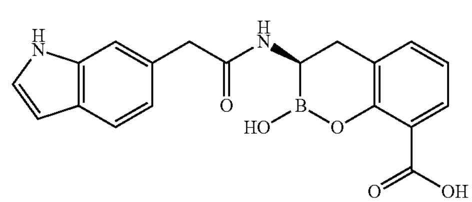 [SMILES: O=C(Cc1ccc2cc[nH]c2c1)N[C@H]1Cc2cccc(C(=O)O)c2OB1O] | 364.2 | 365 |

TABLE 1-continued

Examples of compounds

| Example | Structure | MW | ESI-MS (m/z) for [MH]+ |
|---|---|---|---|
| 47 | 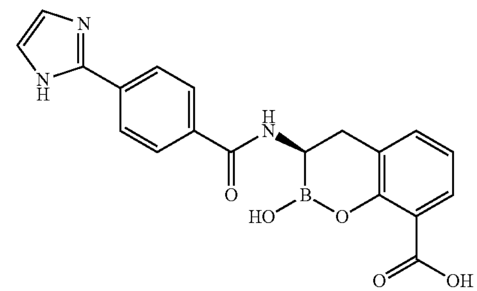 [SMILES: O=C(N[C@H]1Cc2cccc(C(=O)O)c2OB1O)c1ccc(-c2ncc[nH]2)cc1] | 377.2 | 378 |
| 48 | 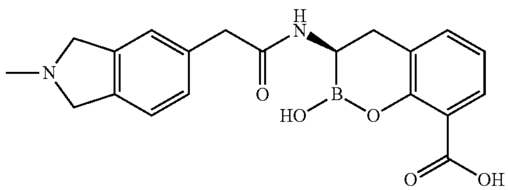 [SMILES: CN1Cc2ccc(CC(=O)N[C@H]3Cc4cccc(C(=O)O)c4OB3O)cc2C1] | 380.2 | 381 |
| 49 | 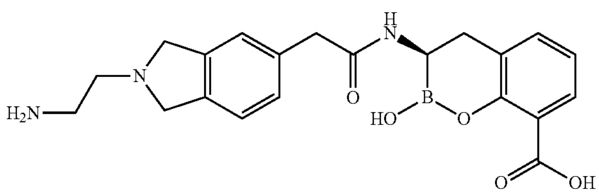 [SMILES: NCCN1Cc2ccc(CC(=O)N[C@H]3Cc4cccc(C(=O)O)c4OB3O)cc2C1] | 409.2 | 410 |
| 50 | 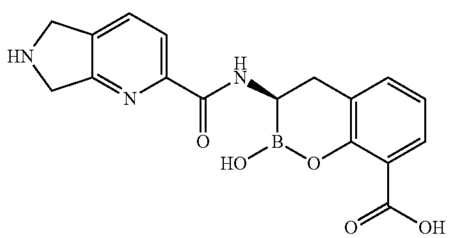 [SMILES: O=C(N[C@H]1Cc2cccc(C(=O)O)c2OB1O)c1ccc2c(n1)CNC2] | 353.1 | 354 |
| 51 | 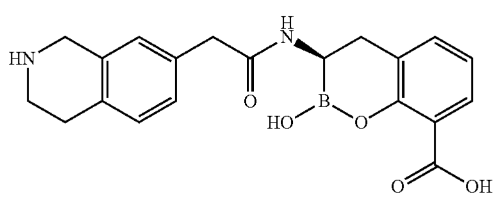 [SMILES: O=C(Cc1ccc2c(c1)CNCC2)N[C@H]1Cc2cccc(C(=O)O)c2OB1O] | 380.2 | 381 |
| 52 | 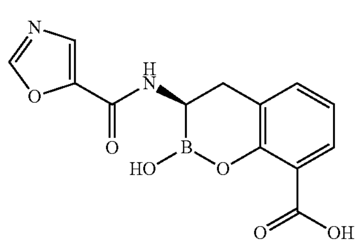 [SMILES: O=C(N[C@H]1Cc2cccc(C(=O)O)c2OB1O)c1cnco1] | 302.0 | 303 |

TABLE 1-continued

Examples of compounds

| Example | Structure | MW | ESI-MS (m/z) for[MH]+ |
|---|---|---|---|
| 53 | 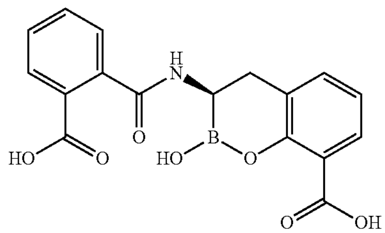 [SMILES: O=C(O)c1ccccc1C(=O)N[C@H]1Cc2cccc(C(=O)O)c2OB1O] | 355.1 | 356 |
| 54 | 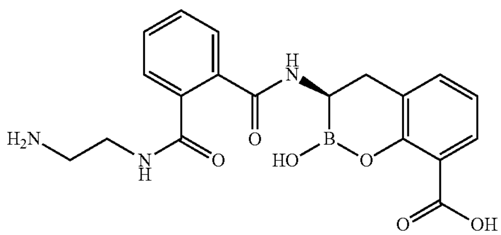 [SMILES: NCCNC(=O)c1ccccc1C(=O)N[C@H]1Cc2cccc(C(=O)O)c2OB1O] | 397.2 | 398 |
| 55 | 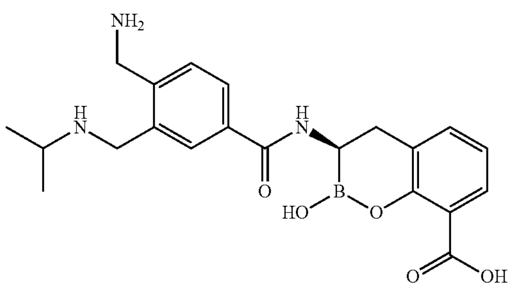 [SMILES: CC(C)NCc1cc(C(=O)N[C@H]2Cc3cccc(C(=O)O)c3OB2O)ccc1CN] | 411.2 | 412 |
| 56 | 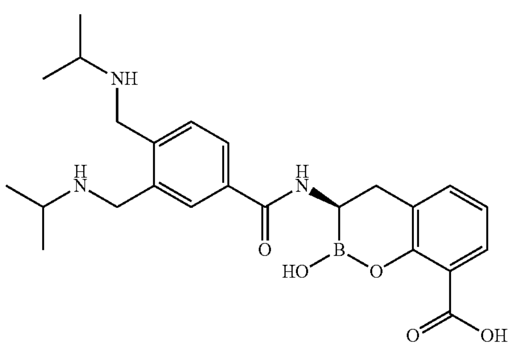 [SMILES: CC(C)NCc1ccc(C(=O)N[C@H]2Cc3cccc(C(=O)O)c3OB2O)cc1CNC(C)C] | 453.2 | 454 |
| 57 | 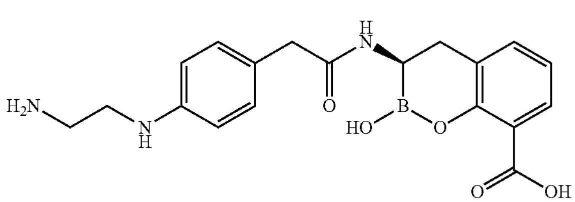 | 383.2 | 384 |
| 58 | 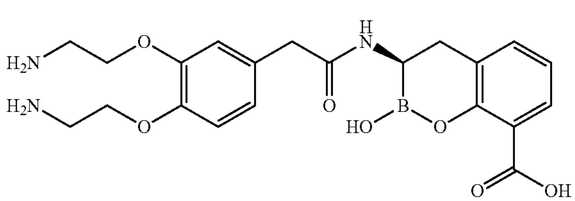 [SMILES: NCCOc1ccc(CC(=O)N[C@H]2Cc3cccc(C(=O)O)c3OB2O)cc1OCCN] | 443.2 | 444 |

TABLE 1-continued

Examples of compounds

| Example | Structure | MW | ESI-MS (m/z) for [MH]+ |
|---|---|---|---|
| 59 | 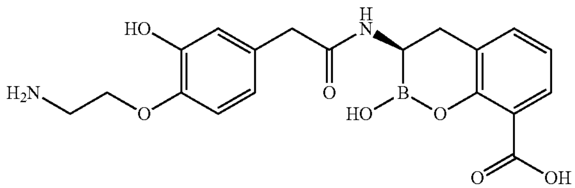 [SMILES: NCCOc1ccc(CC(=O)N[C@H]2Cc3cccc(C(=O)O)c3OB2O)cc1O] | 400.2 | 401 |
| 60 | 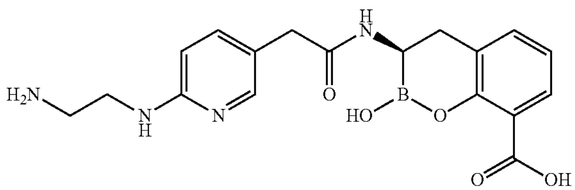 | 384.2 | 385 |
| 61 | 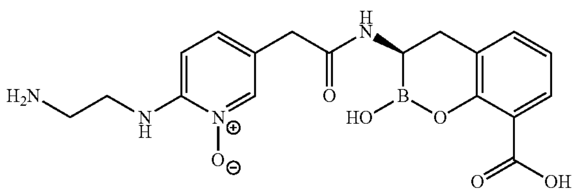 [SMILES: NCCNc1ccc(CC(=O)N[C@H]2Cc3cccc(C(=O)O)c3OB2O)c[n+]1[O-]] | 400.2 | 401 |
| 62 | 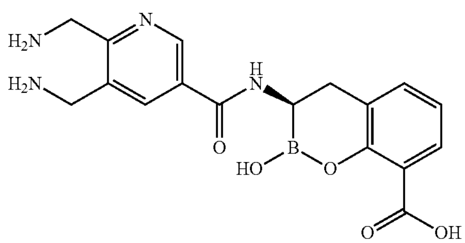 [SMILES: NCc1cc(C(=O)N[C@H]2Cc3cccc(C(=O)O)c3OB2O)cnc1CN] | 370.1 | 371 |
| 63 | 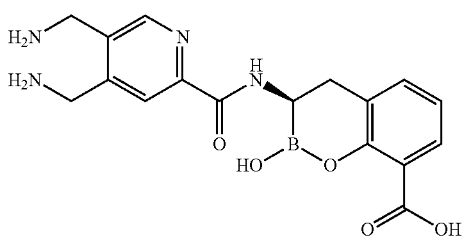 | 370.1 | |
| 64 | 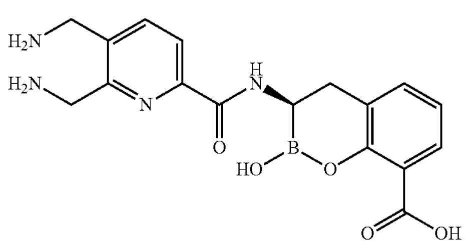 [SMILES: NCc1ccc(C(=O)N[C@H]2Cc3cccc(C(=O)O)c3OB2O)nc1CN] | 370.1 | |
| 65 | 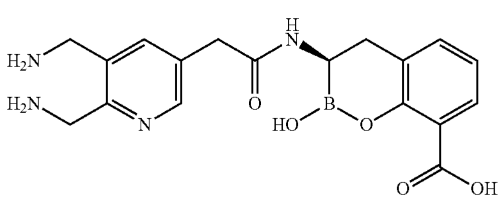 [SMILES: NCc1cc(CC(=O)N[C@H]2Cc3cccc(C(=O)O)c3OB2O)cnc1CN] | 384.2 | |

TABLE 1-continued

Examples of compounds

| Example | Structure | MW | ESI-MS (m/z) for[MH]+ |
|---|---|---|---|
| 66 | 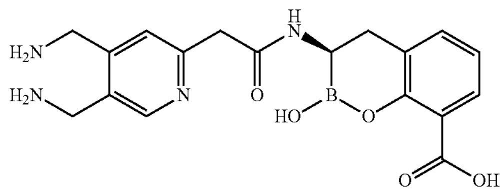 [SMILES: NCc1cnc(CC(=O)N[C@H]2Cc3cccc(C(=O)O)c3OB2O)cc1CN] | 384.2 | |
| 67 | 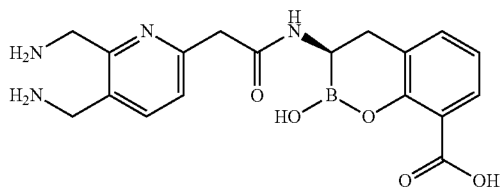 [SMILES: NCc1ccc(CC(=O)N[C@H]2Cc3cccc(C(=O)O)c3OB2O)nc1CN] | 384.2 | |
| 68 | 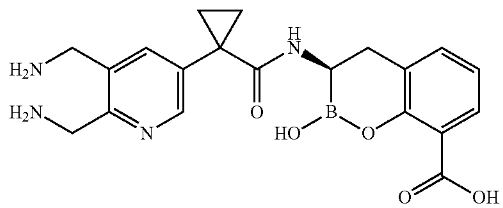 [SMILES: NCc1cc(C2(C(=O)N[C@H]3Cc4cccc(C(=O)O)c4OB3O)CC2)cnc1CN] | 410.2 | |
| 69 | 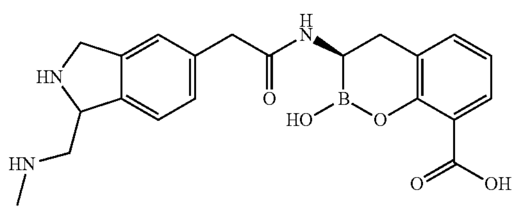 [SMILES: CNCC1NCc2cc(CC(=O)N[C@H]3Cc4cccc(C(=O)O)c4OB3O)ccc21] | 409.2 | |
| 70 | 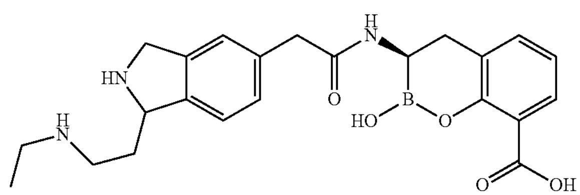 [SMILES: CCNCCC1NCc2cc(CC(=O)N[C@H]3Cc4cccc(C(=O)O)c4OB3O)ccc21] | 437.2 | |
| 71 | 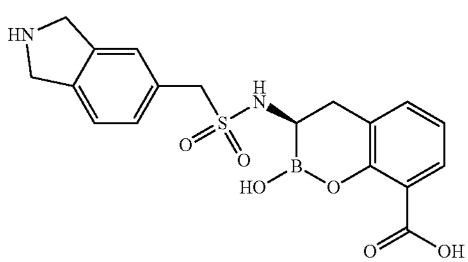 [SMILES: O=C(O)c1cccc2c1OB(O)[C@@H](NS(=O)(=O)Cc1ccc3c(c1)CNC3)C2] | 402.1 | |
| 72 | 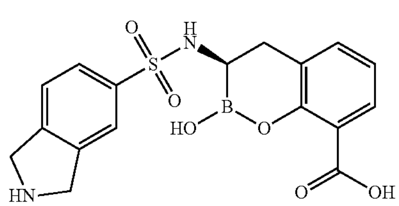 [SMILES: O=C(O)c1cccc2c1OB(O)[C@@H](NS(=O)(=O)c1ccc3c(c1)CNC3)C2] | 388.1 | |

TABLE 1-continued
Examples of compounds
| Example | Structure | MW | ESI-MS (m/z) for[MH]+ |
|---|---|---|---|
| 73 | 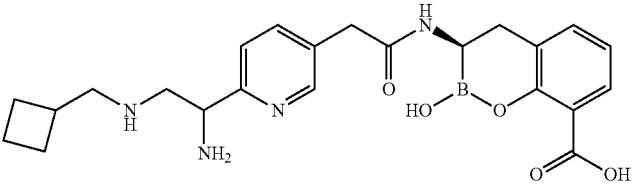 [SMILES: NC(CNCC1CCC1)c1ccc(CC(=O)N[C@H]2Cc3cccc(C(=O)O)c3OB2O)cn1] | 452.2 | |
| 74 | 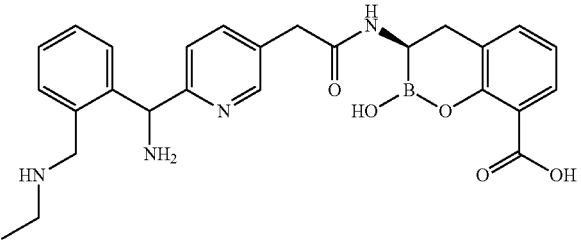 [SMILES: CCNCc1ccccc1C(N)c1ccc(CC(=O)N[C@H]2Cc3cccc(C(=O)O)c3OB2O)cn1] | 488.2 | |
| 75 | 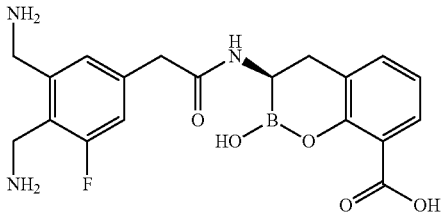 [SMILES: NCc1cc(CC(=O)N[C@H]2Cc3cccc(C(=O)O)c3OB2O)cc(F)c1CN] | 401.2 | |
| 76 | 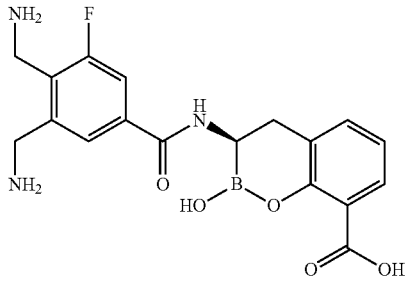 [SMILES: NCc1cc(C(=O)N[C@H]2Cc3cccc(C(=O)O)c3OB2O)cc(F)c1CN] | 387.1 | |
| 77 | 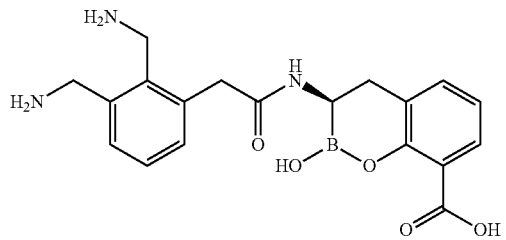 [SMILES: NCc1cccc(CC(=O)N[C@H]2Cc3cccc(C(=O)O)c3OB2O)c1CN] | 383.2 | |
| 78 | 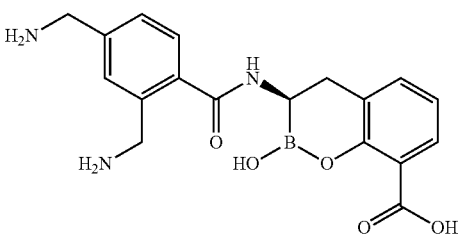 [SMILES: NCc1ccc(C(=O)N[C@H]2Cc3cccc(C(=O)O)c3OB2O)c(CN)c1] | 369.1 | |

TABLE 1-continued

Examples of compounds

| Example | Structure | MW | ESI-MS (m/z) for [MH]+ |
|---|---|---|---|
| 79 | 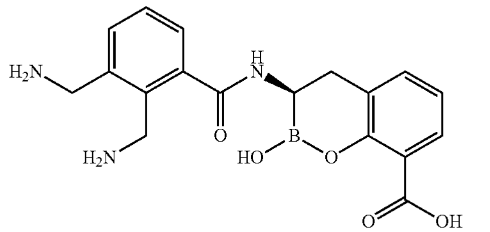 [SMILES: NCc1cccc(C(=O)N[C@H]2Cc3cccc(C(=O)O)c3OB2O)c1CN] | 369.1 | |
| 80 | 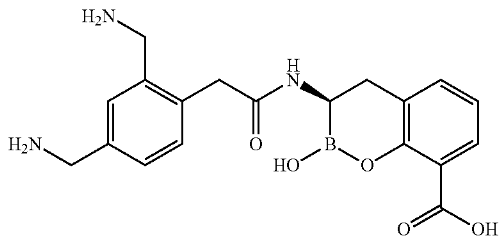 [SMILES: NCc1ccc(CC(=O)N[C@H]2Cc3cccc(C(=O)O)c3OB2O)c(CN)c1] | 383.2 | |
| 81 | 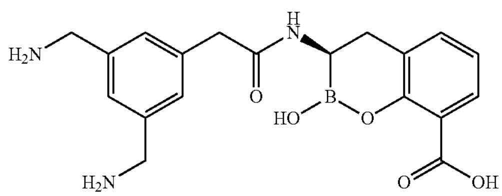 [SMILES: NCc1cc(CN)cc(CC(=O)N[C@H]2Cc3cccc(C(=O)O)c3OB2O)c1] | 383.2 | |
| 82 | 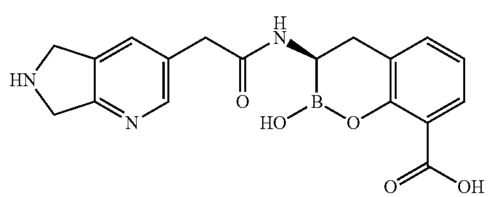 | 367.2 | |
| 83 | 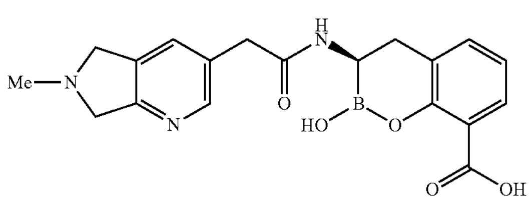 [SMILES: CN1Cc2cc(CC(=O)N[C@H]3Cc4cccc(C(=O)O)c4OB3O)cnc2C1] | 381.2 | |
| 84 | 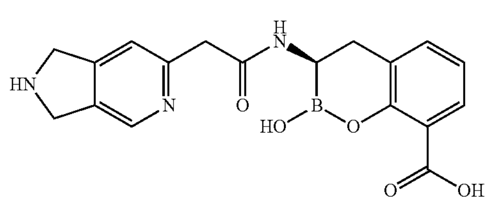 | 367.2 | |
| 85 | 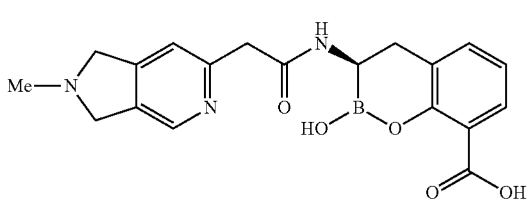 | 381.2 | |

Example 86

Parenteral Composition of a Compound of Formula I or Formula Ia

To prepare a parenteral pharmaceutical composition suitable for administration by injection, 100 mg of a compound of Formula I or Formula Ia, or a water soluble pharmaceutically acceptable salt thereof, is dissolved in DMSO and then mixed with 10 ml of 0.9% sterile saline solution. The mixture is incorporated into a dosage unit suitable for administration by injection.

Example 87

Oral Composition of a Compound of Formula I or Formula Ia

To prepare a pharmaceutical composition for oral delivery, 400 mg of a compound of Formula I or Formula Ia and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

BIOLOGICAL EXAMPLES

Example I

Experimental Method for β-Lactamase Enzyme Assays

Isolation of β-Lactamases.

For SHV-5, Kpc-2, p99AmpC and OXA-1 β-lactamases, E. coli BL21(DE3) bacterial cells carrying expression plasmids (expressed as native untagged proteins) for the individual β-lactamases were grown in 1 L of Superbroth (Teknova Inc. Hollister, CA) supplemented with 100 μg/ml kanamycin selection and 1×5052 (0.5% glycerol, 0.05% glucose and 0.2% α-lactose) at 35° C. for 18-20 hours. Cells were harvested by centrifugation (4,000×g, 4° C., 20 min), resuspended in 50 ml of 10 mM HEPES pH 7.5 (1/20 of the initial volume). The cells were lysed by sonication (5 pulses of 45 seconds) at 45 W on ice. The lysates were clarified by centrifugation at 10,000×g for 40 minutes at 4° C. Samples were diluted 5-fold in 50 mM sodium acetate pH 5.0, stored overnight at 4° C., after which they were centrifuged at 10,000×g for 30 minutes to clarify, and filtered through 0.45 μm filters. The samples were loaded onto a 5 ml Capto S sepharose cation exchange column (GE Healthcare) pre-equilibrated with 50 mM sodium acetate pH 5.0. The column was washed with 5 column volumes of 50 mM sodium acetate pH 5.0 to wash out unbound protein and a linear gradient of NaCl (0 to 500 mM) was used to elute the protein (over 16 CV) from the column. Fractions were assayed for β-lactamase activity using Centa (Calbiochem, Gibbstown, N.J.) or Nitrocefin (EMD Millipore chemicals, Darmstadt, Germany) as a reporter β-lactamase substrate for activity in the isolated fractions. Active fractions were pooled, concentrated and further purified by gel filtration chromatography on a Superdex 75 prep grade gel filtration column (GE Healthcare, Piscataway, N.J.) pre-equilibrated in 50 mM Hepes pH 7.5, 150 mM NaCl. Active fractions were pooled concentrated, quantitated by BCA protein determination (Thermo Scientific, Rockford, Ill.), dialyzed into PBS and frozen at −80° C. in 20% glycerol until use.

For Vim-2 metallo β-lactamase, the procedure was identical with the following exceptions, first the protein was not pH adjusted to pH 5 with 50 mM sodium acetate, second, the chromatography step was changed to a 5 ml Q sepharose anion exchange column pre-equilibrated with 50 mM Hepes pH 7.5, and elution of the protein was achieved by a linear gradient of NaCl (0-600 mM). Finally, the VIM-2 purification required a second run ($3^{rd}$ step) on the Q sepharose anion exchange column to achieve acceptable purity (>90%).

β-Lactamase Inhibition.

To determine the level of inhibition of β-lactamase enzymes, compounds were diluted in PBS at pH 7.4 to yield concentrations ranging from 100 to 0.00005 μM in 96-well microtiter plates. An equal volume of diluted enzyme stock was added, and the plates were incubated at 37° C. for 15 min. Nitrocefin was used as substrate for p99 AmpC, VIM-2 and OXA-1 and dispensed into each well at a final concentration of 100 μM. Absorbance at 486 nm was immediately monitored for 10 min using a Biotek Powerwave XS2 microplate spectrophotometer using the GEN5 softweare package (Biotek Instruments, Winooski Vt.). In an analogous fashion, imipenem was used as substrate for Kpc-2 and Cefotaxime was used for SHV-5, while changes in absorbance upon hydrolysis of the β-lactam ring were monitored at 300 nm and 260 nm respectively in UV-transparent 96-well microtiter assay plates. Maximum rates of hydrolysis were compared to those in control wells (without inhibitors), and percentages of enzyme inhibition were calculated for each concentration of inhibitor. The concentration of inhibitor needed to reduce the initial rate of hydrolysis of substrate by 50% ($IC_{50}$) was calculated as the residual activity of β-lactamase at 486 nm using GraFit version 7 kinetics software package (Erithacus Software, Surrey, UK).

Example II

Inhibition of Diverse β-Lactamases by Exemplary Compounds

Using the methodology described above, examples of the current invention were evaluated for their ability to inhibit β-lactamase enzymes from all four Ambler classifications (A through D). The results of these assays are summarized in Table 2 for representative enzymes across different subtypes (note SHV-5 represents an Ambler Class A Extended Spectrum β-Lactamases, KPC-2 exemplifies a Class A carbapenemase, P99 represents chromosomal Class C AmpC, OXA-1 represents a Class D oxacillinase and VIM-2 represents a class B zinc-dependent metallo-β-lactamase also possessing carbapenemase activity), where A represents an $IC_{50}$ of 10-100 µM, B represents an $IC_{50}$ of 1 to 10 µM, C represents an $IC_{50}$ of 0.1 to 1 µM, and D represents an $IC_{50}$ of <0.1 µM. NT=Not tested.

TABLE 2

Inhibition of Diverse β-Lactamases by Exemplary Compounds

| EXAMPLE | Class A SHV-5 | Class A KPC-2 | Class B VIM-2 | Class C AmpC | Class D OXA-1 |
|---|---|---|---|---|---|
| 1 | D | D | C | D | D |
| 2 | D | D | B | D | D |
| 3 | A | D | B | D | C |
| 4 | D | D | C | D | D |
| 5 | D | D | C | D | D |
| 6 | D | D | B | D | D |
| 7 | D | D | C | D | C |
| 8 | D | C | B | D | NT |
| 9 | D | D | D | D | D |
| 10 | D | D | D | D | D |
| 11 | D | D | C | D | D |
| 12 | D | D | C | D | D |
| 13 | D | C | B | D | D |
| 14 | C | C | D | D | D |
| 15 | D | C | B | D | C |
| 16 | D | D | D | D | D |
| 17 | D | D | D | D | D |
| 18 | D | D | C | D | D |
| 19 | D | D | D | D | D |
| 20 | D | D | D | D | D |
| 21 | C | D | D | D | D |
| 22 | B | C | C | D | D |
| 23 | D | D | C | D | D |
| 24 | D | D | C | D | D |
| 25 | C | D | D | D | C |
| 26 | D | D | C | D | D |
| 27 | D | D | B | D | D |
| 28 | D | D | B | D | D |
| 29 | D | D | B | D | D |
| 30 | C | D | C | D | D |
| 31 | C | D | B | D | D |
| 32 | D | D | C | D | D |
| 33 | D | D | C | D | D |
| 34 | D | D | C | D | D |
| 35 | D | D | C | D | D |
| 36 | D | D | C | D | D |
| 37 | D | D | C | D | D |
| 38 | D | D | C | D | D |
| 39 | C | D | C | D | D |
| 40 | C | D | D | D | D |
| 41 | D | D | D | D | D |
| 42 | D | D | C | D | D |
| 43 | C | D | C | D | D |
| 44 | B | B | B | C | B |
| 45 | C | D | D | D | D |
| 46 | D | D | D | D | D |
| 47 | D | D | C | D | D |
| 48 | D | D | D | D | D |
| 49 | D | D | C | D | D |
| 50 | D | D | C | D | D |
| 51 | D | D | D | D | D |
| 52 | D | D | C | D | D |
| 53 | C | C | B | D | D |
| 54 | C | C | B | D | B |
| 55 | C | B | C | C | C |
| 56 | D | D | C | D | D |
| 57 | D | D | B | D | D |
| 58 | D | D | C | D | D |
| 59 | D | D | C | D | D |
| 60 | D | D | C | D | D |
| 61 | D | D | C | D | D |
| 62 | D | D | C | D | D |
| 63 | C | D | D | D | D |

Example III

In Vitro Antibacterial Assays of β-Lactamase Inhibition

To determine the ability of test compounds to potentiate the inhibition of the growth of bacterial strains that produce beta-lactamase enzymes, classic cell based broth microdilution MIC assays were employed. Six bacteria strains producing beta-lactamase enzymes were used: *E. coli* expressing the Class A Extended Spectrum Beta-Lactamase (ESBL) CTX-M-15, *E. cloacae* expressing the Class C P99, *K. pneumoniae* expressing the Class A carbapenemase KPC-2, *P. aeruginosa* expressing the Class B carbapenemase VIM-2, *K. pneumoniae* expressing the class A carbapenemase KPC-2 and the class B carbapenemase VIM-4, and *S. aureus* producing the Class A penicillinase PC-1. The assay was conducted in Cation Adjusted Mueller Hinton Broth (CAMHB, BD #212322, BD Diagnostic Systems, Sparks, Md.). Bacteria strains were grown for 3-5 hours in CAMBH broth. Test compounds were added to a microtiter plate in 2-fold serial dilutions in CAMHB in a final concentration range of 32 µg/mL to 0.25 µg/ml. An overlay of CAMHB containing a Beta-lactam was added to the compounds at a final static concentration of 4 µg/ml. Ceftazidime (CAZ, Sigma#C3809-1G, Sigma-Aldrich, St. Louis, Mo.) was used as the partner antibiotic for *E. coli* expressing Ambler Class A ESBL CTX-M-15 (MIC alone >128 µg/ml), and *E. cloacae* expressing Class C P99 (MIC alone=128 µg/mL). Meropenem (Mero, U.S. Pat. No. 1,392,454, U.S. Pharmacopeia, Rockville, Md.) was used as the partner antibiotic for *K. pneumoniae* expressing Ambler Class A carbapenemase KPC-3 (MIC alone >128 µg/mL), *P. aeruginosa* expressing Class A carbapenemase VIM-2 (MIC alone=16 g/mL), and *K. pneumoniae* expressing the Ambler Class A carbapenemase KPC-2 and Ambler Class B carbapenemase VIM-4 (MIC alone=64 µg/mL). Piperacillin (Pip, Fisher #ICN15626801, MP Biomidicals, Solon, Ohio) was used as the partner antibiotic for *S. aureus* producing the Class A penicillinase PC-1 (MIC alone=64 µg/ml). Titration of test compounds with MIC readout indicates the concentration of test article needed to sufficiently inhibit beta-lactamase enzyme activity and protect the intrinsic antibacterial activity of the beta-lactam. In addition to the titration of test compounds the MICs of a panel of control beta-lactams is also tested to ensure the strains are behaving consistently from test to test. Once the test compound and antibiotics are added the plates can be inoculated according to CLSI broth microdilution method. After inoculation the plates are incubated for 16-20 hours at 37° C. then the Minimal Inhibitory Concentration (MIC) of the test compound is determined visually.

Example IV

In vitro Antibacterial Activity of Exemplary Compounds

Using the methodology described above in EXAMPLE III, exemplary compounds for Formula I or Formula Ia were evaluated for their ability to inhibit the growth of β-lactamase producing bacteria in the presence of a β-lactam antibiotic.

Representative results are shown in Table 3 where A represents an MIC of the fixed β-lactam antibiotic in the presence of >32 µg/mL of a β-lactamase inhibitor of exemplary compounds, B represents the MIC in the presence of between 8 and 32 µg/mL of a β-lactamase inhibitor of exemplary compounds, and C represents the MIC in the presence of ≤4 µg/mL of a β-lactamase inhibitor of exemplary compounds. NT=Not Tested.

TABLE 3

Broad spectrum inhibition of bacterial growth. MIC of example compounds of the invention in the presence of a fixed amount (4 μg/mL) of designated β-lactam antibiotics ceftazidime (CAZ), meropenem (Mero), Piperacillin (Pip).

| | MIC (μg/mL) of Exemplary Compounds in presence of fixed β-lactams | | | | | |
|---|---|---|---|---|---|---|
| | Fixed CAZ ESBLs (Class A and C) | | Fixed Mero Carbapenemases (Classes A and B) | | | Fixed Pip Penicillinase |
| EXAMPLE | *E. coli* ESBL4 CTX-M-15 | *E. cl.* 144200 p99 AmpC | *K.P.* 156319 KPC-3 | *P. aerug.* Ps296 VIM-2 | *K.P.* A-1797 KPC-2 VIM-4 | *S. aureus* MSSA-7 PC-1 |
| 1 | C | C | B | B | | |
| 2 | C | C | B | B | A | C |
| 3 | C | C | C | B | A | A |
| 4 | C | C | C | A | C | C |
| 5 | C | C | C | A | C | C |
| 6 | C | C | C | A | B | C |
| 7 | C | C | B | A | C | C |
| 8 | C | C | A | C | A | C |
| 9 | C | C | C | C | C | C |
| 10 | C | C | C | B | C | C |
| 11 | C | C | C | A | C | C |
| 12 | B | C | B | A | B | C |
| 13 | C | C | C | B | B | C |
| 14 | C | C | C | C | C | C |
| 15 | C | C | B | C | B | C |
| 16 | C | C | C | C | C | C |
| 17 | C | C | C | B | C | C |
| 18 | C | C | C | C | C | C |
| 19 | C | C | C | C | C | C |
| 20 | C | C | C | C | C | C |
| 21 | C | C | B | A | B | B |
| 22 | C | C | C | A | B | C |
| 23 | C | C | C | B | B | C |
| 24 | C | C | B | B | B | C |
| 25 | C | C | C | C | C | C |
| 26 | C | C | C | B | B | C |
| 27 | C | C | A | A | A | C |
| 28 | C | C | C | A | B | C |
| 29 | C | C | C | A | A | C |
| 30 | C | C | C | C | B | C |
| 31 | C | C | C | B | A | C |
| 32 | C | C | C | C | A | C |
| 33 | C | C | C | C | B | C |
| 34 | C | C | C | C | B | C |
| 35 | C | C | C | C | A | C |
| 36 | C | C | C | C | A | C |
| 37 | C | C | C | C | A | C |
| 38 | C | C | C | B | B | C |
| 39 | C | C | C | B | B | B |
| 40 | C | C | C | C | C | C |
| 41 | C | C | A | B | C | C |
| 42 | C | C | A | C | B | C |
| 43 | C | C | A | A | A | C |
| 44 | B | A | A | A | A | A |
| 45 | C | C | C | C | C | A |
| 46 | C | C | C | C | C | B |
| 47 | C | C | C | B | A | C |
| 48 | C | C | C | C | C | C |
| 49 | C | C | C | C | A | C |
| 50 | C | C | C | C | A | C |
| 51 | C | C | C | C | C | C |
| 52 | C | C | C | B | A | C |
| 53 | C | C | C | A | B | C |
| 54 | C | C | B | C | A | A |
| 55 | C | C | B | C | A | A |
| 56 | C | C | C | C | C | C |
| 57 | C | C | B | C | C | C |
| 58 | C | C | C | C | B | C |
| 59 | C | C | C | C | B | C |
| 60 | C | C | C | C | B | C |
| 61 | C | C | C | C | C | C |
| 62 | C | C | C | C | C | C |
| 63 | C | C | C | C | C | C |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of Formula (I) or Formula (Ia), a pharmaceutically acceptable salt, polymorph, solvate, N-oxide, or isomer thereof:

Formula (I)

$(Y)_p$—(ArA)—$(CR^1R^2)_m$—M—$(CR^1R^2)_n$—Z—N(...) [structure]

Formula (Ia)

$(Y)_p$—(ArA)—$(CR^1R^2)_m$—M—$(CR^1R^2)_n$—Z—N(...) [structure]

wherein:
M is a bond, —O—, —S—, —S(O)—, $SO_2$—, or —N($R^4$)—;
m is 0, 1, or 2;
n is 0, 1, 2, or 3;
provided that
when n is 0, then M is a bond;
p is 2, 3, 4, or 5;
$X^1$ and $X^2$ are independently selected from —OH, —$OR^8$, or F;
Z is >C=O, >C=S, or >$SO_2$;
ArA is an aromatic or heteroaromatic ring system optionally substituted with one or more substituents selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, and —$SR^{10}$;
each Y is selected from the group consisting of —$NR^4R^5$, —$(CR^6R^7)_vNR^4R^5$, —$NR^4(CR^6R^7)_vNR^4R^5$, —$O(CR^6R^7)_vNR^4R^5$, —$S(O)_{0,1,2}(CR^6R^7)_vNR^4R^5$, —$N(R^4)C(O)(CR^6R^7)_vNR^4R^5$, —$(CR^6R^7)_vN(R^4)C(O)(CR^6R^7)_vNR^4R^5$, —$(CR^6R^7)_vNR^4(CR^6R^7)_vNR^4R^5$, —$NR^4(CR^6R^7)_vOR^{10}$, —$NR^4(CR^6R^7)_vS(O)_{0,1,2}R^{10}$, —$C(O)NR^4(CR^6R^7)_vNR^4R^5$, —$S(O)_{0,1,2}NR^4(CR^6R^7)_vNR^4R^5$, —$NR^5C(O)NR^4(CR^6R^7)_vNR^4R^5$, —$OC(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$O(CR^6R^7)_vN(R^4)C(=NR^5)R^6$, —$S(O)_{0,1,2}(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$O(CR^6R^7)_vC(=NR^5)NR^4R^5$, —$S(O)_{0,1,2}(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$O(CR^6R^7)_vN(R^4)C(=NR^5)NR^4R^5$, —$S(O)_{0,1,2}(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$O(CR^6R^7)_vC(=NR^4)NR^5C(=NR^4)NR^4R^5$, —$S(O)_{0,1,2}(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4SO_2R^6$, —$NR^4C(O)R^6$, —$NR^4C(=O)OR^6$, —$C(O)NR^4R^5$, —$(CR^6R^7)_vC(O)NR^4R^5$, —$SO_2NR^4R^5$, -Heteroaryl-$NR^4R^5$, -Heterocyclyl-$NR^4R^5$, -Heteroaryl-$N(R^4)C(=NR^5)NR^4R^5$, -Heterocyclyl-$N(R^4)C(=NR^5)NR^4R^5$, —$N(R^4)$-Heteroaryl-$NR^4R^5$, —$N(R^4)$—Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl-$N(R^4)C(=NR^5)NR^4R^5$, —$(CR^6R^7)_v$Heterocyclyl-$N(R^4)C(=NR^5)NR^4R^5$, —$(CR^6R^7)_v$Heteroaryl, —$(CR^6R^7)_v$Heterocyclyl, —O-Heteroaryl, —O-Heterocyclyl, —$NR^4(CR^6R^7)_v$Heteroaryl, —$NR^4(CR^6R^7)_v$Heterocyclyl, —$O(CR^6R^7)_v$Heteroaryl, —$O(CR^6R^7)_v$Heterocyclyl, —$NR^4(CR^6R^7)_vNR^5$-Heteroaryl, —$NR^4(CR^6R^7)_vNR^5$-Heterocyclyl, —$O(CR^6R^7)_vNR^5$-Heteroaryl, —$O(CR^6R^7)_vNR^5$-Heterocyclyl, —$O(CR^6R^7)_v$O-Heterocyclyl, —$NR^4R^5R^{9+}Q^-$, —$(CR^6R^7)_vNR^4R^5R^{9+}Q^-$, —$NR^4(CR^6R^7)_vNR^4R^5R^{9+}Q^-$, —$NR^4R^{9+}(CR^6R^7)_vNR^4R^5R^{9+}Q^-_2$, —$(CR^6R^7)_v(T)^+Q^-$, and —$O(CR^6R^7)_vNR^4R^5R^{9+}Q^-$;

wherein:
T is pyridine-1-yl, pyrimidin-1-yl, or thiazol-3-yl;
Q is a pharmaceutically acceptable counterion; and
v is 1-4;
or two Ys taken together with the carbon atoms to which they are attached to ArA form an optionally substituted carbocycle or an optionally substituted heterocycle;

$R^a$, $R^b$, and $R^c$ are independently selected from the group consisting of hydrogen, fluoro, chloro, bromo, optionally substituted $C_1$-$C_6$ alkyl, optionally substituted $C_3$-$C_6$ cycloalkyl, optionally substituted heterocyclyl, optionally substituted aryl, optionally substituted heteroaryl, —OH, —$OR^{10}$, —$NR^4R^5$, and —$SR^{10}$;

$R^1$ and $R^2$ are independently selected from the group consisting of hydrogen, fluoro, chloro, bromo, optionally substituted $C_1$-$C_6$ alkyl, optionally substituted $C_3$-$C_6$ cycloalkyl, —OH, —$OR^{10}$, —$SR^{10}$, and —$NR^4R^5$,
or $R^1$ and $R^2$ taken together form an oxo, oxime, or an optionally substituted carbocycle or optionally substituted heterocycle with the carbon to which they are attached;

$R^3$ is hydrogen or optionally substituted $C_1$-$C_6$ alkyl;

$R^d$, $R^4$ and $R^5$ are independently selected from the group consisting of hydrogen, —OH, —CN, optionally substituted $C_1$-$C_6$ alkyl, optionally substituted alkoxyalkyl, optionally substituted hydroxyalkyl, optionally substituted aminoalkyl, optionally substituted cycloalkyl, optionally substituted heterocyclyl, optionally substituted aryl, optionally substituted heteroaryl, optionally substituted cycloalkylalkyl, optionally substituted heterocyclylalkyl, optionally substituted aralkyl, optionally substituted heteroaralkyl, (poly-ethylene-glycol)-ethyl, and an optionally substituted saccharide;

or $R^4$ and $R^5$ taken together form an optionally substituted heterocycle with the nitrogen to which they are attached;

$R^6$ and $R^7$ are independently selected from the group consisting of hydrogen, fluoro, chloro, bromo, optionally substituted $C_1$-$C_6$ alkyl, optionally substituted alkoxyalkyl, optionally substituted hydroxyalkyl, optionally substituted $C_3$-$C_6$ cycloalkyl, —OH, —$OR^{10}$, —$SR^{10}$, —$NR^4R^5$, —$NR^4C(O)R^5$, —$C(O)NR^4R^5$, —$NR^4SO_2R^5$, optionally substituted heterocyclyl, optionally substituted aryl, and optionally substituted heteroaryl;

or $R^6$ and $R^7$ taken together form an oxo, oxime, or an optionally substituted carbocycle or an optionally substituted heterocycle with the carbon to which they are attached;

$R^8$ is optionally substituted $C_1$-$C_6$ alkyl, optionally substituted $C_3$-$C_6$ cycloalkyl, or a pharmaceutically acceptable boronate ester group;

$R^9$ is optionally substituted $C_1$-$C_6$ alkyl;

$R^{10}$ is optionally substituted $C_1$-$C_6$ alkyl or optionally substituted $C_3$-$C_6$ cycloalkyl.

2. The compound of claim 1, wherein $R^a$, $R^b$, and $R^c$ are hydrogen.

3. The compound of claim 1, wherein $R^3$ is hydrogen.

4. The compound of claim 1, wherein $X^1$ and $X^2$ are —OH.

5. The compound of claim 1, wherein $R^d$ is hydrogen.

6. The compound of claim 1, wherein Z is >C=O.

7. The compound of claim 1, wherein:
M is a bond; and
m and n are 0.

8. The compound of claim 1, wherein:
M is a bond; and
m or n are 1.

9. The compound of claim 1, wherein ArA is selected from the group consisting of benzene, pyridine, pyrimidine, thiophene, thiazole, triazole, indole, benzimidazole, azaindole, thienopyrazole, quinoline, quinazoline, and quinoxaline.

10. The compound of claim 1, wherein at least one Y is selected from the group consisting of —$NR^4R^5$, —$(CR^6R^7)_vNR^4R^5$, —$NR^4(CR^6R^7)_vNR^4R^5$, —$O(CR^6R^7)_vNR^4R^5$, —$C(O)NR^4(CR^6R^7)_vNR^4R^5$, —$NR^5C(O)NR^4(CR^6R^7)_vNR^4R^5$, —$NR^5C(=NR^7)NR^4(CR^6R^7)_vNR^4R^5$, —$N(R^4)C(=NR^5)R^6$, —$(CR^6R^7)_vN(R^4)C(=NR^5)R^6$, —$NR^4(CR^6R^7)_vN(R^4)C(=NR^5)R^6$, —$(CR^6R^7)_vC(=NR^5)NR^4R^5$, —$NR^4(CR^6R^7)_vC(=NR^5)NR^4R^5$, —$(CR^6R^7)_vN(R^4)C(=NR^5)NR^4R^5$, —$NR^4(CR^6R^7)_vN(R^4)C(=NR^5)NR^4R^5$, —$NR^4C(=NR^5)NR^4C(=NR^5)NR^4R^5$, —$(CR^6R^7)_vC(=NR^4)NR^5C(=NR^4)NR^4R^5$, —$NR^4(CR^6R^7)_vC(=NR^4)NR^5C(=NR^4)NR^4R^5$, —$NR^4C(=NR^5)NR^4R^5$, —$C(=NR^4)NR^4R^5$, —$C(=NR^4)NR^4C(O)R^6$, —$NR^4C(O)R^6$, —$(CR^6R^7)_vC(O)NR^4R^5$, -Heterocyclyl-$NR^4R^5$, -Heterocyclyl-$N(R^4)C(=NR^4)NR^4R^5$, —$N(R^4)$—Heterocyclyl-$NR^4R^5$, —$(CR^6R^7)_v$Heterocyclyl-$NR^4R^5$, —$(CR^6R^7)_v$Heterocyclyl-$N(R^4)C(=NR^5)NR^4R^5$, —$(CR^6R^7)_v$Heterocyclyl, and —$NR^4(CR^6R^7)_v$Heterocyclyl.

11. The compound of claim 1, wherein two Y groups taken together with the carbon atoms to which they are attached form an optionally substituted carbocycle or an optionally substituted heterocycle.

12. The compound of claim 11, wherein the carbocycle or heterocycle is optionally substituted with one to three substituents selected from the group consisting of fluoro, chloro, bromo, —CN, optionally substituted $C_1$-$C_6$ alkyl, optionally substituted $C_3$-$C_6$ cycloalkyl, optionally substituted heterocycle, optionally substituted aryl, optionally substituted heteroaryl, —OH, —$OR^{10}$, —$SR^{10}$, —$NR^4R^5$, —$(CR^6R^7)_vNR^4R^5$, —$NR^4(CR^6R^7)_vNR^4R^5$, —$O(CR^6R^7)_vNR^4R^5$, —$NR^4C(=NR^5)NR^4R^5$, —$C(=NR^4)NR^4R^5$, -Heteroaryl-$NR^4R^5$, -Heterocyclyl-$NR^4R^5$, —$(CR^6R^7)_v$Heteroaryl-$NR^4R^5$, —$(CR^6R^7)_v$Heterocyclyl-$NR^4R^5$, —$(CR^6R^7)_v$Heteroaryl, and —$(CR^6R^7)_v$Heterocyclyl.

13. The compound of claim 1, wherein p is 2 or 3.

14. The compound of claim 1, wherein $R^4$ and $R^5$ are independently hydrogen or optionally substituted $C_1$-$C_6$ alkyl.

15. The compound of claim 1, wherein each $R^6$ and $R^7$ are independently hydrogen, fluoro, or optionally substituted $C_1$-$C_6$ alkyl.

16. The compound of claim 1, selected from the group represented by the following structures:

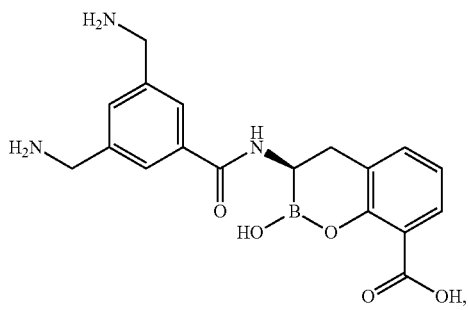

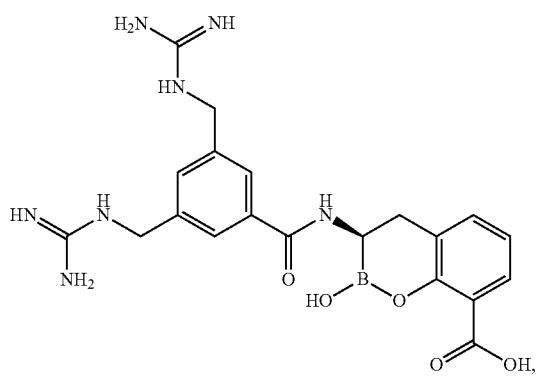

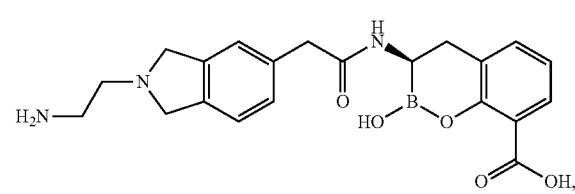

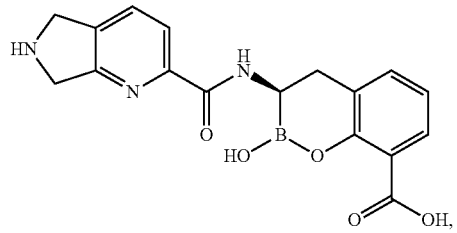

177
-continued
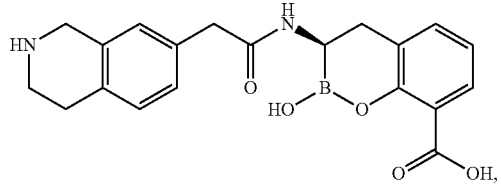
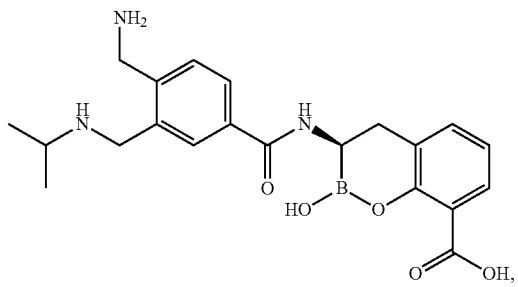
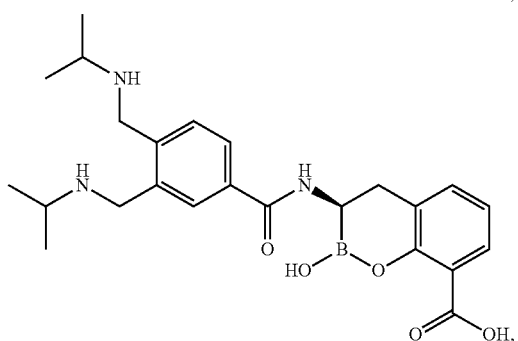
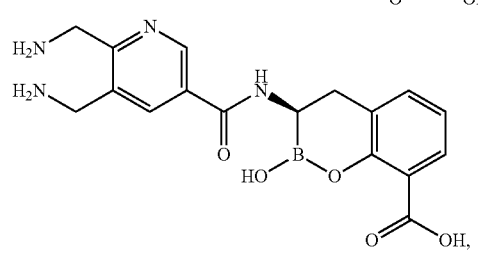
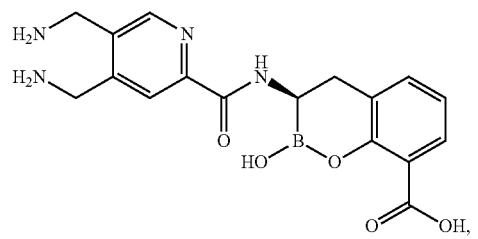
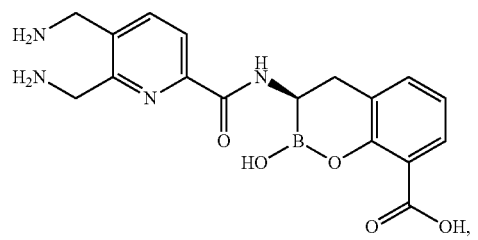
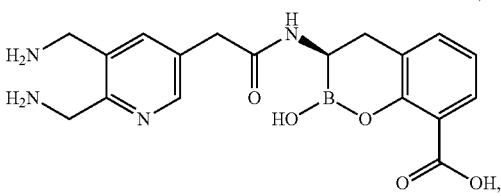
178
-continued
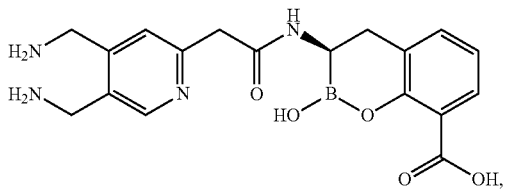
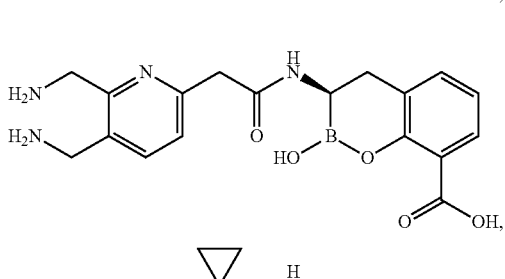
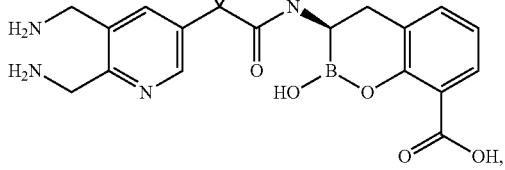
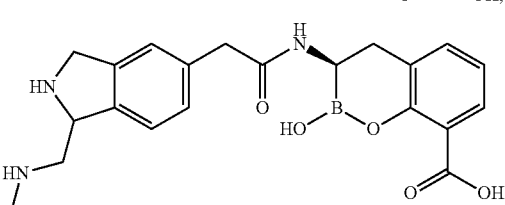
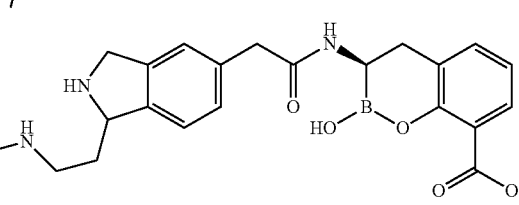
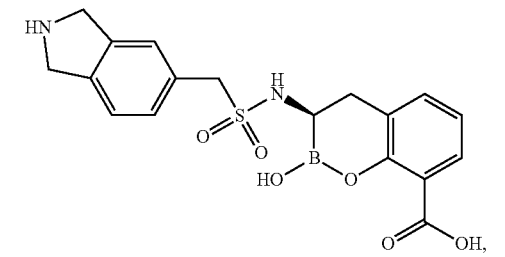
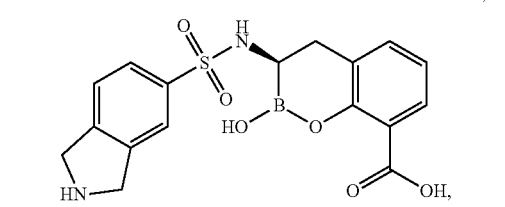
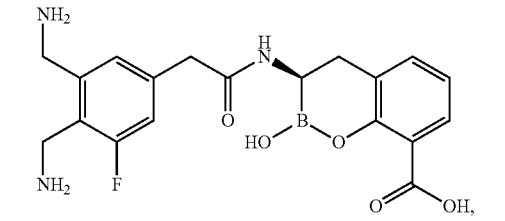

-continued
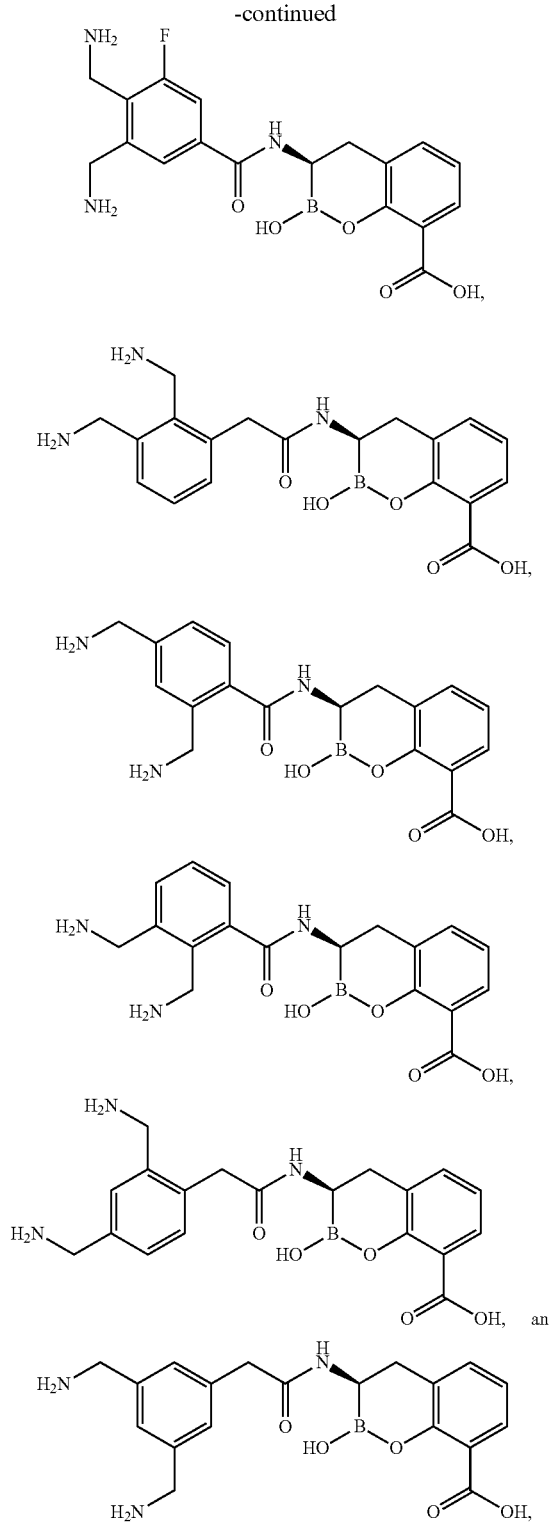
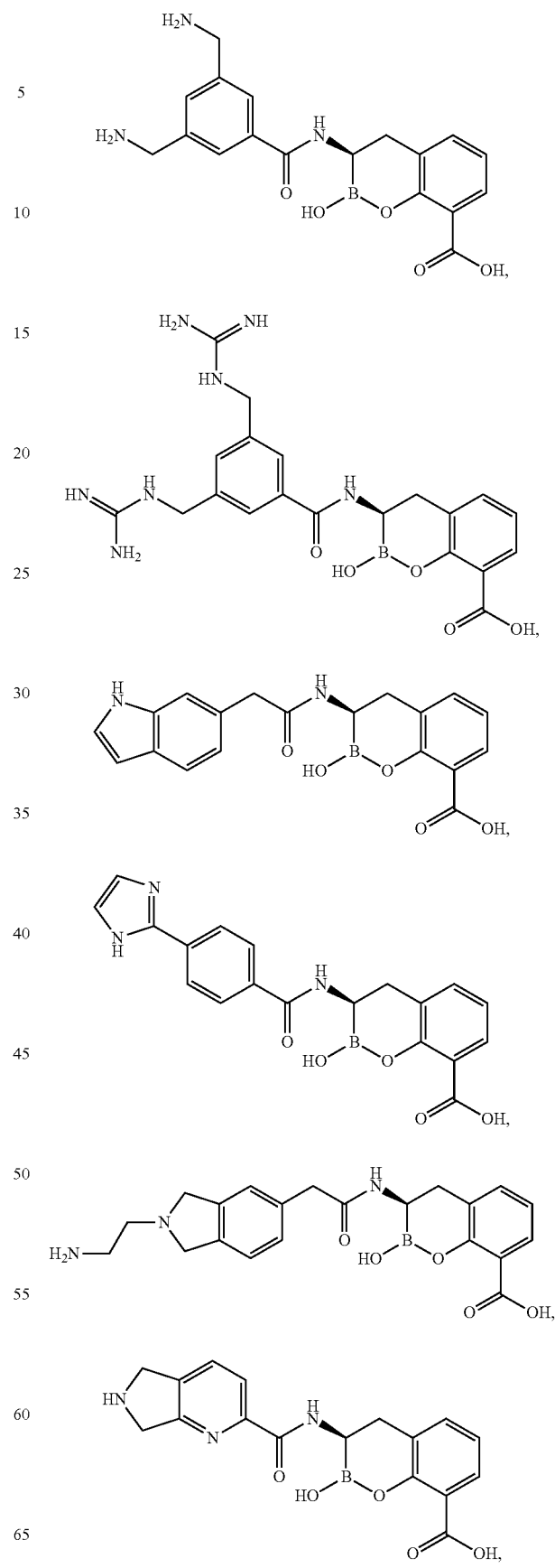
or a pharmaceutically acceptable salt, solvate, polymorph, N-oxide, or isomer thereof, wherein the compound is present in a closed, cyclic form according to Formula I and as shown in the structures above, an open, acyclic form according to Formula Ia, or mixtures thereof.
17. A compound selected from the group represented by the following structures:

181
-continued
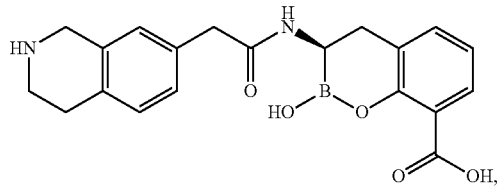
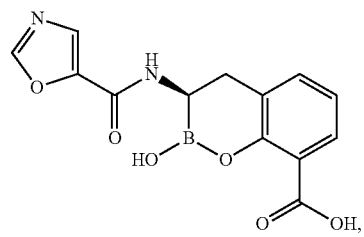
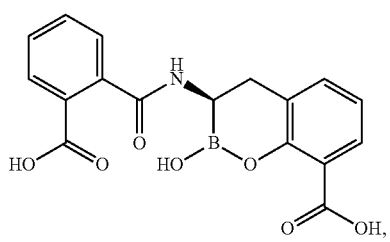
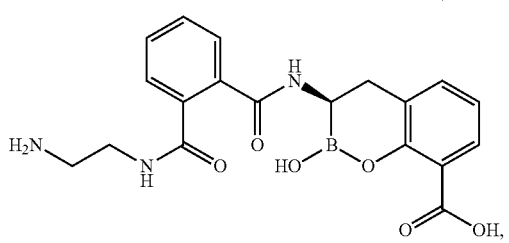
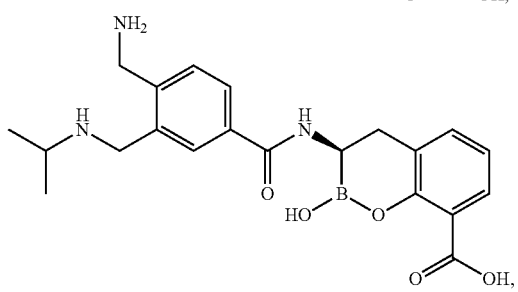
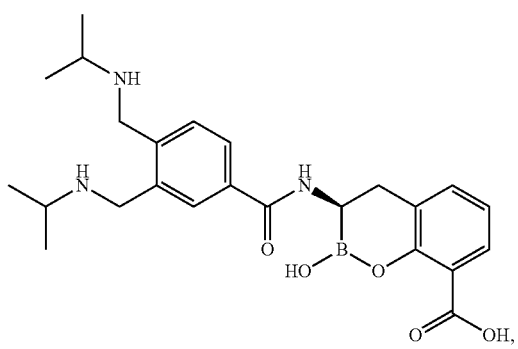
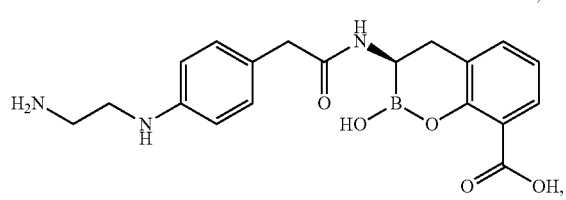
182
-continued
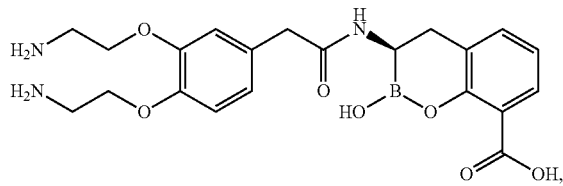
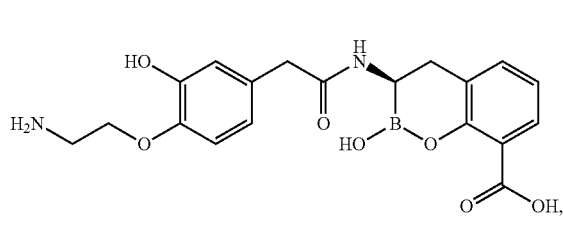
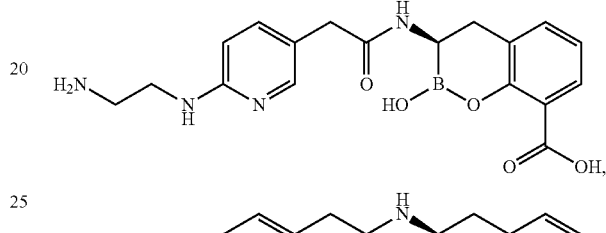
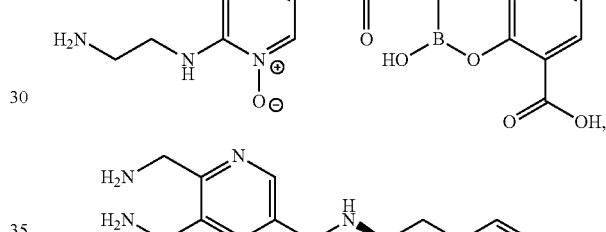
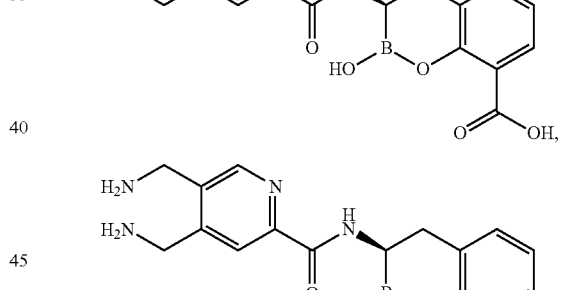
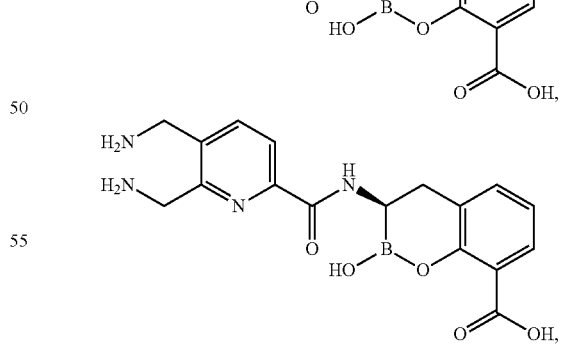
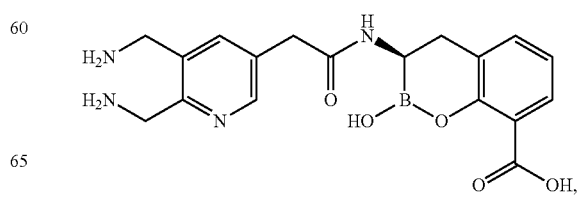

183
-continued
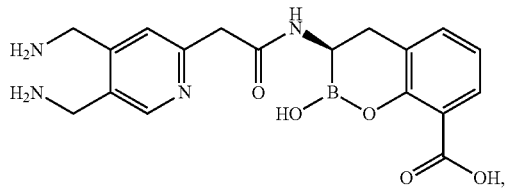
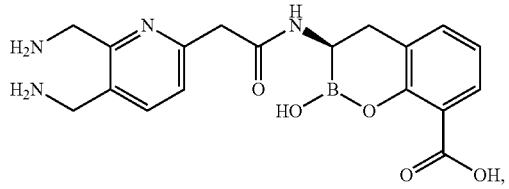
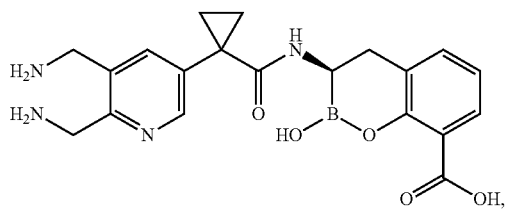
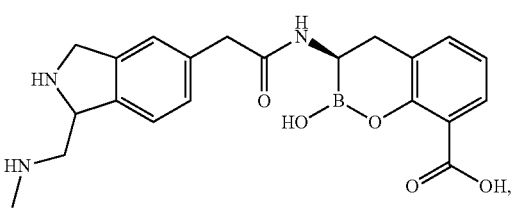
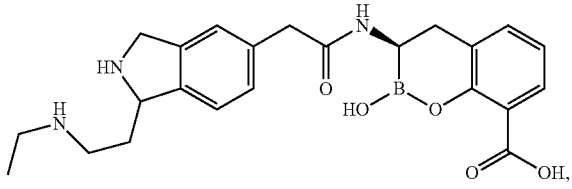
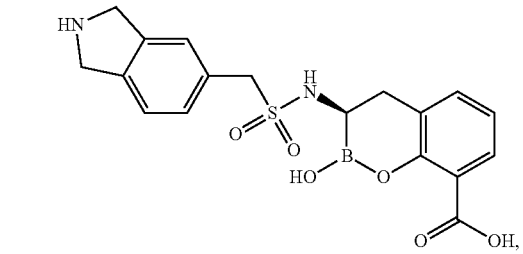
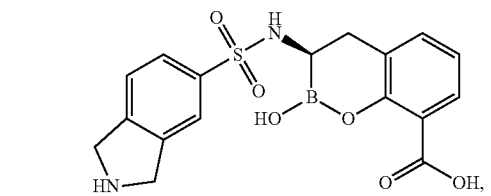
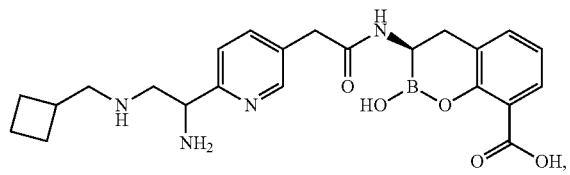
184
-continued
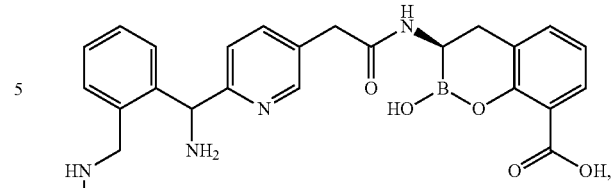
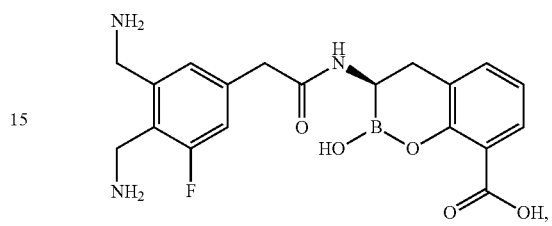
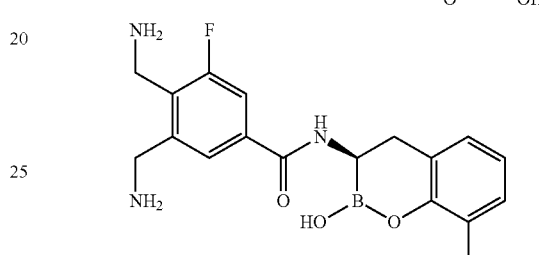
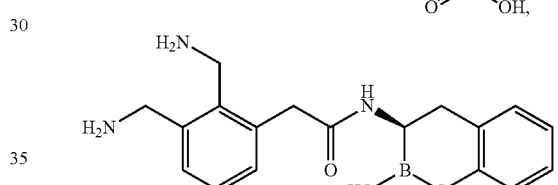
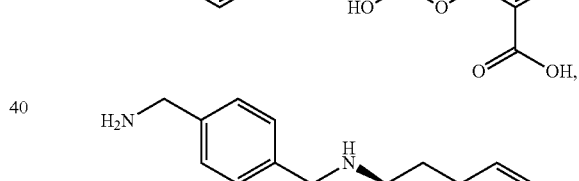
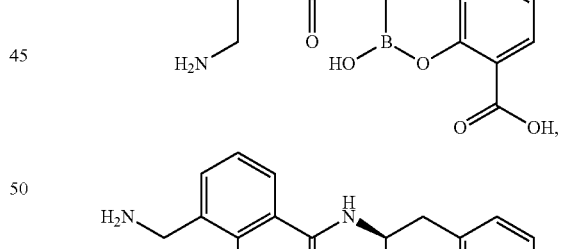
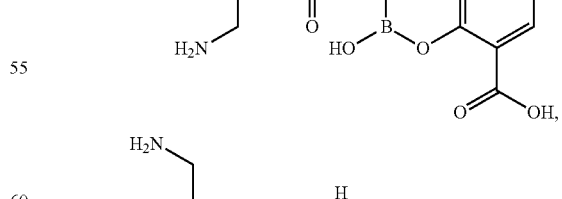
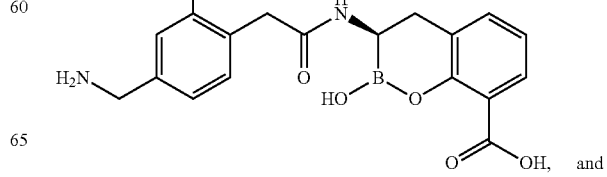
and -continued

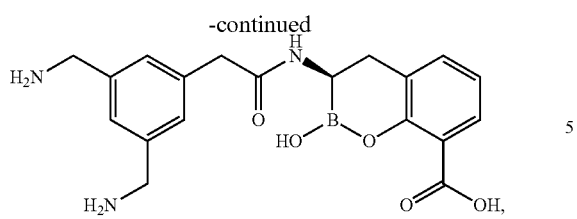

or a pharmaceutically acceptable salt, solvate, polymorph, N-oxide, or isomer thereof, wherein the compound is present in a closed, cyclic form according to Formula I and as shown in the structures above, an open, acyclic form according to Formula Ia, or mixtures thereof.

18. A pharmaceutical composition comprising a compound of claim 1 or a pharmaceutically acceptable salt, polymorph, solvate N-oxide, or isomer thereof, and a pharmaceutically acceptable excipient.

19. The pharmaceutical composition of claim 18, further comprising a beta-lactam antibiotic.

20. A method of treating a bacterial infection in a subject, comprising administering to the subject a pharmaceutical composition of claim 18, optionally in combination with a beta-lactam antibiotic.

* * * * *